(12) United States Patent
Menezes et al.

(10) Patent No.: US 10,794,911 B2
(45) Date of Patent: Oct. 6, 2020

(54) RELIABLE, COMPREHENSIVE, AND RAPID SEXUAL HEALTH ASSESSMENT

(71) Applicant: Simple HealthKit, Inc., San Jose, CA (US)

(72) Inventors: Sheena Ruby Menezes, Los Gatos, CA (US); Jerzy Majka, Foster City, CA (US); Linus Ryan Aranha, Los Gatos, CA (US); Quynh Nga Thi Le, San Jose, CA (US)

(73) Assignee: SIMPLE HEALTHKIT, INC., San Jose, CA (US)

( * ) Notice: Subject to any disclaimer, the term of this patent is extended or adjusted under 35 U.S.C. 154(b) by 0 days.

(21) Appl. No.: 16/571,032

(22) Filed: Sep. 13, 2019

(65) Prior Publication Data

US 2020/0003777 A1   Jan. 2, 2020

Related U.S. Application Data

(63) Continuation of application No. PCT/US2019/016064, filed on Jan. 31, 2019.

(60) Provisional application No. 62/626,010, filed on Feb. 3, 2018, provisional application No. 62/768,618, filed on Nov. 16, 2018.

(51) Int. Cl.
| | | |
|---|---|---|
| *G01N 33/53* | (2006.01) | |
| *G01N 33/571* | (2006.01) | |
| *C12Q 1/00* | (2006.01) | |
| *C12Q 1/68* | (2018.01) | |
| *A61K 49/00* | (2006.01) | |
| *A61B 5/055* | (2006.01) | |
| *A61K 39/095* | (2006.01) | |
| *A61K 39/118* | (2006.01) | |
| *A61K 39/00* | (2006.01) | |
| *G01N 33/569* | (2006.01) | |

(52) U.S. Cl.
CPC ..... *G01N 33/571* (2013.01); *G01N 33/56927* (2013.01); *G01N 2800/26* (2013.01)

(58) Field of Classification Search
CPC ............ G01N 33/6893; G01N 33/571; G01N 33/56927; A61K 38/00; A61K 51/088; A61K 49/085; C12Q 1/689; C07K 14/22; C07K 14/295; C07K 14/14
See application file for complete search history.

(56) References Cited

U.S. PATENT DOCUMENTS

| | | | |
|---|---|---|---|
| 4,094,647 A | 6/1978 | Deutsch et al. | |
| 4,168,146 A | 9/1979 | Grubb et al. | |
| 4,235,601 A | 11/1980 | Deutsch et al. | |
| 4,361,537 A | 11/1982 | Deutsch et al. | |
| 4,730,017 A | 3/1988 | Avar | |
| 4,775,636 A | 10/1988 | Moeremans et al. | |
| 4,855,240 A | 8/1989 | Rosenstein et al. | |
| 4,857,453 A | 8/1989 | Ullman et al. | |
| 4,861,711 A | 8/1989 | Friesen et al. | |
| 4,943,522 A | 7/1990 | Eisinger et al. | |
| 5,415,994 A | 5/1995 | Imrich et al. | |
| 5,602,040 A * | 2/1997 | May ................. | G01N 33/54366 422/401 |
| 5,622,871 A * | 4/1997 | May ................. | G01N 33/54386 422/504 |
| 5,648,274 A * | 7/1997 | Chandler .............. | B01L 3/5023 422/408 |
| 6,093,546 A * | 7/2000 | Ledden ................ | G01N 33/543 435/7.1 |
| 6,136,610 A | 10/2000 | Polito et al. | |
| 2002/0142291 A1* | 10/2002 | Bauer .............. | G01N 33/54386 435/5 |
| 2004/0184954 A1* | 9/2004 | Guo ................... | A61B 10/0051 422/400 |
| 2004/0266025 A1* | 12/2004 | Hickok ................. | A61K 31/20 436/518 |
| 2005/0130120 A1 | 6/2005 | Lambotte et al. | |
| 2005/0227370 A1 | 10/2005 | Ramel et al. | |
| 2006/0008847 A1 | 1/2006 | Ramel et al. | |
| 2006/0105406 A1* | 5/2006 | Warmington .......... | C07K 14/40 435/7.31 |
| 2006/0134804 A1* | 6/2006 | Gao ..................... | G01N 33/558 436/514 |

(Continued)

FOREIGN PATENT DOCUMENTS

| | | |
|---|---|---|
| EP | 0158746 A2 | 10/1985 |
| EP | 0276152 A2 | 7/1988 |

(Continued)

OTHER PUBLICATIONS

Mayo Clinic, https://www.mayoclinic.org/diseases-conditions/gonorrhea/symptoms-causes/syc-20351774, accessed on Dec. 7, 2019 (Year: 2019).*

(Continued)

*Primary Examiner* — Gary B Nickol
*Assistant Examiner* — Lakia J Jackson-Tongue
(74) *Attorney, Agent, or Firm* — Fenwick & West LLP

(57) ABSTRACT

A system and method for detecting status of a health condition in a single-step process includes: a signal output device including a) a loading zone; b) a reaction zone fluidly coupled to the loading zone and including one or more reaction substances conjugated to labels, configured to enable detection of target material associated with the health condition; c) a testing zone fluidly coupled to the reaction zone and including one or more testing substances corresponding to the target material; and d) a control zone including a control substance retained at the control zone. The system and methods can be adapted for assessment of sexual health of one or more subjects, in relation to pregnancy, fertility, and/or sexually transmitted infections caused by one or more agents including, *Chlamydia trachomatis, Neisseria gonorrhoeae, Trichomonas vaginalis, Treponema pallidum, Gardnerella vaginitis*, human immunodeficiency virus, human papillomavirus infection, Hepatitis B, and herpes simplex virus.

28 Claims, 11 Drawing Sheets

Specification includes a Sequence Listing.

(56) References Cited

U.S. PATENT DOCUMENTS

| | | | |
|---|---|---|---|
| 2006/0199277 A1* | 9/2006 | Tang | G01N 33/558 436/514 |
| 2007/0134810 A1 | 6/2007 | Yang et al. | |
| 2008/0090240 A1* | 4/2008 | Ku | C12Q 1/689 435/6.15 |
| 2008/0096189 A1* | 4/2008 | Boone | G01N 33/54366 435/5 |
| 2008/0145272 A1 | 6/2008 | Feaster et al. | |
| 2008/0199851 A1* | 8/2008 | Egan | B01L 3/5023 435/5 |
| 2010/0009387 A1* | 1/2010 | Cheng | C12Q 1/708 435/7.2 |
| 2010/0112725 A1* | 5/2010 | Babu | G01N 33/558 436/518 |
| 2010/0248220 A1* | 9/2010 | Ku | C12Q 1/689 435/6.11 |
| 2010/0304359 A1* | 12/2010 | Egan | G01N 33/54366 435/5 |
| 2010/0323343 A1* | 12/2010 | Egan | C12Q 1/6804 435/5 |
| 2011/0093249 A1* | 4/2011 | Holmes | G06F 19/00 703/6 |
| 2013/0129668 A1 | 5/2013 | Firestein et al. | |
| 2018/0021771 A1 | 1/2018 | Tamir | |

FOREIGN PATENT DOCUMENTS

| | | |
|---|---|---|
| EP | 0306772 A1 | 3/1989 |
| EP | 0451800 A1 | 10/1997 |
| GB | 2204398 A | 11/1988 |
| WO | WO 94/15215 A1 | 7/1994 |
| WO | WO 2003/008583 A2 | 1/2003 |
| WO | WO 2014/139330 A1 | 9/2014 |
| WO | WO 2016/030871 A1 | 3/2016 |
| WO | WO 2017/191274 A2 | 11/2017 |

OTHER PUBLICATIONS

CDC, https://www.cdc.gov/std/trichomonas/stdfact-trichomoniasis.htm, accessed on Dec. 7, 2019 (Year: 2019).*

Medline plus, https://medlineplus.gov/chlamydiainfections.html, accessed on Dec. 7, 2019 (Year: 2019).* antibodies-online.com, "Matched Antibody Pairs (Infectious Diseases)," May 12, 2016, 11 pages [Online] [Retrieved on Apr. 24, 2019] Retrieved from the Internet <URL: https://www.antibodies-online.com/resources/17/1620/matched-antibody-pairs-infectious-diseases/>.

Bamrungsap, S. et al., "Rapid and sensitive lateral flow immunoassay for influenza antigen using fluorescently-doped silica nanoparticles," Microchimica Acta, vol. 181, Iss. 1-2, Oct. 19, 2013, pp. 223-230.

Blaney, L., "Magnetite (Fe3O4): Properties, Synthesis, and Applications," Lehigh Review, vol. 15, Jan. 2007, pp. 33-81.

Chard, T., "Pregnancy tests: a review," Human Reproduction, vol. 7, Iss. 5, May 1992, pp. 701-710.

Chen, R. et al., "Development of a lateral flow fluorescent microsphere immunoassay for the determination of sulfamethazine in milk," Analytical and Bioanalytical Chemistry, vol. 405, Iss. 21, Jul. 9, 2013, pp. 6783-6789.

Chung, K. et al., "The Use of Serial Human Chorionic Gonadotropin Levels to Establish a Viable or a Nonviable Pregnancy," Seminars in Reproductive Medicine, vol. 26, Iss. 5, Sep. 2008, pp. 383-390.

Corstjens, P. et al., "Feasibility of a Lateral Flow Test for Neurocysticercosis Using Novel Up-Converting Nanomaterials and a Lightweight Strip Analyzer," PLOS Neglected Tropical Diseases, vol. 8, Iss. 7, Article e2944, Jul. 3, 2014, pp. 1-12.

Goding, J., "Conjugation of antibodies with fluorochromes: modifications to the standard methods," J. Immunol. Meth, vol. 13, Iss. 3-4, Dec. 1976, pp. 215-226.

Juntunen, E. et al., "Performance of fluorescent europium(III) nanoparticles and colloidal gold reporters in lateral flow bioaffinity assay," Analytical Biochemistry, vol. 428, Iss. 1, Jun. 13, 2012, pp. 31-38.

Liu, H. F. et al., "Recovery and purification process development for monoclonal antibody production," Mabs, vol. 2, Iss. 5, Sep. 1, 2010, pp. 480-499.

Mao, X. et al., "Disposable Nucleic Acid Biosensors Based on Gold Nanoparticle Probes and Lateral Flow Strip," Anal. Chem., vol. 81 Iss. 4, Jan. 21, 2009, pp. 1660-1668.

PCT International Search Report and Written Opinion, PCT Application No. PCT/US19/16064, dated Jul. 17, 2019, 18 pages.

VWR International, LLC, "Anti-Neisseria gonorrhoeae Mouse Monoclonal Antibody [clone: M2110186]," 2019, two pages [Online] [Retrieved on Jul. 8, 2019] Retrieved from the Internet <URL: https://us.vwr.com/store/product/22064262/anti-neisseria-gonorrhoeae-mouse-monoclonal-antibody-clone-m2110186>.

Xu, Y. et al., "Fluorescent Probe-Based Lateral Flow Assay for Multiplex Nucleic Acid Detection," Anal. Chem., vol. 86, Iss. 12, Jun. 3, 2014, pp. 5611-5614.

Zhang, F. et al., "Lanthanide-labeled immunochromatographic strips for the rapid detection of *Pantoea stewartii* subsp. *stewartii*," Biosens. Bioelectron., vol. 51, Jul. 19, 2013, pp. 29-35.

Zhao, Y. et al., "Quantum dots-based lateral flow immunoassay combined with image analysis for semiquantitative detection of IgE antibody to mite," Int. J. Nanomedicine, vol. 12, Jul. 4, 2017, pp. 4805-4812.

Zhuang, L. et al., "Preparation and Characterization of Fe3O4 Particles with Novel Nanosheets Morphology and Magnetochromatic Property by a Modified Solvothermal Method," Scientific Reports, vol. 5, Article No. 9320, Mar. 23, 2015, pp. 1-6.

* cited by examiner

RELIABLE, COMPREHENSIVE, AND RAPID SEXUAL HEALTH ASSESSMENT

CROSS REFERENCE TO RELATED APPLICATIONS

This application is a continuation of International Application No. PCT/US2019/016064, filed on Jan. 31, 2019, which claims the benefit of U.S. Provisional Application Ser. No. 62/626,010 filed Feb. 3, 2018 and U.S. Provisional Application Ser. No. 62/768,618 filed Nov. 16, 2018, all of which are incorporated herein by reference in their entirety for all purposes.

SEQUENCE LISTING

The instant application contains a Sequence Listing which has been submitted via EFS-Web and is hereby incorporated herein by reference in its entirety. Said ASCII copy, created on Sep. 9, 2019, is named 42433_US_Sequence_Listing_ST25_REVISED.txt, and is 346,778 bytes in size.

BACKGROUND

The invention(s) described relate generally to systems and methods for reliably and efficiently assessing sexual health of a subject. Embodiments of the invention(s) described relate to consumer test devices and kits that can be used to detect the presence of one or more infections caused by a sexually transmitted pathogen, optionally in conjunction with the detection of the pregnancy, fertility, and/or other sexual health conditions. Methods for producing the system(s) described are also described.

Sexually transmitted infections (STIs) remain an important focus area for global public health. There are over 1 million sexually transmitted infections (STIs) that are acquired each day and the numbers are growing as 75% of people infected are asymptomatic. However, a high morbidity is associated with STIs, such as the sequelae of reproductive tract infections, cervical cancer, congenital syphilis, ectopic pregnancy and infertility, as well as the morbidity of HIV-related illness and death from acquired immunodeficiency syndrome (AIDS). For example, pregnant women can be infected with sexually transmitted infections (STIs). STIs can complicate pregnancy and may have serious effects on both the pregnant individual and the developing baby. Some of these problems may be seen at birth; however, others may not be discovered until months or years later. In addition, it is well known that having an STI can make it easier for a person to get infected with HIV. A global need for a consumer sensitive and specific rapid test has been established to prevent ectopic pregnancies, pelvic inflammatory disease, infertility and in some cases death.

SUMMARY

The ability to rapidly and reliably assess health (e.g., sexual health) of a subject who is remote from a clinical setting can aid in early detection of abnormal health states. Design of system kit components to facilitate use by an end-user (e.g., in relation to sample provision and processing samples), as well as development of assay components that streamline sample processing to extract target material for single and multiplexed assays can enable such early detection, and thus prevent health complications. The system(s) and method(s) described herein include system components, assay materials, and additional elements for enabling rapid and reliable characterizations of one or more health conditions (e.g., sexual health conditions) of a subject.

In particular, embodiments of the invention(s) described can outperform existing tests for detection of sexual health statuses, in relation to comprehensively and efficiently testing for a panel of different pathogens in a streamlined format. In examples, embodiments of the invention can efficiently test for statuses of infections associated with the following agents in uni-plex and/or multiplexed formats: *Chlamydia trachomatis*, *Neisseria gonorrhoeae*, *Trichomonas vaginalis*, *Treponema pallidum*, *Gardnerella vaginitis*, *Candida Albicans*, *Mycoplasma genitalium*, human immunodeficiency virus, human papillomavirus infection, Hepatitis B, and herpes simplex virus. Embodiments of the invention(s) also produce increased sensitivity and/or specificity in test results by incorporating multiple test lines associated with different target material regions of the agents/biomarkers assessed. Embodiments of the invention(s) also assess other sexual health conditions (e.g., statuses of pregnancy, statuses of fertility).

Embodiments of the invention(s) described also include custom extraction and processing buffer compositions that facilitate easy of sample processing, especially in a consumer kit format. Embodiments of the invention(s) described also include effective reaction and testing substance compositions (e.g., aptamers, antibodies, etc.) that produce appropriate binding characteristics with sample target material and do not cross react, thereby enabling multiplexed format testing.

In one or more embodiments, a system for detecting status of a health condition (e.g., health condition caused by an agent) includes: a signal output device including a) a loading zone; b) a reaction zone fluidly coupled to the loading zone and including: i) a first reaction substance conjugated to a first label, where the first substance is not immobilized and binds to a specific region of a first target of material of the agent; c) a testing zone fluidly coupled to the reaction zone and including: i) a first testing substance retained at the testing zone and that specifically binds to the first target of material of the agent; and d) a control zone including a control substance retained at the control zone, and where the control substance does not preferentially couple to material of the agent. In related embodiments, the reaction zone can optionally include a second reaction substance conjugated to a second label, where the second reaction substance binds to a second target of material of the agent. In related embodiments, the testing zone can optionally include a second testing substance, where the second testing substance is retained at the testing zone and preferentially binds to the second target material of the agent. Related to the system(s), methods for detecting a health status of a subject include: a) collecting a sample from an individual; b) extracting target material of the sample, and receiving the target material into a signal output device which processes the target material and outputs a signal related to the health status.

One or more embodiments of the invention(s) described include devices and apparatus for detecting the presence of a sexually transmitted infection caused by one or more agents including, for example, *Chlamydia trachomatis*, *Neisseria gonorrhoeae*, *Trichomonas vaginalis*, *Treponema pallidum*, *Gardnerella vaginitis*, *Candida Albicans*, *Mycoplasma genitalium*, human immunodeficiency virus, human papillomavirus infection, Hepatitis B, and herpes simplex virus. Extraction compositions for processing samples containing such agents, as well as reaction substances and test substances for enabling detection of such agents are also described. Furthermore, system configurations for multiplexed assays are described.

One or more embodiments of the invention(s) described include devices and apparatus for detecting the presence of a sexually transmitted infection caused by one or more agents, optionally in conjunction with the detection of pregnancy and/or fertility. Such embodiments enable comprehensive characterization of sexual health of a subject.

Additional system elements, including sampling kit components with sample collecting tools are also described where, in embodiments, sample collecting tools are configured to collect a body fluid and/or tissue sample (e.g., a mucosa tissue sample, a urine sample, a blood sample, etc.). In some embodiments, the sample includes vaginal discharge or penile discharge for sexual health analysis.

The system(s) and method(s) described herein can be adapted to be used by subjects who are remote from a research or clinical environment, in a manner that is quick and convenient for the subject.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

1. System

Figure 1A:
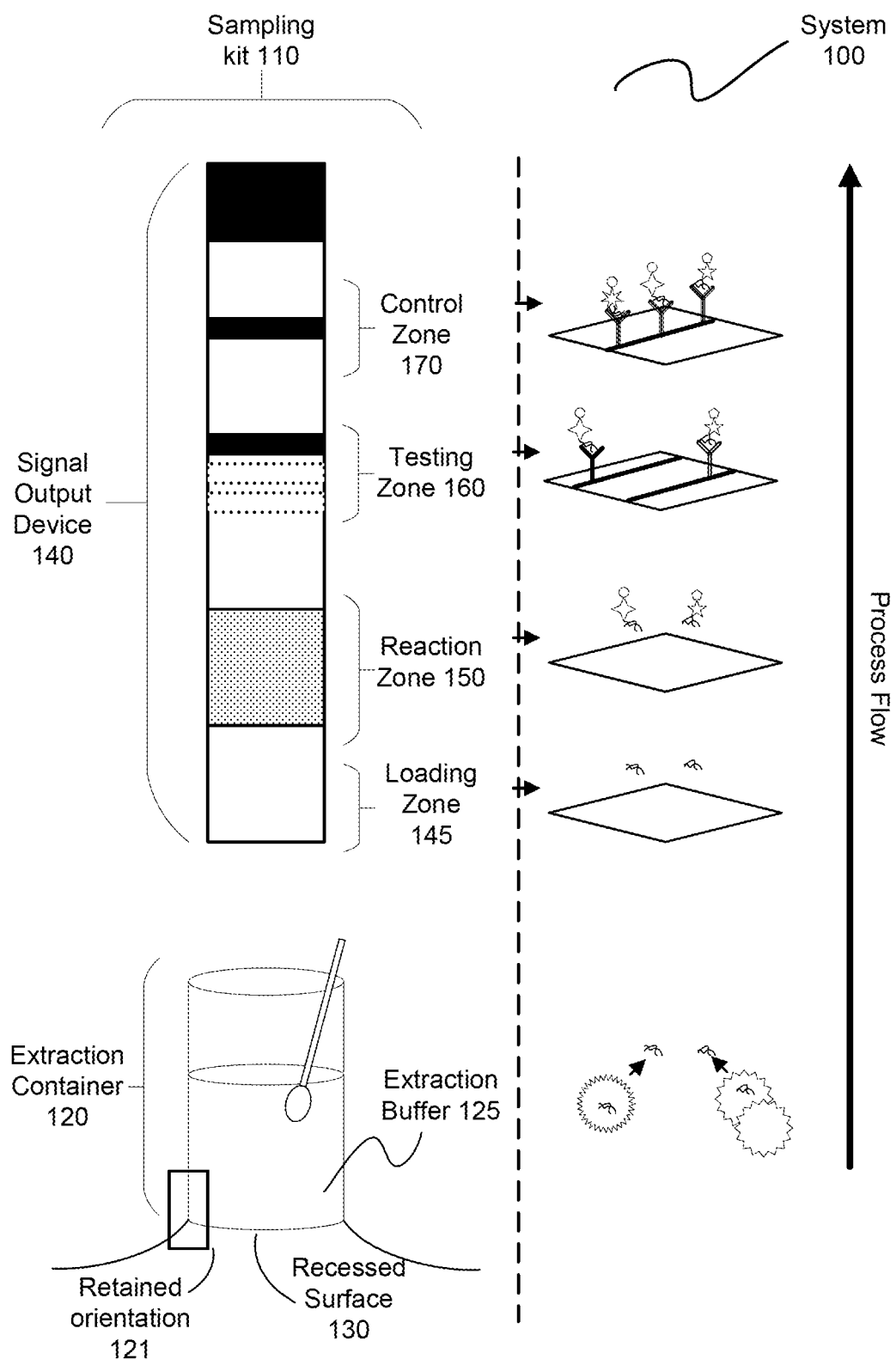
FIG. 1A depicts a system environment for assessing health of a subject, in accordance with one or more embodiments.

FIG. 1A depicts a system environment for assessing health of a subject, in accordance with one or more embodiments. The system 100 shown in FIG. 1A includes: a sampling kit 110 including an extraction container 120 containing an extraction buffer 125 for extracting a target material associated with the health condition; a recessed surface 130 (e.g., of a portion of the sampling kit 110) defining a retained orientation 121 for the extraction container 120; and a signal output device 140, where the signal output device 140 includes: a loading zone 145 insertable into the extraction container 120; a reaction zone 150 fluidly coupled to the loading zone 145 and including at least one reaction substance that preferentially couples to the target material; a testing zone 160 fluidly coupled to the reaction zone and including at least one testing substance retained at the testing zone, where the testing substance(s) preferentially couple(s) to the target material; and a control zone 170 including a control substance retained at the control zone, where the control substance does not preferentially couple to the target material.

The system 100 provides one or more consumer test device and kit components that can be used to detect, in a uni-plexed and/or multiplexed manner, the presence of one or more infections caused by one or more agents (e.g., sexually transmitted pathogens), optionally in conjunction with characterization of other sexual health conditions (e.g., pregnancy, fertility, etc.). In embodiments, the agent(s) can include one or more of (or strains of): *Chlamydia trachomatis, Neisseria gonorrhoeae, Trichomonas vaginalis, Treponema pallidum, Gardnerella vaginitis, Candida Albicans, Mycoplasma genitalium*, human immunodeficiency virus, human papillomavirus infection, Hepatitis B, and herpes simplex virus. Other embodiments can additionally or alternatively target other agents (e.g., non-viral agents, viral agents) in relation to detection of other health conditions states.

Figure 1B:
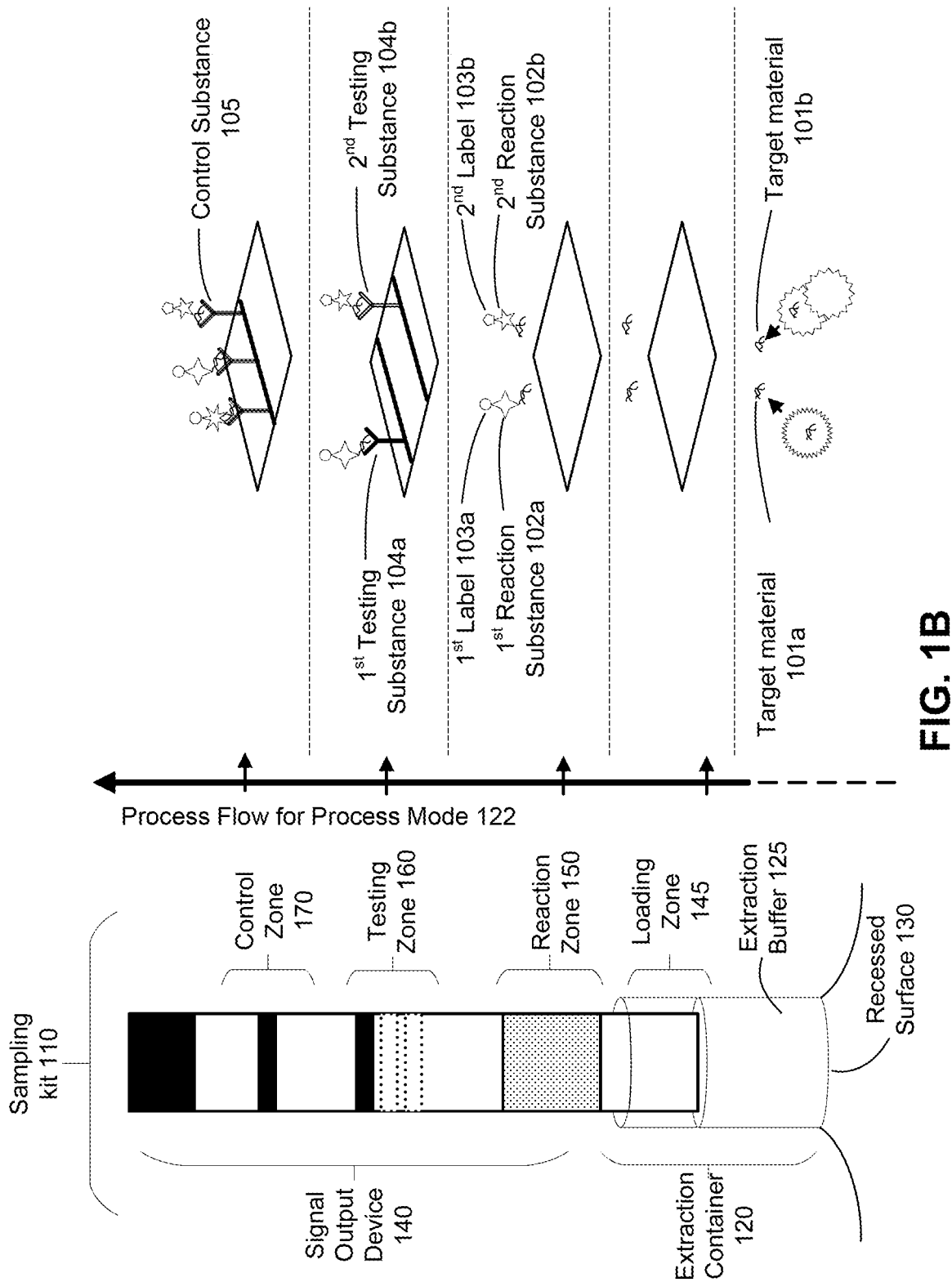
FIG. 1B depicts an expanded schematic of system components shown in FIG. 1A.

FIG. 1B depicts an expanded schematic of system components shown in FIG. 1A. As shown in the process flow of FIG. 1B, individual regions of the sampling kit 110 are configured to enable different phases of sample processing in order to provide one or more output signals that can be used to reliably and rapidly characterize health statuses of the subject. In relation to the extraction container 120 and the extraction buffer 125, the extraction buffer 125, upon contacting a sample from the subject, is configured to extract target material (e.g., target materials 101a and 101b) associated with the health condition(s) of interest. Target materials 101a and 101b can be associated with different regions of the same or different agents (e.g., infectious agents). When received into the loading zone 145 of the signal output device 140, the target material flows to the reaction zone 150, where the reaction zone 150 includes a first reaction substance 102a conjugated to a first label 103a, wherein the first reaction substance 102a preferentially couples to a first target of target material 101a. The reaction zone 150 can optionally include a second reaction substance 102b conjugated to a second label 103b, where the second reaction substance 102b preferentially couples to a second target of target material 101b. In an embodiment, the first reaction substance 102a and the second reaction substance 102b are not immobilized within the reaction zone 150. In embodiments, the reaction zone 150 can include more than two reaction substances conjugated to respective labels, in relation to assays performed on different types of target material (e.g., related to different health conditions).

As shown in the process flow of FIG. 1B, target material-reaction substance complexes flow from the reaction zone 150 to the testing zone 160, where the testing zone 160 includes a first testing substance 104a retained at a first region of the testing zone 160, where the first testing substance 104a preferentially couples to the first target of target material 101a. The testing zone 160 can optionally include a second testing substance 104b retained at a second region of the testing zone 160, where the second testing substance 104b preferentially couples to the second target of target material 101b. In an embodiment, the first testing substance 104a and the second testing substance 104b are thus immobilized within the reaction zone 150, and the first and the second regions, as shown in FIG. 1B, are test lines within the testing zone 160. However, the first and the second regions can alternatively be defined in another manner (e.g., as dots, as areas, as patterns, etc.) within the testing zone 160. Furthermore, in embodiments, the testing zone 160 can include more than two testing substances, in relation to assays performed on different types of target material (e.g., related to different health conditions).

As shown in the process flow of FIG. 1B, sample material including the target material and/or other material flows from the testing zone 160 to the control zone 170, which includes a control substance 105 retained at the control zone 170, where the control substance 105 does not preferentially couple to the target material and/or binds to any substance (e.g., binds non-specifically to different materials). As such, the control substance 105 is immobilized at the control zone 170 and can be immobilized along a line of the control zone 170 or in another manner (e.g., as a dot, as an area, as a pattern).

As shown in FIGS. 1A and 1B, the loading zone 145, the reaction zone 150, the testing zone 160, and the control zone 170 are fluidly coupled. In embodiments, adjacent zones can overlap; however, in other embodiments, one or more adjacent zones of the signal output device 140 may not overlap. Furthermore, as shown in FIGS. 1A and 1B, the sampling kit 110 includes a process mode 122 where, in the process mode 122, the extraction container 120 is retained at the surface 130 in the retained orientation 121, the loading zone 145 is inserted into the extraction container 120, and a sample generated upon extraction of an agent by the extraction buffer 125 flows against gravity through the loading zone 145, the reaction zone 150, the testing zone 160, and the control zone 170. The retained orientation 121 thus positions the extraction container vertically, such that the sample flows against gravity; however, in alternative embodiments, the retained orientation 121 can be a non-vertical orientation.

In more detail, the recessed surface 130 can be a recessed surface of a portion of a component (e.g., housing, packaging, additional element, etc.) of the sampling kit 110, where the recessed surface 130 is complementary to an exterior surface of the extraction container 120. As such, the recessed surface 130 is configured to receive the extraction container 120 with the extraction buffer 125, and to hold it in place so that a user can easily place the signal output device 140 in the extraction container 120 during testing in a consumer environment. The recessed surface 130 thus provides the retained orientation 121 of the sampling kit, by retaining the extraction container 120 in position while it is in contact with the signal output device 140 during testing. The recessed surface 130 can thus be semi-spherical or of another morphology (if the corresponding region of the extraction container 120 is semi-spherical or of another morphology). Additional embodiments of systems including a recessed surface are described in more detail below in relation to FIGS. 6 and 7A.

1.1 System—Applications to Specific STIs 1.1.1 *Chlamydia trachomatis*

In one embodiment, the system 100 is configured to detect presence of *Chlamydia trachomatis* from a sample acquired from the subject, such that the target material (e.g., embodiments of target material 101*a* and 101*b*) includes one or more specific regions of biological material (e.g., tissue content, cellular content, protein content, amino acid content, nucleic acid content, etc.) of *Chlamydia trachomatis*, the reaction substances (e.g., embodiments of reaction substances 102*a* and 102*b*) are configured to bind to specific regions of *Chlamydia trachomatis*, and/or the testing substances (e.g., embodiments of testing substances 104*a* and 104*b*) are configured to bind to specific regions of *Chlamydia trachomatis*.

In specific examples of this embodiment, the target material of *Chlamydia trachomatis* includes individual proteins (and homologs) or a cocktails of proteins (and homologs) including one or more of: Uniprot ID numbers: P26623 (SEQ ID NO 1), A0A0E9CJA7 (SEQ ID NO 2), PODJI1 (SEQ ID NO 3), O84760 (SEQ ID NO 4), P06597 (SEQ ID NO 5), P0C0Z8 (SEQ ID NO 6), A0A0E9CNK8 (SEQ ID NO 7), A0A0E9FM59 (SEQ ID NO 8), B0B7W6 (SEQ ID NO 19), B0B7N4 (SEQ ID NO 20), G4NM26 (SEQ ID NO 21), and P23603 (SEQ ID NO 22). Additionally or alternatively, in specific examples, the target material of *Chlamydia trachomatis* includes lipoglycans or lipopolysaccharides of the *Chlamydia trachomatis* species.

In specific examples of this embodiment, the reaction substances and/or testing substances configured for detection of *Chlamydia trachomatis* include individual or a cocktail of deoxyribonucleic acid (DNA)-based aptamers or any permutation of the sequences listed in TABLE 1 and/or individual or a cocktail of antibody clones listed in TABLE 1.

TABLE 1

Aptamers and Antibodies for *Chlamydia trachomatis*

| Type | Sequence/Identifier |
|---|---|
| Aptamer | AGGGGGCAGGGGGGTTGACTTTACCTTATGCTTAAAGGGGGTGGGCTCGGGAAGAT (SEQ ID NO 12) |
| Aptamer | AGGGGGAGAACGGGGGGGCTTGGGTTGGGGATGGATGTGGGAGGCCGGTCGAGAT (SEQ ID NO 13) |
| Aptamer | TGGCGCGGACGTACTGGCGAATTGGTGAGCCTCGGGCTGGGTGGGGGGTTAGGGAGAT (SEQ ID NO 14) |
| Antibody Clone | M4020310 |
| Antibody Clone | M2103128 |
| Antibody Clone | M61872 |
| Antibody Clone | M61871 |
| Antibody Clone | M4020311 |
| Antibody Clone | HM215 |
| Antibody Clone | HM031 |
| Antibody Clone | 9L102 |
| Antibody Clone | B351M. CL13-256.2.1 |
| Antibody Clone | CT 6703 SP-5 |
| Antibody Clone | CT 6701 SP-5 |

TABLE 1 -continued Aptamers and Antibodies for *Chlamydia trachomatis*

| Type | Sequence/Identifier |
|---|---|
| Antibody Clone | CT 6709 SP-5 |
| Antibody Clone | CL21-335.2.3 |
| Antibody Clone | 027-10347 |

In related embodiments, aptamers (e.g., aptamers listed in TABLE 1) for detection of *Chlamydia trachomatis* are modified by a biotin or —SH group or any other modification at the 5' and/or 3' terminal of the aptamer.

1.1.2 *Neisseria gonorrhoeae*

In one embodiment, the system 100 is configured to detect presence of *Neisseria gonorrhoeae* from a sample acquired from the subject, such that the target material (e.g., embodiments of target material 101a and 101b) includes one or more specific regions of biological material (e.g., tissue content, cellular content, protein content, amino acid content, nucleic acid content, etc.) of *Neisseria gonorrhoeae*, the reaction substances (e.g., embodiments of reaction substances 102a and 102b) are configured to bind to specific regions of *Neisseria gonorrhoeae*, and/or the testing substances (e.g., embodiments of testing substances 104a and 104b) are configured to bind to specific regions of *Neisseria gonorrhoeae*.

In specific examples of this embodiment, the target material of *Neisseria gonorrhoeae* includes individual proteins (and homologs) or a cocktails of proteins (and homologs) including one or more of: Uniprot ID numbers: P95359 (SEQ ID NO 23), A0A1D3HF49 (SEQ ID NO 24), P05430 (SEQ ID NO 25), Q02219 (SEQ ID NO 26), Q51006 (SEQ ID NO 27), Q5F942 (SEQ ID NO 28), B4RQH9 (SEQ ID NO 29), Q5F6W5 (SEQ ID NO 30), P29842 (SEQ ID NO 31), Q5F542 (SEQ ID NO 32), B4RLT9 (SEQ ID NO 33), D6H5Z3 (SEQ ID NO 34), and Q5F651 (SEQ ID NO 35); and GenBank/NCBI Accession Numbers: YP_208979.1 (SEQ ID NO 75), KXI24787.1 (SEQ ID NO 76), SCW17313.1 (SEQ ID NO 77), YP_209073.1 (SEQ ID NO 78), and YP_209148.1 (SEQ ID NO 79). In some embodiments, the target material of *Neisseria gonorrhoeae* includes lipoglycans or lipopolysaccharides of the *Neisseria gonorrhoeae* species.

In specific examples of this embodiment, the reaction substances and/or testing substances configured for detection of *Neisseria gonorrhoeae* include individual or a cocktail of deoxyribonucleic acid (DNA)-based aptamers or any permutation of the sequences listed in TABLE 2 and/or individual or a cocktail of antibody clones listed in TABLE 2.

TABLE 2

Aptamers and Antibodies for *Neisseria gonorrhoeae*

| Type | Sequence or Identifier |
|---|---|
| Aptamer | CTCACACTATTTTTGGCATAGGTGTCGAGGGTGGA CGGGGCGGGGCGGTGAGAT (SEQ ID NO 15) |
| Aptamer | GAGTTAAGTTTGAGTGTTGTCGAGGGTGGACGGGGT GGGGCAAGCTAGTGTGAGAT (SEQ ID NO 16) |

TABLE 2 -continued

Aptamers and Antibodies for *Neisseria gonorrhoeae*

| Type | Sequence or Identifier |
|---|---|
| Antibody Clone | M2110186 |
| Antibody Clone | M1709NG1 |
| Antibody Clone | M1709NG2 |
| Antibody Clone | 386/418 |
| Antibody Clone | M86954 |
| Antibody Clone | 20-NR08 |
| Antibody Clone | 15B441 |
| Antibody Clone | 17E95 |

In related embodiments, aptamers (e.g., aptamers listed in TABLE 2) for detection of *Neisseria Gonorrhoeae* are modified by a biotin or —SH group or any other modification at the 5' and/or 3' terminal of the aptamer.

1.1.3 *Trichomonas vaginalis*

In one embodiment, the system 100 is configured to detect presence of *Trichomonas vaginalis* from a sample acquired from the subject, such that the target material (e.g., embodiments of target material 101a and 101b) includes one or more specific regions of biological material (e.g., tissue content, cellular content, protein content, amino acid content, nucleic acid content, etc.) of *Trichomonas vaginalis*, the reaction substances (e.g., embodiments of reaction substances 102a and 102b) are configured to bind to specific regions of *Trichomonas vaginalis*, and/or the testing substances (e.g., embodiments of testing substances 104a and 104b) are configured to bind to specific regions of *Trichomonas vaginalis*.

In specific examples of this embodiment, the target material of *Trichomonas vaginalis* includes individual proteins (and homologs) or a cocktails of proteins (and homologs) including one or more of: NCBI/GenBank Accession numbers: EAX87747.1 (SEQ ID NO 41), EAY21310.1 (SEQ ID NO 42), EAX96596.1 (SEQ ID NO 43), EAY19137.1 (SEQ ID NO 44), EAY01676.1 (SEQ ID NO 45), EAX86868.1 (SEQ ID NO 46), EAX98121.1 (SEQ ID NO 47), EAY18961.1 (SEQ ID NO 48), AAA91133.1 (SEQ ID NO 49), AAC48339.1 (SEQ ID NO 50), and AAC72899.1 (SEQ ID NO 51). In some embodiments, the target material of *Trichomonas vaginalis* includes lipoglycans or lipopolysaccharides of the *Trichomonas vaginalis* species.

In specific examples of this embodiment, the reaction substances and/or testing substances configured for detection of *Trichomonas vaginalis* include individual or a cocktail of deoxyribonucleic acid (DNA)-based aptamers or any permutation of the sequences listed in TABLE 3 and/or individual or a cocktail of antibody clones listed in TABLE 3.

TABLE 3

Aptamers and Antibodies for *Trichomonas vaginalis*

| Type | Sequence or Identifier |
|---|---|
| Aptamer | TTTATGAGTATATTTCACAATATTTAGTCAGCCAT GACCGGTGCAGTGTGTTCAGAGA (SEQ ID NO 9) |

TABLE 3 -continued

Aptamers and Antibodies for *Trichomonas vaginalis*

| Type | Sequence or Identifier |
|---|---|
| Aptamer | ATTCACTCGTCGGGAAACTATGGGCGTACGGTGCT CGGTTTCCTTCTCTCTGAGTAGA (SEQ ID NO 10) |
| Aptamer | ATTGGGGCGGGAGGGGATGGCGGAGGTTTGTT GTCTGTTCGGGGAGCTGTGTAAGA (SEQ ID NO 11) |
| Antibody Clone | M1011403 |
| Antibody Clone | A19G |
| Antibody Clone | Q65G |
| Antibody Clone | BDI675 |
| Antibody Clone | B985M |
| Antibody Clone | B986M |
| Antibody Clone | 15B485 |
| Antibody Clone | 12K238 |
| Antibody Clone | M1011401 |
| Antibody Clone | M1011404 |
| Antibody Clone | 15B483 |

In related embodiments, aptamers (e.g., aptamers listed in TABLE 3) for detection of *Trichomonas vaginalis* are modified by a biotin or —SH group or any other modification at the 5' and/or 3' terminal of the aptamer.

1.2 System—Uniplexed and Multiplexed Variations

Figure 2:
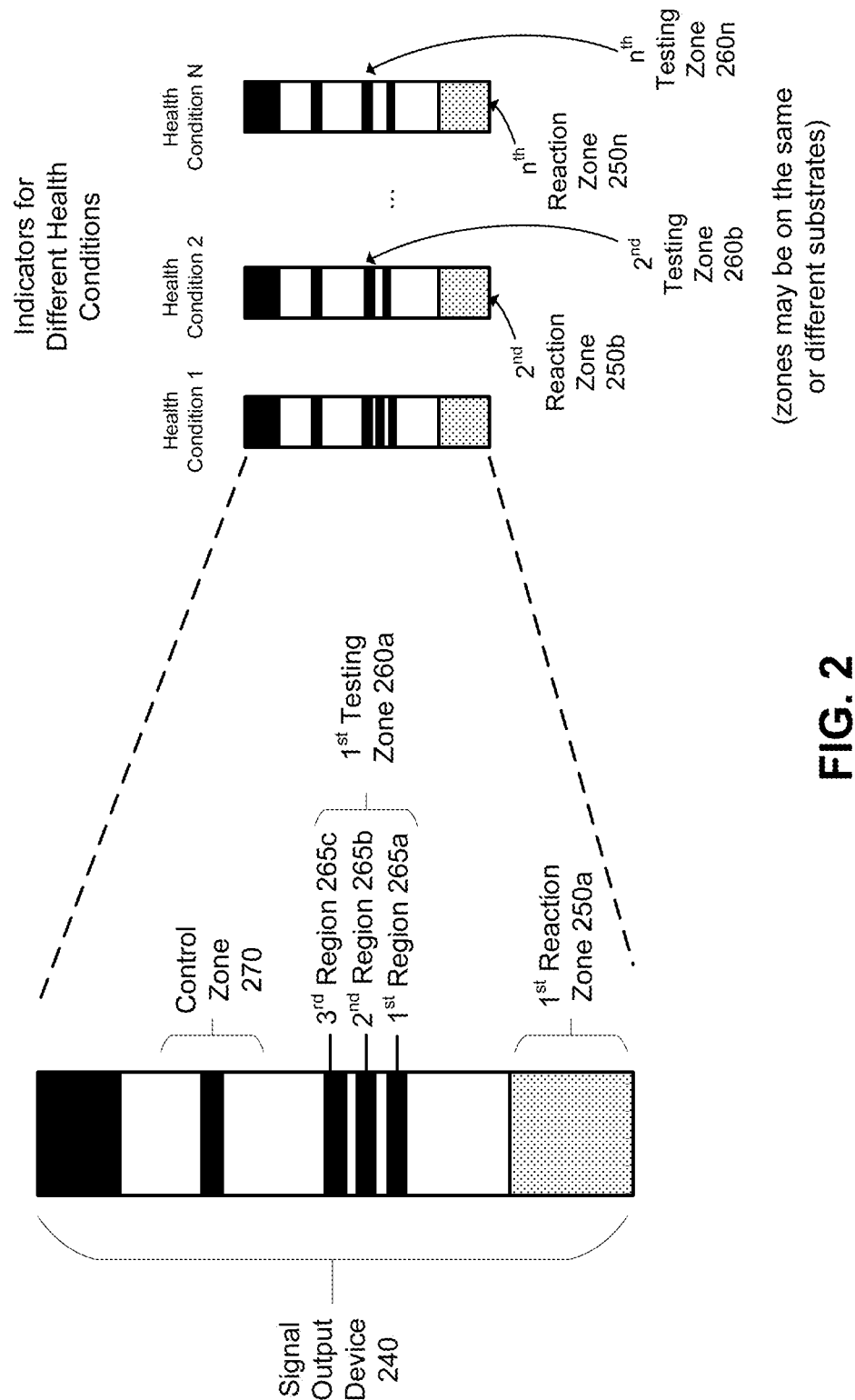
FIG. 2 depicts signal output device portions in accordance with one or more embodiments.

FIG. 2 depicts signal output device portions in accordance with one or more embodiments of the system shown in FIGS. 1A and 1B. As shown in FIG. 2, the system can be configured to indicate statuses of different health conditions in a uni-plexed or a multiplex manner. For each of a set of health conditions (e.g., sexual health conditions), the system can be configured to test a sample for presence of different agents associated with the different health conditions. For instance, for a first health condition, the system can include a signal output device 240 including a first reaction zone 250a with at least one reaction substance that preferentially couples to target material associated with the first health condition; a first testing zone 260a fluidly coupled to the first reaction zone 250a and including at least one testing substance retained at the first testing zone 260a, where the testing substance(s) preferentially couple(s) to the target material; and a control zone 270 including a control substance retained at the control zone 270, where the control substance does not preferentially couple to the target material. The first testing zone 260a includes multiple regions including a first region 265a, a second region 265b, and a third region 265c. The first region 265a, second region 265b, and third region 265c can include the same or different testing substances (e.g., such as the testing substances described in each of TABLES 1-3), to produce output signals that provide for improved characterization of status of the first health condition (e.g., in relation to sensitivity and specificity of an assay). For instance, in relation to the first health condition, if the sample includes target substances of interest associated with the first health condition, the first, second, and third regions 265a, 265b, and 265c of the first testing zone 260a can be configured to indicate a positive test result (e.g., with optical detection of a signal generated at respective regions of the control and testing zones), with greater sensitivity and specificity than if the first testing zone 260a had a single region. However, in alternative embodiments, the first testing zone 260a can additionally or alternatively include fewer or more than three regions.

Also shown in FIG. 2, for a second health condition, the system can include a second reaction zone 250b with at least one reaction substance that preferentially couples to target material associated with the second health condition; and a second testing zone 260b fluidly coupled to the second reaction zone 250b and including at least one testing substance retained at the second testing zone 260a, where the testing substance(s) preferentially couple(s) to the target material associated with the second health condition. Similarly, for an nth health condition, the system can include an nth reaction zone 250n with at least one reaction substance that preferentially couples to target material associated with the nth health condition; and an nth testing zone 260n fluidly coupled to the nth reaction zone 250n and including at least one testing substance retained at the nth testing zone 260n, where the testing substance(s) preferentially couple(s) to the target material associated with the nth health condition.

In various applications, and as described above, the set of health conditions can be associated with STIs associated with one or more of: *Chlamydia trachomatis, Neisseria gonorrhoeae, Trichomonas vaginalis, Treponema pallidum, Gardnerella vaginitis, Candida Albicans, Mycoplasma genitalium*, human immunodeficiency virus, human papillomavirus infection, Hepatitis B, and herpes simplex virus. The set of health conditions can also include non-infection-related health conditions associated with sexual health, such as fertility states and pregnancy states, as detected with appropriate biomarkers. Additionally or alternatively, the set of health conditions can include health conditions not related to sexual health.

1.2.1 Multiplexed Embodiments

Figure 3A:
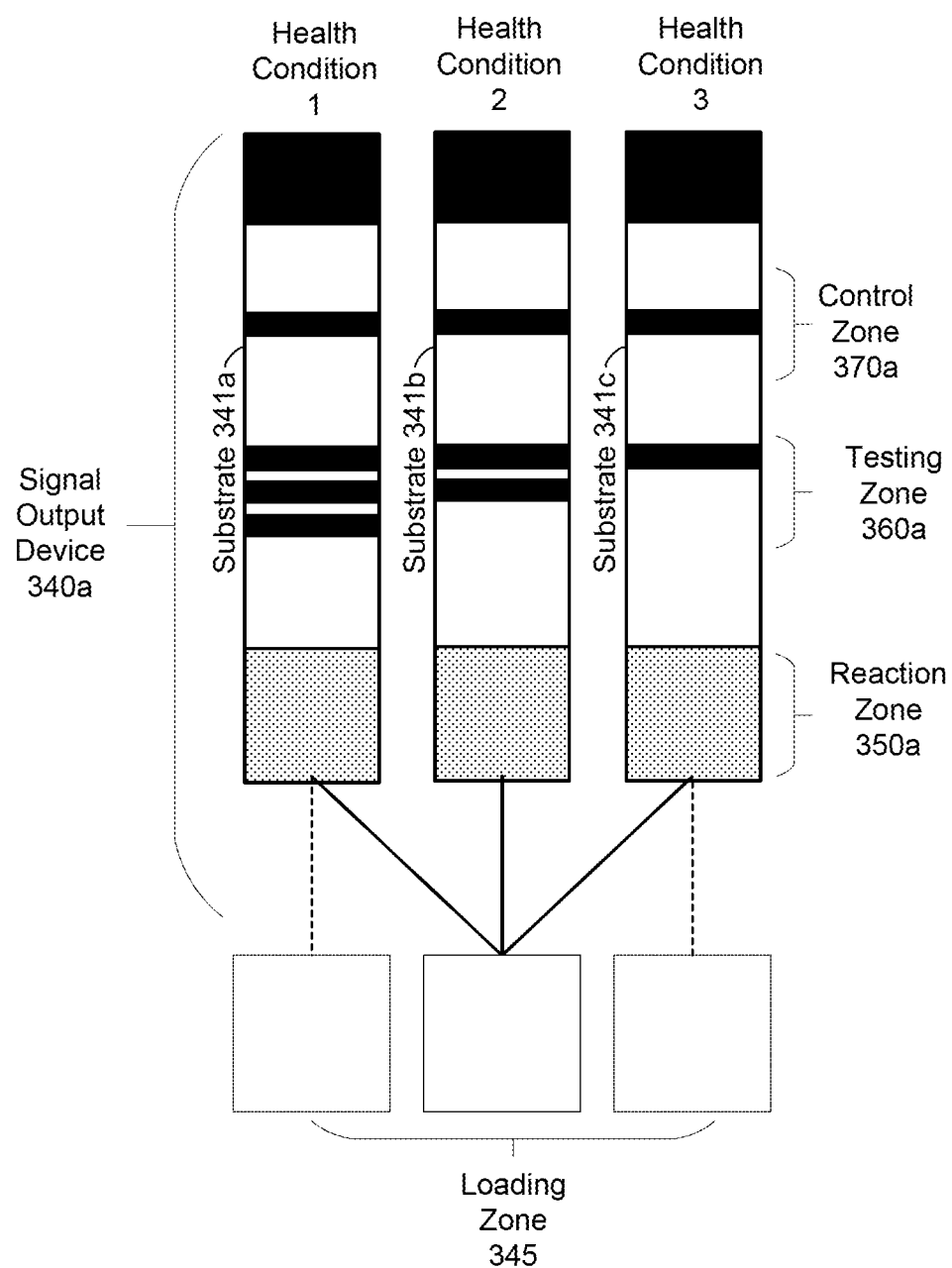
FIG. 3A depicts a schematic of a first embodiment of a signal output device for multiplexed analyses.

FIG. 3A depicts a schematic of an embodiment of a signal output device for multiplexed analyses. As shown in FIG. 3A, the system can include a single signal output device 340a that includes multiple substrates, each of the substrates configured for characterization of an individual health condition. As shown in FIG. 3A, substrate 341a is configured for assessment of a first health condition, substrate 341b is configured for assessment of a second health condition, and substrate 341c is configured for assessment of a third health condition, where the substrates 341a-341c process sample material in parallel and individually output signals for characterizing statuses of their respective health conditions. As such, reaction zones and testing zones corresponding to each health condition can be fluidly isolated from each other in different pathways. For instance, substrates 341a and 341b and be configured to detect different STIs, and substrate 341c can be configured to characterize a state of pregnancy. In more detail, using substrate 341c, substrate 341c includes a reaction zone 350a with at least one reaction substance that preferentially couples to target material associated with the third health condition; a testing zone 360a fluidly coupled to the reaction zone 350a and including at least one testing substance retained at the testing zone 360a, where the testing substance(s) preferentially couple(s) to the target material associated with the third health condition; and a control zone 370a including a control substance retained at the control zone 370a, where the control substance does not preferentially couple to the target material associated with the third health condition. Substrate 341a and substrate 341b also include similar reaction zones and testing zones configured for their respective health conditions, where health condition statuses, during use of the signal output device 340a, are indicated individually from the testing zone and the control zone for each substrate. In embodiments related to the embodiment shown in FIG. 3A, given that the extraction buffer composition (described in more detail in Section 1.3 below) operates to extract target material associated with many health conditions in a single-step mode of operation (e.g., upon contacting a biological sample from a subject), the embodiment of the signal output device 340a shown in FIG. 3A can include a shared loading zone 345 fluidly coupled to the reaction zones of each substrate (i.e., substrates 341a, 341b, and 341c). During sample processing, target material associated with each health condition is extracted using the same extraction buffer, and the extracted target material flows through the shared loading zone 345 to individual reaction zones of each substrate. However, as shown in FIG. 3A, each substrate (i.e., substrates 341a, 341b, and 341c) can include a loading zone that is distinct from the loading zones of the other substrates.

Figure 3B:
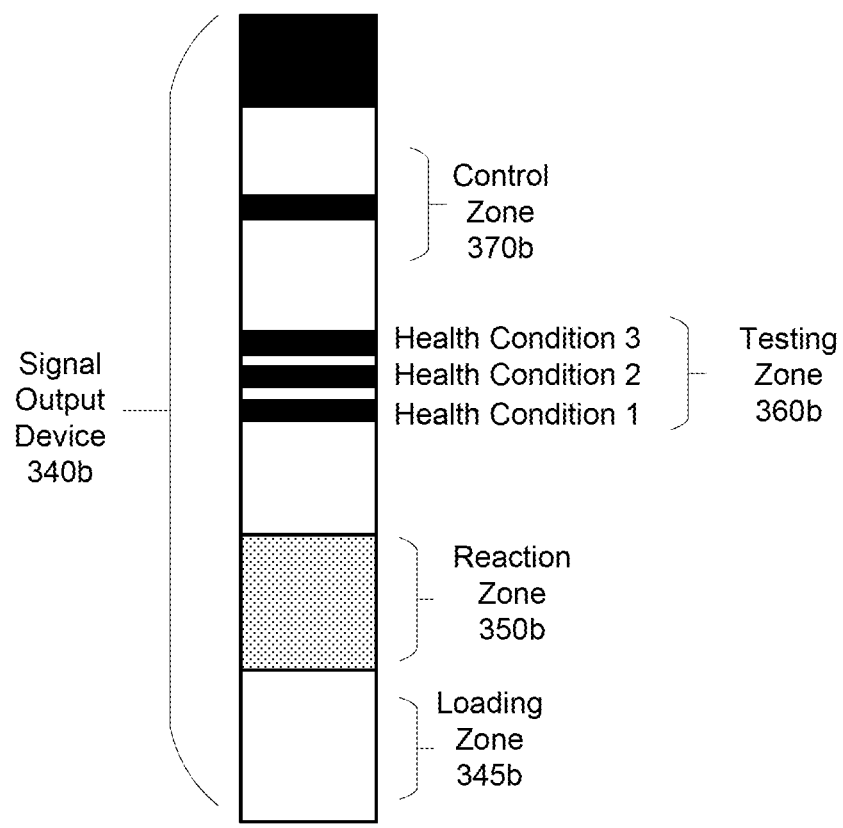
FIG. 3B depicts a schematic of a second embodiment of a signal output device for multiplexed analyses.

FIG. 3B depicts a schematic of another embodiment of a signal output device 340b for multiplexed analyses. As shown in FIG. 3B, the signal output device 340b includes a loading zone 345b and a reaction zone 350b fluidly coupled to the loading zone 345b, where the reaction zone 350b includes reaction substances that preferentially couple to target material associated with each of a first health condition, a second health condition, and a third health condition. For instance, the signal output device 340b includes reaction substances that can each bind to one or more specific regions of target material of different pathogens or biomarkers (e.g., of sexual health). In examples, the reaction zone 350b can include non-immobilized aptamers and/or antibodies listed in TABLES 1-3, such that a sample that has undergone extraction can flow through the reaction zone 350b and individual units of target material associated with each health condition can bind with their respective reaction substances before flowing to the testing zone 360b. The testing zone 360b shown in FIG. 3B includes a first region associated with the first health condition, a second region associated with the second health condition, and a third region associated with the third health condition. In order to provide detectable results, testing substances associated with the first health condition are immobilized at the first region, testing substances associated with the second health condition are immobilized at the second region, and testing substances associated with the third health condition are immobilized at the third region, such that test results (e.g., positive or negative test results) can be observed using the testing zone 360b in a manner that differentiates results for each health condition. As such, reaction zones and testing zones corresponding to each health condition can be fluidly coupled to each other. The signal output device 340b shown in FIG. 3B also includes a control zone 370b including a control substance retained at the control zone 370b, where the control substance does not preferentially couple to and is non-specific to target material associated with any of the health conditions. In related embodiments, given that the extraction buffer composition (described in more detail in Section 1.3 below) operates to extract target material associated with many health conditions in a single-step mode of operation (e.g., upon contacting a biological sample from a subject), and given that the reaction and testing substances used in relation to the system of FIG. 3B are configured to not cross-react, assessments of multiple health conditions can be performed using a single substrate of a signal output device 340b.

Figure 3C:
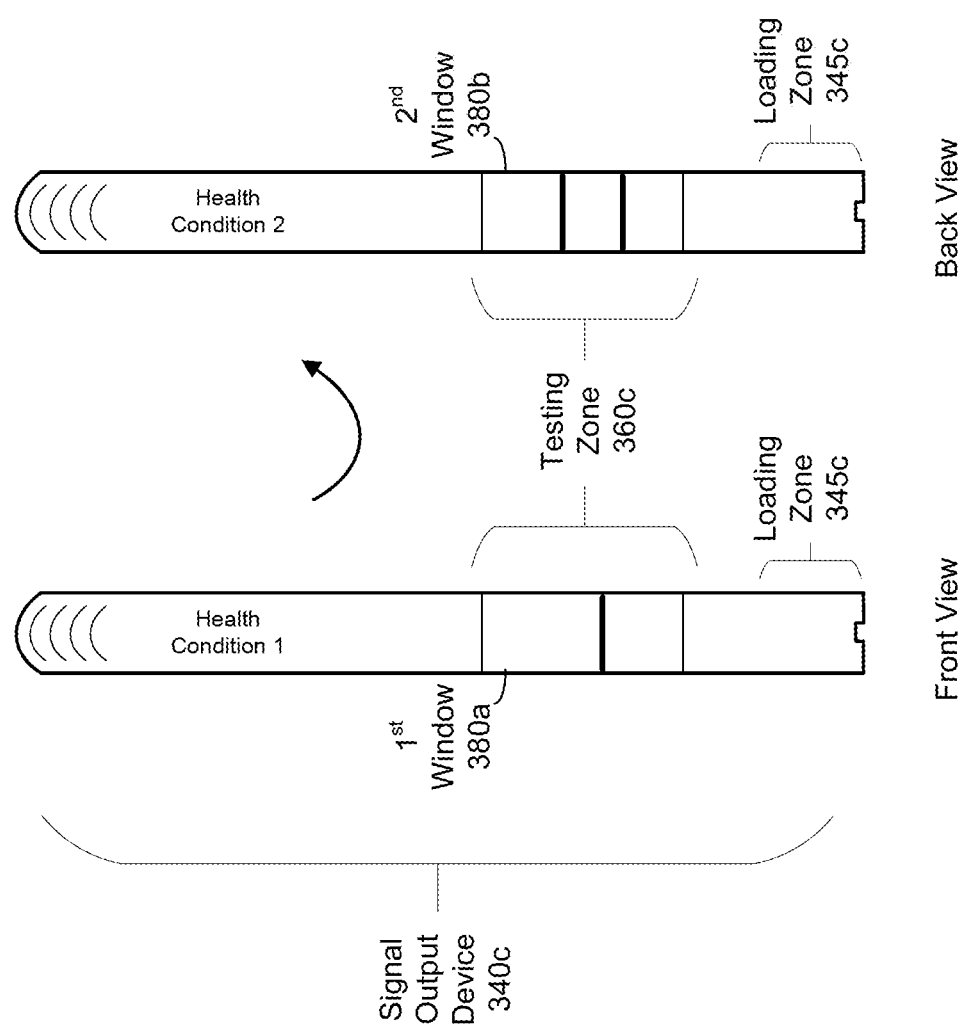
FIG. 3C depicts a schematic of a second embodiment of a signal output device for multiplexed analyses.

FIG. 3C depicts a schematic of another embodiment of a signal output device 340c for multiplexed analyses. As shown in FIG. 3C, the signal output device 340c includes a first side (e.g., front side) and a second side (e.g., back side), where each side is associated with a different health condition (e.g., a first health condition and a second health condition). The signal output device 340c includes a a loading zone 345c and reaction zones (not shown) fluidly coupled to the loading zone 345c, where the reaction zones individually include reaction substances that preferentially couple to target material associated with each of a first health condition and a second health condition. The reaction zone associated with the first health condition can be located at the first side of the signal output device 340c (e.g., within an internal cavity of a housing of the signal output device 340c), and the reaction zone associated with the second health condition can be located at the second side of the signal output device 340c (e.g., within an internal cavity of a housing of the signal output device 340c). In examples, the reaction zone 350b can include non-immobilized aptamers and/or antibodies listed in TABLES 1-3, such that a sample that has undergone extraction can flow through the reaction zone 350b and individual units of target material associated with each health condition can bind with their respective reaction substances before flowing to the testing zone 360c. The testing zone 360c shown in FIG. 3C includes a first side associated with the first health condition and a second side associated with the second health condition. In order to provide detectable results, testing substances associated with the first health condition are immobilized at the first side and testing substances associated with the second health condition are immobilized at the second side, such that test results (e.g., positive or negative test results) can be observed using the testing zone 360c in a manner that differentiates results for each health condition. Each side includes a window (e.g., windows 380a and 380b) that enables observation of test results associated with each side of the testing zone 360c, as relevant to analyses of statuses of each of the first health condition and the second health condition. In related embodiments, given that the extraction buffer composition (described in more detail in Section 1.3 below) operates to extract target material associated with many health conditions in a single-step mode of operation (e.g., upon contacting a biological sample from a subject), and given that the reaction and testing substances used in relation to the system of FIG. 3C are configured to not cross-react, assessments of multiple health conditions can be performed within a single signal output device 340c, for instance, using different sides of a single substrate housed within the signal output device 340c.

1.2.2 Examples of Multiplexed Configurations with Specific Health Conditions

In relation to of multiplexed configurations, examples of configurations for simultaneously assessing multiple health conditions (e.g., sexual health conditions) are described below:

In one example, an embodiment of a signal output device can indicate presence of *Chlamydia trachomatis* in conjunction with the presence of pregnancy, using a single or multiple substrates of a signal output device to indicate *Chlamydia trachomatis* infection status independently of pregnancy status. In this example, reaction substances of a reaction zone and testing substances immobilized at a testing zone of the signal output device can be selected from TABLE 1 for detection of *Chlamydia trachomatis* material. Similarly, reaction substances of a reaction zone and testing substances immobilized at a testing zone of the signal output device can include substances for detection of pregnancy biomarkers.

In another example, an embodiment of a signal output device can indicate presence of *Neisseria gonorrhoeae* in conjunction with the presence of pregnancy, using a single or multiple substrates of a signal output device to indicate *Neisseria gonorrhoeae* infection status independently of pregnancy status. In this example, reaction substances of a reaction zone and testing substances immobilized at a testing zone of the signal output device can be selected from TABLE 2 for detection of *Neisseria gonorrhoeae* material. Similarly, reaction substances of a reaction zone and testing substances immobilized at a testing zone of the signal output device can include substances for detection of pregnancy biomarkers.

In another example, an embodiment of a signal output device can indicate presence of *Trichomonas vaginalis* in conjunction with the presence of pregnancy, using a single or multiple substrates of a signal output device to indicate *Trichomonas vaginalis* infection status independently of pregnancy status. In this example, reaction substances of a reaction zone and testing substances immobilized at a testing zone of the signal output device can be selected from TABLE 3 for detection of *Trichomonas vaginalis* material. Similarly, reaction substances of a reaction zone and testing substances immobilized at a testing zone of the signal output device can include substances for detection of pregnancy biomarkers.

In another example, an embodiment of a signal output device can indicate presence of a target pathogen infection in conjunction with the presence of pregnancy, using a single or multiple substrates of a signal output device to indicate the target pathogen infection status independently of pregnancy status. In this example, reaction substances of a reaction zone and testing substances immobilized at a testing zone of the signal output device can be selected based on specific binding to material of the target pathogen. Similarly, reaction substances of a reaction zone and testing substances immobilized at a testing zone of the signal output device can include substances for detection of pregnancy biomarkers. In some embodiments, the target pathogen is selected from *Chlamydia trachomatis, Neisseria gonorrhoeae, Trichomonas vaginalis, Treponema pallidum, Gardnerella vaginitis, Candida Albicans, Mycoplasma genitalium*, human immunodeficiency virus (HIV), human papillomavirus infection (HPV), Hepatitis B virus (HBV) and herpes simplex virus (HSV).

In another example, an embodiment of a signal output device can indicate presence of *Chlamydia trachomatis* and *Neisseria gonorrhoeae* in conjunction with the presence of pregnancy, using a single or multiple substrates of a signal output device to indicate *Chlamydia trachomatis* infection status, and *Neisseria gonorrhoeae* infection status independently of pregnancy status. In this example, reaction substances of a reaction zone and testing substances immobilized at a testing zone of the signal output device can be selected from TABLE 1 for detection of *Chlamydia trachomatis* material and TABLE 2 for detection of *Neisseria gonorrhoeae* material, where the material(s) from TABLE 1 and TABLE 2 are distinct from each other at respective reaction zones and testing zones. Similarly, reaction substances of a reaction zone and testing substances immobilized at a testing zone of the signal output device can include substances for detection of pregnancy biomarkers.

In another example, an embodiment of a signal output device can indicate presence of *Chlamydia trachomatis* and *Trichomonas vaginalis* in conjunction with the presence of pregnancy, using a single or multiple substrates of a signal output device to indicate *Chlamydia trachomatis* infection status, and *Trichomonas vaginalis* infection status independently of pregnancy status. In this example, reaction substances of a reaction zone and testing substances immobilized at a testing zone of the signal output device can be selected from TABLE 1 for detection of *Chlamydia trachomatis* material and TABLE 3 for detection of *Trichomonas vaginalis* material, where the material(s) from TABLE 1 and TABLE 3 are distinct from each other at respective reaction zones and testing zones. Similarly, reaction substances of a reaction zone and testing substances immobilized at a testing zone of the signal output device can include substances for detection of pregnancy biomarkers.

In another example, an embodiment of a signal output device can indicate presence of *Neisseria gonorrhoeae* and *Trichomonas vaginalis* in conjunction with the presence of pregnancy, using a single or multiple substrates of a signal output device to indicate *Neisseria gonorrhoeae* infection status, and *Trichomonas vaginalis* infection status independently of pregnancy status. In this example, reaction substances of a reaction zone and testing substances immobilized at a testing zone of the signal output device can be selected from TABLE 2 for detection of *Neisseria gonorrhoeae* material and TABLE 3 for detection of *Trichomonas vaginalis* material, where the material(s) from TABLE 2 and TABLE 3 are distinct from each other at respective reaction zones and testing zones. Similarly, reaction substances of a reaction zone and testing substances immobilized at a testing zone of the signal output device can include substances for detection of pregnancy biomarkers.

In another example, an embodiment of a signal output device can indicate presence of *Chlamydia trachomatis, Neisseria gonorrhoeae*, and *Trichomonas vaginalis* in conjunction with the presence of pregnancy, using a single or multiple substrates of a signal output device to indicate *Chlamydia trachomatis* infection status, *Neisseria gonorrhoeae* infection status, and *Trichomonas vaginalis* infection status independently of pregnancy status. In this example, reaction substances of a reaction zone and testing substances immobilized at a testing zone of the signal output device can be selected from TABLE 1 for detection of *Chlamydia trachomatis* material, TABLE 2 for detection of *Neisseria gonorrhoeae* material, and TABLE 3 for detection of *Trichomonas vaginalis* material, where the material(s) from TABLE 1, TABLE 2, and TABLE 3 are distinct from each other at respective reaction zones and testing zones. Similarly, reaction substances of a reaction zone and testing substances immobilized at a testing zone of the signal output device can include substances for detection of pregnancy biomarkers.

1.3 System—Materials and Additional Components 1.3.1 System—Microfluidic and Sample Driving Variations In relation to embodiments of the system described above, embodiments of the sampling kit (such as sampling kit 110) and/or signal output device (such as signal output device 140) can include a capillary driven microfluidic device (e.g., a lateral flow assay (LFA) based device). Alternatively, embodiments of the sampling kit (such as sampling kit 110) and/or signal output device (such as signal output device 140) can include a microfluidic device that is not capillary driven. In some embodiments, sample flow can be driven by pressure (e.g., in embodiments where the system includes a pump), centrifugal forces, electrokinetic forces, or acoustic forces.

In some embodiments, the system is configured for providing "one-step" or "lateral flow" detection of an agent or biomarker in solubilized extract from a sample acquired from a subject. In particular, after target material of the agent or biomarker has been extracted from the sample, it will be necessary only to apply a volume of the extract to the loading zone of the signal output device, wait for a predetermined time, and thereafter read the assay results without performing any additional steps.

1.3.2 System—Samples and Collecting Tool

The samples described herein include any sample that can be obtained from an individual. In some embodiments, the sample can be obtained by an individual without the help of a health care professional, using embodiments of the kit described. In some embodiments, the sample can be obtained under the guidance of a health care professional.

Non-limiting examples of a sample of this invention can include vaginal fluid, vaginal tissue, vaginal wash, vaginal swab, vaginal discharge, cervical swab, cervical tissue urethral swab, urethral discharge, rectal swab, rectal material, rectal wash, urine, blood, serum, plasma, saliva, tears, skin swab, semen, seminal fluid, sputum, bronchial fluid, bronchial wash, peritoneal fluid, peritoneal wash, pleural fluid, pleural wash, cerebrospinal fluid, eye fluid and/or tissue, fluid and/or tissue from lung, liver, heart, brain, kidney, spleen or muscle and any combination thereof. In some embodiments, the sample is a blood sample. In some embodiments, the sample is a urine sample. In some embodiments, the sample is a vaginal discharge or a penile discharge. In some embodiments, the sample is obtained from contacting an ulcer in genital area.

In some embodiments, a sample is collected in a collection unit. In some embodiments, a sample collection unit is configured to receive a volume of the bodily fluid sample. In an instance, the sample collection unit is configured to receive a volume of the bodily fluid sample equivalent to a single drop of blood.

In some embodiments, a sample collection unit includes a sample collecting tool, where the sample collecting tool includes a swab. In some embodiments, the swab is a vaginal swab or urethral swab. In some embodiments, the swab is an endocervical swab. In some embodiments, the sample collecting tool comprises a fluid collecting container. In some embodiments, the fluid collecting container comprises a tube. In some embodiments, the tube is serum tube or a plasma tube. As described below in relation to FIGS. 6 and 7C through 7D, in some embodiments, the sample collecting tool (e.g., swab or other collecting tool) can be integrated with the signal output device. For instance, a swab can be attached to the signal output device in a manner that couples the swab to the sample loading zone (and/or reaction zone) of the signal output device, such that a user can provide a sample to the swab and the swab, integrated with the signal output device, can be transmitted into the extraction container for further sample processing.

In some embodiments, the biological sample of this invention to be used in the methods of this invention can be diluted 1:2, 1:5, 1:10, 1:100, 1:200, 1:300, 1:400, 1:500, 1:600, 1:700, 1:800, 1:900, 1:1000, 1:1500, 1:2000, 1:3000, 1:4000, 1:5000, 1:6000, 1:7000, 1:8000, 1:9000, 1:10,000, 1:20,000, 1:30,000, 1:40,000, 1:50,000, 1:100,000, etc. Such a dilution can be carried out according to protocols well known in the art. In some embodiments, a specific dilution can be used to increase the specificity and/or sensitivity of the method or device as described herein.

1.3.3 System—Pathogens and Target Substances

The methods, devices and kits of the present application are intended for diagnosing an infection of a sexually transmitted pathogen including all of the bacteria, viruses and parasites that can be transmitted through sexual contact. Exemplary pathogens discussed herein are *Chlamydia trachomatis, Neisseria gonorrhoeae, Trichomonas vaginalis, Treponema pallidum, Gardnerella vaginitis, Mycoplasma Genitalium, Candida Albicans* (yeast infection), Human immunodeficiency virus (HIV), Human papillomavirus (HPV), Hepatitis C virus (HCV), Hepatitis B virus (HBV), Herpes simplex virus (HSV).

*Chlamydia trachomatis* (*Chlamydia trachomatis*) serovars A, B, Ba and C are associated with endemic trachoma, which is the most common preventable form of blindness in certain parts of the Mediterranean and Middle East. Serovars L1, L2 and L3 are associated with lymphogranuloma venereum (LGV) in tropical settings. Serovars D through K cause nongonococcal urethritis and epididymitis in men, Reiter's syndrome or proctitis, conjunctivitis in both men and women, and cervicitis, urethritis, endometritis, salpingitis and perihepatitis in women. Between one-half and two-thirds of chlamydial infections in men and women may be asymptomatic and remain undiagnosed and untreated. In women, this may lead to late sequelae such as endometritis, salpingitis, pelvic inflammatory disease, ectopic pregnancy or tubal factor infertility. *Chlamydia trachomatis* in the cervix may be transmitted to a neonate during vaginal delivery, resulting in conjunctivitis and neonatal pneumonia.

In some embodiments, the target material of *Chlamydia trachomatis* is expressed on all strains. In some embodiments, the target substance is expressed on one or more specific strains. In some embodiments, the target substance is a major outer membrane protein of *Chlamydia trachomatis*. In some embodiments, the target substance is evenly distributed on *Chlamydia trachomatis*. In some embodiments, the target substance is unevenly distributed on *Chlamydia trachomatis*.

*Neisseria gonorrhoeae* is an obligate human pathogen and is the etiological agent of gonorrhea. *Neisseria gonorrhoeae* is a Gram-negative coffee bean-shaped diplococci bacteria. Syndromes include cervicitis in women, and urethritis, pharyngitis and proctitis in both sexes. If untreated, women may experience severe sequelae of pelvic inflammatory disease, chronic pelvic pain, ectopic pregnancy and tubal infertility, while men may develop epididymitis, prostatitis and urethral stricture. Occasionally, some individuals may develop disseminated infections with systemic complications, while others may have asymptomatic infections and transmit gonococci unknowingly. Oropharyngeal and anorectal gonococcal infections may be acquired by persons practicing receptive oral or anal intercourse or by contamination from cervical secretions. Occasionally, adults may present with conjunctivitis. In some embodiments, the target material of *Neisseria gonorrhoeae* includes a peptide or protein comprising any portion or the whole of a sequence selected from the sequences described herein.

*Trichomonas vaginalis* (TV) is likely the most common non-viral sexually transmitted infection (STI) in the world. It is as an important source of reproductive morbidity, a facilitator of HIV transmission and acquisition, and thus it is an important public health problem. Despite its importance in human reproductive health and HIV transmission, it is not a reportable disease and surveillance is not generally done. This is problematic since most persons infected with TV are asymptomatic. In some embodiments, the target material of *Trichomonas vaginalis* include a peptide or protein comprising any portion or the whole of a sequence selected from the sequences described herein.

The target material of an agent or biomarker can be anything that is specifically expressed by the agent/biomarker or any component of the agent/biomarker. In some embodiments, the target substance is a polynucleotide. In some embodiments, the target substance is an RNA. In some embodiments, the target substance is an MicroRNA. In some embodiments, the target substance is a DNA. In some embodiments, the target substance is a peptide or protein. In some embodiments, the target substance comprises a peptide or protein comprising any portion or the whole of a sequence selected from the sequences described herein in Section X. In some embodiments, the target substance is a lipid. In some embodiments, the target substance is a polysaccharide. In some embodiments, the target substance is a lipopolysaccharide.

1.3.4 System—Extraction Buffer

In some embodiments, as described above, the extraction buffer is configured for "single-step" extraction of target material from one or more agents associated with health conditions. In some embodiments, the extraction buffer comprises: 1-100% PBS (phosphate buffered saline), 1-100% TBS (Tris buffered saline), 1-100% HBS (HEPES buffered saline) and extraction substance. The extraction substance is selected from one or more substances in this group: 0.01%-100% 3-[(3-Cholamidopropyl) dimethylammonio]-1-propanesulfonate, 0.1%-100% BugBuster™, 0.01%-100% octylthioglucoside, 5-5000 mM sodium hydroxide, 0.01%-100% Triton X-100, 0.01%-100% octyl glucoside. In embodiments, the extraction buffer is used at concentration between 0.001% and 100%; however, in alternative embodiments, the extraction buffer can be used at another concentration.

1.3.5 System—Substrate Materials

In relation to embodiments of the system described above, embodiments of the loading zone (such as loading zone 145) can include or be composed of cellulose and/or glass fiber. In some embodiments, the loading zone is capable of transporting the sample to other parts of the device (e.g., by way of fluid coupling). In some embodiments, the transportation of the sample through different zones from the loading zone is in a continuous and/or homogenous manner. In some embodiments, the loading zone includes materials or reagents that pretreat the sample before its transportation. In some embodiments, the loading zone includes pretreating materials/reagents configured for one or more of: separation of sample components, removal of interfering materials, and/or adjustment of pH.

In relation to embodiments of the system described above, the system can include substrate materials and/or structures that provide for lateral flow of a sample from a loading zone to a testing zone (such as testing zone 160). In some instances, the devices include a bibulous material or member that readily absorbs liquid and provides for liquid flow through the member. Examples of bibulous materials include: organic or inorganic polymers and natural and synthetic polymers. More specific examples of suitable solid supports include, without limitation, glass fiber, cellulose, nylon, cross-linked dextran, various chromatographic papers and nitrocellulose. In some embodiments, the bibulous member includes a membrane, and in a specific example, the membrane is a nitrocellulose membrane. In some embodiments, the membrane is located in testing zone and/or control line zone, described in more detail below.

While the bibulous member and overall configuration of a lateral flow assay device implemented in embodiments of the system may vary, in certain embodiments the bibulous member can have a strip configuration, some embodiments of which are described in relation to FIGS. 1A-1B, 2, and 3A-3C above. Where the bibulous material is configured as a strip, the bibulous member can have a length that is longer than its width. In some examples, the length is longer than the width by 1.5 fold or more, such as 2-fold or more, e.g., 10 fold or more, including 20-fold or more. In some examples, the length of the bibulous member ranges from 0.5 to 20 cm, such as 1.0 to 15 cm, e.g., 2.0 to 10 cm, while the width ranges 0.1 to 10.0 cm, such as 0.5 to 2.5 cm, e.g., 1 to 2 cm. The thickness of the bibulous member may also vary, ranging in some instances from 0.01 to 0.05 cm, such as 0.1 to 0.4 cm, e.g., 0.1 to 0.25 cm.

Optionally, the signal output device of the system can include an absorbent pad downstream from the reaction zone and any control region, e.g., at the end distal from the sample loading zone, where the absorbent pad is configured to absorb fluid and reagents present therein that have flowed through the bibulous member. While the configuration of the absorbent pad may vary, in some instances it is configured to absorb a volume of liquid that is substantially the same as the volume of sample that is applied to the sample loading zone during use.

1.3.6 System—Configuration of Loading Zone

As such, embodiments of the loading zone can include a terminal zone (e.g., a most upstream zone) of the bibulous member, e.g., positioned closer to one end of the bibulous member. Alternatively, embodiments of the loading zone may be distinct from the bibulous member, but configured to provide for fluid communication of sample into the bibulous member upon application of sample to the sample loading zone. The loading zone may be configured to receive samples of varying volumes, where in some instances the sample zone is configured to receive a sample having a volume ranging from 0.1 ul to 20 ml such as 5 ul to 20 ml.

In some instances, the loading zone may include a metering device configured to meter a specific amount of sample into the bibulous member.

1.3.7 System—Configuration of Reaction Zone

Embodiments of the reaction zone can be positioned at some distance downstream from the loading zone. The distance between the loading zone and the reaction zone may vary. In some embodiments, the distance ranges from 0.1 to 10 cm, such as 0.1 to 3 cm and including 0.5 to 2 cm. In some embodiments, the reaction zone overlaps with the loading zone in a portion or full. In some embodiments, the reaction zone overlaps with the loading zone in about 25%, 50%, 75%, and 100%.

As described above, in some embodiments, the reaction substances implemented for detection are not immobilized at the reaction zone(s). In relation to immobilization, a substance and the bibulous member maintain their position relative to each other in space under the conditions of use, e.g., under the assay conditions. As such, a not immobilized reaction substance is not stably associated with the bibulous member and can migrate under the capillary pressure or other drivers of sample flow. In some embodiments, examples of which are described above, a reaction substance binds to a specific region of a target material of a pathogen or other agent.

In some embodiments (some of which are described above), the reaction zone includes two or more reaction substances that are conjugated to the same or different labels. In some embodiments, the two or more reaction substances are not immobilized. In some embodiments, the two or more substances each bind to the same specific region of the same target material of an agent or biomarker. In some embodiments, the two or more substances each bind to two or more different specific regions of the same target material of an agent or biomarker. In some embodiments, the two or more substances each bind to a specific region of two or more different target materials of an agent or biomarker. In some embodiments, the two or more substances each bind to a specific region of target materials of two or more different agents or biomarkers.

1.3.7.1 System—Reaction Zone Substances

The reaction substances in the reaction zone that bind to specific agent/biomarker regions of target material of interest can include one or more of: a protein, a peptide or its analogs (e.g., an antibody, antigen, peptoid, D-peptide, beta-peptide), or a nucleic acid (e.g., an aptamer) or its analogs.

Antibodies

In some embodiments, the reaction substances include antibodies. In some embodiments, an antibody used is a monoclonal antibody. In some embodiments, the antibody is a polyclonal antibody. In some embodiments, the antibody is a bispecific antibody that binds to two separate regions of an agent, or two separate regions of two different agents. In some embodiments, the substance is a fragment or a variant of an antibody (e.g., Fab fragment or single chain variable fragment).

In some embodiments, the reaction substances include monoclonal antibodies that bind to a specific region of target substance on an agent (e.g., *Chlamydia trachomatis, Neisseria gonorrhoeae, Trichomonas vaginalis, Treponema pallidum, Gardnerella vaginitis, Mycoplasma genitalium, Candida Albicans* (yeast infection), Human immunodeficiency virus (HIV), Human papillomavirus (HPV), Hepatitis C virus (HCV), Hepatitis B virus (HBV), Herpes simplex virus (HSV)). Such monoclonal antibodies can be generated using a hybridoma technique. For example, monoclonal antibodies can be produced from a single B-lymphocyte clone involving immunizing a certain species (e.g., a mouse, rat, rabbit, or goat) against the specific region on a target substance and obtaining the B-lymphocytes from the spleen of the species. The B-lymphocytes are then fused (by chemical- or virus-induced methods) with an immortal myeloma cell line lacking the hypoxanthine-guanine-phosphoribosyltransferase (HGPRT) gene and not containing any other immunoglobulin-producing cell. These hybridoma cells are then cultured in vitro in selective medium (i.e. medium containing hypoxanthine-aminopterinthymidine) where only the hybridomas (i.e. the fusion between the primary B-lymphocytes and myeloma cells) survive as they have inherited immortality from the myeloma cells and selective resistance from the primary B-lymphocytes (as the myeloma cells lack HGPRT, they cannot synthesize nucleotides de novo as this is inhibited by aminopterin in the selective medium). The initial culture of hybridomas contains a mixture of antibodies derived from many different primary B-lymphocyte clones, each secreting its own individual specific antibody into the culture medium (i.e. the antibodies are still polyclonal). Each individual clone can be separated by dilution into different culture wells. The cell culture medium can then be screened from many hundreds of different wells for the specific antibody activity required and the desired B-lymphocytes grown from the positive wells and then recloned and retested for activity. The positive hybridomas and monoclonal antibodies generated can then be stored away in liquid nitrogen.

Monoclonal antibodies can also be generated using phage display. This involves isolating B-lymphocytes from the blood of humans and then isolating the mRNA and converting it into cDNA using PCR to amplify all the VH and VL segments. These segments can then be cloned into a vector (usually as scFv) next to the PIII protein of a bacteriophage. This vector is then introduced into *E. coli* cells in order to generate a library containing approximately $10^{10}$ clones of antibody fragments. *E. coli* can then secrete the bacteriophage containing the VH and VL segments as part of the bacteriophage coat. Specific VH and VL segments against the target substance can then be selected and used to re-infect *E. coli* with the bacteriophage. Cells containing the plasmid can then be isolated and sequenced. Its advantages include: once the library is made, the same library can be used to generate new antibodies and does not have to be remade, no immunizations are required as the entire process is done in vitro, antibodies can be obtained much more quickly than the traditional hybridoma technique and the library can be used to generate antibodies to toxic target substances that could not be used to immunize an animal.

In some embodiments, monoclonal antibodies can also be improved in multiple aspects. For example, binding affinity to the target substance can be improved by using phage display libraries to isolate antibodies with strong affinities for the target substance.

In some embodiments, monoclonal antibodies are recovered and/or purified with a process comprising one or more of the following steps: 1) harvest antibodies with centrifugation/filgration thereby removing cells and cell debris; 2) protein A and/or protein G chromatograph which yields highly purified product in a single step; 3) low pH hold to inactivate endogenous/adventitious viruses; 4) additional chromatography steps to further remove impurities and viruses; 5) filtration to further remove endogenous/adventitious viruses; and 6) ultrafiltration/diafiltration.

In some embodiments (some of which are described above), the reaction zone includes reaction substances including antibodies listed in TABLES 1, 2, and 3.

Aptamers

In some embodiments, the reaction substance that binds to a specific region of an agent is an aptamer or aptamers. In some embodiments, the aptamer is generated by an in vitro process known as SELEX (systematic evolution of ligands by exponential enrichment). In some embodiments, the aptamer is an organic molecule.

In some embodiments, the aptamer has a molecular weight of about 50 to 100 Da, 50 to 200 Da, 50 to 500 Da, 50 to 1000 Da, 50 to 2,000 Da, 50 to 3,000 Da, 50 to 4,000 Da, 50 to 5,000 Da, 50 to 6,000 Da, 50 to 7,000 Da, 50 to 8,000 Da, 50 to 9,000 Da, 50 to 10,000 Da, 50 to 11,000 Da, 50 to 12,500 Da, 50 to 15,000 Da, 100 to 200 Da, 100 to 500 Da, 100 to 1000 Da, 100 to 2,000 Da, 100 to 3,000 Da, 100 to 4,000 Da, 100 to 5,000 Da, 100 to 6,000 Da, 100 to 7,000 Da, 100 to 8,000 Da, 100 to 9,000 Da, 100 to 10,000 Da, 100 to 11,000 Da, 100 to 12,500 Da, 100 to 15,000 Da, 200 Da to 500 Da, 200 to 1000 Da, 200 to 2,000 Da, 200 to 3,000 Da, 200 to 4,000 Da, 200 to 5,000 Da, 200 to 6,000 Da, 200 to 7,000 Da, 200 to 8,000 Da, 200 to 9,000 Da, 200 to 10,000 Da, 200 to 11,000 Da, 200 to 12,500 Da, 200 to 15,000 Da, 500 to 1000 Da, 500 to 2,000 Da, 500 to 3,000 Da, 500 to 4,000 Da, 500 to 5,000 Da, 500 to 6,000 Da, 500 to 7,000 Da, 500 to 8,000 Da, 500 to 9,000 Da, 500 to 10,000 Da, 500 to 11,000 Da, 500 to 12,500 Da, 500 to 15,000 Da, 1,000 to 2,000 Da, 1,000 to 3,000 Da, 1,000 to 4,000 Da, 1,000 to 5,000 Da, 1,000 to 6,000 Da, 1,000 to 7,000 Da, 1,000 to 8,000 Da, 1,000 to 9,000 Da, 1,000 to 10,000 Da, 1,000 to 11,000 Da, 1,000 to 12,500 Da, 1,000 to 15,000 Da, 2,000 to 3,000 Da, 2,000 to 4,000 Da, 2,000 to 5,000 Da, 2,000 to 6,000 Da, 2,000 to 7,000 Da, 2,000 to 8,000 Da, 2,000 to 9,000 Da, 2,000 to 10,000 Da, 2,000 to 11,000 Da, 2,000 to 12,500 Da, 2,000 to 15,000 Da, 3,000 Da to 4,000 Da, 3,000 to 5,000 Da, 3,000 to 6,000 Da, 3,000 to 7,000 Da, 3,000 to 8,000 Da, 3,000 to 9,000 Da, 3,000 to 10,000 Da, 3,000 to 11,000 Da, 3,000 to 12,500 Da, 3,000 to 15,000 Da, 4,000 to 5,000 Da, 4,000 to 6,000 Da, 4,000 to 7,000 Da, 4,000 to 8,000 Da, 4,000 to 9,000 Da, 4,000 to 10,000 Da, 4,000 to 11,000 Da, 4,000 to 12,500 Da, 4,000 to 15,000 Da, 5,000 to 6,000 Da, 5,000 to 7,000 Da, 5,000 to 8,000 Da, 5,000 to 9,000 Da, 5,000 to 10,000 Da, 5,000 to 11,000 Da, 5,000 to 12,500 Da, 5,000 to 15,000 Da, 6,000 to 7,000 Da, 6,000 to 8,000 Da, 6,000 to 9,000 Da, 6,000 to 10,000 Da, 6,000 to 11,000 Da, 6,000 to 12,500 Da, 6,000 to 15,000 Da, 7,000 to 8,000 Da, 7,000 to 9,000 Da, 7,000 to 10,000 Da, 7,000 to 11,000 Da, 7,000 to 12,500 Da, 7,000 to 15,000 Da, 8,000 to 9,000 Da, 8,000 to 10,000 Da, 8,000 to 11,000 Da, 8,000 to 12,500 Da, 8,000 to 15,000 Da, 9,000 to 10,000 Da, 9,000 to 11,000 Da, 9,000 to 12,500 Da, 9,000 to 15,000 Da, 10,000 to 11,000 Da, 10,000 to 12,500 Da, 10,000 to 15,000 Da, or 12,000 to 15,000 Da, each inclusive. In some embodiments, the aptamer has a molecular weight of about 100 to 10,000 Da.

In some embodiments (some of which are described above), the reaction zone includes reaction substances including aptamers listed in TABLES 1, 2, and 3.

Molecular Beacons

In some embodiments, the reaction substance that binds to a specific region of an agent includes a molecular beacon or molecular beacons. Molecular beacons are a specific DNA hairpin structure with fluorophore at one end and quencher at the other end. Fluorophore cannot produce fluorescence in the absence of an analyte (e.g., a target substance of a pathogen) because of closely located quencher. When complementary DNA sequence (e.g., a target substance of a pathogen) is present as a target analyte, stem and loop portions of the beacons are opened as a result of a force and fluorescence signal is observed. In some embodiments, the molecular beacon binds to a target substance of a pathogen, wherein the target substance comprises a nucleic acid, a toxin, and/or a protein or peptide. In some embodiments, the molecular beacon comprises a loop region and/or a double stranded stem region. In some embodiments, the loop region is complementary to a target substance (e.g., a DNA, an mRNA, a toxin or a protein of a pathogen).

In some embodiments, the molecular beacon has about 10 to 15, 10 to 20, 10 to 25, 10 to 30, 10 to 35, 10 to 40, 10 to 45, 10 to 50, 15 to 20, 15 to 25, 15 to 30, 15 to 35, 15 to 40, 15 to 45, 15 to 50, 20 to 25, 20 to 30, 20 to 35, 20 to 40, 20 to 45, 20 to 50, 25 to 30, 25 to 35, 25 to 40, 25 to 45, 25 to 50, 30 to 35, 30 to 40, 30 to 45, 30 to 50, 35 to 40, 35 to 45, 35 to 50, 40 to 45, 40 to 50 or 45 to 50 base pairs in the loop region, each inclusive, wherein the loop is complimentary to a target substance. In some embodiments, the molecular beacon has about 15 to 30 base pairs in the loop, wherein the loop is complimentary to a target substance.

In some embodiments, the molecular beacon has about 3 to 4, 3 to 5, 3 to 6, 3 to 7, 3 to 8, 3 to 9, 4 to 5, 4 to 6, 4 to 7, 4 to 8, 4 to 9, 5 to 6, 5 to 7, 5 to 8, 5 to 9, 6 to 7, 6 to 8, 6 to 9, 7 to 8, 7 to 9 or 8 to 9 base pairs at the double stranded stem region.

DNA Probes

In some embodiments, the reaction substance that binds to a specific region of a pathogen includes a DNA probe.

Pregnancy and Fertility Biomarkers

In some embodiments (some of which are described above), the reaction zone further includes a substance that binds to a biomarker of pregnancy. In some embodiments, the biomarker(s) include one or more of: human chorionic gonadotropin (hCG), activin A, pregnancy-associated plasma protein-A (PAPP-A), human placental lactogen (hPL), A disintegrin and Metalloprotease-12 (ADAM-12), pregnancy-specific beta glycoprotein 1 (SP-1), placental mRNAs, progestrerone, Inhibin A, Vascular Endothelial Growth Factor (VEGF), Placental-like growth factor (P1GF), Leukemic Inhibitory Factor, Glycodelin, Mucin-1, Adrenomedullin, and other biomarkers.

In some embodiments (some of which are described above), the reaction zone further includes a substance that binds to a biomarker of fertility. In some embodiments, the biomarker(s) include one or more of: oestrone-3-glucuronide (E3G0, luteinizing hormone, follicle stimulating hormone (FSH), estrogen, progesterone, testosterone, dehydroepiandrosterone (DHEA), cortisol, sex hormone binding globulin (SHBG), triiodothyronine (T3), Thyroxine (T4), thyroid stimulating hormone (TSH), thyroid peroxidase antibodies (TPO antibodies), and other biomarkers.

1.3.7.2 System—Reaction Zone Labels

In some embodiments, the labels used (e.g., labels to which reaction substances are conjugated) include one or more of: gold nanoparticles, colored latex beads, magnetic particles, carbon nanoparticles, cellulose nano beads, selenium nanoparticles, silver nanoparticles, quantum dots, up converting phosphors, organic fluorophores, textile dyes, enzymes, liposomes and labels.

In some embodiments, the conjugation of the substance that binds to a specific region of a pathogen and the label is stable for at least about 1, 3, 5, 7, 10, 12, or 14 or more days. In some embodiments, the conjugation is stable for at least about 1, 2, 3, 4, 5, 6, 7, 8, 9, 10 or more weeks. In some embodiments, the conjugation is stable for at least about 1, 2, 3, 4, 5, 6, 7, 8, 9, 10, 11, 12 or more months. In some embodiments, the conjugation is stable for at least about 1, 2, 3, 4, 5, or more months. The conjugation is stable when at least 50%, 60%, 70%, 80%, 90%, 95%, 98%, 99%, 99.5% of the conjugates are functional (e.g., labeling the true positive and/or not labeling the false negative) and/or at most 30%, 25%, 20%, 15%, 10%, 5%, 2.5%, 1% or 0.5% of the conjugates are not functional (e.g., labeling the false positive and/or not labeling the true positive).

In some embodiments, the concentration of the label is at least about $10^{-12}$, $10^{-11}$, $10^{-10}$, $10^{-9}$, $10^{-8}$, $10^{-7}$, or $10^{-6}$ M. In some embodiments, the concentration of the label is at most about $10^{-11}$, $10^{-10}$, 10–9, $10^{-8}$, $10^{-7}$, $10^{-6}$, $10^{-5}$ or $10^{-4}$ M. In some embodiments, the concentration of the label is about $10^{-12}$, $10^{-11}$, $10^{-10}$, $10^{-9}$, $10^{-8}$, $10^{-7}$, or $10^{-6}$ M.

In some embodiments, the label is capable of generate a direct signal after encountering the analyte (e.g., the specific region that the conjugated substance binds to). In some embodiments, the label generates a signal after an additional step.

In some embodiments, the device comprises more than one label. In some embodiments, the more than one label can be composed of same or different material(s). In some embodiments, the more than one label can generate same or different signals.

Cellulose NanoBeads

In some embodiments, the labels used (e.g., labels to which reaction substances are conjugated) include Cellulose NanoBeads. Cellulose NanoBeads (e.g., NanoAc™) are inert and spherical, which have high affinity to biomolecules and can be functionalized. Cellulose nanobeads are highly stable, deeply colored particles that have demonstrated appropriate performance.

Latex Beads

In some embodiments, the labels used (e.g., labels to which reaction substances are conjugated) include latex beads. Latex beads are inert and spherical, which have high affinity to biomolecules and can be functionalized.

Gold Nanoparticles

In some embodiments, the labels used (e.g., labels to which reaction substances are conjugated) include gold nanoparticles. In some embodiments, the gold nanoparticles include colloidal gold. Colloidal gold is inert and spherical, which have high affinity to biomolecules and can be functionalized. In some embodiments, the average diameter of the gold nanoparticles is about 5 to 150 nm. In some embodiments, the average diameter of the gold nanoparticles is no greater than 150 nm or 200 nm. In some embodiments, the average diameter of the gold nanoparticles is about 40 nm. In some embodiments, the average diameter of the gold nanoparticles is about 30 nm. In some embodiments, the average diameter of the gold nanoparticles is about 60 nm. In some embodiments, the average diameter of the gold nanoparticles is about 5 to 25, 5 to 50, 5 to 75, 5 to 100, 5 to 125, 5 to 150, 5 to 175, 5 to 200, 25 to 50, 25 to 75, 25 to 100, 25 to 125, 25 to 150, 25 to 175, 25 to 200, 50 to 75, 50 to 100, 50 to 125, 50 to 150, 50 to 175, 50 to 200, 75 to 100, 75 to 125, 75 to 150, 75 to 175, 75 to 200, 100 to 125, 100 to 150, 100 to 175, 100 to 200, 125 to 150, 125 to 175, 125 to 200, 150 to 175, 150 to 200, or 175 to 200 nm, each inclusive.

Europium Ions

In some embodiments, the labels used (e.g., labels to which reaction substances are conjugated) include Europium ions. In some embodiments, Europium ion is chelated by isothiocyanate. Isothiocyanate can be functionalized and has high affinity to biomolecules. Europium ions are highly fluorescent and have demonstrated appropriate performance over standard labels in lateral flow applications.

Magnetic Particles or Aggregates

In some embodiments, the labels used (e.g., labels to which reaction substances are conjugated) include a magnetic particle or aggregate. In some embodiments, the magnetic particle or aggregate can produce a signal, wherein the signal can be read by an optical strip reader or magnetic assay reader. In some embodiments, the magnetic particle or aggregate comprises one or more iron oxide particle. In some embodiments, the one or more iron particles comprise $Fe_3O_4$ particles. In some embodiments, the one or more iron oxide particles are modified with polyethylene glycol. In some embodiments, the one or more iron oxide particles are crosslinked with poly-L-lysine.

Fluorescent and/or Luminescent Materials

In some embodiments, the labels used (e.g., labels to which reaction substances are conjugated) include a fluorescent or luminescent material. In some embodiments, the label includes an organic fluorophore (e.g., rhodamine). In some embodiments, the label includes a fluorescent microsphere. In some embodiments, the label includes a nanomaterial. In some embodiments, the nanomaterial includes quantum dots. In some embodiments, the quantum dots are encapsuled into a nanobead, thereby improving the detection sensitivity.

In some embodiments, the labels used include at least two or more different quantum dots, wherein the different quantum dots generate different colors.

In some embodiments, the labels used include upconverting phosphors (UCP). In some embodiments, the UCP are characterized with their excitation in infra-red region and emission in high energy visible region. In some embodiments, the UCP are characterized with the absence of auto fluorescence or the absence a significant level of auto fluorescence. In some embodiments, the average diameter of UCP is about 10 nm to 1 um. In some embodiments, the average diameter of UCP is about 10 to 50, 10 to 100, 10 to 200, 10 to 300, 10 to 400, 10 to 500, 10 to 750, 50 to 100, 50 to 200, 50 to 300, 50 to 400, 50 to 500, 50 to 750, 50 to 1,000, 100 to 200, 100 to 300, 100 to 400, 100 to 500, 100 to 750, 100 to 1,000, 200 to 300, 200 to 400, 200 to 500, 200 to 750, 200 to 1,000, 300 to 400, 300 to 500, 300 to 750, 300 to 1,000, 400 to 500, 400 to 750, 400 to 1,000, 500 to 750, 500 to 1,000, or 750 to 1,000 nm, each inclusive. In some embodiments, the average diameter of UCP is about 40 to 400 nm. In some embodiments, the average diameter of UCP is about 40 nm.

In some embodiments, the labels used include fluorescent europium nanoparticles. In some embodiments, the fluorescent europium nanoparticles comprise europium III nanoparticles. In some embodiments, the average diameter of europium nanoparticles is about 100 to 1,000 nm. In some embodiments, the average diameter of europium nanoparticles is about 400 to 600 nm. In some embodiments, the average diameter of europium nanoparticles is about 500 nm (e.g., 520 nm).

In some embodiments, the labels used include silica nanoparticles. In some embodiments, the label comprises lanthanide chelate-loaded silica nanoparticles.

In some embodiments, the labels used include a fluorescent microsphere.

Enzymes

In some embodiments, the labels used (e.g., labels to which reaction substances are conjugated) include an enzyme. In some embodiments, the enzyme is horse-radish peroxidase (HRP). In some embodiments, the enzyme is alkaline phosphatase (AP). In some embodiments, the enzyme is Glucose oxidase. In some embodiments, the enzyme is Urease. In some embodiments, the amplification of the detectable signal is obtained by reacting the enzyme with one or more substrates or additional enzymes and substrates to produce a detectable reaction product.

Colloidal Carbon

In some embodiments, the labels used (e.g., labels to which reaction substances are conjugated) include colloidal carbon. Unstabilized carbon can be used to produce carbon sols suitable for protein adsorption. Their carbon sols are formed by suspending carbon particles of well-defined particle sizes in distilled water or low ionic strength buffers, sonicated or vigorously agitated, followed by centrifugation. These unstabilized carbon sols were flocculated easily by salt. However, when coated with macromolecules such as antibodies, they were "protected" from flocculation. In practice, increasing amounts of a macromolecule are incubated with a fixed amount of non-stabilized carbon aqueous sol under defined conditions to determine the "minimal protective amount". The optimal pH for adsorption can be determined by one of ordinary skill in the art. Unlike colloidal gold, in which the conjugation of protein to colloidal gold is near instantaneous, adsorption onto colloidal carbon takes a longer time from one to several hours.

Colloidal carbon has appropriate properties in terms of stability and high color contrast on a membrane.

1.3.8 System—Configuration of Testing Zone

In some embodiments (some of which are described above), the system includes a testing zone. The testing zone can be positioned at some distance downstream from the reaction zone. The distance between the reaction zone and the testing zone may vary. In some embodiments, the distance ranges from 0.1 to 10 cm, such as 1 to 5 cm.

As described above, in some embodiments, the testing zone includes one or more immobilized substances. In some embodiments, the immobilized substances bind to specific regions of target material of agents or biomarkers associated with the health condition(s) of interest). In some embodiments, the specific region(s) are the same as the region(s) that the non-immobilized (i.e. capable of migrating downstream) substance in the reaction zone binds to. In some embodiments, the specific region(s) are different from the region(s) that the non-immobilized (i.e. capable of migrating downstream) substance(s) in the reaction zone bind to.

In some embodiments, the testing zone can include two or more testing substances, examples of which are described above. In some embodiments, the two or more testing substances are immobilized. In some embodiments, the testing zone includes two or more immobilized testing substances when the reaction zone includes two or more non-immobilized corresponding reaction substances. In some embodiments, the two or more non-immobilized reaction substances in the reaction region bind to the same target substance of an agent or biomarker, and the two or more immobilized corresponding testing substances in the testing zone each binds to the same target substance of the agent or biomarker (can bind to the same specific region or a different region that the non-immobilized reaction substance binds to). In some embodiments, the two or more non-immobilized reaction substances in the reaction zone bind to two or more different target materials of an agent or biomarker, and the two or more immobilized testing substances in the testing zone each bind to the same two or more target materials of the same agent or biomarker (e.g., can bind to the same specific region or a different region that the non-immobilized reaction substance binds to). In some embodiments, the two or more non-immobilized reaction substances in the reaction zone bind to a specific region of target material of two or more different agents or biomarkers, and the two or more immobilized testing substances in the testing zone each bind to the same target material of the two or more different agents or biomarkers.

In some embodiments, the two or more immobilized testing substances in the testing zone are configured in a non-overlapping manner. In some embodiments, the two or more immobilized testing substances are separated from each other in different regions of the testing zone with of distance of about 0.1 cm to 10 cm. In some embodiments, the two or more immobilized testing substances are separated from each other in different regions of the testing zone with a distance of about at least 0.01-5 cm.

In some embodiments, the two or more immobilized testing substances in the testing zone are configured to be at least partially overlapping. In some embodiments, the two or more immobilized substances completely overlap with each other.

In some embodiments, the affinity between the immobilized or non-immobilized substance(s) and the target material to which the substance(s) specifically bind when they are specifically bound to each other in a binding complex is characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower KD.

In some embodiments, the affinity between the immobilized testing substance in the testing zone and the target material of interest from the sample is about equal to or strong than the affinity between the non-immobilized reaction substance in the reaction zone and the same target material. In some embodiments, the affinity between the immobilized testing substance in the testing zone and the target material is at least about 1.5-fold, 2-fold, 3-fold, 4-fold, 5-fold than the affinity between the non-immobilized reaction substance in the reaction zone and the same target material.

In some embodiments, the affinity between the immobilized testing substance in the testing zone and the target material of interest from the sample is about equal to or weaker than the affinity between the non-immobilized reaction substance in the reaction zone and the same target material. In some embodiments, the affinity between the immobilized testing substance in the testing zone and the target material is at most about 90%, 80%, 70%, 60%, or 50% of the affinity between the non-immobilized reaction substance in the reaction zone and the same target material.

In some embodiments (some of which are described above), the testing zone further includes a substance that binds to a biomarker of pregnancy. In some embodiments, the biomarker(s) include one or more of: human chorionic gonadotropin (hCG), activin A, pregnancy-associated plasma protein-A (PAPP-A), human placental lactogen (hPL), A disintegrin and Metalloprotease-12 (ADAM-12), pregnancy-specific beta glycoprotein 1 (SP-1), placental mRNAs, progestrerone, Inhibin A, Vascular Endothelial Growth Factor (VEGF), Placental-like growth factor (P1GF), Leukemic Inhibitory Factor, Glycodelin, Mucin-1, Adrenomedullin, and other biomarkers.

In some embodiments (some of which are described above), the testing zone further includes a substance that binds to a biomarker of fertility. In some embodiments, the biomarker(s) include one or more of: oestrone-3-glucuronide (E3G0, luteinizing hormone, follicle stimulating hormone (FSH), estrogen, progesterone, testosterone, dehydroepiandrosterone (DHEA), cortisol, sex hormone binding globulin (SHBG), triiodothyronine (T3), Thyroxine (T4), thyroid stimulating hormone (TSH), thyroid peroxidase antibodies (TPO antibodies), and other biomarkers.

1.3.9 System—Configuration of Testing Zone

In some embodiments (some of which are described above), the system also includes a control zone. When present, the control zone is located downstream from the loading zone. In some embodiments, the control zone is located upstream or downstream from, or overlaps with the reaction zone. In some embodiments, the control zone is located upstream or downstream, or overlaps from the testing zone. In some embodiments, the control zone is located downstream from both the reaction zone and the testing zone.

In some embodiments, the control zone includes a control substance. In some embodiments, the control substance is immobilized. In some embodiments, the control substance binds to any particle. In some embodiments, the substance binds to a mobile control binding agent (a control binding agent that is not immobilized). In some embodiments, the mobile control binding agent is or includes the non-immobilized reaction substance in the reaction zone. In some embodiments, the mobile control binding agent is or includes an agent in the sample or a solution the sample is prepared in. In some embodiments, the control zone includes two or more substances that bind to two or more mobile control binding agents. In some embodiments, the two or more mobile control binding agents are from different sources (e.g., one is from the sample or a solution the sample is prepared in, and another from the non-immobilized substance originally in the reaction zone.)

1.3.10 System—Sensitivity and Specificity

In some embodiments, the system achieves a sensitivity of detecting the presence of a specific agent or biomarker of at least about 50%, 55%, 60%, 65%, 70%, 75%, 80%, 82.5%, 85%, 90%, 92.5%, 95%, 96%, 97%, 98%, or 99%. In some embodiments, the system detects two or more different agents or biomarkers with a sensitivity for at least two agents/biomarkers being both about or more than 50%, 55%, 60%, 65%, 70%, 75%, 80%, 82.5%, 85%, 90%, 92.5%, 95%, 96%, 97%, 98%, or 99%. In some embodiments, the system detects three or more different agents or biomarkers with a sensitivity for at least three agents/biomarkers being both about or more than 50%, 55%, 60%, 65%, 70%, 75%, 80%, 82.5%, 85%, 90%, 92.5%, 95%, 96%, 97%, 98%, or 99%.

In some embodiments, the system achieves a specificity of detecting the presence of a specific agent or biomarker of at least about 50%, 55%, 60%, 65%, 70%, 75%, 80%, 82.5%, 85%, 90%, 92.5%, 95%, 96%, 97%, 98%, or 99%. In some embodiments, the system detects two or more different agents or biomarkers with a specificity for at least two agents/biomarkers being both about or more than 50%, 55%, 60%, 65%, 70%, 75%, 80%, 82.5%, 85%, 90%, 92.5%, 95%, 96%, 97%, 98%, or 99%. In some embodiments, the system detects three or more different agents or biomarkers with specificity for at least three agents/biomarkers being both about or more than 50%, 55%, 60%, 65%, 70%, 75%, 80%, 82.5%, 85%, 90%, 92.5%, 95%, 96%, 97%, 98%, or 99%.

1.3.11 System—Detection System

In some embodiments, the system includes, is coupled to, or otherwise communicates with a detection system. In some embodiments, the detection system includes an optical reader (e.g., an optical strip reader). In some embodiments, the optical reader measures the intensity of colors produced at test and control lines. In some embodiments, the intensity of colors is recorded by an imaging software (e.g., an application on a computer, such as a mobile app). In some embodiments, the intensity of colors are recorded by a camera and then processed by an imaging software. In some embodiments, the optical system comprises a source of light. In some embodiments, the source of light comprises a monochromatic light. In some embodiments, the optical system is an automated system. In some embodiments, the optical system is a manual system.

In some embodiments, the detection system includes a fluorescence reader (e.g., a fluorescence strip reader). In some embodiments, the fluorescence reader measures the fluorescence intensity of test and control lines.

In some embodiments, the detection system includes a photoelectric sensor. In some embodiments, the photoelectric sensor measures photoelectrons produced as a result of the colloidal gold being exposed to a light source.

In some embodiments, the detection system includes a magnetic reader (e.g., a magnetic strip reader). In some embodiments, the detection system comprises an electrochemical detector.

In some embodiments, the system does not include an external detection system. In some embodiments, the systems described herein produce a signal that can be assessed by the eye (e.g., with visual observation).

1.4 System—Component Variations

Figure 4:
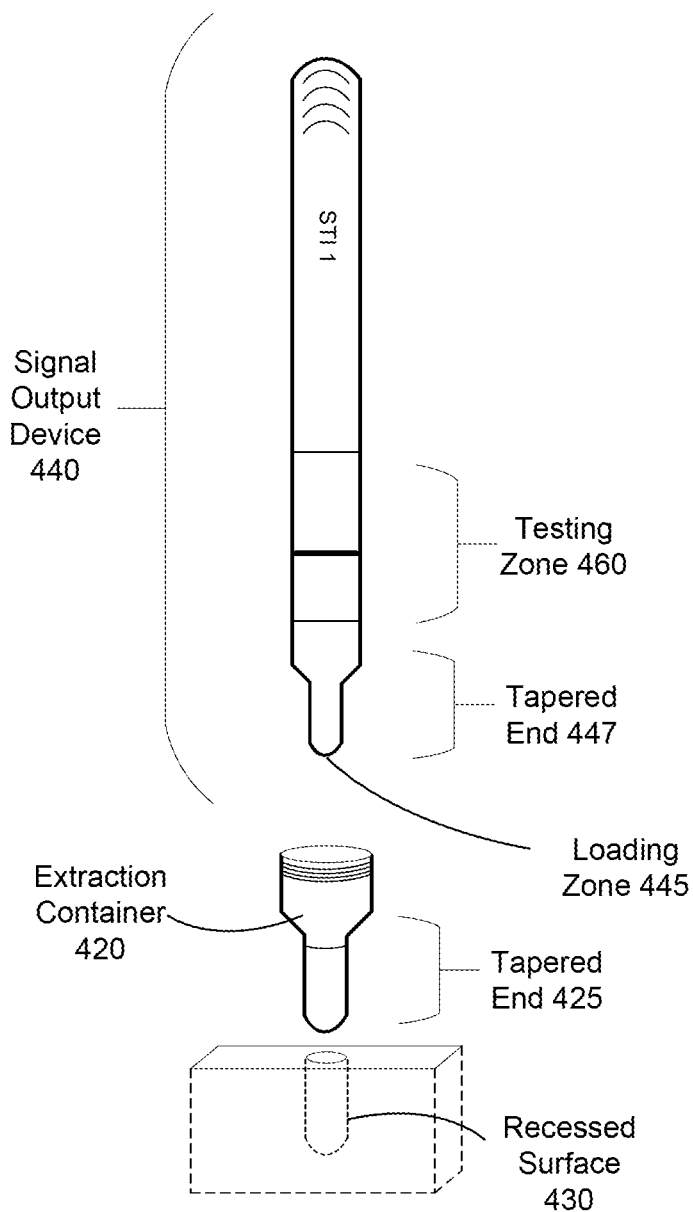
FIG. 4 depicts an embodiment of kit components configured to adjust sample extraction and processing parameters.

FIG. 4 depicts an embodiment of kit components configured to adjust sample extraction and processing parameters. As shown in FIG. 4, the embodiment of the extraction container 420 includes a tapered end 425 for containing an extraction buffer. Such a configuration reduces sample volume required and increases sample concentration within the extraction buffer. The tapered end 425 of the extraction container 420 is configured to be complementary to the recessed surface 430 of the sampling kit. Similarly, the signal output device 440 includes a loading zone 445 with a tapered end 447 configured to fit within the tapered end 425 of the extraction container 420 and displace fluid within the extraction container 420, in order to facilitate transmission of the extracted target material from the sample to the testing zone 460 of the signal output device 440.

2. Method

Figure 5:
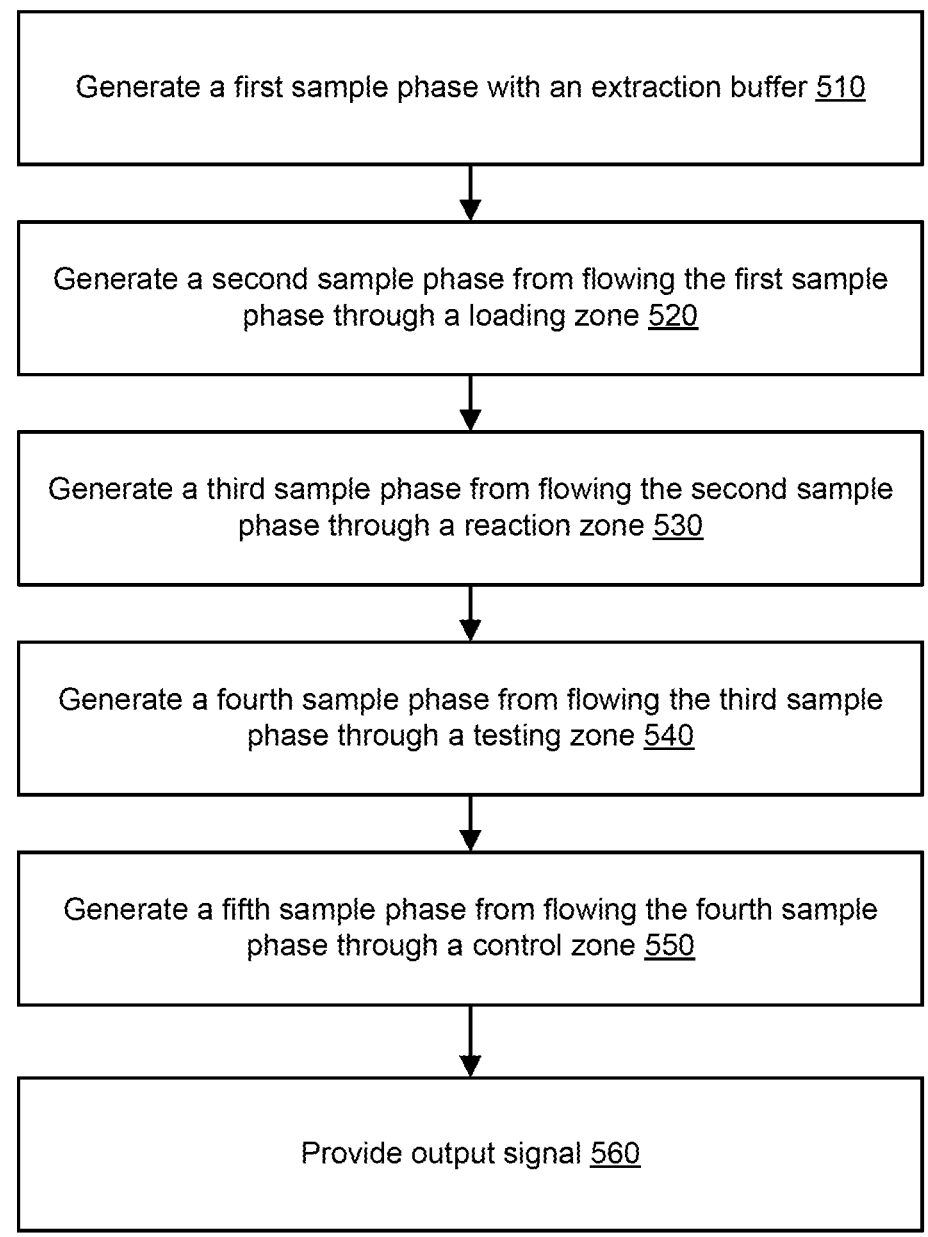
FIG. 5 depicts a flowchart of a method for assessing health of a subject, in accordance with one or more embodiments.

FIG. 5 depicts a flowchart of a method for assessing health of a subject, in accordance with one or more embodiments. The method 500 can be implemented by one or more embodiments of the system(s) described above. As such, as shown in FIG. 5, once a sample is taken from a subject, the extraction container of a sampling kit can generate a first sample phase 510 including a target material associated with the health condition, upon receiving a sample acquired directly from a subject into the extraction container containing an extraction buffer. The sampling kit and signal output device then generates a second sample phase 520 upon receiving a signal output device into the extraction container and flowing the first sample phase through a loading zone of the signal output device. The sampling kit and signal output device then generates a third sample phase 530 upon flowing the second sample phase through a reaction zone fluidly coupled to the loading zone and comprising a first reaction substance conjugated to a first label, where the first reaction substance preferentially couples to the target material. The sampling kit and signal output device then generates a fourth sample phase 540 upon flowing the third sample phase through a testing zone comprising a first testing substance retained at the testing zone, where the first testing substance preferentially couples to the target material. The sampling kit and signal output device then generates a fifth sample phase 550 upon flowing the fourth sample phase through a control zone comprising a control substance immobilized at the control zone, where the control substance does not preferentially couple with the target material. Finally, the sampling kit and signal output device provide an optically detected signal 560 characterizing status of the health condition from the testing zone and the control zone.

The method 500 is configured to operate with embodiments of the extraction containers, extraction buffers, loading zones, reaction zones, testing zones, control zones, substances, and labels described above. The method 500 is configured for detection of one or more health conditions, including sexual health conditions described above.

Figure 6:
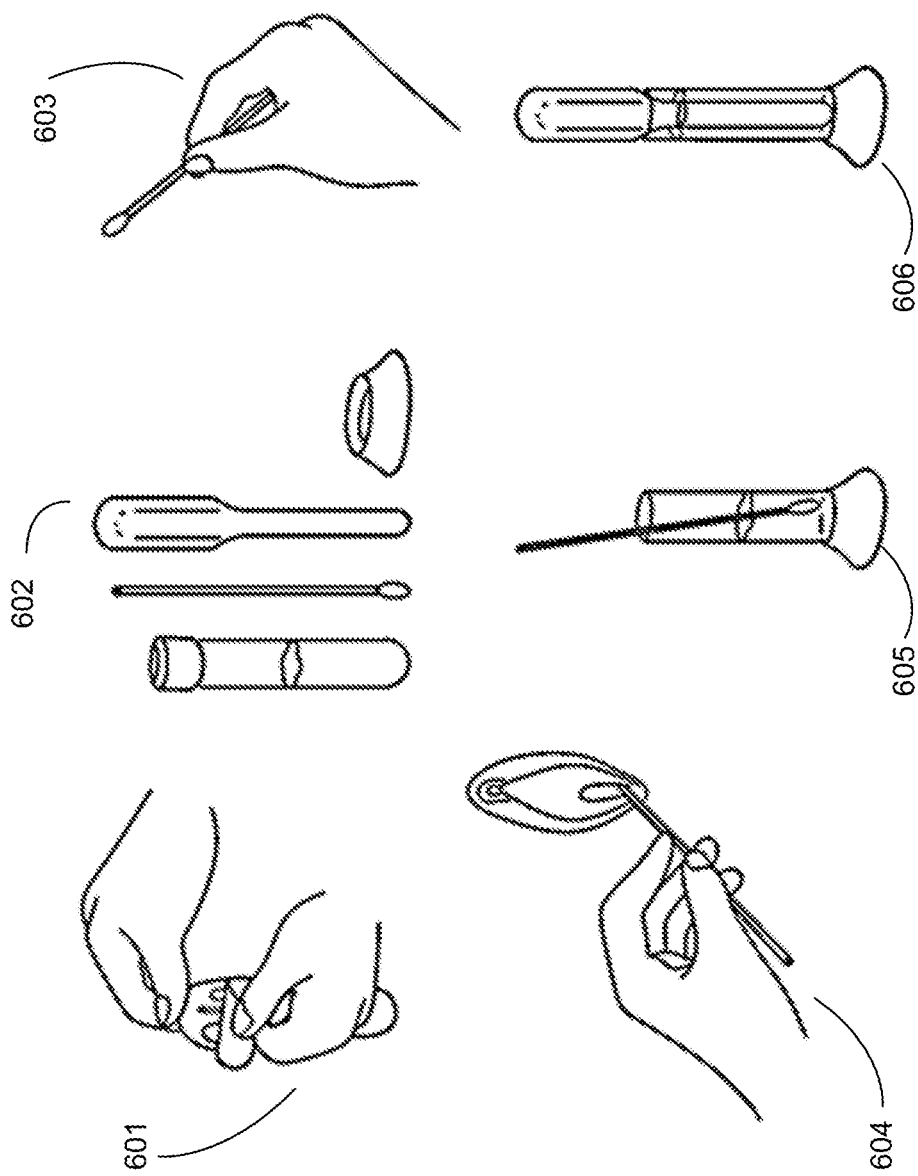
FIG. 6 depicts a schematic of a method for providing and processing a sample, in accordance with one or more embodiments.

FIG. 6 depicts a schematic of a method for providing and processing a sample, in accordance with one or more embodiments. As shown in FIG. 6, an entity (e.g., a subject, an entity associated with the subject) opens 601 packaging of a sampling kit of the system, which contains embodiments 602 of an extraction container, sample collecting tool, signal output device, and retention surface, as described above. The collection tool is operated upon 603 and receives 604 a sample from the subject. The sample collecting tool with the sample is then transmitted 605 into the extraction container to interact with an extraction buffer. Then, the signal output device is received 606 into the extraction container, in order to transmit target material through the signal output device (e.g., as in steps 520-560 described above). In a related embodiment, as described in relation to FIGS. 7C and 7D below, the sample collecting tool can be integrated with the signal output device, such that the user can provide a sample to the sample collecting tool (e.g., by swabbing a collection site of the user's body), and then transmit 605 the sample collection tool, which is coupled to the signal output device, into the extraction container.

Non-limiting examples of a sample can include vaginal fluid, vaginal tissue, vaginal washing, vaginal swab, vaginal discharge, cervical swab, cervical tissue urethral swab, urethral discharge, rectal swab, rectal material, rectal washing, urine, blood, serum, plasma, saliva, tears, skin swab, semen, seminal fluid, sputum, bronchial fluid, bronchial washing, peritoneal fluid, peritoneal washing, pleural fluid, pleural washing, cerebrospinal fluid, eye fluid and/or tissue, fluid and/or tissue from lung, liver, heart, brain, kidney, spleen or muscle and any combination thereof. In some embodiments, the sample is a blood sample. In some embodiments, the sample is a urine sample. In some embodiments, the sample is a vaginal discharge or a penile discharge. In some embodiments, the sample is obtained from contacting an ulcer in genital area.

In some embodiments, the sample can be preabsorbed, e.g., to reduce or minimize cross-reactivity and/or background. As nonlimiting examples, in some embodiments, the biological sample can be preabsorbed with a lysate of bacteria expressing glutathione-S-transferase (GST) and/or a lysate of normal (e.g., non-pathogen infected mammalian cells). In some embodiments, absorption of the sample can be with a lysate of pathogen-infected mammalian cells, to remove and/or block chlamydial antigen-specific antibodies from human samples, which can help confirm the specificity of human antibody binding to the test analyte.

In some embodiments, the biological sample is obtained with a sample collecting tool. In some embodiments, the sample collecting tool includes a swab. In some embodiments, the swab is a vaginal swab or urethral swab. In some embodiments, the swab is an endocervical swab. In some embodiments, the sample collecting tool comprises a fluid collecting container. In some embodiments, the fluid collecting container comprises a tube. In some embodiments, the tube is serum tube or a plasma tube.

In some embodiments, the sample is or is recommended to be collected at a specific time or in a specific period of time. In some embodiments, the sample is or is recommended to be collected in the morning. In some embodiments, the sample is or is recommended to be collected within 1, 2, 3, 4, 5, 6, or more hours before urinating. In some embodiments, the sample is or is recommended to be collected at noon. In some embodiments, the sample is or is recommended to be collected in the evening. In some embodiments, the sample is or is recommended to be collected before the shower. In some embodiments, the sample is or is recommended to be collected before the individual having sex. In some embodiments, the sample is or is recommended to be collected after the individual having sex. In some embodiments, the sample is or is recommended to be collected within 1, 2, 3, 4, 5, 6 or more hours before or after the individual having sex. In some embodiments, the sample is or is recommended to be collected at least 4, 5, 6, 7, 8, 9, 10, 12 days after the individual ovulates.

In some embodiments, the biological sample is stable at room temperature for at least 1, 2, 4, 8, 12, 16, 20, 24 hours after obtained. In some embodiments, the sample is or is recommended to be tested within 1, 2, 3, 4, 5, 6 hours after it is obtained. In some embodiments, the sample is or is recommended to be tested shortly after it is obtained (for example, within an hour).

Figure 7A:
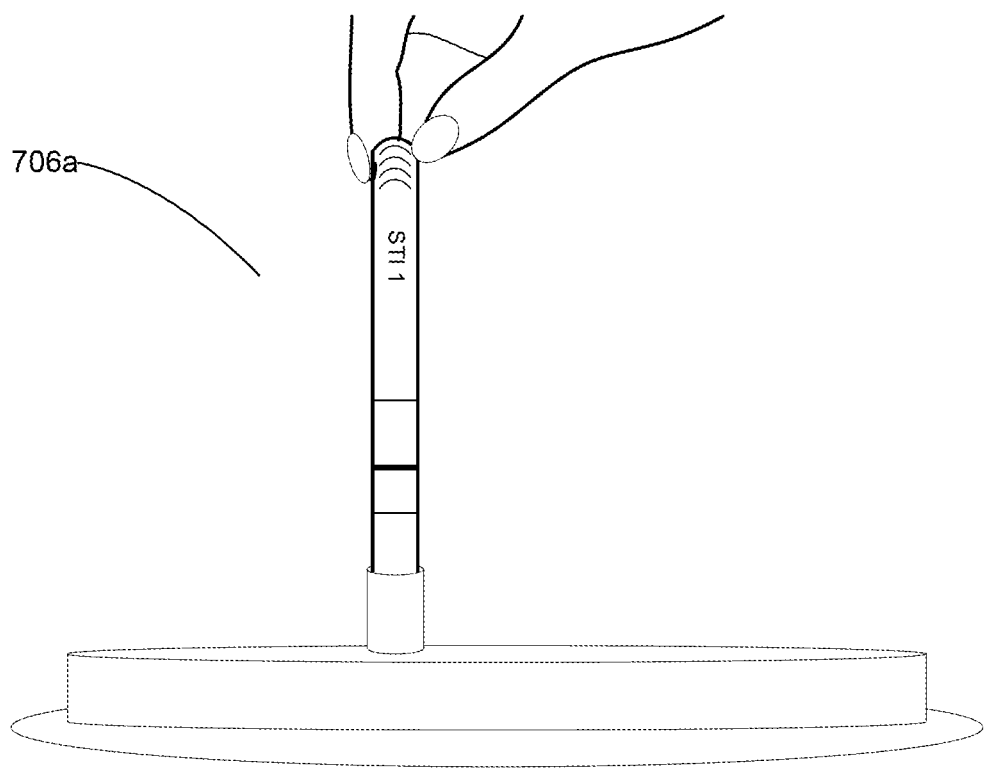
FIG. 7A depicts a phase of usage of system components, in accordance with the methods shown in FIGS. 5 and 6.

FIG. 7A depicts a phase of usage of system components, in accordance with the methods shown in FIGS. 5 and 6. As shown in FIG. 7A, a specific example of the signal output device is received 706a into an extraction container in a manner analogous to that of step 606 described above, in order to transmit target material through the signal output device (e.g., as in steps 520-560 described above). In the example of FIG. 7A, the packaging of the sampling kit provides a retention surface (similar to that of recessed surface 130 described above) to perform the experiment in a resource limiting space.

Figure 7B:
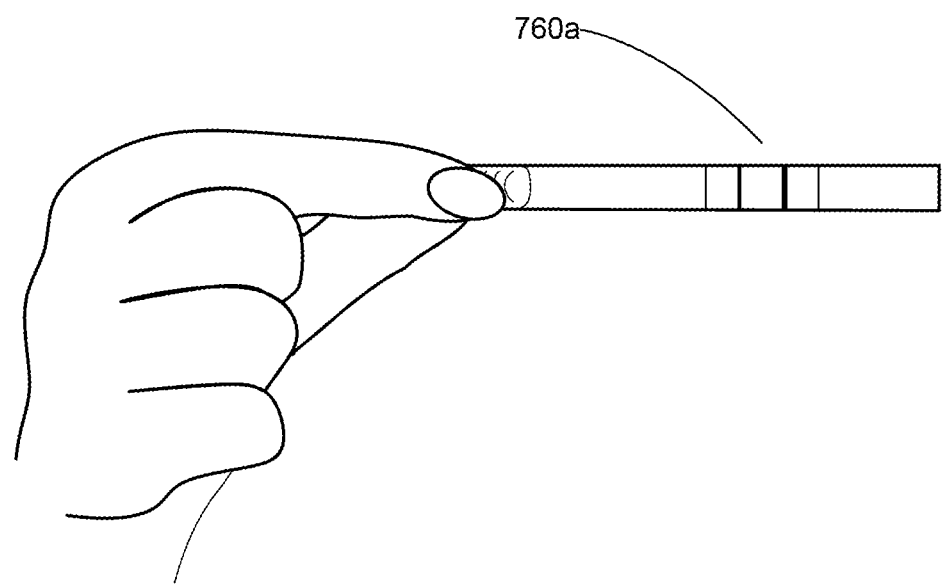
FIG. 7B depicts another phase of usage of system components, in accordance with the method shown in FIGS. 5 and 6.

FIG. 7B depicts another phase of usage of system components, in accordance with the method shown in FIGS. 5 and 6. As shown in FIG. 7B, the specific example of the signal output device provides 760a an output signal indicative of statuses of one or more health conditions in a manner analogous to that of Step 560 above. In a specific example of Step 760a, a result can be read from the signal output within 5-10 minutes of providing a sample.

Figure 7C:
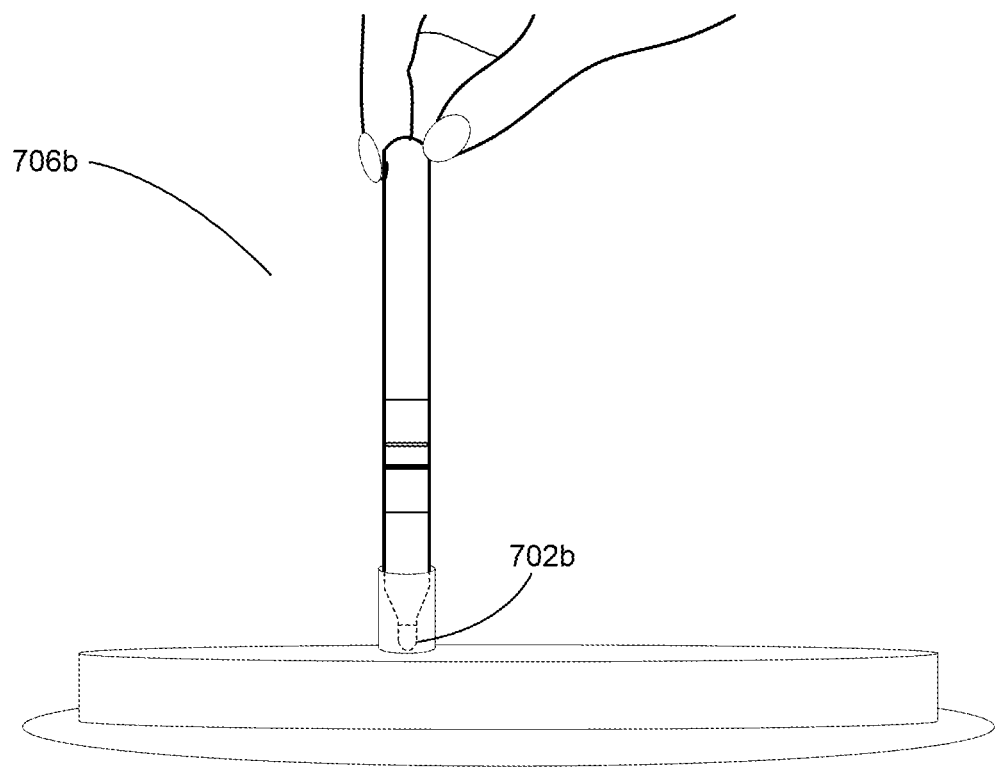
FIG. 7C depicts a phase of usage of an alternative embodiment of system components, in accordance with the methods shown in FIGS. 5 and 6.

FIG. 7C depicts a phase of usage of an alternative embodiment of system components, in accordance with the methods shown in FIGS. 5 and 6. As shown in FIG. 7C, a specific example of the signal output device is received 706b into an extraction container in a manner analogous to that of step 606 described above, in order to transmit target material through the signal output device (e.g., as in steps 520-560 described above). In the example of FIG. 7C, the packaging of the sampling kit provides a retention surface (similar to that of recessed surface 130 described above) to perform the experiment in a resource limiting space. Furthermore, in the example of FIG. 7C, the embodiment of the signal output device includes a sample collecting tool (e.g., swab) 702b integrated with a distal region of the signal output device configured to be inserted into extraction container. As such, the signal output device can include an integrated sample collecting tool described in relation to FIG. 6 above, where, during use, the user can provide a sample with the sample collecting tool end of the signal output device, and transfer the sample collecting tool end of the signal output device into the extraction container for sample processing with the extraction buffer, as described above.

Figure 7D:
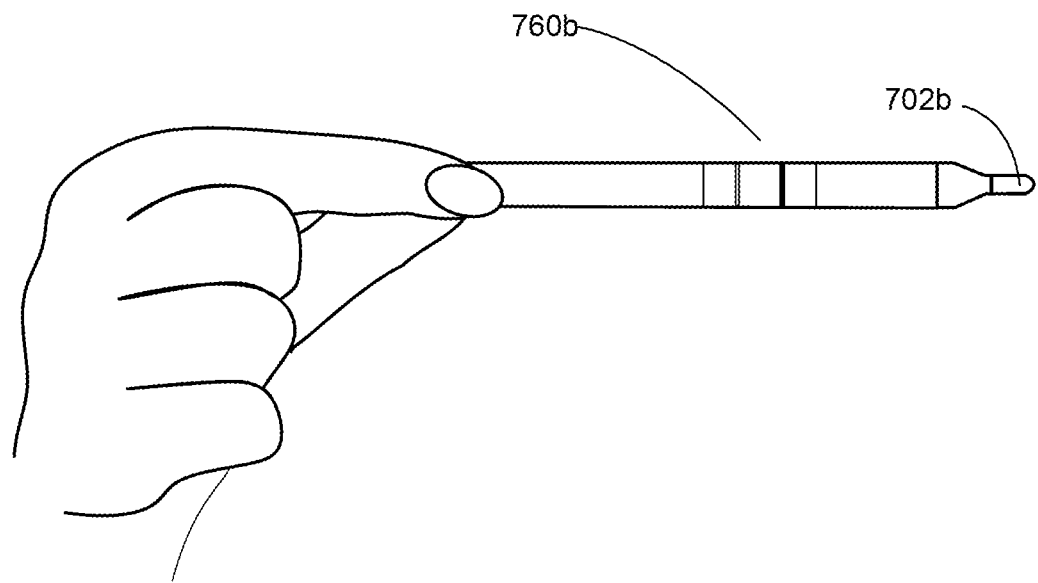
FIG. 7D depicts another phase of usage of an alternative embodiment of system components, in accordance with the method shown in FIGS. 5 and 6.

FIG. 7D depicts another phase of usage of an alternative embodiment of system components, in accordance with the method shown in FIGS. 5 and 6. As shown in FIG. 7B, the specific example of the signal output device provides 760b an output signal indicative of statuses of one or more health conditions in a manner analogous to that of Step 560 above. In a specific example of Step 760b, a result can be read from the signal output within 5-10 minutes of providing a sample.

3. Conclusion

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any of the steps, operations, or processes described herein may be performed or implemented with one or more hardware or software modules, alone or in combination with other devices.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, one implementation of which is set forth in the following claims.

What is claimed is:

1. A system for detection of a sexually transmitted infection, the system comprising:
   a sampling kit comprising:
   a sample collecting tool for collecting a biological sample;
   a container for receiving the sample collecting tool;
   a buffer for being held within the container and for extracting, from the sample on the sample collecting tool, a target material associated with the sexually transmitted infection, the target material comprising a biomarker of a pathogen that causes the sexually transmitted infection, wherein the buffer comprises one or more of: phosphate buffered saline, Tris-buffered saline, 4-(2-hydroxyethyl)-1-piperazineethanesulfonic acid (HEPES) buffered saline, and an extraction substance comprising one or more of: 3-[(3-Cholamidopropyl) dimethylammonio]-1-propanesulfonate, a protein extraction reagent, octyl-thioglucoside, sodium hydroxide, Triton X-100, and octyl glucoside;
   a signal output device, wherein the signal output device comprises:
   a loading zone at a proximal end of the signal output device, the loading zone insertable into the container such that the loading zone receives the target material extracted in the buffer upon insertion of the loading zone into the container,
   a reaction zone in fluid communication with the loading zone such that the received target material is able to pass from the loading zone to the reaction zone, the reaction zone comprising a first reaction substance conjugated to a first label, wherein the first reaction substance is capable of preferentially coupling to a first target of the received target material,
   a testing zone in fluid communication with the reaction zone such that the first reaction substance and the first target material are able to pass from the reaction zone to the testing zone, the testing zone comprising a first testing substance retained at a first region of the testing zone, wherein the first testing substance is capable of preferentially coupling to the first target of the received target material such that the testing zone is able to visually display an indication of the detection of the sexually transmitted infection when the sexually transmitted infection is present; and
   a control zone in fluid communication with the reaction zone such that the first reaction substance and the first target are able to pass through the testing zone to the control zone, the control zone comprising a control substance retained at the control zone, wherein the control substance is not capable of preferentially coupling to the target material;
   wherein the sexual transmitted infection is an infection associated with at least one of: *Chlamydia trachomatis, Neisseria gonorrhoeae,* or *Trichomonas vaginalis*; and
   wherein the first reaction substance and the first testing substance each comprise at least one of the following aptamers: SEQ ID NO 9, SEQ ID NO 10, SEQ ID NO 11, SEQ ID NO 12, SEQ ID NO 13, SEQ ID NO 14, SEQ ID NO 15, or SEQ ID NO 16, or at least one of the following antibodies: M4020310, M2103128, M61872, M61871, M4020311, HM215, HM031, 9L102, B351M, CL13-256.2.1, CT 6703 SP-5, CT 6701 SP-5, CT 6709 SP-5, CL21-335.2.3, 027-10347, M2110186, M1709NG1, M1709NG2, 386/418, M86954, 20-NR08, 15B441, 17E95, M1011403, A19G, Q65G, BDI675, B985M, B986M, 15B485, 12K238, M1011401, M1011404, or 15B483.

2. The system of claim 1, wherein the sexually transmitted infection is an infection associated with *Chlamydia trachomatis*.

3. The system of claim 2, wherein the first reaction substance and the first testing substance each comprise at least one of the following aptamers: SEQ ID NO 12, SEQ ID NO 13, and SEQ ID NO 14, or
at least one of the following antibodies: M4020310, M2103128, M61872, M61871, M4020311, HM215, HM031, 9L102, B351M, CL13-256.2.1, CT 6703 SP-5, CT 6701 SP-5, CT 6709 SP-5, CL21-335.2.3 and 027-10347.

4. The system of claim 1, wherein the sexually transmitted infection is an infection associated with *Neisseria gonorrhoeae*.

5. The system of claim 4, wherein the first reaction substance and the first testing substance each comprise at least one of the following aptamers: SEQ ID NO 15 and SEQ ID NO 16, or
at least one of the following antibodies: M2110186, M1709NG1, M1709NG2, 386/418, M86954, 20-NR08, 15B441, and 17E95.

6. The system of claim 1, wherein the sexually transmitted infection is an infection associated with *Trichomonas vaginalis*.

7. The system of claim 6, wherein the first reaction substance and the first testing substance each comprise at least one of the following aptamers: SEQ ID NO 9, SEQ ID NO 10, and SEQ ID NO 11,
or at least one of the following antibodies: M1011403, A19G, Q65G, BDI675, B985M, B986M, 15B485, 12K238, M1011401, M1011404, and 15B483.

8. The system of claim 1, wherein the loading zone is inserted insertable into the container, and a sample generated upon extraction of an agent by the buffer flows against gravity through the loading zone, the reaction zone, the testing zone, and the control zone.

9. The system of claim 1, wherein the system further comprises a recessed surface of a housing of the sampling kit, the recessed surface capable of retaining the container in a retained orientation.

10. The system of claim 1, wherein the biological sample is a urine or blood sample.

11. The system of claim 1, wherein the biological sample is vaginal discharge or penile discharge.

12. The system of claim 1, wherein the biological sample is obtained from contacting an ulcer in a genital area.

13. The system of claim 1, wherein the sample collecting tool is a vaginal swab, a cervical swab, or an endocervical swab.

14. The system of claim 1, wherein the first label comprises one or more of: gold nanoparticles, colored latex beads, magnetic particles, cellulose nanobeads, carbon nanoparticles, selenium nanoparticles, silver nanoparticles, quantum dots, up converting phosphors, europium, organic fluorophores, textile dyes, enzymes, and liposomes.

15. The system of claim 1, wherein the container contains the buffer for extracting the target material from the biological sample on the sample collecting tool in one or more steps, the buffer comprising of one or more of: phosphate buffered saline, Tris-buffered saline, HEPES buffered saline, and an extraction substance comprising one or more of: hydrochloric acid, 3-[(3-Cholamidopropyl) dimethylammonio]-1-propanesulfonate, a protein extraction reagent, 3-([3-Cholamidopropyl]dimethylammonio)-2-hydroxy-1-propanesulfonate octylthioglucoside, sodium hydroxide, Triton X-100, and octyl glucoside.

16. The system of claim 1, wherein the first target comprises material from a first biomarker of a first sexually transmitted infection.

17. The system of claim 1, wherein the buffer is capable of extracting target material associated with a set of sexually transmitted infections associated with a set of infectious agents.

18. The system of claim 17, wherein the first target comprises material from a first infectious agent associated with a first sexual sexually transmitted infection of the set of sexually transmitted infections.

19. The system of claim 1, wherein the first region of the testing zone is defined in a first pathway and wherein a second region of the testing zone is fluidly isolated from the first pathway.

20. The system of claim 1, wherein the reaction zone of the signal output device further comprises a second reaction substance conjugated to a second label, wherein the second reaction substance is capable of preferentially coupling to a second target of the target material, and wherein the testing zone of the signal output device further comprises a second testing substance retained at a second region of the testing zone, wherein the second testing substance is capable of preferentially coupling to the second target of the target material.

21. The system of claim 1, wherein the signal output device is a test strip, and wherein the sampling kit is a multiplex assay with more than one test line on the test strip to test for more than one sexually transmitted infection.

22. The system of claim 21, wherein the multiplex assay tests for two or more of the following on the test strip: *Chlamydia trachomatis, Neisseria gonorrhoeae, Trichomonas vaginalis*, pregnancy status, and fertility status.

23. The system of claim 21, wherein the multiplex assay tests for three or more of the following on the test strip: *Chlamydia trachomatis, Neisseria gonorrhoeae, Trichomonas vaginalis*, pregnancy status, and fertility status.

24. The system of claim 1, wherein the first reaction substance is a protein or nucleic acid conjugated to the first label and capable of binding a specific region of the target material when it passes through the reaction zone to form a target material/reaction substance complex.

25. The system of claim 24, wherein the testing substance is an immobilized protein or nucleic acid capable of binding the first target of the target material in the target material/reaction substance complex when it passes through the testing zone.

26. The system of claim 25, wherein the reaction substance and the testing substance each comprise:
at least one of the following aptamers: SEQ ID NO 9, SEQ ID NO 10, SEQ ID NO 11, SEQ ID NO 12, SEQ ID NO 13, SEQ ID NO 14, SEQ ID NO 15, and SEQ ID NO 16, or at least one of the following antibodies: M4020310, M2103128, M61872, M61871, M4020311, HM215, HM031, 9L102, B351M, CL13-256.2.1, CT 6703 SP-5, CT 6701 SP-5, CT 6709 SP-5, CL21-335.2.3, 027-10347, M2110186, M1709NG1, M1709NG2, 386/418, M86954, 20-NR08, 15B441, 17E95, M1011403, A19G, Q65G, BDI675, B985M, B986M, 15B485, 12K238, M1011401, M1011404, and 15B483.

27. The system of claim 1, wherein the first reaction substance or the first testing substance comprise at least one of the following aptamers: SEQ ID NO 9, SEQ ID NO 10, SEQ ID NO 11, SEQ ID NO 12, SEQ ID NO 13, SEQ ID NO 14, SEQ ID NO 15, and SEQ ID NO 16.

28. The system of claim 1, wherein the first reaction substance or the first testing substance comprise at least one of at least one of the following antibodies: M4020310, M2103128, M61872, M61871, M4020311, HM215, HM031, 9L102, B351M, CL13-256.2.1, CT 6703 SP-5, CT 6701 SP-5, CT 6709 SP-5, CL21-335.2.3, 027-10347, M2110186, M1709NG1, M1709NG2, 386/418, M86954, 20-NR08, 15B441, 17E95, M1011403, A19G, Q65G, BDI675, B985M, B986M, 15B485, 12K238, M1011401, M1011404, and 15B483.

* * * * *

SEQUENCE LISTING

```
<160> NUMBER OF SEQ ID NOS: 90

<210> SEQ ID NO 1
<211> LENGTH: 243
<212> TYPE: PRT
<213> ORGANISM: Chlamydia trachomatis (strain D/UW-3/Cx)

<400> SEQUENCE: 1

Met Lys Asn Ile Leu Ser Trp Met Leu Met Phe Ala Val Ala Leu Pro
1               5                   10                  15

Ile Val Gly Cys Asp Asn Gly Gly Ser Gln Thr Ser Ala Thr Glu
            20                  25                  30

Lys Ser Met Val Glu Asp Ser Ala Leu Thr Asp Asn Gln Lys Leu Ser
            35                  40                  45

Arg Thr Phe Gly His Leu Leu Ser Arg Gln Leu Ser Arg Thr Glu Asp
    50                  55                  60

Phe Ser Leu Asp Leu Val Glu Val Ile Lys Gly Met Gln Ser Glu Ile
65                  70                  75                  80

Asp Gly Gln Ser Ala Pro Leu Thr Asp Thr Glu Tyr Glu Lys Gln Met
                85                  90                  95

Ala Glu Val Gln Lys Ala Ser Phe Glu Ala Lys Cys Ser Glu Asn Leu
                100                 105                 110

Ala Ser Ala Glu Lys Phe Leu Lys Glu Asn Lys Glu Lys Ala Gly Val
            115                 120                 125

Ile Glu Leu Glu Pro Asn Lys Leu Gln Tyr Arg Val Val Lys Glu Gly
        130                 135                 140

Thr Gly Arg Val Leu Ser Gly Lys Pro Thr Ala Leu Leu His Tyr Thr
145                 150                 155                 160

Gly Ser Phe Ile Asp Gly Lys Val Phe Asp Ser Ser Glu Lys Asn Lys
                165                 170                 175

Glu Pro Ile Leu Leu Pro Leu Thr Lys Val Ile Pro Gly Phe Ser Gln
            180                 185                 190

Gly Met Gln Gly Met Lys Glu Gly Val Arg Val Leu Tyr Ile His
        195                 200                 205

Pro Asp Leu Ala Tyr Gly Thr Ala Gly Gln Leu Pro Pro Asn Ser Leu
    210                 215                 220

Leu Ile Phe Glu Val Lys Leu Ile Glu Ala Asn Asp Asp Asn Val Ser
225                 230                 235                 240

Val Thr Glu

<210> SEQ ID NO 2
<211> LENGTH: 264
<212> TYPE: PRT
```

<213> ORGANISM: Chlamydia trachomatis

<400> SEQUENCE: 2

Met Gly Asn Ser Gly Phe Tyr Leu Tyr Asn Thr Glu Asn Cys Val Phe
1 5 10 15

Ala Asp Asn Ile Lys Val Gly Gln Met Thr Glu Pro Leu Lys Asp Gln
20 25 30

Gln Ile Ile Leu Gly Thr Lys Ser Thr Pro Val Ala Ala Lys Met Thr
35 40 45

Ala Ser Asp Gly Ile Ser Leu Thr Val Ser Asn Asn Ser Ser Thr Asn
50 55 60

Ala Ser Ile Thr Ile Gly Leu Asp Ala Glu Lys Ala Tyr Gln Leu Ile
65 70 75 80

Leu Glu Lys Leu Gly Asn Gln Ile Leu Asp Gly Ile Ala Asp Thr Ile
85 90 95

Val Asp Ser Thr Val Gln Asp Ile Leu Asp Lys Ile Thr Thr Asp Pro
100 105 110

Ser Leu Gly Leu Leu Lys Ala Phe Asn Asn Phe Pro Ile Thr Asn Lys
115 120 125

Ile Gln Cys Asn Gly Leu Phe Thr Pro Ser Asn Ile Glu Thr Leu Leu
130 135 140

Gly Gly Thr Glu Ile Gly Lys Phe Thr Val Thr Pro Lys Ser Ser Gly
145 150 155 160

Ser Met Phe Leu Val Ser Ala Asp Ile Ile Ala Ser Arg Met Glu Gly
165 170 175

Gly Val Val Leu Ala Leu Val Arg Glu Gly Asp Ser Lys Pro Cys Ala
180 185 190

Ile Ser Tyr Gly Tyr Ser Ser Gly Val Pro Asn Leu Cys Ser Leu Arg
195 200 205

Thr Ser Ile Thr Asn Thr Gly Leu Thr Pro Thr Thr Tyr Ser Leu Arg
210 215 220

Val Gly Gly Leu Glu Ser Gly Val Val Trp Val Asn Ala Leu Ser Asn
225 230 235 240

Gly Asn Asp Ile Leu Gly Ile Thr Asn Thr Ser Asn Val Ser Phe Leu
245 250 255

Glu Val Ile Pro Gln Thr Asn Ala
260

<210> SEQ ID NO 3
<211> LENGTH: 88
<212> TYPE: PRT
<213> ORGANISM: Chlamydia trachomatis

<400> SEQUENCE: 3

Met Lys Lys Thr Ala Leu Leu Ala Ala Leu Cys Ser Val Val Ser Leu
1 5 10 15

Ser Ser Cys Cys Arg Ile Val Asp Cys Cys Phe Glu Asp Pro Cys Ala
20 25 30

Pro Ile Gln Cys Ser Pro Cys Glu Ser Lys Lys Lys Asp Val Asp Gly
35 40 45

Gly Cys Asn Ser Cys Asn Gly Tyr Val Pro Ala Cys Lys Pro Cys Gly
50 55 60

Gly Asp Thr His Gln Asp Ala Glu His Gly Pro Gln Ala Arg Glu Ile
65 70 75 80

Pro Val Asp Gly Lys Cys Arg Gln

<210> SEQ ID NO 4
<211> LENGTH: 512
<212> TYPE: PRT
<213> ORGANISM: Chlamydia trachomatis (strain D/UW-3/Cx)

<400> SEQUENCE: 4

```
Met Pro His Asp Asn Asn Glu Met His Arg Asn Thr Ile His Gln Leu
1               5                   10                  15
Phe Thr Gly Leu Asp Lys Ala Tyr Gln Ile Val Lys Gly Phe Tyr Gly
                20                  25                  30
Pro Ala Tyr Ser Ser Ser Lys Asp Phe Phe Lys Gly Arg Gly Tyr
            35                  40                  45
His Ile Leu Ser Arg Ile Glu Leu Ser Asp Pro Phe Glu Arg Ile Gly
        50                  55                  60
Val Tyr Phe Ala Arg Ser Leu Ala Lys Arg Ile His Lys Arg His Ala
65                  70                  75                  80
Asp Gly Val Ile Ser Ser Val Ile Leu Leu Arg Ala Phe Leu Lys Ala
                85                  90                  95
Ser Ile Pro Phe Ile Asp Gln Gly Leu Ser Pro Arg Leu Leu Ala Ser
            100                 105                 110
Ala Leu Ala Ser Gln Lys Glu Ala Val Cys Ala Tyr Leu His Ser His
        115                 120                 125
Ser Phe Leu Leu Lys Asp Ala Ser Lys Val Leu Gly Leu Ile Arg Ser
    130                 135                 140
His Leu Pro Asp Pro Leu Ile Gly Glu Ala Phe Ala Glu Ala Val Ala
145                 150                 155                 160
Tyr Thr Gly His Glu Gly Ala Val Ala Leu Ser Gln Arg Ser Gly Ser
                165                 170                 175
Thr Leu His Leu Val Lys Gly Ile Gln Thr Gln Lys Gly Tyr Arg Val
            180                 185                 190
Pro Ser Phe Phe Pro His Asp Ser Phe His Glu Asn Pro Ile Val Ala
        195                 200                 205
Pro Lys Ile Phe Val Thr Asp Gln Lys Ile His Cys Leu Phe Pro Phe
    210                 215                 220
Leu Pro Leu Leu Lys Lys Phe Ser Glu Glu Gln Thr Pro Leu Ile Ile
225                 230                 235                 240
Phe Cys Lys Glu Ile Ala Pro Asp Pro Leu Ala Thr Cys Ile Ala Asn
                245                 250                 255
Arg Ile Ala Gly Leu Leu Asp Val Leu Val Thr Ile Pro Asp Thr
            260                 265                 270
Thr Leu Leu Glu Asp Ile Ala Leu Leu Thr Gly Thr Thr Val Phe Ser
        275                 280                 285
Ser Pro Pro Phe Ser Asn Lys Pro Pro Ile Glu Leu Pro Leu Leu Gly
    290                 295                 300
Ser Cys Thr Trp Ala Glu Leu Ser Arg Asp His Thr Leu Leu Val Cys
305                 310                 315                 320
Glu Asn Leu Val Pro Glu Val Val Lys Leu Lys Val Arg Gln Leu Asp
                325                 330                 335
His Ala Ile His Asn Ala Glu Asp Glu Thr Ser Arg Lys Leu Leu Lys
            340                 345                 350
Lys Arg Lys His Arg Leu Glu Asn Ser Ile Ala Ile Ile Pro Val Lys
        355                 360                 365
```

```
Gln Asp Thr Thr Pro Leu His Glu Leu Ala Leu Lys Thr Leu Asn Ser
    370                 375                 380

Thr Gln Glu Ser Gly Phe Val Leu Gly Gly Ala Ala Leu Leu Tyr
385                 390                 395                 400

Ala Thr Gln Ser Leu Ser Ser Pro Glu His Ser Gln Glu Gln
                405                 410                 415

Ala Ala Val Gln Ile Leu Gln Thr Ala Cys Arg Thr Leu Leu Glu Gln
                420                 425                 430

Leu Val Asn Ser Val Tyr Met Asp Gly Lys Leu Val Ala Asp Lys Leu
                435                 440                 445

Cys Ser Leu Gly Thr Pro Ser Leu Gly Phe Asn Val Val Ser Gln Gln
450                 455                 460

Ile Glu Asp Met Ile Ser Ala Gly Ile Ile Thr Pro Leu Asn Val Val
465                 470                 475                 480

Leu Asp Ile Phe Ser Cys Ser Leu His Thr Ala Val Asp Leu Leu Leu
                485                 490                 495

Ala Ser Phe Thr Thr Pro Pro Thr Pro Ala Ala Lys Glu Lys Lys Thr
                500                 505                 510

<210> SEQ ID NO 5
<211> LENGTH: 394
<212> TYPE: PRT
<213> ORGANISM: Chlamydia trachomatis serovar L2 (strain 434/Bu/ATCC VR-
      902-B)

<400> SEQUENCE: 5

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
                35                  40                  45

Asp Pro Cys Thr Thr Trp Cys Asp Ala Ile Ser Met Arg Met Gly Tyr
50                  55                  60

Tyr Gly Asp Phe Val Phe Asp Arg Val Leu Gln Thr Asp Val Asn Lys
65                  70                  75                  80

Glu Phe Gln Met Gly Ala Lys Pro Thr Thr Ala Thr Gly Asn Ala Ala
                85                  90                  95

Ala Pro Ser Thr Cys Thr Ala Arg Glu Asn Pro Ala Tyr Gly Arg His
                100                 105                 110

Met Gln Asp Ala Glu Met Phe Thr Asn Ala Ala Tyr Met Ala Leu Asn
                115                 120                 125

Ile Trp Asp Arg Phe Asp Val Phe Cys Thr Leu Gly Ala Thr Ser Gly
130                 135                 140

Tyr Leu Lys Gly Asn Ser Ala Ser Phe Asn Leu Val Gly Leu Phe Gly
145                 150                 155                 160

Asp Asn Glu Asn His Ala Thr Val Ser Asp Ser Lys Leu Val Pro Asn
                165                 170                 175

Met Ser Leu Asp Gln Ser Val Val Glu Leu Tyr Thr Asp Thr Thr Phe
                180                 185                 190

Ala Trp Ser Ala Gly Ala Arg Ala Ala Leu Trp Glu Cys Gly Cys Ala
                195                 200                 205

Thr Leu Gly Ala Ser Phe Gln Tyr Ala Gln Ser Lys Pro Lys Val Glu
210                 215                 220

Glu Leu Asn Val Leu Cys Asn Ala Ala Glu Phe Thr Ile Asn Lys Pro
```

```
                225                 230                 235                 240
    Lys Gly Tyr Val Gly Gln Glu Phe Pro Leu Asp Leu Lys Ala Gly Thr
                    245                 250                 255

Asp Gly Val Thr Gly Thr Lys Asp Ala Ser Ile Asp Tyr His Glu Trp
                260                 265                 270

Gln Ala Ser Leu Ala Leu Ser Tyr Arg Leu Asn Met Phe Thr Pro Tyr
                275                 280                 285

Ile Gly Val Lys Trp Ser Arg Ala Ser Phe Asp Ala Asp Thr Ile Arg
                290                 295                 300

Ile Ala Gln Pro Lys Ser Ala Thr Thr Val Phe Asp Val Thr Leu
    305                 310                 315                 320

Asn Pro Thr Ile Ala Gly Ala Gly Asp Val Lys Ala Ser Ala Glu Gly
                    325                 330                 335

Gln Leu Gly Asp Thr Met Gln Ile Val Ser Leu Gln Leu Asn Lys Met
                    340                 345                 350

Lys Ser Arg Lys Ser Cys Gly Ile Ala Val Gly Thr Thr Ile Val Asp
                    355                 360                 365

Ala Asp Lys Tyr Ala Val Thr Val Glu Thr Arg Leu Ile Asp Glu Arg
                    370                 375                 380

Ala Ala His Val Asn Ala Gln Phe Arg Phe
    385                 390

<210> SEQ ID NO 6
<211> LENGTH: 102
<212> TYPE: PRT
<213> ORGANISM: Chlamydia trachomatis (strain D/UW-3/Cx)

<400> SEQUENCE: 6

Met Ser Asp Gln Ala Thr Thr Leu Lys Ile Lys Pro Leu Gly Asp Arg
1               5                   10                  15

Ile Leu Val Lys Arg Glu Glu Ala Ser Thr Ala Arg Gly Gly Ile
            20                  25                  30

Ile Leu Pro Asp Thr Ala Lys Lys Gln Asp Arg Ala Glu Val Leu
        35                  40                  45

Ala Leu Gly Thr Gly Lys Lys Asp Asp Lys Gly Gln Gln Leu Pro Phe
    50                  55                  60

Glu Val Gln Val Gly Asn Ile Val Leu Ile Asp Lys Tyr Ser Gly Gln
65                  70                  75                  80

Glu Leu Thr Val Glu Gly Glu Tyr Val Ile Val Gln Met Ser Glu
                85                  90                  95

Val Ile Ala Val Leu Gln
            100

<210> SEQ ID NO 7
<211> LENGTH: 102
<212> TYPE: PRT
<213> ORGANISM: Chlamydia trachomatis

<400> SEQUENCE: 7

Met Ser Asp Gln Ala Thr Thr Leu Lys Ile Lys Pro Leu Gly Asp Arg
1               5                   10                  15

Ile Leu Val Lys Arg Glu Glu Ala Ser Thr Ala Arg Gly Gly Ile
            20                  25                  30

Ile Leu Pro Asp Thr Ala Lys Lys Gln Asp Arg Ala Glu Val Leu
        35                  40                  45

Ala Leu Gly Thr Gly Lys Lys Asp Asp Lys Gly Gln Gln Leu Pro Phe
```

```
              50                  55                  60
Glu Val Gln Val Gly Asn Ile Val Leu Ile Asp Lys Tyr Ser Gly Gln
 65                  70                  75                  80

Glu Leu Thr Val Glu Gly Glu Tyr Val Ile Val Gln Met Ser Glu
                 85                  90                  95

Val Ile Ala Val Leu Gln
            100

<210> SEQ ID NO 8
<211> LENGTH: 89
<212> TYPE: PRT
<213> ORGANISM: Chlamydia trachomatis

<400> SEQUENCE: 8

Met Leu Lys Pro Leu Lys Asp Arg Val Val Ile Gln Met Val Glu Gln
  1               5                  10                  15

Glu Glu Lys Thr Ala Gly Gly Leu Phe Leu Pro Thr Ala Ala Gln Glu
                 20                  25                  30

Lys Leu Gln Phe Ala Thr Val Leu Ala Val Ser Glu Phe Thr Glu Glu
             35                  40                  45

Lys Asp Arg Gln Val Gln Val Gly Asp Arg Val Phe Glu Lys Tyr
 50                  55                  60

Thr Gly Thr Glu Val Lys Leu Asp Gly Gln Glu Tyr Ile Ile Val Lys
 65                  70                  75                  80

Glu Gln Asp Ile Ile Ala Ile Val Gln
                 85

<210> SEQ ID NO 9
<211> LENGTH: 58
<212> TYPE: DNA
<213> ORGANISM: Artificial Sequence
<220> FEATURE:
<223> OTHER INFORMATION: DNA-based aptamer

<400> SEQUENCE: 9
atttcacaat atttagtcag ccatgaccgg tgcagtttat gagtattgtg ttcagaga          58

<210> SEQ ID NO 10
<211> LENGTH: 58
<212> TYPE: DNA
<213> ORGANISM: Artificial Sequence
<220> FEATURE:
<223> OTHER INFORMATION: DNA-based aptamer

<400> SEQUENCE: 10
attcactcgt cgggaaacta tgggcgtacg gtgctcggtt tccttctctc tgagtaga           58

<210> SEQ ID NO 11
<211> LENGTH: 58
<212> TYPE: DNA
<213> ORGANISM: Artificial Sequence
<220> FEATURE:
<223> OTHER INFORMATION: DNA-based aptamer

<400> SEQUENCE: 11
attgggggcg ggaggggat ggcggaggtt tgttgtctgt tcggggagct gtgtaaga           58

<210> SEQ ID NO 12
<211> LENGTH: 56
<212> TYPE: DNA
<213> ORGANISM: Artificial Sequence
<220> FEATURE:
```

<223> OTHER INFORMATION: DNA-based aptamer

<400> SEQUENCE: 12 aggggcagg gggttgact ttaccttatg cttaaagggg gtgggctcgg gaagat    56

<210> SEQ ID NO 13
<211> LENGTH: 55
<212> TYPE: DNA
<213> ORGANISM: Artificial Sequence
<220> FEATURE:
<223> OTHER INFORMATION: DNA-based aptamer

<400> SEQUENCE: 13 aggggagaa cgggggggct tgggttgggg atggatgtgg gaggccggtc gagat    55

<210> SEQ ID NO 14
<211> LENGTH: 58
<212> TYPE: DNA
<213> ORGANISM: Artificial Sequence
<220> FEATURE:
<223> OTHER INFORMATION: DNA-based aptamer

<400> SEQUENCE: 14
tggcgcggac gtactggcga attggtgagc ctcgggctgg gtgggggtt agggagat    58

<210> SEQ ID NO 15
<211> LENGTH: 55
<212> TYPE: DNA
<213> ORGANISM: Artificial Sequence
<220> FEATURE:
<223> OTHER INFORMATION: DNA-based aptamer

<400> SEQUENCE: 15
ctcacactat tttttggcat aggtgtcgag ggtggacggg gcggggcggt gagat    55

<210> SEQ ID NO 16
<211> LENGTH: 56
<212> TYPE: DNA
<213> ORGANISM: Artificial Sequence
<220> FEATURE:
<223> OTHER INFORMATION: DNA-based aptamer

<400> SEQUENCE: 16
gagttaagtt tgagtgttgt cgagggtgga cggggtgggg caagctagtg tgagat    56

<210> SEQ ID NO 17
<211> LENGTH: 243
<212> TYPE: PRT
<213> ORGANISM: Chlamydia trachomatis (strain D/UW-3/Cx)

<400> SEQUENCE: 17

Met Lys Asn Ile Leu Ser Trp Met Leu Met Phe Ala Val Ala Leu Pro
1               5                   10                  15

Ile Val Gly Cys Asp Asn Gly Gly Gly Ser Gln Thr Ser Ala Thr Glu
            20                  25                  30

Lys Ser Met Val Glu Asp Ser Ala Leu Thr Asp Asn Gln Lys Leu Ser
        35                  40                  45

Arg Thr Phe Gly His Leu Leu Ser Arg Gln Leu Ser Arg Thr Glu Asp
    50                  55                  60

Phe Ser Leu Asp Leu Val Glu Val Ile Lys Gly Met Gln Ser Glu Ile
65                  70                  75                  80

Asp Gly Gln Ser Ala Pro Leu Thr Asp Thr Glu Tyr Glu Lys Gln Met
                85                  90                  95

```
Ala Glu Val Gln Lys Ala Ser Phe Glu Ala Lys Cys Ser Glu Asn Leu
                100                 105                 110

Ala Ser Ala Glu Lys Phe Leu Lys Glu Asn Lys Glu Lys Ala Gly Val
            115                 120                 125

Ile Glu Leu Glu Pro Asn Lys Leu Gln Tyr Arg Val Val Lys Glu Gly
        130                 135                 140

Thr Gly Arg Val Leu Ser Gly Lys Pro Thr Ala Leu Leu His Tyr Thr
145                 150                 155                 160

Gly Ser Phe Ile Asp Gly Lys Val Phe Asp Ser Ser Glu Lys Asn Lys
                165                 170                 175

Glu Pro Ile Leu Leu Pro Leu Thr Lys Val Ile Pro Gly Phe Ser Gln
        180                 185                 190

Gly Met Gln Gly Met Lys Glu Gly Glu Val Arg Val Leu Tyr Ile His
            195                 200                 205

Pro Asp Leu Ala Tyr Gly Thr Ala Gly Gln Leu Pro Pro Asn Ser Leu
        210                 215                 220

Leu Ile Phe Glu Val Lys Leu Ile Glu Ala Asn Asp Asp Asn Val Ser
225                 230                 235                 240

Val Thr Glu

<210> SEQ ID NO 18
<211> LENGTH: 264
<212> TYPE: PRT
<213> ORGANISM: Chlamydia trachomatis

<400> SEQUENCE: 18

Met Gly Asn Ser Gly Phe Tyr Leu Tyr Asn Thr Glu Asn Cys Val Phe
1               5                   10                  15

Ala Asp Asn Ile Lys Val Gly Gln Met Thr Glu Pro Leu Lys Asp Gln
            20                  25                  30

Gln Ile Ile Leu Gly Thr Lys Ser Thr Pro Val Ala Ala Lys Met Thr
        35                  40                  45

Ala Ser Asp Gly Ile Ser Leu Thr Val Ser Asn Asn Ser Ser Thr Asn
    50                  55                  60

Ala Ser Ile Thr Ile Gly Leu Asp Ala Glu Lys Ala Tyr Gln Leu Ile
65                  70                  75                  80

Leu Glu Lys Leu Gly Asn Gln Ile Leu Asp Gly Ile Ala Asp Thr Ile
                85                  90                  95

Val Asp Ser Thr Val Gln Asp Ile Leu Asp Lys Ile Thr Thr Asp Pro
            100                 105                 110

Ser Leu Gly Leu Leu Lys Ala Phe Asn Asn Phe Pro Ile Thr Asn Lys
        115                 120                 125

Ile Gln Cys Asn Gly Leu Phe Thr Pro Ser Asn Ile Glu Thr Leu Leu
    130                 135                 140

Gly Gly Thr Glu Ile Gly Lys Phe Thr Val Thr Pro Lys Ser Ser Gly
145                 150                 155                 160

Ser Met Phe Leu Val Ser Ala Asp Ile Ile Ala Ser Arg Met Glu Gly
                165                 170                 175

Gly Val Val Leu Ala Leu Val Arg Glu Gly Asp Ser Lys Pro Cys Ala
            180                 185                 190

Ile Ser Tyr Gly Tyr Ser Ser Gly Val Pro Asn Leu Cys Ser Leu Arg
        195                 200                 205

Thr Ser Ile Thr Asn Thr Gly Leu Thr Pro Thr Thr Tyr Ser Leu Arg
    210                 215                 220
```

```
Val Gly Gly Leu Glu Ser Gly Val Val Trp Val Asn Ala Leu Ser Asn
225                 230                 235                 240

Gly Asn Asp Ile Leu Gly Ile Thr Asn Thr Ser Asn Val Ser Phe Leu
            245                 250                 255

Glu Val Ile Pro Gln Thr Asn Ala
            260
```

<210> SEQ ID NO 19
<211> LENGTH: 660
<212> TYPE: PRT
<213> ORGANISM: Chlamydia trachomatis serovar L2 (strain 434/Bu/ATCC VR-902-B)

<400> SEQUENCE: 19

```
Met Ser Glu Lys Arg Lys Ser Asn Lys Ile Ile Gly Ile Asp Leu Gly
1               5                   10                  15

Thr Thr Asn Ser Cys Val Ser Val Met Glu Gly Gly Gln Pro Lys Val
            20                  25                  30

Ile Ala Ser Ser Glu Gly Thr Arg Thr Thr Pro Ser Ile Val Ala Phe
        35                  40                  45

Lys Gly Gly Glu Thr Leu Val Gly Ile Pro Ala Lys Arg Gln Ala Val
    50                  55                  60

Thr Asn Pro Glu Lys Thr Leu Ala Ser Thr Lys Arg Phe Ile Gly Arg
65                  70                  75                  80

Lys Phe Ser Glu Val Glu Ser Glu Ile Lys Thr Val Pro Tyr Lys Val
                85                  90                  95

Ala Pro Asn Ser Lys Gly Asp Ala Val Phe Asp Val Glu Gln Lys Leu
            100                 105                 110

Tyr Thr Pro Glu Glu Ile Gly Ala Gln Ile Leu Met Lys Met Lys Glu
        115                 120                 125

Thr Ala Glu Ala Tyr Leu Gly Glu Thr Val Thr Glu Ala Val Ile Thr
    130                 135                 140

Val Pro Ala Tyr Phe Asn Asp Ser Gln Arg Ala Ser Thr Lys Asp Ala
145                 150                 155                 160

Gly Arg Ile Ala Gly Leu Asp Val Lys Arg Ile Ile Pro Glu Pro Thr
                165                 170                 175

Ala Ala Ala Leu Ala Tyr Gly Ile Asp Lys Glu Gly Asp Lys Lys Ile
            180                 185                 190

Ala Val Phe Asp Leu Gly Gly Gly Thr Phe Asp Ile Ser Ile Leu Glu
        195                 200                 205

Ile Gly Asp Gly Val Phe Glu Val Leu Ser Thr Asn Gly Asp Thr His
    210                 215                 220

Leu Gly Gly Asp Asp Phe Asp Gly Val Ile Ile Asn Trp Met Leu Asp
225                 230                 235                 240

Glu Phe Lys Lys Gln Glu Gly Ile Asp Leu Ser Lys Asp Asn Met Ala
                245                 250                 255

Leu Gln Arg Leu Lys Asp Ala Ala Glu Lys Ala Lys Ile Glu Leu Ser
            260                 265                 270

Gly Val Ser Ser Thr Glu Ile Asn Gln Pro Phe Ile Thr Ile Asp Ala
        275                 280                 285

Asn Gly Pro Lys His Leu Ala Leu Thr Leu Thr Arg Ala Gln Phe Glu
    290                 295                 300

His Leu Ala Ser Ser Leu Ile Glu Arg Thr Lys Gln Pro Cys Ala Gln
305                 310                 315                 320
```

```
Ala Leu Lys Asp Ala Lys Leu Ser Ala Ser Asp Ile Asp Asp Val Leu
                325                 330                 335

Leu Val Gly Gly Met Ser Arg Met Pro Ala Val Gln Ala Val Val Lys
            340                 345                 350

Glu Ile Phe Gly Lys Glu Pro Asn Lys Gly Val Asn Pro Asp Glu Val
        355                 360                 365

Val Ala Ile Gly Ala Ala Ile Gln Gly Gly Val Leu Gly Gly Glu Val
    370                 375                 380

Lys Asp Val Leu Leu Leu Asp Val Ile Pro Leu Ser Leu Gly Ile Glu
385                 390                 395                 400

Thr Leu Gly Gly Val Met Thr Pro Leu Val Glu Arg Asn Thr Thr Ile
                405                 410                 415

Pro Thr Gln Lys Lys Gln Ile Phe Ser Thr Ala Ala Asp Asn Gln Pro
            420                 425                 430

Ala Val Thr Ile Val Val Leu Gln Gly Glu Arg Pro Met Ala Lys Asp
        435                 440                 445

Asn Lys Glu Ile Gly Arg Phe Asp Leu Thr Asp Ile Pro Pro Ala Pro
    450                 455                 460

Arg Gly His Pro Gln Ile Glu Val Thr Phe Asp Ile Asp Ala Asn Gly
465                 470                 475                 480

Ile Leu His Val Ser Ala Lys Asp Ala Ala Ser Gly Arg Glu Gln Lys
                485                 490                 495

Ile Arg Ile Glu Ala Ser Ser Gly Leu Lys Glu Asp Glu Ile Gln Gln
            500                 505                 510

Met Ile Arg Asp Ala Glu Leu His Lys Glu Asp Lys Gln Arg Lys
        515                 520                 525

Glu Ala Ser Asp Val Lys Asn Glu Ala Asp Gly Met Ile Phe Arg Ala
    530                 535                 540

Glu Lys Ala Val Lys Asp Tyr His Asp Lys Ile Pro Ala Glu Leu Val
545                 550                 555                 560

Lys Glu Ile Glu Glu His Ile Glu Lys Val Arg Gln Ala Ile Lys Glu
                565                 570                 575

Asp Ala Ser Thr Thr Ala Ile Lys Ala Ala Ser Asp Glu Leu Ser Thr
            580                 585                 590

Arg Met Gln Lys Ile Gly Glu Ala Met Gln Ala Gln Ser Ala Ser Ala
        595                 600                 605

Ala Ala Ser Ser Ala Ala Asn Ala Gln Gly Gly Pro Asn Ile Asn Ser
    610                 615                 620

Glu Asp Leu Lys Lys His Ser Phe Ser Thr Arg Pro Pro Ala Gly Gly
625                 630                 635                 640

Ser Ala Ser Ser Thr Asp Asn Ile Glu Asp Ala Asp Val Glu Ile Val
                645                 650                 655

Asp Lys Pro Glu
            660

<210> SEQ ID NO 20
<211> LENGTH: 232
<212> TYPE: PRT
<213> ORGANISM: Chlamydia trachomatis serovar L2 (strain 434/Bu/ATCC VR-
      902-B)

<400> SEQUENCE: 20

Met Thr Lys His Gly Lys Arg Ile Arg Gly Ile Gln Glu Thr Tyr Asp
1               5                   10                  15

Leu Ala Lys Ser Tyr Ser Leu Gly Glu Ala Ile Asp Ile Leu Lys Gln
```

```
            20                  25                  30
Cys Pro Thr Val Arg Phe Asp Gln Thr Val Asp Val Ser Val Lys Leu
        35                  40                  45
Gly Ile Asp Pro Arg Lys Ser Asp Gln Gln Ile Arg Gly Ser Val Ser
    50                  55                  60
Leu Pro His Gly Thr Gly Lys Val Leu Arg Ile Leu Val Phe Ala Ala
65                  70                  75                  80
Gly Asp Lys Ala Ala Glu Ala Ile Glu Ala Gly Ala Asp Phe Val Gly
                85                  90                  95
Ser Asp Asp Leu Val Glu Lys Ile Lys Gly Gly Trp Val Asp Phe Asp
            100                 105                 110
Val Ala Val Ala Thr Pro Asp Met Met Arg Glu Val Gly Lys Leu Gly
        115                 120                 125
Lys Val Leu Gly Pro Arg Asn Leu Met Pro Thr Pro Lys Ala Gly Thr
    130                 135                 140
Val Thr Thr Asp Val Val Lys Thr Ile Ala Glu Leu Arg Lys Gly Lys
145                 150                 155                 160
Ile Glu Phe Lys Ala Asp Arg Ala Gly Val Cys Asn Val Gly Val Ala
                165                 170                 175
Lys Leu Ser Phe Asp Ser Ala Gln Ile Lys Glu Asn Val Glu Ala Leu
            180                 185                 190
Cys Ala Ala Leu Val Lys Ala Lys Pro Ala Thr Ala Lys Gly Gln Tyr
        195                 200                 205
Leu Val Asn Phe Thr Ile Ser Ser Thr Met Gly Pro Gly Val Thr Val
    210                 215                 220
Asp Thr Arg Glu Leu Ile Ala Leu
225                 230

<210> SEQ ID NO 21
<211> LENGTH: 1014
<212> TYPE: PRT
<213> ORGANISM: Chlamydia trachomatis serovar A (strain A2497)

<400> SEQUENCE: 21

Met Met Gln Thr Ser Phe His Lys Phe Phe Leu Ser Met Ile Leu Ala
1               5                   10                  15
Tyr Ser Cys Cys Ser Leu Asn Gly Gly Gly Tyr Ala Ala Glu Ile Met
            20                  25                  30
Val Pro Gln Gly Ile Tyr Asp Gly Glu Thr Leu Thr Val Ser Phe Pro
        35                  40                  45
Tyr Thr Val Ile Gly Asp Pro Ser Gly Thr Thr Val Phe Ser Ala Gly
    50                  55                  60
Glu Leu Thr Leu Lys Asn Leu Asp Asn Ser Ile Ala Ala Leu Pro Leu
65                  70                  75                  80
Ser Cys Phe Gly Asn Leu Leu Gly Ser Phe Thr Val Leu Gly Arg Gly
                85                  90                  95
His Ser Leu Thr Phe Glu Asn Ile Arg Thr Ser Thr Asn Gly Ala Ala
            100                 105                 110
Leu Ser Asp Ser Ala Asn Ser Gly Leu Phe Thr Ile Glu Gly Phe Lys
        115                 120                 125
Glu Leu Ser Phe Ser Asn Cys Asn Ser Leu Leu Ala Val Leu Pro Ala
    130                 135                 140
Ala Thr Thr Asn Asn Gly Ser Gln Thr Pro Thr Thr Thr Ser Thr Pro
145                 150                 155                 160
```

-continued

Ser Asn Gly Thr Ile Tyr Ser Lys Thr Asp Leu Leu Leu Asn Asn
                165                 170                 175

Glu Lys Phe Ser Phe Tyr Ser Asn Leu Val Ser Gly Asp Gly Gly Ala
            180                 185                 190

Ile Asp Ala Lys Ser Leu Thr Val Gln Gly Ile Ser Lys Leu Cys Val
        195                 200                 205

Phe Gln Glu Asn Thr Ala Gln Ala Asp Gly Gly Ala Cys Gln Val Val
    210                 215                 220

Thr Ser Phe Ser Ala Met Ala Asn Glu Ala Pro Ile Ala Phe Val Ala
225                 230                 235                 240

Asn Val Ala Gly Val Arg Gly Gly Ile Ala Ala Val Gln Asp Gly
                245                 250                 255

Gln Gln Gly Val Ser Ser Thr Ser Thr Glu Asp Pro Val Val Ser
            260                 265                 270

Phe Ser Arg Asn Thr Ala Val Glu Phe Asp Gly Asn Val Ala Arg Val
        275                 280                 285

Gly Gly Gly Ile Tyr Ser Tyr Gly Asn Val Ala Phe Leu Asn Asn Gly
    290                 295                 300

Lys Thr Leu Phe Leu Asn Asn Val Ala Ser Pro Val Tyr Ile Ala Ala
305                 310                 315                 320

Glu Gln Pro Thr Asn Gly Gln Ala Ser Asn Thr Ser Asp Asn Tyr Gly
                325                 330                 335

Asp Gly Gly Ala Ile Phe Cys Lys Asn Gly Ala Gln Ala Ala Gly Ser
            340                 345                 350

Asn Asn Ser Gly Ser Val Ser Phe Asp Gly Glu Gly Val Val Phe Phe
        355                 360                 365

Ser Ser Asn Val Ala Ala Gly Lys Gly Gly Ala Ile Tyr Ala Lys Lys
    370                 375                 380

Leu Ser Val Ala Asn Cys Gly Pro Val Gln Phe Leu Gly Asn Ile Ala
385                 390                 395                 400

Asn Asp Gly Gly Ala Ile Tyr Leu Gly Glu Ser Gly Glu Leu Ser Leu
                405                 410                 415

Ser Ala Asp Tyr Gly Asp Met Ile Phe Asp Gly Asn Leu Lys Arg Thr
            420                 425                 430

Ala Lys Glu Asn Ala Ala Asp Val Asn Gly Val Thr Val Ser Ser Gln
        435                 440                 445

Ala Ile Ser Met Gly Ser Gly Gly Lys Ile Thr Thr Leu Arg Ala Lys
    450                 455                 460

Ala Gly His Gln Ile Leu Phe Asn Asp Pro Ile Glu Met Ala Asn Gly
465                 470                 475                 480

Asn Asn Gln Pro Ala Gln Ser Ser Glu Pro Leu Lys Ile Asn Asp Gly
                485                 490                 495

Glu Gly Tyr Thr Gly Asp Ile Val Phe Ala Asn Gly Asn Ser Thr Leu
            500                 505                 510

Tyr Gln Asn Val Thr Ile Glu Gln Gly Arg Ile Val Leu Arg Glu Lys
        515                 520                 525

Ala Lys Leu Ser Val Asn Ser Leu Ser Gln Thr Gly Gly Ser Leu Tyr
    530                 535                 540

Met Glu Ala Gly Ser Thr Leu Asp Phe Val Thr Pro Gln Pro Pro Gln
545                 550                 555                 560

Gln Pro Pro Ala Ala Asn Gln Leu Ile Thr Leu Ser Asn Leu His Leu
                565                 570                 575

Ser Leu Ser Ser Leu Leu Ala Asn Asn Ala Val Thr Asn Pro Pro Thr

-continued

```
                580                 585                 590
Asn Pro Pro Ala Gln Asp Ser His Pro Ala Val Ile Gly Ser Thr Thr
            595                 600                 605

Ala Gly Ser Val Thr Ile Ser Gly Pro Ile Phe Phe Glu Asp Leu Asp
            610                 615                 620

Asp Thr Ala Tyr Asp Arg Tyr Asp Trp Leu Gly Ser Asn Gln Lys Ile
625                 630                 635                 640

Asp Val Leu Lys Leu Gln Leu Gly Thr Gln Pro Pro Ala Asn Ala Pro
                645                 650                 655

Ser Asp Leu Thr Leu Gly Asn Glu Met Pro Lys Tyr Gly Tyr Gln Gly
            660                 665                 670

Ser Trp Lys Leu Ala Trp Asp Pro Asn Thr Ala Asn Asn Gly Pro Tyr
            675                 680                 685

Thr Leu Lys Ala Thr Trp Thr Lys Thr Gly Tyr Asn Pro Gly Pro Glu
            690                 695                 700

Arg Val Ala Ser Leu Val Pro Asn Ser Leu Trp Gly Ser Ile Leu Asp
705                 710                 715                 720

Ile Arg Ser Ala His Ser Ala Ile Gln Ala Ser Val Asp Gly Arg Ser
                725                 730                 735

Tyr Cys Arg Gly Leu Trp Val Ser Gly Val Ser Asn Phe Phe Tyr His
            740                 745                 750

Asp Arg Asp Ala Leu Gly Gln Gly Tyr Arg Tyr Ile Ser Gly Gly Tyr
            755                 760                 765

Ser Leu Gly Ala Asn Ser Tyr Phe Gly Ser Ser Met Phe Gly Leu Ala
            770                 775                 780

Phe Thr Glu Val Phe Gly Arg Ser Lys Asp Tyr Val Val Cys Arg Ser
785                 790                 795                 800

Asn His His Ala Cys Ile Gly Ser Val Tyr Leu Ser Thr Lys Gln Ala
                805                 810                 815

Leu Cys Gly Ser Tyr Val Phe Gly Asp Ala Phe Ile Arg Ala Ser Tyr
            820                 825                 830

Gly Phe Gly Asn Gln His Met Lys Thr Ser Tyr Thr Phe Ala Glu Glu
            835                 840                 845

Ser Asp Val Arg Trp Asp Asn Asn Cys Leu Val Gly Glu Ile Gly Val
850                 855                 860

Gly Leu Pro Ile Val Ile Thr Pro Ser Lys Leu Tyr Leu Asn Glu Leu
865                 870                 875                 880

Arg Pro Phe Val Gln Ala Glu Phe Ser Tyr Ala Asp His Glu Ser Phe
                885                 890                 895

Thr Glu Glu Gly Asp Gln Ala Arg Ala Phe Arg Ser Gly His Leu Met
            900                 905                 910

Asn Leu Ser Val Pro Val Gly Val Lys Phe Asp Arg Cys Ser Ser Thr
            915                 920                 925

His Pro Asn Lys Tyr Ser Phe Met Gly Ala Tyr Ile Cys Asp Ala Tyr
            930                 935                 940

Arg Thr Ile Ser Gly Thr Gln Thr Thr Leu Leu Ser His Gln Glu Thr
945                 950                 955                 960

Trp Thr Thr Asp Ala Phe His Leu Ala Arg His Gly Val Ile Val Arg
                965                 970                 975

Gly Ser Met Tyr Ala Ser Leu Thr Ser Asn Ile Glu Val Tyr Gly His
            980                 985                 990

Gly Arg Tyr Glu Tyr Arg Asp Thr  Ser Arg Gly Tyr Gly  Leu Ser Ala
            995                 1000                1005
```

Gly Ser Lys Val Arg Phe
            1010

<210> SEQ ID NO 22
<211> LENGTH: 547
<212> TYPE: PRT
<213> ORGANISM: Chlamydia trachomatis

<400> SEQUENCE: 22

Met Asn Lys Leu Ile Arg Arg Ala Val Thr Ile Phe Ala Val Thr Ser
1               5                   10                  15

Val Ala Ser Leu Phe Ala Ser Gly Val Leu Glu Thr Ser Met Ala Glu
            20                  25                  30

Ser Leu Ser Thr Asn Val Ile Ser Leu Ala Asp Thr Lys Ala Lys Asp
        35                  40                  45

Asn Thr Ser His Lys Ser Lys Ala Arg Lys Asn His Ser Lys Glu
    50                  55                  60

Thr Leu Val Asp Arg Lys Glu Val Ala Pro Val His Glu Ser Lys Ala
65                  70                  75                  80

Thr Gly Pro Lys Gln Asp Ser Cys Phe Gly Arg Met Tyr Thr Val Lys
                85                  90                  95

Val Asn Asp Asp Arg Asn Val Glu Ile Thr Gln Ala Val Pro Glu Tyr
            100                 105                 110

Ala Thr Val Gly Ser Pro Tyr Pro Ile Glu Ile Thr Ala Thr Gly Lys
        115                 120                 125

Arg Asp Cys Val Asp Val Ile Thr Gln Gln Leu Pro Cys Glu Ala
130                 135                 140

Glu Phe Val Arg Ser Asp Pro Ala Thr Thr Pro Thr Ala Asp Gly Lys
145                 150                 155                 160

Leu Val Trp Lys Ile Asp Arg Leu Gly Gln Gly Glu Lys Ser Lys Ile
                165                 170                 175

Thr Val Trp Val Lys Pro Leu Lys Glu Gly Cys Cys Phe Thr Ala Ala
            180                 185                 190

Thr Val Cys Ala Cys Pro Glu Ile Arg Ser Val Thr Lys Cys Gly Gln
        195                 200                 205

Pro Ala Ile Cys Val Lys Gln Glu Gly Pro Glu Asn Ala Cys Leu Arg
210                 215                 220

Cys Pro Val Val Tyr Lys Ile Asn Val Val Asn Gln Gly Thr Ala Ile
225                 230                 235                 240

Ala Arg Asn Val Val Glu Asn Pro Val Pro Asp Gly Tyr Ala His
                245                 250                 255

Ser Ser Gly Gln Arg Val Leu Thr Phe Thr Leu Gly Asp Met Gln Pro
            260                 265                 270

Gly Glu His Arg Thr Ile Thr Val Glu Phe Cys Pro Leu Lys Arg Gly
        275                 280                 285

Arg Ala Thr Asn Ile Ala Thr Val Ser Tyr Cys Gly Gly His Lys Asn
290                 295                 300

Thr Ala Ser Val Thr Thr Val Ile Asn Glu Pro Cys Val Gln Val Ser
305                 310                 315                 320

Ile Ala Gly Ala Asp Trp Ser Tyr Val Cys Lys Pro Val Glu Tyr Val
                325                 330                 335

Ile Ser Val Ser Asn Pro Gly Asp Leu Val Leu Arg Asp Val Val Val
            340                 345                 350

Glu Asp Thr Leu Ser Pro Gly Val Thr Val Leu Glu Ala Ala Gly Ala

```
            355                 360                 365
Gln Ile Ser Cys Asn Lys Val Val Trp Thr Val Lys Glu Leu Asn Pro
370                 375                 380
Gly Glu Ser Leu Gln Tyr Lys Val Leu Val Arg Ala Gln Thr Pro Gly
385                 390                 395                 400
Gln Phe Thr Asn Asn Val Val Lys Ser Cys Ser Asp Cys Gly Thr
            405                 410                 415
Cys Thr Ser Cys Ala Glu Ala Thr Thr Tyr Trp Lys Gly Val Ala Ala
            420                 425                 430
Thr His Met Cys Val Val Asp Thr Cys Asp Pro Val Cys Val Gly Glu
            435                 440                 445
Asn Thr Val Tyr Arg Ile Cys Val Thr Asn Arg Gly Ser Ala Glu Asp
            450                 455                 460
Thr Asn Val Ser Leu Met Leu Lys Phe Ser Lys Glu Leu Gln Pro Val
465                 470                 475                 480
Ser Phe Ser Gly Pro Thr Lys Gly Thr Ile Thr Gly Asn Thr Val Val
            485                 490                 495
Phe Asp Ser Leu Pro Arg Leu Gly Ser Lys Glu Thr Val Glu Phe Ser
            500                 505                 510
Val Thr Leu Lys Ala Val Ser Ala Gly Asp Ala Arg Gly Glu Ala Ile
            515                 520                 525
Leu Ser Ser Asp Thr Leu Thr Val Pro Val Ser Asp Thr Glu Asn Thr
530                 535                 540
His Ile Tyr
545

<210> SEQ ID NO 23
<211> LENGTH: 792
<212> TYPE: PRT
<213> ORGANISM: Neisseria gonorrhoeae

<400> SEQUENCE: 23

Met Lys Leu Lys Gln Ile Ala Ser Ala Leu Met Met Leu Gly Ile Ser
1               5                   10                  15
Pro Leu Ala Phe Ala Asp Phe Thr Ile Gln Asp Ile Arg Val Glu Gly
            20                  25                  30
Leu Gln Arg Thr Glu Pro Ser Thr Val Phe Asn Tyr Leu Pro Val Lys
        35                  40                  45
Val Gly Asp Thr Tyr Asn Asp Thr His Gly Ser Ala Ile Ile Lys Ser
    50                  55                  60
Leu Tyr Ala Thr Gly Phe Phe Asp Asp Val Arg Val Glu Thr Ala Asp
65                  70                  75                  80
Gly Leu Leu Leu Leu Thr Val Ile Val Cys Pro Thr Ile Gly Ser Leu
                85                  90                  95
Asn Ile Thr Gly Ala Lys Met Leu Gln Asn Asp Ala Ile Lys Lys Asn
            100                 105                 110
Leu Glu Ser Phe Gly Leu Ala Gln Ser Gln Tyr Phe Asn Gln Ala Thr
        115                 120                 125
Leu Asn Gln Ala Val Ala Gly Leu Lys Glu Glu Tyr Leu Gly Arg Gly
    130                 135                 140
Lys Leu Asn Ile Gln Ile Thr Pro Lys Val Thr Lys Leu Ala Arg Asn
145                 150                 155                 160
Arg Val Asp Ile Asp Ile Thr Ile Asp Glu Gly Lys Ser Ala Lys Ile
                165                 170                 175
```

-continued

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asp Arg Phe Asp Arg Gln Lys Phe Ala Gln Asp Met Glu Lys
210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Arg Gln Thr Ile Lys
            245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
        290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Gly Thr Lys Thr Val Asp
            325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
            355                 360                 365

Leu Arg Gln Met Glu Ser Ala Pro Tyr Asp Thr Ser Lys Leu Gln Arg
370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
            405                 410                 415

Ser Leu Thr Glu Arg Ser Thr Gly Ser Leu Asp Leu Ser Ala Gly Trp
        420                 425                 430

Val Gln Asp Thr Gly Leu Val Met Ser Ala Gly Val Ser Gln Asp Asn
            435                 440                 445

Leu Phe Gly Thr Gly Lys Ser Ala Ala Leu Arg Ala Ser Arg Ser Lys
450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Ile Tyr Gly Lys Ala Phe Asp Pro
            485                 490                 495

Arg Lys Ala Ser Thr Ser Val Lys Gln Tyr Lys Thr Thr Ala Gly
            500                 505                 510

Gly Gly Val Arg Met Gly Ile Pro Val Thr Glu Tyr Asp Arg Val Asn
        515                 520                 525

Phe Gly Leu Ala Ala Glu His Leu Thr Val Asn Thr Tyr Asn Lys Ala
        530                 535                 540

Pro Lys Arg Tyr Ala Asp Phe Ile Lys Gln Tyr Gly Lys Thr Asp Gly
545                 550                 555                 560

Ala Asp Gly Ser Phe Lys Gly Leu Leu Tyr Lys Gly Thr Val Gly Trp
            565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr

```
                595                 600                 605
Tyr Ser Ala Thr His Asn Gln Thr Trp Phe Phe Pro Leu Ser Lys Thr
610                     615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Arg Thr Tyr Thr Ala Ala Glu Asn Gly Asn Asn Lys Ser Val Tyr Ser
                725                 730                 735

Glu Asn Ala His Lys Ser Thr Phe Thr Asn Glu Leu Arg Tyr Ser Ala
            740                 745                 750

Gly Gly Ala Val Thr Trp Leu Ser Pro Leu Gly Pro Met Lys Phe Ile
        755                 760                 765

Tyr Ala Tyr Pro Leu Lys Lys Pro Glu Asp Glu Ile Gln Arg Phe
770                 775                 780

Gln Phe Gln Leu Gly Thr Thr Phe
785                 790

<210> SEQ ID NO 24
<211> LENGTH: 792
<212> TYPE: PRT
<213> ORGANISM: Neisseria gonorrhoeae

<400> SEQUENCE: 24

Met Lys Leu Lys Gln Ile Ala Ser Ala Leu Met Met Leu Gly Ile Ser
1               5                   10                  15

Pro Leu Ala Phe Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175
```

-continued

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asp Arg Phe Asp Arg Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Arg Gln Thr Ile Lys
            245                 250                 255

Ile Thr Val His Glu Gly Gly Arg Phe Arg Trp Gly Lys Val Ser Ile
        260                 265                 270

Glu Gly Asp Thr Asn Glu Val Pro Lys Ala Glu Leu Glu Lys Leu Leu
    275                 280                 285

Thr Met Lys Pro Gly Lys Trp Tyr Glu Arg Gln Gln Met Thr Ala Val
290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Gly Thr Lys Thr Val Asp
            325                 330                 335

Phe Val Leu His Ile Glu Pro Gly Arg Lys Ile Tyr Val Asn Glu Ile
        340                 345                 350

His Ile Thr Gly Asn Asn Lys Thr Arg Asp Glu Val Val Arg Arg Glu
    355                 360                 365

Leu Arg Gln Met Glu Ser Ala Pro Tyr Asp Thr Ser Lys Leu Gln Arg
370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
            405                 410                 415

Ser Leu Thr Glu Arg Ser Thr Gly Ser Leu Asp Leu Ser Ala Gly Trp
        420                 425                 430

Val Gln Asp Thr Gly Leu Val Met Ser Ala Gly Val Ser Gln Asp Asn
    435                 440                 445

Leu Phe Gly Thr Gly Lys Ser Ala Ala Leu Arg Ala Ser Arg Ser Lys
450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Ile Tyr Gly Lys Ala Phe Asp Pro
            485                 490                 495

Arg Lys Ala Ser Thr Ser Val Lys Gln Tyr Lys Thr Thr Ala Gly
        500                 505                 510

Gly Gly Val Arg Met Gly Ile Pro Val Thr Glu Tyr Asp Arg Val Asn
    515                 520                 525

Phe Gly Leu Ala Ala Glu His Leu Thr Val Asn Thr Tyr Asn Lys Ala
530                 535                 540

Pro Lys Arg Tyr Ala Asp Phe Ile Lys Gln Tyr Gly Lys Thr Asp Gly
545                 550                 555                 560

Ala Asp Gly Ser Phe Lys Gly Leu Leu Tyr Lys Gly Thr Val Gly Trp
            565                 570                 575

Gly Arg Asn Lys Thr Asp Ser Ala Leu Trp Pro Thr Arg Gly Tyr Leu
        580                 585                 590

Thr Gly Val Asn Ala Glu Ile Ala Leu Pro Gly Ser Lys Leu Gln Tyr

```
                595                 600                 605
Tyr Ser Ala Thr His Asn Gln Thr Trp Phe Phe Pro Leu Ser Lys Thr
            610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                            645                 650                 655

Gly Ser Val Arg Gly Tyr Glu Ser Gly Thr Leu Gly Pro Lys Val Tyr
                660                 665                 670

Asp Glu Tyr Gly Glu Lys Ile Ser Tyr Gly Gly Asn Lys Lys Ala Asn
                675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Arg Thr Tyr Thr Ala Ala Glu Asn Gly Asn Asn Lys Ser Val Tyr Ser
                            725                 730                 735

Glu Asn Ala His Lys Ser Thr Phe Thr Asn Glu Leu Arg Tyr Ser Ala
                740                 745                 750

Gly Gly Ala Val Thr Trp Leu Ser Pro Leu Gly Pro Met Lys Phe Ser
                755                 760                 765

Tyr Ala Tyr Pro Leu Lys Lys Lys Pro Glu Asp Glu Ile Gln Arg Phe
770                 775                 780

Gln Phe Gln Leu Gly Thr Thr Phe
785                 790

<210> SEQ ID NO 25
<211> LENGTH: 326
<212> TYPE: PRT
<213> ORGANISM: Neisseria gonorrhoeae

<400> SEQUENCE: 25

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Ala His His Gly Ala Gln Ala Asp Arg Val Lys
        35                  40                  45

Thr Ala Thr Glu Ile Ala Asp Leu Gly Ser Lys Ile Gly Phe Lys Gly
    50                  55                  60

Gln Glu Asp Leu Gly Asn Gly Leu Lys Ala Ile Trp Gln Leu Glu Gln
65                  70                  75                  80

Lys Ala Tyr Val Ser Gly Thr Asp Thr Gly Trp Gly Asn Arg Gln Ser
                85                  90                  95

Phe Ile Gly Leu Lys Gly Gly Phe Gly Lys Val Arg Val Gly Arg Leu
            100                 105                 110

Asn Ser Val Leu Lys Asp Thr Gly Gly Phe Asn Pro Trp Glu Gly Lys
        115                 120                 125

Ser Tyr Tyr Leu Gly Leu Ser Asn Ile Ala Gln Pro Glu Glu Arg His
    130                 135                 140

Val Ser Val Arg Tyr Asp Ser Pro Glu Phe Ala Gly Phe Arg Ala Val
145                 150                 155                 160

Gln Tyr Val Pro Asn Asp Asn Ser Gly Lys Asn His Ser Glu Ser Tyr
                165                 170                 175
```

```
His Ala Gly Phe Asn Tyr Lys Asn Ser Gly Phe Phe Val Gln Tyr Ala
                180                 185                 190
Gly Phe Tyr Lys Arg His Ser Tyr Thr Thr Glu Lys His Gln Val His
            195                 200                 205
Arg Leu Val Gly Gly Tyr Asp His Asp Ala Leu Tyr Ala Ser Val Ala
        210                 215                 220
Val Gln Gln Gln Asp Ala Lys Leu Thr Trp Arg Asn Asp Asn Ser His
225                 230                 235                 240
Asn Ser Gln Thr Glu Val Ala Thr Ala Tyr Arg Phe Gly Asn
                245                 250                 255
Val Thr Pro Arg Val Ser Tyr Ala His Gly Phe Lys Gly Ser Val Tyr
            260                 265                 270
Asp Ala Asp Asn Asp Asn Thr Tyr Asp Gln Val Val Gly Ala Glu
        275                 280                 285
Tyr Asp Phe Ser Lys Arg Thr Ser Ala Leu Val Ser Ala Gly Trp Leu
    290                 295                 300
Gln Arg Gly Lys Gly Thr Glu Lys Phe Val Ala Thr Val Gly Gly Val
305                 310                 315                 320
Gly Leu Arg His Lys Phe
                325

<210> SEQ ID NO 26
<211> LENGTH: 392
<212> TYPE: PRT
<213> ORGANISM: Neisseria gonorrhoeae

<400> SEQUENCE: 26

Met Lys Arg Gln Ala Leu Ala Ala Met Ile Ala Ser Leu Phe Ala Leu
1               5                   10                  15
Ala Ala Cys Gly Gly Glu Gln Ala Gln Ala Pro Ala Glu Thr Pro
            20                  25                  30
Ala Ala Ser Ala Glu Ala Ala Ser Ser Ala Ala Gln Ala Thr Ala Glu
        35                  40                  45
Thr Pro Ala Gly Glu Leu Pro Val Ile Asp Ala Val Thr Thr His Ala
    50                  55                  60
Pro Glu Val Pro Pro Ala Ile Asp Arg Asp Tyr Pro Ala Lys Val Arg
65                  70                  75                  80
Val Lys Met Glu Thr Val Glu Lys Thr Met Lys Met Asp Asp Gly Val
                85                  90                  95
Glu Tyr Arg Tyr Trp Thr Phe Asp Gly Asp Val Pro Gly Arg Met Ile
            100                 105                 110
Arg Val Arg Glu Gly Asp Thr Val Glu Val Glu Phe Ser Asn Asn Pro
        115                 120                 125
Ser Ser Thr Val Pro His Asn Val Asp Phe His Ala Thr Gly Gln
    130                 135                 140
Gly Gly Gly Ala Ala Thr Phe Thr Ala Pro Gly Arg Thr Ser Thr
145                 150                 155                 160
Phe Ser Phe Lys Ala Leu Gln Pro Gly Leu Tyr Ile Tyr His Cys Ala
                165                 170                 175
Val Ala Pro Val Gly Met His Ile Ala Asn Gly Met Tyr Gly Leu Ile
            180                 185                 190
Leu Val Glu Pro Lys Glu Gly Leu Pro Lys Val Asp Lys Glu Phe Tyr
        195                 200                 205
Ile Val Gln Gly Asp Phe Tyr Thr Lys Gly Lys Lys Gly Ala Gln Gly
    210                 215                 220
```

-continued

```
Leu Gln Pro Phe Asp Met Asp Lys Ala Val Ala Glu Gln Pro Glu Tyr
225                 230                 235                 240

Val Val Phe Asn Gly His Val Gly Ser Ile Ala Gly Asp Asn Ala Leu
            245                 250                 255

Lys Ala Lys Ala Gly Glu Thr Val Arg Met Tyr Val Gly Asn Gly Gly
        260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
            340                 345                 350

Ile Met Thr Gln Lys Leu Ser Asp Thr Ala Tyr Ala Gly Ser Gly Ala
        355                 360                 365

Ala Ser Ala Pro Ala Ala Ser Ala Pro Ala Ala Ser Ala Pro Ala Ala
    370                 375                 380

Ser Ala Ser Glu Lys Ser Val Tyr
385                 390

<210> SEQ ID NO 27
<211> LENGTH: 467
<212> TYPE: PRT
<213> ORGANISM: Neisseria gonorrhoeae

<400> SEQUENCE: 27

Met Asn Thr Thr Leu Lys Thr Thr Leu Thr Ser Val Ala Ala Ala Phe
1               5                   10                  15

Ala Leu Ser Ala Cys Thr Met Ile Pro Gln Tyr Glu Gln Pro Lys Val
            20                  25                  30

Glu Val Ala Glu Thr Phe Gln Asn Asp Thr Ser Val Ser Ser Ile Arg
        35                  40                  45

Ala Val Asp Leu Gly Trp His Asp Tyr Phe Ala Asp Pro Arg Leu Gln
    50                  55                  60

Lys Leu Ile Asp Ile Ala Leu Glu Arg Asn Thr Ser Leu Arg Thr Ala
65                  70                  75                  80

Val Leu Asn Ser Glu Ile Tyr Arg Lys Gln Tyr Met Ile Glu Arg Asn
                85                  90                  95

Asn Leu Leu Pro Thr Leu Ala Ala Asn Ala Asn Gly Ser Arg Gln Gly
            100                 105                 110

Ser Leu Ser Gly Gly Asn Val Ser Ser Ser Tyr Asn Val Gly Leu Gly
        115                 120                 125

Ala Ala Ser Tyr Glu Leu Asp Leu Phe Gly Arg Val Arg Ser Ser Ser
    130                 135                 140

Glu Ala Ala Leu Gln Gly Tyr Phe Ala Ser Val Ala Asn Arg Asp Ala
145                 150                 155                 160

Ala His Leu Ser Leu Ile Ala Thr Val Ala Lys Ala Tyr Phe Asn Glu
                165                 170                 175

Arg Tyr Ala Glu Glu Ala Met Ser Leu Ala Gln Arg Val Leu Lys Thr
            180                 185                 190

Arg Glu Glu Thr Tyr Asn Ala Val Arg Ile Ala Val Gln Gly Arg Arg
```

```
                195                 200                 205
Asp Phe Arg Arg Pro Ala Pro Ala Glu Ala Leu Ile Glu Ser Ala
    210                 215                 220

Lys Ala Asp Tyr Ala His Ala Arg Ser Arg Glu Gln Ala Arg Asn
225                 230                 235                 240

Ala Leu Ala Thr Leu Ile Asn Arg Pro Ile Pro Glu Asp Leu Pro Ala
            245                 250                 255

Gly Leu Pro Leu Asp Lys Gln Phe Phe Val Glu Lys Leu Pro Ala Gly
        260                 265                 270

Leu Ser Ser Glu Val Leu Leu Asp Arg Pro Asp Ile Arg Ala Ala Glu
    275                 280                 285

His Ala Leu Lys Gln Ala Asn Ala Asn Ile Gly Ala Ala Arg Ala Ala
290                 295                 300

Phe Phe Pro Ser Ile Arg Leu Thr Gly Ser Val Gly Thr Gly Ser Val
305                 310                 315                 320

Glu Leu Gly Gly Leu Phe Lys Ser Gly Thr Gly Val Trp Ala Phe Ala
            325                 330                 335

Pro Ser Ile Thr Leu Pro Ile Phe Thr Trp Gly Thr Asn Lys Ala Asn
            340                 345                 350

Leu Asp Val Ala Lys Leu Arg Gln Gln Ala Gln Ile Val Ala Tyr Glu
        355                 360                 365

Ser Ala Val Gln Ser Ala Phe Gln Asp Val Ala Asn Ala Leu Ala Ala
    370                 375                 380

Arg Glu Gln Leu Asp Lys Ala Tyr Asp Ala Leu Ser Lys Gln Ser Arg
385                 390                 395                 400

Ala Ser Lys Glu Ala Leu Arg Leu Val Gly Leu Arg Tyr Lys His Gly
            405                 410                 415

Val Ser Gly Ala Leu Asp Leu Leu Asp Ala Glu Arg Ser Ser Tyr Ser
            420                 425                 430

Ala Glu Gly Ala Ala Leu Ser Ala Gln Leu Thr Arg Ala Glu Asn Leu
        435                 440                 445

Ala Asp Leu Tyr Lys Ala Leu Gly Gly Gly Leu Lys Arg Asp Thr Gln
    450                 455                 460

Thr Gly Lys
465

<210> SEQ ID NO 28
<211> LENGTH: 594
<212> TYPE: PRT
<213> ORGANISM: Neisseria gonorrhoeae (strain ATCC 700825 / FA 1090)

<400> SEQUENCE: 28

Met Ala Leu Val Glu Leu Lys Val Pro Asp Ile Gly Gly His Glu Asn
1               5                   10                  15

Val Asp Ile Ile Ala Val Glu Val Asn Val Gly Asp Thr Ile Ala Val
            20                  25                  30

Asp Asp Thr Leu Ile Thr Leu Glu Thr Asp Lys Ala Thr Met Asp Val
        35                  40                  45

Pro Ala Glu Val Ala Gly Val Ile Lys Glu Val Lys Val Lys Val Gly
    50                  55                  60

Asp Lys Ile Ser Glu Gly Gly Leu Ile Val Val Val Glu Ala Glu Gly
65              70                  75                  80

Ala Ala Ala Ala Pro Lys Ala Glu Ala Ala Ala Pro Ala Gln Glu
            85                  90                  95
```

```
Ala Pro Lys Ala Ala Pro Ala Pro Gln Ala Ala Gln Phe Gly Gly
            100                 105                 110

Ala Ala Asp Ala Glu Tyr Asp Val Val Leu Gly Gly Gly Pro Gly
            115                 120                 125

Gly Tyr Ser Ala Ala Phe Ala Ala Asp Glu Gly Leu Lys Val Ala
            130                 135                 140

Ile Val Glu Arg Tyr Lys Thr Leu Gly Gly Val Cys Leu Asn Val Gly
145                 150                 155                 160

Cys Ile Pro Ser Lys Ala Leu Leu His Asn Ala Ala Val Ile Asp Glu
                165                 170                 175

Val Arg His Leu Ala Ala Asn Gly Ile Lys Tyr Pro Lys Pro Glu Leu
            180                 185                 190

Asp Ile Asp Met Leu Arg Ala Tyr Lys Asp Gly Val Val Ser Arg Leu
            195                 200                 205

Thr Gly Gly Leu Ala Gly Met Ala Lys Ser Arg Lys Val Asp Val Ile
            210                 215                 220

Gln Gly Asp Gly Gln Phe Leu Asp Pro His His Leu Glu Val Ser Leu
225                 230                 235                 240

Thr Ala Gly Asp Ala Tyr Glu Gln Ala Ala Pro Thr Gly Glu Lys Lys
                245                 250                 255

Ile Val Ala Phe Lys Asn Cys Ile Ile Ala Ala Gly Ser Arg Val Thr
                260                 265                 270

Lys Leu Pro Phe Ile Pro Glu Asp Pro Arg Ile Ile Asp Ser Ser Gly
            275                 280                 285

Ala Leu Ala Leu Lys Glu Val Pro Gly Lys Leu Leu Ile Ile Gly Gly
            290                 295                 300

Gly Ile Ile Gly Leu Glu Met Gly Thr Val Tyr Ser Thr Leu Gly Ser
305                 310                 315                 320

Arg Leu Asp Val Val Glu Met Met Asp Gly Leu Met Gln Gly Ala Asp
                325                 330                 335

Arg Asp Leu Val Lys Val Trp Gln Lys Gln Asn Glu Tyr Arg Phe Asp
            340                 345                 350

Asn Ile Met Val Asn Thr Lys Thr Val Ala Val Glu Pro Lys Glu Asp
            355                 360                 365

Gly Val Tyr Val Thr Phe Glu Gly Ala Asn Ala Pro Lys Glu Pro Gln
            370                 375                 380

Arg Tyr Asp Ala Val Leu Val Ala Ala Gly Arg Ala Pro Asn Gly Lys
385                 390                 395                 400

Leu Ile Ser Ala Glu Lys Ala Gly Val Ala Val Thr Asp Arg Gly Phe
                405                 410                 415

Ile Glu Val Asp Lys Gln Met Arg Thr Asn Val Pro His Ile Tyr Ala
                420                 425                 430

Ile Gly Asp Ile Val Gly Gln Pro Met Leu Ala His Lys Ala Val His
            435                 440                 445

Glu Gly His Val Ala Ala Glu Asn Cys Ala Gly His Lys Ala Tyr Phe
            450                 455                 460

Asp Ala Arg Val Ile Pro Gly Val Ala Tyr Thr Ser Pro Glu Val Ala
465                 470                 475                 480

Trp Val Gly Glu Thr Glu Leu Ser Ala Lys Ala Ser Gly Arg Lys Ile
                485                 490                 495

Thr Lys Ala Asn Phe Pro Trp Ala Ala Ser Gly Arg Ala Ile Ala Asn
                500                 505                 510

Gly Cys Asp Asn Gly Phe Thr Lys Leu Ile Phe Asp Ala Glu Thr Gly
```

```
                515                 520                 525
Arg Ile Ile Gly Gly Gly Ile Val Gly Pro Asn Gly Gly Asp Met Ile
        530                 535                 540
Gly Glu Val Cys Leu Ala Ile Glu Met Gly Cys Asp Ala Ala Asp Ile
545                 550                 555                 560
Gly Lys Thr Ile His Pro His Pro Thr Leu Gly Glu Ser Ile Gly Met
            565                 570                 575
Ala Ala Glu Val Ala Leu Gly Val Cys Thr Asp Leu Pro Pro Gln Lys
                580                 585                 590
Lys Lys

<210> SEQ ID NO 29
<211> LENGTH: 236
<212> TYPE: PRT
<213> ORGANISM: Neisseria gonorrhoeae (strain NCCP11945)

<400> SEQUENCE: 29

Met Thr Lys Gln Leu Lys Leu Ser Ala Leu Phe Val Ala Leu Leu Ala
1               5                   10                  15
Ser Gly Thr Ala Val Ala Gly Glu Ala Ser Val Gln Gly Tyr Thr Val
            20                  25                  30
Ser Gly Gln Ser Asn Glu Ile Val Arg Asn Asn Tyr Gly Glu Cys Trp
        35                  40                  45
Lys Asn Ala Tyr Phe Asp Lys Ala Ser Gln Gly Arg Val Glu Cys Gly
    50                  55                  60
Asp Ala Val Ala Val Pro Glu Pro Glu Pro Ala Pro Val Ala Val Val
65                  70                  75                  80
Glu Gln Ala Pro Gln Tyr Val Asp Glu Thr Ile Ser Leu Ser Ala Lys
                85                  90                  95
Thr Leu Phe Gly Phe Asp Lys Asp Ser Leu Arg Ala Glu Ala Gln Asp
            100                 105                 110
Asn Leu Lys Val Leu Ala Gln Arg Leu Ser Arg Thr Asn Val Gln Ser
        115                 120                 125
Val Arg Val Glu Gly His Thr Asp Phe Met Gly Ser Glu Lys Tyr Asn
    130                 135                 140
Gln Ala Leu Ser Glu Arg Arg Ala Tyr Val Val Ala Asn Asn Leu Val
145                 150                 155                 160
Ser Asn Gly Val Pro Ala Ser Arg Ile Ser Ala Val Gly Leu Gly Glu
                165                 170                 175
Ser Gln Ala Gln Met Thr Gln Val Cys Gln Ala Glu Val Ala Lys Leu
            180                 185                 190
Gly Ala Lys Ala Ser Lys Ala Lys Arg Glu Ala Leu Ile Ala Cys
        195                 200                 205
Ile Glu Pro Asp Arg Arg Val Asp Val Lys Ile Arg Ser Ile Val Thr
    210                 215                 220
Arg Gln Val Val Pro Ala Arg Asn His His Gln His
225                 230                 235

<210> SEQ ID NO 30
<211> LENGTH: 642
<212> TYPE: PRT
<213> ORGANISM: Neisseria gonorrhoeae (strain ATCC 700825 / FA 1090)

<400> SEQUENCE: 30

Met Ala Lys Val Ile Gly Ile Asp Leu Gly Thr Thr Asn Ser Cys Leu
1               5                   10                  15
```

-continued

Ala Ile Ser Glu Asn Gly Gln Thr Lys Val Ile Glu Asn Ala Glu Gly
        20                  25                  30

Ala Arg Thr Thr Pro Ser Ile Ile Ala Tyr Leu Asp Gly Gly Glu Ile
            35                  40                  45

Leu Val Gly Ala Pro Ala Lys Arg Gln Ala Val Thr Asn Ala Lys Asn
50                  55                  60

Thr Ile Tyr Ala Ala Lys Arg Leu Ile Gly His Lys Phe Glu Asp Lys
65                  70                  75                  80

Glu Val Gln Arg Asp Ile Glu Ser Met Pro Phe Glu Ile Ile Lys Ala
                85                  90                  95

Asp Asn Gly Asp Ala Trp Val Lys Ala Gln Gly Lys Glu Leu Ser Pro
            100                 105                 110

Pro Gln Ile Ser Ala Glu Val Leu Arg Lys Met Lys Glu Ala Ala Glu
        115                 120                 125

Ala Tyr Leu Gly Glu Lys Val Thr Glu Ala Val Ile Thr Val Pro Ala
130                 135                 140

Tyr Phe Asn Asp Ser Gln Arg Gln Ala Thr Lys Asp Ala Gly Arg Ile
145                 150                 155                 160

Ala Gly Leu Asp Val Lys Arg Ile Ile Asn Glu Pro Thr Ala Ala Ala
                165                 170                 175

Leu Ala Phe Gly Met Asp Lys Gly Asp Asn Lys Asp Arg Lys Ile Ala
            180                 185                 190

Val Tyr Asp Leu Gly Gly Gly Thr Phe Asp Ile Ser Ile Ile Glu Ile
        195                 200                 205

Ala Asn Leu Asp Gly Asp Lys Gln Phe Glu Val Leu Ala Thr Asn Gly
210                 215                 220

Asp Thr Phe Leu Gly Gly Glu Asp Phe Asp Gln Arg Leu Ile Asp Tyr
225                 230                 235                 240

Ile Ile Asp Glu Phe Lys Lys Glu Gln Gly Ile Asp Leu Lys Gln Asp
                245                 250                 255

Val Met Ala Leu Gln Arg Leu Lys Glu Ala Ala Glu Lys Ala Lys Ile
            260                 265                 270

Glu Leu Ser Ser Gly Gln Gln Thr Glu Ile Asn Leu Pro Tyr Ile Thr
        275                 280                 285

Met Asp Ala Thr Gly Pro Lys His Leu Ala Met Lys Ile Thr Arg Ala
290                 295                 300

Lys Phe Glu Ser Leu Val Glu Asp Leu Ile Ala Arg Ser Ile Glu Pro
305                 310                 315                 320

Cys Arg Thr Ala Leu Lys Asp Ala Gly Leu Ser Thr Gly Asp Ile Asp
                325                 330                 335

Asp Val Ile Leu Val Gly Gly Gln Ser Arg Met Pro Lys Val Gln Glu
            340                 345                 350

Ala Val Lys Asp Phe Phe Gly Lys Glu Pro Arg Lys Asp Val Asn Pro
        355                 360                 365

Asp Glu Ala Val Ala Val Gly Ala Ala Ile Gln Gly Glu Val Leu Ser
370                 375                 380

Gly Gly Arg Ser Asp Val Leu Leu Asp Val Thr Pro Leu Ser Leu
385                 390                 395                 400

Gly Ile Glu Thr Met Gly Gly Val Met Thr Lys Leu Ile Gln Lys Asn
                405                 410                 415

Thr Thr Ile Pro Thr Lys Ala Ser Gln Val Phe Ser Thr Ala Glu Asp
            420                 425                 430

-continued

Asn Gln Ser Ala Val Thr Ile His Val Leu Gln Gly Glu Arg Glu Arg
            435                 440                 445

Ala Ser Ala Asn Lys Ser Leu Gly Gln Phe Asn Leu Gly Asp Ile Ala
450                 455                 460

Pro Ala Pro Arg Gly Met Pro Gln Ile Glu Val Thr Phe Asp Ile Asp
465                 470                 475                 480

Ala Asn Gly Ile Leu His Val Ser Ala Lys Asp Lys Gly Thr Gly Lys
                485                 490                 495

Ala Ala Asn Ile Thr Ile Gln Gly Ser Ser Gly Leu Ser Glu Glu
                500                 505                 510

Ile Glu Arg Met Val Lys Asp Ala Glu Ala Asn Ala Glu Asp Lys
            515                 520                 525

Lys Leu Thr Glu Leu Val Ala Ser Arg Asn Gln Ala Glu Ala Leu Ile
530                 535                 540

His Ser Val Lys Lys Ser Leu Ala Asp Tyr Gly Asp Lys Leu Asp Ala
545                 550                 555                 560

Ala Glu Lys Glu Lys Ile Glu Ala Ala Leu Lys Glu Ala Glu Ala
                565                 570                 575

Val Lys Gly Asp Asp Lys Thr Ala Ile Asp Ala Lys Ala Glu Ala Leu
                580                 585                 590

Gly Thr Ala Ser Gln Lys Leu Gly Glu Met Val Tyr Ala Gln Ala Gln
            595                 600                 605

Ala Glu Ala Gln Ala Gly Glu Gly Ala Gln Ala Asn Ala Ser Ala Lys
            610                 615                 620

Lys Asp Asp Asp Val Val Asp Ala Asp Phe Glu Glu Val Lys Asp Asp
625                 630                 635                 640

Lys Lys

<210> SEQ ID NO 31
<211> LENGTH: 544
<212> TYPE: PRT
<213> ORGANISM: Neisseria gonorrhoeae

<400> SEQUENCE: 31

Met Ala Ala Lys Asp Val Gln Phe Gly Asn Glu Val Arg Gln Lys Met
1               5                   10                  15

Val Asn Gly Val Asn Ile Leu Ala Asn Ala Val Arg Val Thr Leu Gly
                20                  25                  30

Pro Lys Gly Arg Asn Val Val Asp Arg Ala Phe Gly Gly Pro His
            35                  40                  45

Ile Thr Lys Asp Gly Val Thr Val Ala Lys Glu Ile Glu Leu Lys Asp
50                  55                  60

Lys Phe Glu Asn Met Gly Ala Gln Met Val Lys Glu Val Ala Ser Lys
65                  70                  75                  80

Thr Asn Asp Val Ala Gly Asp Gly Thr Thr Thr Ala Thr Val Leu Ala
                85                  90                  95

Gln Ser Ile Val Ala Glu Gly Ile Lys Ala Val Thr Ala Gly Met Asn
                100                 105                 110

Pro Thr Asp Leu Lys Arg Gly Ile Asp Lys Ala Val Ala Ala Leu Val
            115                 120                 125

Glu Glu Leu Lys Asn Ile Ala Lys Pro Cys Asp Thr Ser Lys Glu Ile
    130                 135                 140

Ala Gln Val Gly Ser Ile Ser Ala Asn Ser Asp Glu Gln Val Gly Ala
145                 150                 155                 160

Ile Ile Ala Glu Ala Met Glu Lys Val Gly Lys Glu Gly Val Ile Thr
            165                 170                 175

Val Glu Asp Gly Lys Ser Leu Glu Asn Glu Leu Asp Val Val Glu Gly
        180                 185                 190

Met Gln Phe Asp Arg Gly Tyr Leu Ser Pro Tyr Phe Ile Asn Asp Ala
    195                 200                 205

Glu Lys Gln Ile Ala Gly Leu Asp Asn Pro Phe Val Leu Leu Phe Asp
210                 215                 220

Lys Lys Ile Ser Asn Ile Arg Asp Leu Leu Pro Val Leu Glu Gln Val
225                 230                 235                 240

Ala Lys Ala Ser Arg Pro Leu Leu Ile Ile Ala Glu Asp Val Glu Gly
                245                 250                 255

Glu Ala Leu Ala Thr Leu Val Val Asn Asn Ile Arg Gly Val Leu Lys
            260                 265                 270

Thr Val Ala Val Lys Ala Pro Gly Phe Gly Asp Arg Arg Lys Ala Met
        275                 280                 285

Leu Gln Asp Ile Ala Ile Leu Thr Gly Ala Val Ile Ser Glu Glu
    290                 295                 300

Val Gly Leu Ser Leu Glu Lys Ala Thr Leu Asp Asp Leu Gly Gln Ala
305                 310                 315                 320

Lys Arg Ile Glu Ile Gly Lys Glu Asn Thr Thr Val Ile Asp Gly Phe
                325                 330                 335

Gly Asp Ala Ala Gln Ile Glu Ala Arg Val Ala Glu Ile Arg Gln Gln
            340                 345                 350

Ile Glu Thr Ala Thr Ser Asp Tyr Asp Lys Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Asp Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Leu Arg Ala Arg Ala Ala Leu Glu Asn Leu His Thr Gly
            420                 425                 430

Asn Ala Asp Gln Asp Ala Gly Val Gln Ile Val Leu Arg Ala Val Glu
        435                 440                 445

Ser Pro Leu Arg Gln Ile Val Ala Asn Ala Gly Gly Glu Pro Ser Val
    450                 455                 460

Val Val Asn Lys Val Leu Glu Gly Lys Gly Asn Tyr Gly Tyr Asn Ala
465                 470                 475                 480

Gly Ser Gly Glu Tyr Gly Asp Met Ile Gly Met Gly Val Leu Asp Pro
                485                 490                 495

Ala Lys Val Thr Arg Ser Ala Leu Gln His Ala Ala Ser Ile Ala Gly
            500                 505                 510

Leu Met Leu Thr Thr Asp Cys Met Ile Ala Glu Ile Pro Glu Glu Lys
        515                 520                 525

Pro Ala Val Pro Asp Met Gly Gly Met Gly Gly Met Gly Gly Met Met
    530                 535                 540

<210> SEQ ID NO 32
<211> LENGTH: 96
<212> TYPE: PRT
<213> ORGANISM: Neisseria gonorrhoeae (strain ATCC 700825 / FA 1090)

<400> SEQUENCE: 32

```
Met Thr Ile Arg Pro Leu His Asp Arg Val Val Lys Arg Leu Glu
1               5                   10                  15

Ala Glu Glu Lys Thr Ala Ser Gly Ile Val Leu Pro Gly Ala Ala
                20                  25                  30

Glu Lys Pro Asp Met Gly Glu Val Ile Ala Val Gly Ala Gly Lys Ile
                35                  40                  45

Gly Lys Asp Gly Ala Arg Arg Pro Leu Asp Val Lys Ala Gly Asp Lys
50                  55                  60

Ile Ile Phe Gly Lys Tyr Ser Gly Gln Thr Val Lys Ala Asp Gly Glu
65                  70                  75                  80

Glu Leu Leu Val Met Arg Glu Glu Asp Ile Phe Gly Ile Val Glu Lys
                85                  90                  95
```

<210> SEQ ID NO 33
<211> LENGTH: 89
<212> TYPE: PRT
<213> ORGANISM: Neisseria gonorrhoeae (strain NCCP11945)

<400> SEQUENCE: 33

```
Met Asn Lys Ser Glu Leu Ile Glu Ala Ile Ala Gln Glu Ala Asp Ile
1               5                   10                  15

Ser Lys Ala Ala Ala Gln Lys Ala Leu Asp Ala Thr Thr Asn Ala Val
                20                  25                  30

Thr Asn Ala Leu Lys Gln Gly Asp Thr Val Thr Leu Val Gly Phe Gly
                35                  40                  45

Thr Phe Tyr Val Gly Glu Arg Ala Glu Arg Gln Gly Arg Asn Pro Lys
50                  55                  60

Thr Gly Glu Pro Leu Thr Ile Ala Ala Ala Lys Thr Leu Lys Phe Arg
65                  70                  75                  80

Ala Gly Lys Ala Leu Lys Asp Ala Leu
                85
```

<210> SEQ ID NO 34
<211> LENGTH: 236
<212> TYPE: PRT
<213> ORGANISM: Neisseria gonorrhoeae DGI2

<400> SEQUENCE: 34

```
Met Thr Lys Gln Leu Lys Leu Ser Ala Leu Phe Val Ala Leu Leu Ala
1               5                   10                  15

Ser Gly Thr Ala Val Ala Gly Glu Ala Ser Val Gln Gly Tyr Thr Val
                20                  25                  30

Ser Gly Gln Ser Asn Glu Ile Val Arg Asn Asn Tyr Gly Glu Cys Trp
                35                  40                  45

Lys Asn Ala Tyr Phe Asp Lys Ala Ser Gln Gly Arg Val Glu Cys Gly
    50                  55                  60

Asp Ala Val Ala Val Pro Glu Pro Glu Pro Ala Pro Val Ala Val Val
65                  70                  75                  80

Glu Gln Ala Pro Gln Tyr Val Asp Gly Thr Ile Ser Leu Ser Ala Lys
                85                  90                  95

Thr Leu Phe Gly Phe Asp Lys Asp Ser Leu Arg Ala Glu Ala Gln Asp
                100                 105                 110

Asn Leu Lys Val Leu Ala Gln Arg Leu Ser Arg Thr Asn Val Gln Ser
                115                 120                 125

Val Arg Val Glu Gly His Thr Asp Phe Met Gly Ser Glu Lys Tyr Asn
                130                 135                 140
```

Gln Ala Leu Ser Glu Arg Arg Ala Tyr Val Val Ala Asn Asn Leu Val
145                 150                 155                 160

Ser Asn Gly Val Pro Ala Ser Arg Ile Ser Ala Val Gly Leu Gly Glu
                165                 170                 175

Ser Gln Ala Gln Met Thr Gln Val Cys Gln Ala Glu Val Ala Lys Leu
            180                 185                 190

Gly Ala Lys Ala Ser Lys Ala Lys Arg Glu Ala Leu Ile Ala Cys
        195                 200                 205

Ile Glu Pro Asp Arg Arg Val Asp Val Lys Ile Arg Ser Ile Val Thr
210                 215                 220

Arg Gln Val Val Pro Ala Arg Asn His His Gln His
225                 230                 235

<210> SEQ ID NO 35
<211> LENGTH: 801
<212> TYPE: PRT
<213> ORGANISM: Neisseria gonorrhoeae (strain ATCC 700825 / FA 1090)

<400> SEQUENCE: 35

Met Ala Arg Leu Phe Ser Leu Lys Pro Leu Val Leu Ala Leu Gly Phe
1               5                   10                  15

Cys Phe Gly Thr His Cys Ala Ala Asp Thr Val Ala Ala Glu Glu Ala
                20                  25                  30

Asp Gly Arg Val Ala Glu Gly Ala Gln Gly Ala Ser Glu Ser Ala
            35                  40                  45

Gln Ala Ser Asp Leu Thr Leu Gly Ser Thr Cys Leu Phe Cys Ser Asn
50                  55                  60

Glu Ser Gly Ser Pro Glu Arg Thr Glu Ala Ala Val Gln Gly Ser Gly
65                  70                  75                  80

Glu Ala Ser Val Pro Glu Asp Tyr Thr Arg Ile Val Ala Asp Arg Met
                85                  90                  95

Glu Gly Gln Ser Lys Val Lys Val Arg Ala Glu Gly Ser Val Ile Ile
            100                 105                 110

Glu Arg Asp Gly Ala Val Leu Asn Thr Asp Trp Ala Asp Tyr Asp Gln
        115                 120                 125

Ser Gly Asp Thr Val Thr Val Gly Asp Arg Phe Ala Leu Gln Gln Asp
130                 135                 140

Gly Thr Leu Ile Arg Gly Glu Thr Leu Thr Tyr Asn Leu Asp Gln Gln
145                 150                 155                 160

Thr Gly Glu Ala His Asn Val Arg Met Glu Thr Glu Gln Gly Gly Arg
                165                 170                 175

Arg Leu Gln Ser Val Ser Arg Thr Ala Glu Met Leu Gly Glu Gly Arg
            180                 185                 190

Tyr Lys Leu Thr Glu Thr Gln Phe Asn Thr Cys Ser Ala Gly Asp Ala
        195                 200                 205

Gly Trp Tyr Val Lys Ala Ser Val Glu Ala Asp Arg Gly Lys Gly
210                 215                 220

Ile Gly Val Ala Lys His Ala Ala Phe Val Phe Gly Val Pro Leu
225                 230                 235                 240

Phe Tyr Thr Pro Trp Ala Asp Phe Pro Leu Asp Gly Asn Arg Lys Ser
                245                 250                 255

Gly Leu Leu Val Pro Ser Val Ser Ala Gly Ser Asp Gly Val Ser Leu
            260                 265                 270

Ser Val Pro Tyr Tyr Phe Asn Leu Ala Pro Asn Phe Asp Ala Thr Phe

```
            275                 280                 285
Ala Pro Gly Ile Ile Gly Glu Arg Gly Ala Thr Phe Asp Gly Gln Ile
290                 295                 300
Arg Tyr Leu Arg Pro Asp Tyr Ser Gly Gln Thr Asp Leu Thr Trp Leu
305                 310                 315                 320
Pro His Asp Lys Lys Ser Gly Arg Asn Asn Arg Tyr Gln Ala Lys Trp
                    325                 330                 335
Gln His Arg His Asp Ile Ser Asp Thr Leu Gln Ala Gly Val Asp Phe
                340                 345                 350
Asn Gln Val Ser Asp Ser Gly Tyr Tyr Arg Asp Phe Tyr Gly Gly Glu
                355                 360                 365
Glu Ile Ala Gly Asn Val Asn Leu Asn Arg Arg Val Trp Leu Asp Tyr
370                 375                 380
Gly Gly Arg Ala Ala Gly Gly Ser Leu Asn Ala Gly Leu Ser Val Gln
385                 390                 395                 400
Lys Tyr Gln Thr Leu Ala Asn Gln Ser Gly Tyr Lys Asp Glu Pro Tyr
                    405                 410                 415
Ala Ile Met Pro Arg Leu Ser Ala Asp Trp His Lys Asn Ala Gly Arg
                420                 425                 430
Ala Gln Ile Gly Val Ser Ala Gln Phe Thr Arg Phe Ser His Asp Gly
                435                 440                 445
Arg Gln Asp Gly Ser Arg Leu Val Val Tyr Pro Gly Ile Lys Trp Asp
450                 455                 460
Phe Ser Asn Ser Trp Gly Tyr Val Arg Pro Lys Leu Gly Leu His Ala
465                 470                 475                 480
Thr Tyr Tyr Ser Leu Asp Ser Phe Gly Gly Lys Ala Ser Arg Ser Val
                    485                 490                 495
Gly Arg Val Leu Pro Val Val Asn Ile Asp Gly Gly Thr Thr Phe Glu
                500                 505                 510
Arg Asn Thr Arg Leu Phe Gly Gly Val Val Gln Thr Ile Glu Pro
                515                 520                 525
Arg Leu Phe Tyr Asn Tyr Ile Pro Ala Lys Ser Gln Asn Asp Leu Pro
530                 535                 540
Asn Phe Asp Ser Ser Glu Ser Ser Phe Gly Tyr Gly Gln Leu Phe Arg
545                 550                 555                 560
Glu Asn Leu Tyr Tyr Gly Asn Asp Arg Ile Asn Ala Ala Asn Ser Leu
                    565                 570                 575
Ser Thr Ala Val Gln Ser Arg Ile Leu Asp Gly Ala Thr Gly Glu Glu
                580                 585                 590
Arg Phe Arg Ala Gly Ile Gly Gln Lys Phe Tyr Phe Lys Asp Asp Ala
                595                 600                 605
Val Met Leu Asp Gly Ser Val Gly Lys Asn Pro Arg Ser Arg Ser Asp
                610                 615                 620
Trp Val Ala Phe Ala Ser Gly Gly Ile Gly Gly Arg Phe Thr Leu Asp
625                 630                 635                 640
Ser Ser Ile His Tyr Asn Gln Asn Asp Lys Arg Ala Glu His Tyr Ala
                    645                 650                 655
Val Gly Ala Gly Tyr Arg Pro Ala Pro Gly Lys Val Leu Asn Ala Arg
                660                 665                 670
Tyr Lys Tyr Gly Arg Asn Glu Lys Ile Tyr Leu Gln Ala Asp Gly Ser
                675                 680                 685
Tyr Phe Tyr Asp Lys Leu Ser Gln Leu Asp Leu Ser Ala Gln Trp Pro
690                 695                 700
```

```
Leu Thr Arg Asn Leu Ser Ala Val Val Arg Tyr Asn Tyr Gly Phe Glu
705                 710                 715                 720

Ala Lys Lys Pro Ile Glu Met Leu Ala Gly Ala Glu Tyr Lys Ser Ser
                725                 730                 735

Cys Gly Cys Trp Gly Ala Gly Val Tyr Ala Gln Arg Tyr Val Thr Gly
            740                 745                 750

Glu Asn Thr Tyr Lys Asn Ala Val Phe Phe Ser Leu Gln Leu Lys Asp
        755                 760                 765

Leu Ser Ser Val Gly Arg Asn Pro Ala Gly Arg Met Asp Val Ala Val
    770                 775                 780

Pro Gly Tyr Ile Pro Ala His Ser Leu Ser Ala Gly Arg Asn Lys Arg
785                 790                 795                 800

Pro

<210> SEQ ID NO 36
<211> LENGTH: 635
<212> TYPE: PRT
<213> ORGANISM: Neisseria gonorrhoeae (strain ATCC 700825 / FA 1090)

<400> SEQUENCE: 36

Met Pro Ser Glu Ala Ser Arg Pro Val Arg Thr Val Leu Glu Ser Lys
1               5                   10                  15

Ser Ala Thr Pro Met His Asp Thr Arg Thr Met Met Ile Lys Pro Thr
                20                  25                  30

Ala Leu Leu Leu Pro Ala Leu Phe Phe Phe Pro His Ala Tyr Ala Pro
            35                  40                  45

Ala Ala Asp Leu Ser Glu Asn Lys Ala Ala Gly Phe Ala Leu Phe Lys
        50                  55                  60

Ser Lys Ser Pro Asp Thr Glu Val Lys Leu Lys Pro Lys Phe Pro
65                  70                  75                  80

Val Arg Ile Asp Thr Gln Asp Ser Glu Ile Lys Asp Met Val Glu Glu
                85                  90                  95

His Leu Pro Leu Ile Thr Gln Gln Glu Glu Val Leu Asp Lys Glu
                100                 105                 110

Gln Thr Gly Phe Leu Ala Glu Ala Pro Asp Asn Val Lys Thr Met
            115                 120                 125

Leu Arg Ser Lys Gly Tyr Phe Ser Ser Lys Val Ser Leu Thr Glu Lys
130                 135                 140

Asp Gly Ala Tyr Thr Val His Ile Thr Pro Gly Pro Arg Thr Lys Ile
145                 150                 155                 160

Ala Asn Val Gly Val Ala Ile Leu Gly Asp Ile Leu Ser Asp Gly Asn
                165                 170                 175

Leu Ala Glu Tyr Tyr Arg Asn Ala Leu Glu Asn Trp Gln Gln Pro Val
            180                 185                 190

Gly Ser Asp Phe Asp Gln Asp Ser Trp Glu Asn Ser Lys Thr Ser Val
        195                 200                 205

Leu Gly Ala Val Thr Arg Lys Gly Tyr Pro Leu Ala Lys Leu Gly Asn
    210                 215                 220

Thr Arg Ala Ala Val Asn Pro Asp Thr Ala Thr Ala Asp Leu Asn Val
225                 230                 235                 240

Val Val Asp Ser Gly Arg Pro Ile Ala Phe Gly Asp Phe Glu Ile Thr
                245                 250                 255

Gly Thr Gln Arg Tyr Pro Glu Gln Thr Val Ser Gly Leu Ala Arg Phe
            260                 265                 270
```

Gln Pro Gly Thr Pro Tyr Asp Leu Asp Leu Leu Asp Phe Gln Gln
            275                 280                 285

Ala Leu Glu Gln Asn Gly His Tyr Ser Gly Ala Ser Val Gln Ala Asp
        290                 295                 300

Phe Asp Arg Leu Gln Gly Asp Arg Val Pro Val Lys Val Ser Val Thr
305                 310                 315                 320

Glu Val Lys Arg His Lys Leu Glu Thr Gly Ile Arg Leu Asp Ser Glu
                325                 330                 335

Tyr Gly Leu Gly Gly Lys Ile Ala Tyr Asp Tyr Asn Leu Phe Asn
            340                 345             350

Lys Gly Tyr Ile Gly Ser Val Val Trp Asp Met Asp Lys Tyr Glu Thr
        355                 360                 365

Thr Leu Ala Ala Gly Ile Ser Gln Pro Arg Asn Tyr Arg Gly Asn Tyr
370                 375                 380

Trp Thr Ser Asn Val Ser Tyr Asn Arg Ser Thr Thr Gln Asn Leu Glu
385                 390                 395                 400

Lys Arg Ala Phe Ser Gly Gly Ile Trp Tyr Val Arg Asp Arg Ala Gly
                405                 410                 415

Ile Asp Ala Arg Leu Gly Ala Glu Phe Leu Ala Glu Gly Arg Lys Ile
            420                 425                 430

Pro Gly Ser Asp Val Asp Leu Gly Asn Ser His Ala Thr Met Leu Thr
        435                 440                 445

Ala Ser Trp Lys Arg Gln Leu Leu Asn Asn Val Leu His Pro Glu Asn
    450                 455                 460

Gly His Tyr Leu Asp Gly Lys Ile Gly Thr Thr Leu Gly Thr Phe Leu
465                 470                 475                 480

Ser Ser Thr Ala Leu Ile Arg Thr Ser Ala Arg Ala Gly Tyr Phe Phe
                485                 490                 495

Thr Pro Glu Asn Lys Lys Leu Gly Thr Phe Ile Ile Arg Gly Gln Ala
            500                 505                 510

Gly Tyr Thr Val Ala Arg Asp Asn Ala Asp Val Pro Ser Gly Leu Met
        515                 520                 525

Phe Arg Ser Gly Gly Ala Ser Ser Val Arg Gly Tyr Glu Leu Asp Ser
    530                 535                 540

Ile Gly Leu Ala Gly Pro Asn Gly Ser Val Leu Pro Glu Arg Ala Leu
545                 550                 555                 560

Leu Val Gly Ser Leu Glu Tyr Gln Leu Pro Phe Thr Arg Thr Leu Ser
                565                 570                 575

Gly Ala Val Phe His Asp Met Gly Asp Ala Ala Ala Asn Phe Lys Arg
            580                 585                 590

Met Lys Leu Lys His Gly Ser Gly Leu Gly Val Arg Trp Phe Ser Pro
        595                 600                 605

Leu Ala Pro Phe Ser Phe Asp Ile Ala Tyr Gly His Ser Asp Lys Lys
    610                 615                 620

Ile Arg Trp His Ile Ser Leu Gly Thr Arg Phe
625                 630                 635

<210> SEQ ID NO 37
<211> LENGTH: 467
<212> TYPE: PRT
<213> ORGANISM: Neisseria gonorrhoeae

<400> SEQUENCE: 37

Met Lys Lys Ile Gln Ala Asp Ile Val Val Ile Gly Gly Gly Thr Ala

-continued

```
1               5                   10                  15
Gly Met Gly Ala Phe Arg Asn Ala Arg Leu His Ser Asp Asn Val Tyr
                20                  25                  30
Leu Ile Glu Asn Asn Val Phe Gly Thr Thr Cys Ala Arg Val Gly Cys
                35                  40                  45
Met Pro Ser Lys Leu Leu Ile Ala Ala Glu Ala Arg His His Ala
        50                  55                  60
Leu His Thr Asp Pro Phe Gly Val His Leu Asp Lys Asp Ser Ile Val
65                      70                  75                  80
Val Asn Gly Glu Glu Val Met Arg Arg Val Lys Ser Glu Arg Asp Arg
                    85                  90                  95
Phe Val Gly Phe Val Val Thr Asp Val Glu Glu Trp Pro Ala Asp Lys
                    100                 105                 110
Arg Ile Met Gly Ser Ala Lys Phe Ile Asp Glu His Thr Val Gln Ile
                    115                 120                 125
Asp Asp His Ile Gln Ile Ala Ala Lys Ser Phe Val Ile Ala Thr Gly
                    130                 135                 140
Ser Arg Pro Val Ile Leu Pro Gln Trp Gln Ser Leu Gly Asp Arg Leu
145                 150                 155                 160
Ile Ile Asn Asp Asp Val Phe Ser Trp Asp Thr Leu Pro Lys Arg Val
                    165                 170                 175
Ala Val Phe Gly Pro Gly Val Ile Gly Leu Glu Leu Gly Gln Ala Leu
                    180                 185                 190
His Arg Leu Gly Val Lys Val Glu Ile Phe Gly Leu Gly Gly Ile Ile
                    195                 200                 205
Gly Gly Ile Ser Asp Pro Val Val Ser Asp Glu Ala Lys Ala Val Phe
                    210                 215                 220
Gly Glu Glu Leu Lys Leu His Leu Asp Ala Lys Thr Glu Val Lys Leu
225                 230                 235                 240
Asp Ala Asp Gly Asn Val Glu Val His Trp Glu Gln Asp Gly Glu Lys
                    245                 250                 255
Gly Val Phe Val Ala Glu Tyr Met Leu Ala Ala Val Gly Arg Arg Pro
                    260                 265                 270
Asn Val Asp Asn Ile Gly Leu Glu Asn Ile Asn Ile Asp Lys Asp Ala
                    275                 280                 285
Arg Gly Val Pro Val Ala Asp Pro Leu Thr Met Gln Thr Ser Ile Pro
                    290                 295                 300
His Ile Phe Ile Ala Gly Asp Ala Ser Asn Gln Leu Pro Leu Leu His
305                 310                 315                 320
Glu Ala Ala Asp Gln Gly Lys Ile Ala Gly Asp Asn Ala Gly Arg Tyr
                    325                 330                 335
Pro Asn Ile Gly Ser Gly Leu Arg Arg Ser Thr Ile Gly Val Val Phe
                    340                 345                 350
Thr Ser Pro Gln Ile Gly Phe Val Gly Leu Lys Tyr Ala Gln Val Ala
                    355                 360                 365
Ala Gln Tyr Gln Ala Asp Glu Phe Val Ile Gly Glu Val Ser Phe Lys
                    370                 375                 380
Asn Gln Gly Arg Ser Arg Val Met Leu Val Asn Lys Gly His Met Arg
385                 390                 395                 400
Leu Tyr Ala Glu Lys Ala Thr Gly Arg Phe Ile Gly Ala Glu Ile Val
                    405                 410                 415
Gly Pro Ala Ala Glu His Leu Ala His Leu Leu Ala Trp Ala His Gln
                    420                 425                 430
```

Met Lys Met Thr Val Pro Gln Met Leu Asp Met Pro Phe Tyr His Pro
              435                 440                 445

Val Ile Glu Glu Gly Leu Arg Thr Ala Leu Arg Asp Ala Asp Ala Lys
    450                 455                 460

Leu Lys Ala
465

<210> SEQ ID NO 38
<211> LENGTH: 297
<212> TYPE: PRT
<213> ORGANISM: Neisseria gonorrhoeae

<400> SEQUENCE: 38

Met Ile Ile Ala Glu Asp Val Glu Gly Glu Ala Leu Ala Thr Leu Val
1               5                   10                  15

Val Asn Asn Ile Arg Gly Ile Leu Lys Thr Val Ala Val Lys Ala Pro
            20                  25                  30

Gly Phe Gly Asp Arg Arg Lys Ala Met Leu Gln Asp Ile Ala Ile Leu
        35                  40                  45

Thr Gly Gly Val Val Ile Ser Glu Glu Val Gly Leu Ser Leu Glu Lys
    50                  55                  60

Ala Thr Leu Asp Asp Leu Gly Gln Ala Lys Arg Ile Glu Ile Gly Lys
65                  70                  75                  80

Glu Asn Thr Thr Val Ile Asp Gly Phe Gly Asp Ala Ala Gln Ile Glu
                85                  90                  95

Ala Arg Val Ala Glu Ile Arg Gln Gln Ile Glu Thr Ala Thr Ser Asp
            100                 105                 110

Tyr Asp Lys Glu Lys Leu Gln Glu Arg Val Ala Lys Leu Ala Gly Gly
        115                 120                 125

Val Ala Val Ile Lys Val Gly Ala Ala Thr Glu Val Glu Met Lys Glu
    130                 135                 140

Lys Lys Asp Arg Val Glu Asp Ala Leu His Ala Thr Arg Ala Ala Val
145                 150                 155                 160

Glu Glu Gly Val Val Ala Gly Gly Val Ala Leu Leu Arg Ala Arg
                165                 170                 175

Ala Ala Leu Glu Asn Leu His Thr Gly Asn Ala Asp Gln Asp Ala Gly
            180                 185                 190

Val Gln Ile Val Leu Arg Ala Val Glu Ser Pro Leu Arg Gln Ile Val
        195                 200                 205

Ala Asn Ala Gly Gly Glu Pro Ser Val Val Asn Lys Val Leu Glu
    210                 215                 220

Gly Lys Gly Asn Tyr Gly Tyr Asn Ala Gly Ser Gly Glu Tyr Gly Asp
225                 230                 235                 240

Met Ile Gly Met Gly Val Leu Asp Pro Ala Lys Val Thr Arg Ser Ala
                245                 250                 255

Leu Gln His Ala Ala Ser Ile Ala Gly Leu Met Leu Thr Thr Asp Cys
            260                 265                 270

Met Ile Ala Glu Ile Pro Glu Glu Lys Pro Ala Val Pro Asp Met Gly
        275                 280                 285

Gly Met Gly Gly Met Gly Gly Met Met
    290                 295

<210> SEQ ID NO 39
<211> LENGTH: 90
<212> TYPE: PRT

<213> ORGANISM: Neisseria gonorrhoeae (strain ATCC 700825 / FA 1090)

<400> SEQUENCE: 39

```
Met Arg Lys Thr Phe Leu Ile Leu Thr Val Ser Ala Ala Leu Leu Ser
1               5                   10                  15

Gly Cys Ala Trp Glu Thr Tyr Gln Asp Gly Asn Gly Lys Thr Ala Val
            20                  25                  30

Arg Gln Lys Tyr Pro Ala Gly Thr Pro Val Tyr Tyr Gln Asp Gly Ser
        35                  40                  45

Tyr Ser Lys Asn Met Asn Tyr Asn Gln Tyr Arg Pro Glu Arg Arg Ala
    50                  55                  60

Val Leu Pro Asp Gln Thr Gly Asn Asn Ala Asp Glu Glu His Arg Gln
65                  70                  75                  80

His Trp Gln Lys Pro Lys Phe Gln Asn Arg
                85                  90
```

<210> SEQ ID NO 40
<211> LENGTH: 288
<212> TYPE: PRT
<213> ORGANISM: Neisseria gonorrhoeae (strain ATCC 700825 / FA 1090)

<400> SEQUENCE: 40

```
Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ser Ala
            20                  25                  30

Ala Ala Pro Ser Ala Asp Asn Gly Ala Ala Lys Lys Glu Ile Val Phe
        35                  40                  45

Gly Thr Thr Val Gly Asp Phe Gly Asp Met Val Lys Glu Gln Ile Gln
    50                  55                  60

Ala Glu Leu Glu Lys Lys Gly Tyr Thr Val Lys Leu Val Glu Phe Thr
65                  70                  75                  80

Asp Tyr Val Arg Pro Asn Leu Ala Leu Ala Glu Gly Glu Leu Asp Ile
                85                  90                  95

Asn Val Phe Gln His Lys Pro Tyr Leu Asp Asp Phe Lys Lys Glu His
            100                 105                 110

Asn Leu Asp Ile Thr Glu Ala Phe Gln Val Pro Thr Ala Pro Leu Gly
        115                 120                 125

Leu Tyr Pro Gly Lys Leu Lys Ser Leu Glu Glu Val Lys Asp Gly Ser
    130                 135                 140

Thr Val Ser Ala Pro Asn Asp Pro Ser Asn Phe Ala Arg Ala Leu Val
145                 150                 155                 160

Met Leu Asn Glu Leu Gly Trp Ile Lys Leu Lys Asp Gly Ile Asn Pro
                165                 170                 175

Leu Thr Ala Ser Lys Ala Asp Ile Ala Glu Asn Leu Lys Asn Ile Lys
            180                 185                 190

Ile Val Glu Leu Glu Ala Ala Gln Leu Pro Arg Ser Arg Ala Asp Val
        195                 200                 205

Asp Phe Ala Val Val Asn Gly Asn Tyr Ala Ile Ser Ser Gly Met Lys
    210                 215                 220

Leu Thr Glu Ala Leu Phe Gln Glu Pro Ser Phe Ala Tyr Val Asn Trp
225                 230                 235                 240

Ser Ala Val Lys Thr Ala Asp Lys Asp Ser Gln Trp Leu Lys Asp Val
                245                 250                 255

Thr Glu Ala Tyr Asn Ser Asp Ala Phe Lys Ala Tyr Ala His Lys Arg
```

```
                    260                 265                 270
Phe Glu Gly Tyr Lys Tyr Pro Ala Ala Trp Asn Glu Gly Ala Ala Lys
            275                 280                 285

<210> SEQ ID NO 41
<211> LENGTH: 751
<212> TYPE: PRT
<213> ORGANISM: Trichomonas vaginalis G3

<400> SEQUENCE: 41

Met Phe Cys Ser Leu Leu Ile Thr Ser Ala Phe Ala Ile His Asn Arg
1               5                   10                  15

Thr Glu Asn Ile Thr Leu Lys Asp Asp Gln Thr Leu Val Tyr Ser His
            20                  25                  30

Leu Lys Asn Gly Ser Tyr Leu Met Pro Leu Tyr Val Lys Asp Ile Trp
        35                  40                  45

Pro Glu Cys Glu Asn Asp Thr Ser Ile Thr Phe Cys Trp Tyr Tyr Leu
    50                  55                  60

Thr Arg Gly Asn Ala Trp Asp Phe Gly Tyr Ala Lys Leu Pro Asn Gly
65                  70                  75                  80

Val Gln His Pro Gln Lys Gly Gln Tyr Cys Thr Asp Phe Asp Val Leu
                85                  90                  95

Tyr Arg Gly Ala Trp Thr Thr Phe Ala Lys Thr Gly Trp Trp Pro Ile
            100                 105                 110

Trp Ser Ile Asp Asp Ser Ile Tyr Tyr Arg Ile His Gly Ser Glu Asn
        115                 120                 125

Gly Thr Asn Thr Leu Arg Asn Val Thr Ile Arg Thr Lys Ile Thr Gln
130                 135                 140

Pro Ala Gly Pro Asn Tyr Leu Leu Ile Glu Phe Ile Ala His Asn His
145                 150                 155                 160

Asp Ser Gln Pro His Ile Val Asn Val Leu Ser Tyr Thr Asp Val Met
                165                 170                 175

Ile Gly Asn Lys Asp Ser Ala Pro Ile Lys Trp Tyr Pro Pro Asn Thr
            180                 185                 190

His Asn Gly Phe Ser Met Glu Asn Glu Ala Asn Arg Thr Leu Val
        195                 200                 205

Leu Ile Gly Lys Asn Gly Phe Gly Val Asn Pro Val Asp Tyr Leu Trp
    210                 215                 220

Phe Gly Leu Tyr Ser Glu Gly Gln Thr Tyr Lys Phe Asn Lys Thr Asp
225                 230                 235                 240

Glu Ser Pro Thr Pro Ile Gly Arg Asp Thr Ala Phe Ser Leu Gly Trp
                245                 250                 255

Thr Asn Arg Arg Ile Tyr Pro Gly Gln Asn Leu Ser Phe Gly Val Leu
            260                 265                 270

Leu Gly Ile Gly Glu Phe Asn Gln Leu Lys Phe Pro Pro Thr Ile Thr
        275                 280                 285

Val Asp Glu Ser Lys Phe Lys Ile Asn Tyr Ala Pro Gly Glu Lys Ile
    290                 295                 300

Lys Ile Pro Ile Arg Val Gln Asp Lys Leu Thr Gly Ser Tyr Gly Leu
305                 310                 315                 320

Arg Val Thr Cys Glu Phe Pro Asn Asn Glu Ser Lys Thr His Asn Ile
                325                 330                 335

Ser Lys Thr Glu Gly Thr Val Asn Glu Pro Val Glu Phe Glu Tyr Asp
            340                 345                 350
```

```
Leu Gly Gln Asn Ile Ser Arg Tyr Pro Val Lys Cys Tyr Ala Glu Asn
            355                 360                 365

Tyr Asp Ile Thr Lys Thr Asp His Pro Gly Pro Lys Ser Asn Asp Phe
370                 375                 380

Asn Arg Val Phe Leu Val Asn Glu Ala Pro Arg Leu Thr Leu Thr Ser
385                 390                 395                 400

Gln Ile Asn Asp Gln Tyr Gly Arg Gly Gly Tyr Val Asn Ile Asp Gly
            405                 410                 415

Ile Val Trp Asp Asp Thr Arg Val Thr Met Thr Tyr Gln Val Asp Asp
            420                 425                 430

Asn Phe Tyr Tyr Arg Ala Asp Gly Asp Ile Thr Cys Asp Lys Gln Glu
            435                 440                 445

Lys Leu Phe Ser Lys Gln Ile Gln Ile Ser Pro Ser Tyr Ser Tyr Gly
450                 455                 460

Lys His Thr Leu Gln Ile Trp Ala Glu Asp Glu Phe Gly Val Lys Ser
465                 470                 475                 480

Pro Ile Val Lys Lys Glu Phe Ser Val Gln Asn His Pro Pro Glu
            485                 490                 495

Val Asn Ile Thr Glu Val Asp Asp Asn Lys Ser Gly Asn Tyr Tyr Asn
            500                 505                 510

Ser Pro Ile Thr Phe Lys Leu Gln Val Arg Asp Val Asp Val Asp Asp
            515                 520                 525

Val Ile Leu Leu Met Val Lys Thr Pro Gly Thr Asn Gln Phe Ala Gln
            530                 535                 540

Ile Met Thr Thr Pro Ala Lys Gln Gln Glu Trp Ile Asn Phe Thr Tyr
545                 550                 555                 560

Thr Tyr Asp Val Glu Ala Leu His Glu Glu Gly Asn Tyr Ala Ile Ile
            565                 570                 575

Phe Gln Ala Thr Asp Arg Ile Gly Ser Pro Ser Arg Asn Lys Glu Tyr
            580                 585                 590

Thr Phe Ile Phe Lys Lys His Pro Val Pro Thr Pro Ala Gln Pro Arg
            595                 600                 605

Ser Glu Lys Thr Asp Asn Ser Gly Asn Ile Glu Gln Cys Ala Met Val
610                 615                 620

Thr Asp Ala Asn Gly Asp Ser Phe Leu Asn Cys Thr Met Thr His Val
625                 630                 635                 640

Ile Ile Asp Val Asn Gln Lys Thr Pro Ser Ala Ser Asn Asp Asp Gly
            645                 650                 655

Asp Ala Phe Ser Asn Gly Asp Ala Asn Lys Ser Asn Ser Lys Lys
            660                 665                 670

Lys Asp Lys Tyr Leu Ile Ile Gly Ile Ala Ala Ala Val Val Ala
            675                 680                 685

Ala Ala Ala Ile Ile Ala Ala Ile Leu Ile Ala Lys Glu Ala Ser Lys
            690                 695                 700

Lys Ala Asn Asp Phe Gly Phe Asn Pro Glu Thr Glu Glu Ala Leu Gln
705                 710                 715                 720

Ala Asn Asn Asp Phe Val Gln Glu Lys Glu Asn Pro Val Tyr Asn Glu
                725                 730                 735

Asn Ala Gln Asp Asp Pro Phe Ala Asn Glu Phe Glu Asp Val Asp
            740                 745                 750

<210> SEQ ID NO 42
<211> LENGTH: 748
<212> TYPE: PRT
```

<213> ORGANISM: Trichomonas vaginalis G3

<400> SEQUENCE: 42

Met Leu Pro Leu Phe Tyr Thr Leu Ile Ser Asp Asp Tyr Ile Val
1               5                   10                  15

Lys Thr Lys Tyr Leu Arg Ala Tyr Tyr Cys Arg His Tyr Tyr Asp
            20                  25                  30

Pro Trp Thr Asp Ile Asn Ile Gln Tyr Asn Glu Arg Ala Asp Ser Thr
        35                  40                  45

Ser Gly Gly Glu Arg Trp Val Pro Thr Thr Tyr Ser Asp Gly Gly Trp
    50                  55                  60

Phe Pro Ile Phe Lys Val Asp Asp Pro Thr Lys Val Arg Ile Leu
65                  70                  75                  80

Gly Ser Asn Arg Gly Val Ser Asn Tyr Lys Gly Ile Tyr Ala Ser Thr
                85                  90                  95

Asn Val Thr Tyr His Pro Glu Ile Gly Glu Lys Tyr Leu Leu Ile Thr
            100                 105                 110

Tyr Ser Phe Lys Asn Gln Asp Thr Arg Pro His Thr Leu His Val Ala
            115                 120                 125

Ser His Thr Asp Val Gln Ile Arg Ser Asn Asp Arg Ala Thr Cys Lys
    130                 135                 140

Trp Tyr Tyr Gly Lys Arg Gly Leu Thr Met Lys Asp Pro Gly Thr Gly
145                 150                 155                 160

Ile Thr Leu Thr Leu Leu Ile Lys Gly Gly Tyr His Val Thr Asp Val
                165                 170                 175

Asp Thr Phe Trp Phe Gly Arg Trp Gln Gly Pro Asn Thr Asn Leu His
            180                 185                 190

Tyr Phe Asp Asn Tyr Thr Asp Ser Gly Asp Asn Asp Leu Val Asn Thr
            195                 200                 205

Asp Ser Ala Phe Ser Ile Gly Trp Leu Asn Arg His Ile Tyr Pro Asn
    210                 215                 220

Glu Thr Leu Asp Phe Ser Val Leu Leu Gly Val Gly Ala Asn Leu Lys
225                 230                 235                 240

Asn Pro Ala Val Leu Thr Val Asn Asp Asn Phe Ala Asp Asn Asn Met
                245                 250                 255

Pro Asn Gln Glu Ile Thr Val Thr Gly Thr Val Asn Asp Phe Asp Pro
            260                 265                 270

Asp Glu Asn Val Thr Val Tyr Tyr Gln Phe Asn Gly Gly Pro Glu Thr
            275                 280                 285

Lys Val Glu Thr Phe Pro Thr Gly Ala Ser Gly Gly Ile Ser Asn Gly
    290                 295                 300

Ala Phe Ser Phe Lys Val Thr Leu Gly Pro Asp Val Ala Gln Tyr Pro
305                 310                 315                 320

Leu Lys Val Tyr Ala Arg Asp Ser Phe Gly Leu Thr Ser Asn Val Phe
                325                 330                 335

Glu Lys Asn Leu Leu Val Asn Glu Ile Pro Arg Leu Val Leu Thr Arg
            340                 345                 350

Ala Pro Pro Ser Thr Phe Phe Thr Gly Thr Val Ile Leu Glu Gly
    355                 360                 365

Thr Ile Trp Asp Asp Arg Lys Ala Thr Leu Lys Tyr Gln Val Asp Asn
    370                 375                 380

Gly Tyr Asn Trp Asn Thr Gly Asp Glu Glu Phe Val Cys Asn Arg Ala
385                 390                 395                 400

```
Thr Lys Pro Phe Arg Lys Ser Phe Pro Ile Gln Glu Asp Tyr Ile Asn
                405                 410                 415
Tyr Gly His His Val Ile Lys Ile Trp Ala Gln Asp Asp Phe Gly Val
            420                 425                 430
Gln Ser Glu Pro Ile Ile Ala Glu Phe Asp Tyr Val Gln Leu His Ala
        435                 440                 445
Pro Glu Met Lys Pro Ser Gln Ala Gln Thr Ser Ile Pro Glu Val His
    450                 455                 460
Val Gly Lys Lys Phe Thr Ile Ser Gly Gln Ala Arg Asp Ile Asp Ser
465                 470                 475                 480
Gly Glu Arg Val Ser Val Tyr Tyr Lys Tyr Pro Glu Asp Thr Pro Gly
                485                 490                 495
Thr Gln Pro Arg Pro Leu Phe Thr Phe Asp Ser Asn Thr Gly Trp Gln
            500                 505                 510
Glu Trp Glu Ile Glu Tyr Glu Val Pro Asp Arg Lys Leu Pro Phe Asp
        515                 520                 525
Gln Glu Val Lys Val Ile Leu Tyr Ala Glu Asp Thr Arg Gly Gly Thr
    530                 535                 540
Ser Ala Asp Leu Glu Phe Lys Phe Ile Val Lys Lys Val Gln Thr Ile
545                 550                 555                 560
Pro Pro Thr Pro Tyr Asp Gly Glu Val Pro Pro Asn Pro Ser Asp Asn
                565                 570                 575
Pro Asn Ile Pro Asp Ser Ser Tyr Ser Gly Leu Thr Ala Thr Ser Glu
            580                 585                 590
Val Pro Thr Ile Val Cys Glu Glu His Thr Asp Val Asn Gly Asp Thr
        595                 600                 605
Tyr Thr Arg Cys Asp Leu Gly Thr Thr Tyr Ile Val Ile Thr Thr Asp
    610                 615                 620
Ala Thr Pro Ala Pro Thr Gln Ser Ala Thr Pro Ser Ala Ser Pro Glu
625                 630                 635                 640
Pro Gly Ala Phe Pro Glu Glu Asp Asn Ala Lys Glu Val Ser Ala Ser
                645                 650                 655
Lys Glu Lys Ser Asn Lys Lys Lys Met Leu Ile Ile Gly Leu Ala Ala
            660                 665                 670
Gly Gly Val Ala Ala Ala Val Val Ala Ala Ile Ile Ile His
        675                 680                 685
Glu Ala Thr Lys Ala Pro Lys Asp Phe Val Phe Asn Glu Glu Asn Gly
    690                 695                 700
Glu Phe Met Glu Val Asp Gly Asp Ala Cys Gln Asp Ala Asp Asn Pro
705                 710                 715                 720
Ile Tyr Asp Glu Asn Gly Ala Asp Asp Pro Phe Ala Asn Glu Phe Asp
                725                 730                 735
Glu Asp Asp Gly Pro Val Glu Gly Ile Phe Pro Ala
            740                 745

<210> SEQ ID NO 43
<211> LENGTH: 613
<212> TYPE: PRT
<213> ORGANISM: Trichomonas vaginalis G3

<400> SEQUENCE: 43

Met Phe Asn Leu Phe Leu Ala Thr Val Ser Ser Glu Lys Arg Pro Gln
1               5                   10                  15
Ile Glu Ala Asp Lys Val Arg Phe Gln Gly Tyr Gly Lys Phe Ser Lys
                20                  25                  30
```

```
Thr Gly His Gln Ile Ala Ile Ser Ser Asn Gln Arg Leu Tyr Tyr Tyr
        35                  40                  45

Ala Ser Val His Ile Ile Asn Ala Tyr Phe Ser Asn Cys Val Ala Asn
        50                  55                  60

Asp Leu Asn Leu Lys Trp Gln Met Ser Cys Gly Gly Ala Ile Phe Leu
65                  70                  75                  80

Asn Lys Gly Ser Leu Tyr Phe Glu Arg Lys Asp Gly Ser Tyr Ser Ser
                85                  90                  95

Ser Phe Asp Gln Cys Gln Ala Thr Asp Lys Gly Gly Ala Ile Tyr Ala
                100                 105                 110

Tyr Asp Ser Ala Cys Asp Ile Phe Gln Val Asn Phe Phe Arg Cys Lys
                115                 120                 125

Ala Gly Asn Glu Gly Gly Ala Tyr Tyr His Asp Gly Met Arg Tyr Ser
        130                 135                 140

Arg Pro Tyr Tyr Ala Asn Ala Lys Tyr Asn Thr Leu Ile Ile Glu Tyr
145                 150                 155                 160

Cys Thr Phe Lys Gly Asn Leu Ala Asp Ser Tyr Gly Gly Ala Leu Ala
                165                 170                 175

Val Lys Gly Ala Val Pro Phe Thr Leu Lys Asn Ser Lys Phe Leu Asn
        180                 185                 190

Asn Gly Ala Val Ala Gly Gly Ala Leu Tyr Gly Asp Tyr Ser Asp Ile
        195                 200                 205

Thr Met Thr Asn Asn Leu Phe Val Leu Asn Phe Gly Asp His Thr Arg
        210                 215                 220

Pro Cys Gln Asn Asn Lys Lys Cys Gly Ser Pro Asn Tyr Gln Ser Phe
225                 230                 235                 240

Lys Tyr Val Pro Ala Gly Ala Ile Leu Ile Arg Ser Ser Pro Glu Tyr
                245                 250                 255

Phe Pro Val Asp Val Tyr Ser Ala Glu Asn Cys Phe Asn Gln Asn Phe
                260                 265                 270

Leu Leu Asn Asn Arg Trp Pro Asp Lys Ser Lys Thr Ser Val Asn Ile
        275                 280                 285

Leu Leu Leu Phe Ala Val Arg Phe Lys Ser Val Asn Asp Lys Met Lys
        290                 295                 300

Trp His Thr Val Asn Val Ile Asp Asn Met Thr Leu Ala Lys Lys Phe
305                 310                 315                 320

Asn Tyr Pro Lys Glu Tyr Pro Ser Lys Tyr Ile Gln Leu Arg Ala Asn
                325                 330                 335

Gly Ile Asn Ile Arg Ser Phe Glu Met Thr Gly Thr Arg Gln Asp Val
                340                 345                 350

Glu Gly Cys Lys Ile Asp Gly Phe Pro Ala Val Thr Pro Ile Pro Pro
        355                 360                 365

Ala Thr Pro Ile Pro Thr Pro Tyr Pro Thr Val Pro Thr Pro Asp Pro
370                 375                 380

Thr Gln Pro Pro Pro Thr Arg Ser Leu Ala Thr Pro Tyr Pro
385                 390                 395             400

Thr Ile Pro Pro Arg Thr Pro Phe Pro Ser Ala Thr Ile Pro Pro
                405                 410                 415

Ala Thr Lys Lys Lys Asp Thr Pro Phe Pro Thr Leu Ala Pro Pro Gln
                420                 425                 430

Thr Pro Ala Pro Thr Pro Ser Pro Ile Pro Thr Arg Glu Pro Thr Ala
                435                 440                 445
```

```
Pro Pro Thr Ala Thr Pro Ala Ala Thr Arg Ser Ala Ile Pro Thr Pro
    450                 455                 460

Ile Ser Val Pro Pro Thr Ile Asn Ile Thr Ile Pro Ala Asn Ala Ser
465                 470                 475                 480

Val Asp Glu Glu Ile Asn Thr Ser Asp Cys Gly Glu Met Cys Lys Thr
                485                 490                 495

Glu His Ile Pro Met Arg Thr Pro Asn Ala Ile Thr Ile Asn Tyr Glu
                500                 505                 510

Ser Pro Val Pro Asn Thr Glu Asp Ser Ala Asn Asn Ala Lys Asn Ala
            515                 520                 525

Val Ile Gly Arg Asn Thr Ala Ala Pro Asp Glu Ser Ala Val Gly Phe
    530                 535                 540

Val Ile Ala Ala Val Ala Ala Val Ala Ala Val Gly Val Ile Ala Gly
545                 550                 555                 560

Ile Ile Tyr Thr Leu Thr Arg Ser Lys Pro Pro Met Asp Leu Glu
                565                 570                 575

Asn Ala Glu Arg Val Asn Met Gly Asn Asp Asn Asn Ala Val Glu Asn
                580                 585                 590

Asp Asn Pro Ile Tyr Asn Asn Asn Ala Ala Gln Asp Pro Phe Ala Asp
            595                 600                 605

Glu Phe Glu Asp Ala
            610

<210> SEQ ID NO 44
<211> LENGTH: 596
<212> TYPE: PRT
<213> ORGANISM: Trichomonas vaginalis G3

<400> SEQUENCE: 44

Met Ser Ser Asp Lys Ser Ser Arg Val Thr Ser Glu Glu Asn Ile Glu
1               5                   10                  15

Lys Thr Thr Thr Thr Gly Phe Glu Met Phe Glu Cys Leu Lys Leu Phe
                20                  25                  30

Arg Asn Lys Ala Ile Leu Phe Leu Val Tyr Phe Ile Ser Leu Gly Asn
            35                  40                  45

Gly Ala Leu Pro Ile Phe Asn Met Met Ile Leu Gly Asp Val Thr Ser
    50                  55                  60

Ser Ala Ser Thr Asp Pro Thr Lys Thr Ala Thr Lys Leu Met Thr Pro
65                  70                  75                  80

Leu Leu Leu Lys Leu Thr Tyr Ile Ser Ile Ala Gln Ala Val Ile Leu
                85                  90                  95

Leu Ile Thr Ile Met Cys Lys Ser Tyr Ile Ile Pro Thr Phe Thr Val
                100                 105                 110

Asp Ile Arg Gln Ala Met Phe Asn Ser Ile Met Thr Gln Pro Ile Asp
            115                 120                 125

Phe Phe Asp Lys Thr Ser Ser Gly Val Leu Met Gly Arg Phe Ser Glu
    130                 135                 140

Asp Ile Thr Ile Ile Arg Asp Val Tyr Ile Glu Lys Asn Cys Ala Met
145                 150                 155                 160

Leu Gln Gly Met Thr Met Ser Leu Ile Ala Ile Met Gly Phe Ile
                165                 170                 175

Arg Leu Pro Tyr Val Ser Leu Ser Tyr Phe Val Ala Ile Pro Leu Leu
            180                 185                 190

Val Ala Ser Tyr Ile Leu Ser Glu Lys Tyr Ile Asp Lys Leu Trp Lys
    195                 200                 205
```

```
Asn His Asn Ile Gln Ser Thr Ser Ile Ala Ser Lys Thr Glu Glu Val
    210                 215                 220

Ile Ser Gln Tyr Arg Thr Val Lys Ala Phe Asp Cys Glu Lys Lys Glu
225                 230                 235                 240

Cys Asp Asp Tyr Asn Asp Leu Leu Asp Asn Val Asp Asp Ile Tyr Arg
                245                 250                 255

Lys Thr Ala Ile Ala Gln Gly Leu Lys Glu Ala Phe Ser Ser Ile Ile
                260                 265                 270

Ala Asn Gly Leu Thr Val Phe Val Tyr Phe Ile Ala Tyr Leu Met
                275                 280                 285

Met Val Lys Lys Asn Thr Lys Val Lys Ser Gly Asp Ser Leu Ser Met
290                 295                 300

Met Met Tyr Ile Met Leu Gly Thr Met Gly Phe Ser Gln Ile Leu Ser
305                 310                 315                 320

Ala Ser Asp Ser Tyr Lys Lys Ala Asn Met Ala Ala Leu Lys Ile Leu
                325                 330                 335

Asn Ile Ile Asn Arg Lys Val Glu Asn Asp Ser Glu Asn Gln Thr Glu
                340                 345                 350

Ile Gly Lys Ile Glu Gly Lys Ile Glu Phe Gln Asn Val Ser Phe Lys
                355                 360                 365

Tyr Ser Thr Arg Asp Glu Tyr Ala Ile Arg Asn Leu Thr Phe Glu Ile
370                 375                 380

Lys Pro Gly Glu Thr Val Ala Leu Val Gly Glu Ser Gly Cys Gly Lys
385                 390                 395                 400

Thr Thr Thr Leu Ser Leu Leu Gln Arg Phe Tyr Asp Val Ser Glu Gly
                405                 410                 415

Lys Ile Leu Ile Asp Gly Lys Asp Ile Ser Asn Phe Ser Ala Ser Ser
                420                 425                 430

Leu Arg Ser Gln Ile Ser Cys Val Pro Gln Ser Pro Val Leu Phe Ser
                435                 440                 445

Met Ser Ile Leu Asp Asn Val Lys Tyr Gly Lys Pro Glu Ser Ser Phe
                450                 455                 460

Asp Glu Val Lys Thr Ala Ala Glu Ile Gly Asn Ala His Asn Phe Ile
465                 470                 475                 480

Cys Gln Met Glu Asn Gln Tyr Asp Gln Glu Val Gln Gln Ile Ser Leu
                485                 490                 495

Ser Gly Gly Gln Lys Gln Arg Ile Cys Ile Ser Arg Ala Val Leu Cys
                500                 505                 510

Asn Ala Pro Ile Leu Leu Leu Asp Glu Ala Thr Ala Ser Leu Asp Ala
                515                 520                 525

Glu Ser Glu Gln Leu Val Gln Glu Ser Leu Glu Lys Val Arg Lys Gly
                530                 535                 540

Lys Thr Ala Ile Ile Val Ala His Arg Leu Ser Thr Val Lys Asn Ala
545                 550                 555                 560

Asp Arg Ile Leu Val Phe Asp Asn Gly Thr Ile Val Glu Thr Gly Thr
                565                 570                 575

His Glu Glu Leu Leu Glu Lys Gly Gly Ile Tyr Ser Asn Leu Val Lys
                580                 585                 590

Phe Gln Leu Gln
            595

<210> SEQ ID NO 45
<211> LENGTH: 846
```

<212> TYPE: PRT
<213> ORGANISM: Trichomonas vaginalis G3

<400> SEQUENCE: 45

```
Met Tyr Leu Gly Phe Leu Ile Ser Phe Ala Ser Ser Asn Gln Asn Lys
1               5                   10                  15

Pro Val Leu Glu Asn Cys Asn Tyr Tyr Ser Thr Tyr Asn Tyr Ser Cys
            20                  25                  30

Ala Thr Ile Pro Ser Gly Met Asn Tyr Ile Asp Gly Leu Leu Arg Cys
        35                  40                  45

Asn Ser Ser Ser Gln Val Ile Asp Leu Thr Ser Asp Glu Met Thr Cys
    50                  55                  60

Ile Asp Tyr Ala Ser Gly Thr Lys Val Leu Tyr Asp Thr Ala Val Val
65                  70                  75                  80

Ser Glu Asn Thr Thr Gly Leu Ser Lys Met Ile Val Phe Phe Asp
                85                  90                  95

Gln Ser Asp Lys Phe Ser Ser Arg Leu Ser Thr Asp Tyr Gly Asn Leu
            100                 105                 110

Leu Asp Asp Ala Val Lys Ala Cys Lys Ser Asn Tyr Ala Gln Met Tyr
        115                 120                 125

Thr Pro Cys Gln Ile Val Ala Ser Gly Cys Ala Leu Ser Ser Tyr Tyr
    130                 135                 140

Pro His Ser Pro Ala Cys Ile Ala Tyr Asn Ala Leu Pro Ala Ala Asn
145                 150                 155                 160

Ser Thr Thr Tyr Glu Tyr Lys Tyr Trp Pro Ala Asn Arg Pro Phe Ile
                165                 170                 175

Glu Tyr Gly Val Gln Ala Ser Lys Val Ile Asp Glu His Ile Met Asn
            180                 185                 190

Thr Thr Phe Ser Lys Glu Glu Gln Ile Asn Ile Val Leu Ala Arg Tyr
        195                 200                 205

Ser Gln Asn Gly Thr Phe Leu Gly Tyr Val Pro Leu Thr Asn Gln Phe
    210                 215                 220

Asp Ile Cys Thr Glu Lys Arg Asp Val Asn Leu Met Trp Gln Leu Tyr
225                 230                 235                 240

Gly Thr Gly Tyr Val Ser Glu Cys Glu Val Asn Ile Met Asp Ile Phe
                245                 250                 255

Asn Ser Thr Thr Thr Asp Val Tyr Asp Pro Phe Leu Val Gln Glu Val
            260                 265                 270

Ser Gly Thr Asn Val Leu Arg Pro Ile Pro Val Asn Val Leu Ser Tyr
        275                 280                 285

Arg Asp Ala Asn Glu Ile Pro Val Asn Gln Arg Ser Ile Glu Arg Lys
    290                 295                 300

Lys Arg Leu Phe Arg Arg Phe Ala Leu Asp Asn Tyr Thr Asn Pro
305                 310                 315                 320

Ile Phe Ile Gln Tyr Leu Ser Ser Met Ser Ile Lys Phe Glu His Phe
                325                 330                 335

Asn Glu Thr Ser Glu Glu Arg Ile Pro Val Ile Thr Val Gly Tyr Thr
            340                 345                 350

Thr Val Arg Arg Ser Asp Leu Gln Glu Ser Asp Tyr Pro Ile Tyr Leu
        355                 360                 365

Asp Val Glu Ser Phe Thr Thr Ser Asn Tyr Ser Phe Ser Ile Glu Phe
    370                 375                 380

Ser Thr Asn Ile Glu Ser Tyr Trp Glu Ala Ala Leu Ile Thr Leu Ile
385                 390                 395                 400
```

```
Val Leu Ala Ile Ile Cys Ile Ile Ile Trp Leu Tyr Arg Ala Val Val
                405                 410                 415

Thr Val Lys Arg Tyr Gly Thr Glu Gly Ile Asp Phe Lys Val Ile Ala
                420                 425                 430

Ala Leu Phe Ala Glu Ala Phe Asn Ile Val Ala Trp Leu Leu Phe Ile
                435                 440                 445

Met Ala Phe Val Phe Ser Phe Ala Ile Phe Cys Ala Tyr Lys Trp Thr
            450                 455                 460

Pro Ser Ser Lys Tyr Thr Ile Leu Gly Asn Glu Phe Gly Ile Leu Thr
465                 470                 475                 480

Gly Phe Ile Trp Ala Ala Trp Val Leu Ser Phe Ile Gly Leu Val Ile
                485                 490                 495

Lys Tyr Val Leu Met Leu Thr Ser Thr Phe Leu Ile Asp Trp Glu
                500                 505                 510

Pro Arg Arg Pro Ser Ile Pro Val Ser Ala Trp Arg Arg Ile Leu Val
                515                 520                 525

Gly Asn Glu Phe Leu Lys Leu His Thr Arg Arg Ser Tyr Asn Ile Pro
                530                 535                 540

Phe Thr Val Ile Thr Leu Val Phe Ile Leu Gly Gly Phe Gly Val Asp
545                 550                 555                 560

Lys Leu Gln Ala Val Leu Pro Ser Ser Thr Leu Ile Glu Ser Gly Ser
                565                 570                 575

Asn Tyr Gly Val Leu Arg Phe Ala Ile Val Thr Phe Ile Tyr Ile Leu
                580                 585                 590

Leu Leu Ile Phe Gln Tyr Ile Val Thr Arg Ile Val Trp Leu Ile Ser
                595                 600                 605

Gly Ser Pro Tyr Glu Asp Phe Ala Arg Leu Cys Gly Thr Ala Asn Val
                610                 615                 620

Ser Val Leu Thr Leu Leu Ser Pro Ser Trp Ala Ile Tyr Leu Asn Gly
625                 630                 635                 640

Arg Ala Met Lys Pro Ala Asp Glu Gly Asp Ile Lys Leu Ile Gln Ser
                645                 650                 655

Ile Ser Glu Ala Glu Lys Gly Ala Leu Ser Ile Lys Pro Leu Ser Glu
                660                 665                 670

Asn Arg Pro Glu Gln Val Tyr Glu Cys Phe Phe Ala Pro Lys Leu Arg
                675                 680                 685

Glu Pro Leu Tyr Gln Ala Tyr Asp Arg Ile Val Glu Met His His Met
                690                 695                 700

Arg Pro Lys Asn Leu Lys Arg Ala Asn Thr Ser Ile Val Ser Leu Glu
705                 710                 715                 720

Ala Met Ser Ser Phe Glu Gln Leu Asn Val Phe Leu Gln Arg Phe Phe
                725                 730                 735

Gly Ala Glu Gly Lys Asp Arg Glu Tyr Asp Val Trp Lys Thr Pro Phe
                740                 745                 750

Gly Tyr Lys Leu Ser Arg Met Pro Pro Glu Pro Pro Glu Arg Ser Leu
                755                 760                 765

Leu Tyr Ala Gln Ser Thr Asn Ser Leu Arg Lys Ala Ile Asp Gly Tyr
                770                 775                 780

Gly Glu Trp Leu Leu Ala Leu Phe Asp Leu Leu Leu Phe Val Cys Val
785                 790                 795                 800

Asp Tyr Gln Ala Ser Ser Thr Pro Ile Ala Ala Phe Val Thr Leu Ile
                805                 810                 815
```

Ile Asp Ala Val Met Met Ala Ala Trp Arg Ser Ala Ala Lys Arg Asn
            820                 825                 830

Leu Ala Arg Lys Ser Leu Ile Asp Asn Arg Phe Phe Leu Asn
            835                 840                 845

<210> SEQ ID NO 46
<211> LENGTH: 454
<212> TYPE: PRT
<213> ORGANISM: Trichomonas vaginalis G3

<400> SEQUENCE: 46

Met Gly Glu Asp Val Ser Glu Val Asp Glu Gln Ser Pro Lys Ser Asn
1               5                   10                  15

Leu Leu Lys Trp Ile Phe Ile Ala Val Ala Val Val Val Ile Val
            20                  25                  30

Ile Ile Val Thr Val Thr Val Val Leu Val Leu Lys Lys Lys Arg Asn
            35                  40                  45

Glu Lys Tyr Pro Gly Phe Leu Tyr Leu Asn Asp Ile His Ile Asp Leu
        50                  55                  60

Ser Tyr Asn Pro Lys Ser Asn Lys Asp Trp Cys His Ser Gln Thr Asn
65                  70                  75                  80

Asn Leu Leu Glu Ser Trp Glu Phe Gly Gln Tyr Asn Cys Asp Pro Pro
                85                  90                  95

Pro Lys Leu Tyr Asp Ser Leu Val Glu Ser Leu Lys Thr Asn Val Pro
            100                 105                 110

Ser Val Asp Phe Ile Leu Leu Gly Gly Asp Leu Pro Ser His Asp Leu
        115                 120                 125

Gly Gly Asn Tyr Thr Phe Leu Lys Glu His Phe Arg Leu Ile Thr Asp
130                 135                 140

Pro Leu Glu Lys Leu Tyr Pro Asn Lys Lys Ile Phe Ile Thr Leu Gly
145                 150                 155                 160

Asn Asn Asp Phe Gln Glu Asn Tyr Gly Ser Phe Lys Thr Asp Leu Lys
                165                 170                 175

Asp Phe Glu Asn Ala His Glu Val Phe Gly Lys Trp Met Asn Glu Glu
            180                 185                 190

Gln Ser Lys Thr Phe Lys Lys Gly Gly Tyr Tyr Glu Asp Met Pro
        195                 200                 205

Glu Leu Lys Leu Arg Leu Leu Leu Asn Thr Val Met Tyr Thr Asn
210                 215                 220

Thr Lys Ser Arg Val Phe Asn Glu Ser Leu Lys Asp Pro Tyr Asp Gln
225                 230                 235                 240

Phe Ala Trp Ile Arg Gln Thr Tyr Lys Glu Gly Val Asp Lys Gly Tyr
                245                 250                 255

Lys Val Gly Val Ala Leu His Val Pro Pro Gly Ile Val Tyr Tyr Lys
            260                 265                 270

Gly Ile Pro Gly Phe Pro Ser Met Tyr Leu Glu Glu Phe Gly Lys Val
        275                 280                 285

Phe Glu Glu Cys Asp Phe Ser Phe Thr Ile Ser Gly His Ser His Ile
290                 295                 300

Asp Thr Leu Asn Pro Leu Tyr Lys Ala Asn Val Glu Glu Asp Asn Ile
305                 310                 315                 320

Gln Tyr Ser Leu Ser Ala Val Ser Val Ser Pro Ser His Tyr Asn Asn
                325                 330                 335

Pro Gly Tyr Arg Tyr Phe Glu Ile Lys Asp Gly Val Leu Gln Asp Tyr
            340                 345                 350

```
Thr Gln Phe Tyr Ala Asp Ile Met Met Asn Pro Asp Ser Pro Lys Trp
            355                 360                 365

Glu Val Glu Tyr Lys Phe Arg Asp Ala Tyr Lys Val Lys Asp Leu Ser
        370                 375                 380

Lys Lys Ser Leu Asn Asp Ala Thr Arg Tyr Ile Arg Ser Lys Gly Ser
385                 390                 395                 400

Val Ile Trp Ser Tyr Arg Gly Tyr Ile Tyr Ser Gln Ala Glu Lys Tyr
                405                 410                 415

Asn Pro Phe Phe Tyr Cys Ala Leu Arg Ala Leu Thr Lys Glu Asp Val
            420                 425                 430

Phe Lys Cys Ser Leu Asp Leu Asn Val Asn Leu Ser Ser Ile Met Pro
        435                 440                 445

Tyr Ser Asn Arg Gly Asp
    450

<210> SEQ ID NO 47
<211> LENGTH: 1576
<212> TYPE: PRT
<213> ORGANISM: Trichomonas vaginalis G3

<400> SEQUENCE: 47

Met Asn Pro Ser Glu Ser Ser Val Ser Lys Ser Thr Ser Ser Val Ser
1               5                   10                  15

Ser Ile Gly Val Asn Lys Asp Ser Val Ile Gln Gly Lys Tyr Ser Leu
            20                  25                  30

Ser Asp Gln Ile Phe Pro Val Tyr Asp Gln Met Met Gln Lys Ala Ile
        35                  40                  45

Leu Pro Lys Trp Phe Leu Ala Phe Val Ala Phe Tyr Ile Met Leu Gln
    50                  55                  60

Ile Leu Ile Ile Ala Phe Trp Val Tyr Thr Glu Pro Phe Leu Arg Ile
65                  70                  75                  80

Asn Ser Lys Tyr Ser Lys Phe Phe Glu Ile Phe Leu Lys Val Phe Ile
                85                  90                  95

Tyr Gly Asp Ala Ile His Tyr Thr Glu Val Lys Gly Leu Asn Met Tyr
            100                 105                 110

Arg Thr Leu Ile Val Ser Leu Phe Ala Phe Phe Trp Val Phe Phe Val
        115                 120                 125

Ile Tyr Tyr His Lys Leu Lys Tyr Ser Ile Pro Val Pro Leu Leu Tyr
    130                 135                 140

Ile Thr Ser Leu Ile Val Asp Ile Leu Val Pro Val Phe Ile Thr Pro
145                 150                 155                 160

Ser Ala Tyr Val Ala Cys His Gly Ile Val Asn Leu Lys Tyr Ala His
                165                 170                 175

Asn Ser Thr Ile Ile Gly Glu Ile Ile Gly Phe Ile Ser Tyr Gly
            180                 185                 190

Ile Thr Leu Met Asn Phe Ser Ile Thr Thr Leu Lys Ala Arg Ser
        195                 200                 205

Val Ala Leu Thr Asn Leu Thr Phe Pro Leu Phe Asp Ser Ser Ser Ile
    210                 215                 220

Val Val Trp Thr Ile Ser Thr Thr Leu Cys Cys Ile Leu Ser Ala Ile
225                 230                 235                 240

Leu Thr Tyr Phe Glu Asn Trp Thr Gln Ile Ile Val Ile Val Ile His
                245                 250                 255

Ala Ile Ile Ser Cys Tyr Leu Cys Tyr Arg Leu Leu Phe Ile Pro Phe
```

```
                260                 265                 270
Tyr Asp Leu Tyr Arg Asn Ala Ser Val Leu Ala Phe Ala Ile Thr Ser
            275                 280                 285
Ile Val Leu Asp Ile Tyr Ser Ile Leu Met Gln Leu Ile Lys Ser Ile
            290                 295                 300
Pro Tyr Glu Tyr Ile Pro Phe Ile Leu Ile Gly Ser Leu Ile Ile Ser
305                 310                 315                 320
Phe Ile Phe Ala Ser Ile Phe Tyr Lys Arg Lys Val Lys Gln Ile Lys
                325                 330                 335
Glu Asp Leu Thr Phe Arg Thr Asp Asn Pro Lys Ala Pro Glu Tyr Leu
            340                 345                 350
Ala Ser Leu Asn Ile Asp Ser Thr Gln Leu Arg Ala Met Glu Tyr Ile
            355                 360                 365
Val Val Gly Leu Thr Gln Ile Cys Asp Tyr Phe Val Asp Gly Ser Leu
            370                 375                 380
Thr Asp Tyr Ile Ile Lys Val Asp Glu Phe Glu Gly Ile Leu Ala Ile
385                 390                 395                 400
Leu Leu Gln Val Val Thr Phe Phe Pro Cys Glu Ser Arg Lys Met Asp
                405                 410                 415
Val Leu Tyr Lys Lys Leu Ile Met Lys Arg Lys Leu Ser Phe Ala Asp
                420                 425                 430
Arg Phe Leu Leu Tyr Gln Val Tyr Arg Ile Lys Thr Arg Arg Leu Val
            435                 440                 445
Thr Asp Thr Lys Ser Thr Leu Glu Thr Tyr Thr Lys Leu Lys Ala Arg
            450                 455                 460
Asn Asp Glu Cys Lys Gln Ser Ile Arg Ser Phe Trp Asp Phe Pro Ser
465                 470                 475                 480
Cys Lys Ile Asn Tyr Leu Ser Ser Leu Ser Ile Thr Val Asn Asp Ile
                485                 490                 495
Asn Ser Leu Phe Ile Asn Thr Ile Gln Glu Asn Pro Asn Asn Val Arg
            500                 505                 510
Ile Ala Thr Glu Tyr Ser Asp Phe Leu Ile Glu Cys Met Thr Asn Phe
            515                 520                 525
Asp Glu Ala Ile Arg Gln Lys Val Lys Val Glu Arg Ile Leu Asn Gly
            530                 535                 540
Thr Asn Phe Asn Val Asp Ile Ser Phe Arg Ser Leu Val Asn Lys Phe
545                 550                 555                 560
Pro Arg Tyr Leu Lys Asp Lys Ile Leu Asp Thr Lys Gly Arg Leu Ile
                565                 570                 575
Met Arg Leu Lys Glu Arg Asn Ser Asp Pro Leu Asn Asp Asn Ser Ser
            580                 585                 590
Asn Gln Ser Lys Ser Gly Ser Ser Lys Glu Thr Asn Thr Ser Thr
            595                 600                 605
Leu Thr Val Asp Leu Glu Thr Gln Glu Val Val Ser Lys Arg Val Leu
            610                 615                 620
Arg Asp Ser Lys Val Arg Leu Ala Phe His Gln Ser Ile His Thr Leu
625                 630                 635                 640
His Pro His His Met Lys Asn Leu Thr Ile Leu Ala Asn Ser Ile Leu
                645                 650                 655
Val Val Cys Phe Ser Ile Phe Ile Ala Tyr Tyr Ala Tyr Gln Lys Asp
                660                 665                 670
Lys Leu Lys Trp Arg Arg Asp Ala Phe Val Glu Phe Arg Tyr Met Ser
            675                 680                 685
```

-continued

```
Leu Ala Leu Asp Lys Thr Tyr Tyr Ala Ser Phe Val Leu Thr Leu Glu
    690             695                 700

Trp Ala Arg Met His Asp Arg Tyr Asp Asn Ser Thr Glu Ile Met Gly
705             710                 715                 720

Asn Ile Ser Ile Asp Phe Glu Asp Asn Pro Ile Ala Lys Asn Lys Trp
                725                 730                 735

Glu Pro Ala Tyr Glu Thr Ile Tyr Gln Thr Val Asp Gln Ala Lys Asp
                740                 745                 750

Phe Leu Glu Thr Leu Tyr Gln Ser Met Ala Asp Ser Ala Arg Thr Glu
        755                 760                 765

Asp Ile Tyr Glu Ile Ile Pro Leu Leu Leu Lys Pro Arg Ser Lys Ile
770                 775                 780

Tyr Ala Cys Thr Asn Tyr Glu Ile Ser His Asp Met Pro Gly Asn Leu
785                 790                 795                 800

Lys Asp Gln Phe Val Ile Ile His Phe Phe Gln Asp Asn Phe Ala Gly
                805                 810                 815

Asp Phe His Val Met Asp Lys Asp Ile Pro Asn Ile Tyr Gln Asn Asp
                820                 825                 830

Phe Tyr Cys Gln Leu Phe Ala Asn Ser Tyr Ile Leu Ser Lys Asn Ala
        835                 840                 845

Glu Glu Ser Ile Glu Asn Ile Leu Asp Tyr Ser Val Glu Lys Ser Gln
850                 855                 860

Lys Leu Ile Asp Asp Val Trp Leu Trp Thr Gly Ile Gly Gly Gly Ile
865                 870                 875                 880

Val Leu Phe Val Thr Phe Ile Pro Met Ile Ile Ile Ile Asn Tyr
                885                 890                 895

Tyr Lys Ile Val Asn Gly Leu Leu Lys Val Leu Leu Glu Leu Pro Asn
        900                 905                 910

Ser Ala Lys Glu Asp Ala Lys Lys Arg Leu Asn Ile Glu Asn Thr Asp
        915                 920                 925

Glu Ile Val Glu Thr Ser Asn Lys Thr Lys Lys Ser Lys Leu Leu Glu
    930                 935                 940

Ile Ser Ile Phe Ile Tyr Phe Ala Ser Ala Ala Leu Ile Thr Val Leu
945                 950                 955                 960

Tyr Cys Leu Ser Gly Leu Tyr Thr Tyr Tyr Phe Asn Asp Leu Met Ala
                965                 970                 975

Asn Leu Leu Asp Trp Tyr Tyr Ile Ser Cys Val Arg Asn Val Ala Ser
                980                 985                 990

Ser Glu Leu Arg Asn Asn Ile Leu  His Ile Ile Leu Leu  Asn Asp Ser
            995                 1000                1005

Leu Pro  Asn Lys Ile Ile Pro  Leu Glu Asp Ile Tyr  Gln Ala Ala
    1010                1015                1020

Leu Asp  Glu Ile Asp Leu Leu  Lys Arg Tyr Asn Gln  Tyr Leu Ile
    1025                1030                1035

Glu Gly  Gly Asn Asn Phe Glu  Arg Phe Ile Gly Phe  Asp Ala Glu
    1040                1045                1050

Ser Asp  Ser Tyr Gln Phe Met  Glu Val Cys Glu Leu  Gly Arg Asp
    1055                1060                1065

Pro Lys  Ser Met His Asp Met  Tyr Ala Cys Ser Ser  Ile Asp Lys
    1070                1075                1080

Gln Ile  Ala Phe Leu Thr Thr  Asn Val Arg Asp Ile  Met Lys Asn
    1085                1090                1095
```

-continued

Pro Asp Lys Leu Ser Gly Ala Ile Asn Asp Glu Val Thr Gln Asn
1100                1105                1110

Val Met His Leu Ile Asn Asn His Phe Tyr Pro Leu Thr Val Leu
1115                1120                1125

Ala Ala Thr Arg Val Lys Ser Leu Leu Gln Asp Asn Phe Asp Ala
1130                1135                1140

Gly Met Lys Lys Leu Thr Ile Tyr Leu Val Ile Glu Leu Leu Ile
1145                1150                1155

Ser Leu Phe Leu Phe Ile Leu Pro Leu Phe Ile Arg Ala Val Ile
1160                1165                1170

Trp Glu Asn Tyr Lys Met Leu Leu Met Leu Leu Lys His Leu Pro
1175                1180                1185

Pro Gln Val Ile Ile Asp Thr Pro Glu Ile Leu Asp Phe Phe Arg
1190                1195                1200

Glu Lys Ser Lys His His His Thr Glu Ala Met Thr Ile Ser Lys
1205                1210                1215

Ser Val Val Tyr Asn Thr Ser Glu Cys Ile Ala Ile Thr Asn Gln
1220                1225                1230

Asn Ala Ile Ile Glu Ile Val Asn Gln Ser Leu Thr Ala Asn Ile
1235                1240                1245

Asn Ile Thr Pro Asp Gln Ile Leu Gly Gln Ser Ile Thr Asn Ile
1250                1255                1260

Ile Ser Leu Ser Glu His Asp Arg Ile Gly Asn Gln Ile Gln Leu
1265                1270                1275

Met Thr Thr Gly Gln Gly Ser Ser Val Trp Gln Asp His Thr Lys
1280                1285                1290

Leu Val Lys Asp Asp Gly Ser Glu Val Pro Phe Gly Ile Thr Ile
1295                1300                1305

Ile Gly Met Lys Glu Asn Glu Gly Ser Ala Asp Ile Thr Ser Leu
1310                1315                1320

Val Phe Ile Leu Glu Asn Glu Glu Lys Ile Lys Gln Lys Lys
1325                1330                1335

Leu Ala Glu Glu Ser Lys Ala Lys Ser Glu Lys Leu Leu Tyr Gln
1340                1345                1350

Ile Leu Pro Lys Asp Ile Val Val Arg Leu Asn Arg Gly Glu Thr
1355                1360                1365

Asp Ile Ser Phe Thr Ile Pro Ser Ala Thr Ile Phe Phe Ile Asp
1370                1375                1380

Ile Val Lys Phe Ser Ser Tyr Ala Glu Leu Leu Thr Pro Ser Glu
1385                1390                1395

Ile Met Ala Asn Leu Ser Leu Val Phe Ala Thr Phe Asp Gly Ile
1400                1405                1410

Val Ser Glu Phe Gln Ser Ile Thr Lys Ile Lys Leu Ile Gly Asp
1415                1420                1425

Val Tyr Met Ala Ala Ala Gly Leu Phe Gln Asp Pro Lys Glu Glu
1430                1435                1440

Ser Lys Gln His Ala Glu Asp Ala Val Arg Cys Cys Leu Lys Cys
1445                1450                1455

Ala Lys Ser Met Glu Glu Ile Asn Met Lys Leu Asn Ala Ser Leu
1460                1465                1470

Glu Val Arg Ile Gly Cys Asn Ser Gly Gly Pro Leu Ile Gly Gly
1475                1480                1485

Val Leu Gly Thr Asp Lys Pro Thr Phe Asp Ile Ile Gly Asp Thr

```
                    1490                1495                1500

Ile Asn Val Ala Ala Arg Leu Gln Ser Thr Asp Ile Pro Gly Asn
1505                1510                1515

Val Gln Ile Ser Ala Ser Thr Lys Glu Met Ile Glu His Leu Asp
1520                1525                1530

Phe Val Ile Glu Glu Arg Gly Leu Ile Tyr Leu Lys Gly Lys Gly
1535                1540                1545

Lys Gln Met Thr Tyr Phe Val Ser Phe Lys Asn Asn Asp Gly Asn
1550                1555                1560

Lys Ser Ser Phe Asp Ser Ser Phe Thr Leu Lys Leu Asn
1565                1570                1575

<210> SEQ ID NO 48
<211> LENGTH: 370
<212> TYPE: PRT
<213> ORGANISM: Trichomonas vaginalis G3

<400> SEQUENCE: 48

Met Phe Arg Gln Leu Leu Ala Gly Ser Leu Pro Thr Asp Met Ile Val
1               5                   10                  15

Pro Asn Phe Thr His Val Tyr Pro Glu Cys Asp Lys Lys Leu Glu Lys
            20                  25                  30

Thr Met Asn Phe Thr Thr Leu Tyr Thr Lys Glu Leu Glu Ala Gly Glu
        35                  40                  45

Ile Ile Cys Phe Tyr Lys Thr Tyr Ala Ile Ala Gly Asn Ala Ala Tyr
    50                  55                  60

Thr Val Asn Ala Thr Tyr Phe Asn Pro Glu Asn Thr Ser Ile Tyr Glu
65                  70                  75                  80

Thr Lys Phe Ala Glu Ser Pro Phe Leu Val Ser Gly Pro Ile Ser Pro
                85                  90                  95

Lys Val Ile Pro Val Ser Lys Val Ala Cys Lys Asp Ser Ser Lys Lys
            100                 105                 110

Cys Lys Ile Gln Phe Ile Ser Ile Thr Pro Ser Gly His Gln Lys Leu
        115                 120                 125

Glu Glu Ser Asp Leu Tyr Val Asp Asn Ile Phe Asp Ser Tyr Leu Ser
    130                 135                 140

Thr Lys Lys Lys Gln Ser Phe Ser Lys Ser Tyr Ser Met Glu Phe His
145                 150                 155                 160

Ile Ser Ser Lys Asn Asn Lys Val Lys Arg Val Met Asn Ser Ser Thr
                165                 170                 175

Phe Ile Ser Thr His Ile Gly Ser Lys Ser Arg Thr Ile Thr Val Ser
            180                 185                 190

Pro Asp Ser Leu Tyr Val Phe Ala Asp Gly Lys Lys Gln Glu Lys Asn
        195                 200                 205

Thr Gly Thr Gly Lys Ala Leu Ser Phe Ala Pro Ser Gln Glu Phe Ser
    210                 215                 220

Leu Ser Leu Val Asn Met Ser Glu Leu Gln Thr Lys Ile Gln Thr Asp
225                 230                 235                 240

Lys Lys Asp Gly Lys Ile Asn Asp Ser Tyr Lys Ile Asp Lys Lys Gly
                245                 250                 255

Ser Gln Thr Ile Thr Val Ser Ile Ser Glu Pro Lys Ser Ser Ser Glu
            260                 265                 270

Asp Glu Glu Phe Phe Asp Glu Asp Lys Glu Tyr Tyr Leu Lys Gly
        275                 280                 285
```

```
Asp Ala Ser Leu Lys Ser Lys Glu Val Glu Asp Thr Lys Glu
    290                 295                 300

Asn Pro Pro Gly Ser Ser Phe Pro Ala Trp Glu Ile Ala Val Ile
305                 310                 315                 320

Val Ile Val Ile Ile Leu Ile Ile Val Ile Ile Ile Ile Ile Phe
                    325                 330                 335

Cys Cys Cys Cys Cys Cys Ser Cys Cys Ser Cys Lys Lys Gly Ser
                340                 345                 350

Ser Asn Val Gly Ser Ala Lys Asp Asp Glu Asp Ser Gly Ser Gly Val
        355                 360                 365

Asn Val
    370

<210> SEQ ID NO 49
<211> LENGTH: 567
<212> TYPE: PRT
<213> ORGANISM: Trichomonas vaginalis

<400> SEQUENCE: 49

Met Leu Ala Ser Ser Val Ala Ala Pro Val Arg Asn Ile Cys Arg Ala
1               5                   10                  15

Lys Leu Pro Ala Leu Lys Thr Gly Met Thr Leu Leu Gln Asp Gly Asp
            20                  25                  30

Leu Ser Lys Gly Ser Ala Phe Thr Lys Glu Glu Arg Asp Arg Leu Asn
        35                  40                  45

Leu Arg Gly Leu Leu Pro Tyr Lys Val Phe Thr Lys Asp Glu Gln Ala
    50                  55                  60

Ala Arg Ile Arg Arg Gln Phe Glu Leu Met Pro Thr Pro Leu Leu Lys
65                  70                  75                  80

Tyr Ile Phe Leu Ala Asn Glu Arg Glu Lys Asn Ser Gln Ser Phe Trp
                85                  90                  95

Arg Phe Leu Phe Thr His Pro Pro Thr Glu Thr Met Pro Val Leu Tyr
            100                 105                 110

Thr Pro Thr Val Gly Glu Ala Cys Gln Lys Trp Ala Thr His Arg Gln
        115                 120                 125

Ser Tyr Arg Gly Ile Tyr Ile Thr Pro Glu Asp Ser Gly Lys Ile Lys
    130                 135                 140

Asp Ile Leu Arg Asn Tyr Pro Arg Gln Asp Ile Arg Cys Ile Val Val
145                 150                 155                 160

Thr Asp Gly Gly Arg Ile Leu Gly Leu Gly Asp Leu Gly Ala Ser Gly
                165                 170                 175

Leu Gly Ile Pro Val Gly Lys Leu Met Leu Tyr Thr Leu Ile Gly Gln
            180                 185                 190

Val His Pro Asp Gln Thr Leu Pro Val Gln Leu Asp Met Gly Thr Asp
        195                 200                 205

Arg Lys Glu Ile Leu Ala Asp Pro Leu Tyr His Gly Trp Arg His Pro
    210                 215                 220

Arg Ile Arg Gly Pro Glu His Thr Lys Phe Val Ala Glu Phe Val Asp
225                 230                 235                 240

Ala Val Lys Glu Val Phe Gly Glu Thr Cys Leu Val Gln Phe Glu Asp
                245                 250                 255

Phe Glu Met Glu Thr Ala Phe Lys Leu Leu Asp His Phe Arg Trp Arg
            260                 265                 270

Cys Asn Cys Phe Asn Asp Asp Ile Glu Gly Thr Ala Ala Val Ala Ala
        275                 280                 285
```

```
Ala Thr Leu Ala Ser Ala Thr His Met Glu Gly Val Pro Asp Leu Lys
        290                 295                 300

Asn Gln Lys Ile Ile Phe Ile Gly Ala Gly Ser Ala Ala Thr Gly Ile
305                 310                 315                 320

Ala Asn Leu Ile Val Asp Met Ala Val Ser Arg Gly Gly Ile Ser Arg
                325                 330                 335

Lys Asp Ala Glu Arg Asn Ile Ile Met Phe Asp His Lys Gly Met Val
            340                 345                 350

His Ala Asp Arg Lys Asp Leu Tyr Asp Phe Asn Lys Pro Tyr Met His
        355                 360                 365

Asp Met Glu Val Tyr Gly Ser Val Leu Glu Gly Val Lys Lys Phe Lys
    370                 375                 380

Ala Thr Cys Val Ile Gly Val Ser Gly Val Pro Gly Leu Ile Thr Lys
385                 390                 395                 400

Glu Ile Val Gln Ala Thr Cys Ala Asn Cys Glu Arg Pro Val Ile Met
                405                 410                 415

Pro Leu Ser Asn Pro Thr Val Lys Ala Glu Ala Lys Pro His Asp Val
            420                 425                 430

Tyr Gln Trp Ser Asn Gly Lys Ala Leu Cys Ala Thr Gly Ser Pro Phe
        435                 440                 445

Pro Val Glu Thr Val Asn Gly Lys Lys Thr Ile Thr Ala Gln Ala Asn
    450                 455                 460

Asn Ser Trp Ile Phe Pro Ala Val Gly Tyr Ala Leu Val Thr Thr Arg
465                 470                 475                 480

Ala Arg His Cys Pro Gly Lys Val Phe Glu Val Ala Ala Glu Ser Leu
                485                 490                 495

Ala Ser Leu Val Lys Lys Glu Asp His Asp Met Gly Asn Leu Leu Pro
            500                 505                 510

Pro Leu Asp Lys Ile Arg Glu Tyr Ser Phe Gly Ile Ala Leu Asp Val
        515                 520                 525

Ala Lys Tyr Leu Ile Lys Asn Glu Leu Ala Thr Ala Leu Pro Pro Lys
    530                 535                 540

Gly Thr Glu Leu Lys Asp Trp Leu Lys Ala Gln Leu Phe Asp Pro Gln
545                 550                 555                 560

Ala Glu Tyr Glu Gln Leu Tyr
                565

<210> SEQ ID NO 50
<211> LENGTH: 309
<212> TYPE: PRT
<213> ORGANISM: Trichomonas vaginalis

<400> SEQUENCE: 50

Met Leu Ser Ser Ser Phe Glu Arg Asn Leu His Gln Pro Leu Leu Phe
1               5                   10                  15

Ile Asp Lys Asp Thr Lys Val Val Ile Gln Gly Ile Gly Asn Gln Gly
            20                  25                  30

Gln Phe His Ser Arg Leu Met Arg Gln Tyr Gly Thr Lys Val Val Gly
        35                  40                  45

Ala Val His Pro Lys Lys Ala Gly Ser Ile Ala Gly Leu Pro Ile
    50                  55                  60

Phe Lys Asn Met Lys Glu Val Val Lys Arg Thr Asp Ala Asn Ala Ser
65                  70                  75                  80

Leu Ile Phe Val Pro Ala Pro Gly Ala Ala Ala Ala Cys Ile Glu Ala
```

```
                 85                  90                  95
Ala Gln Ala Gly Met Gly Leu Val Val Cys Ile Thr Glu His Ile Pro
            100                 105                 110

Gln His Asp Met Ile Lys Val Lys Lys Val Met Lys Glu Thr Gly Cys
            115                 120                 125

Gln Leu Ile Gly Pro Asn Cys Pro Gly Leu Ile Gln Pro Gly Thr His
            130                 135                 140

Thr Lys Leu Gly Ile Ile Pro Thr Asn Ile Phe Asn Asn Gly Lys Ile
145                 150                 155                 160

Gly Ile Val Ser Arg Ser Gly Thr Leu Thr Tyr Glu Ala Ala Tyr Ala
                165                 170                 175

Thr Thr Leu Ala Gly Leu Gly Gln Ser Thr Val Val Gly Ile Gly Gly
            180                 185                 190

Asp Pro Phe Ala Gly Gln Leu His Thr Asp Val Val Lys Arg Phe Ala
            195                 200                 205

Ala Asp Pro Gln Thr Glu Gly Ile Ile Leu Ile Gly Glu Ile Gly Gly
            210                 215                 220

Thr Ser Glu Glu Asp Ala Ala Glu Trp Ile Ala Lys Thr Lys Leu Thr
225                 230                 235                 240

Gln Glu Lys Pro Val Val Ala Phe Ile Ala Gly Ala Thr Ala Pro Pro
                245                 250                 255

Gly Lys Arg Met Gly His Ser Gly Ala Ile Val Ser Gly Gly Lys Gly
            260                 265                 270

Thr Ala Glu Gly Lys Tyr Lys Ala Leu Glu Ala Ala Gly Val Arg Ile
            275                 280                 285

Ala Arg His Pro Gly Asn Met Gly Lys Phe Ile Phe Glu Glu Met Lys
            290                 295                 300

Arg Met Gly Lys Ile
305

<210> SEQ ID NO 51
<211> LENGTH: 931
<212> TYPE: PRT
<213> ORGANISM: Trichomonas vaginalis

<400> SEQUENCE: 51

Met Ser Val Arg Arg Glu Gly Leu Leu Asp Asp Ala Trp Glu Lys Thr
1               5                   10                  15

Gln Ile Lys Val Phe Ser Arg Trp Val Gln Lys Gln Leu Leu Ala Arg
            20                  25                  30

Gln Ile Gln Phe Glu Thr Ile Glu Thr Asp Phe Glu Asp Gly Thr Lys
            35                  40                  45

Leu Leu Asn Leu Leu Glu Ile Ile Gly Lys Glu Pro Met Pro Ser Lys
        50                  55                  60

Trp His Lys Gln Pro Lys Met Met Val Gln Lys Arg Glu Asn Val Asp
65                  70                  75                  80

Leu Ala Leu Lys Tyr Ile Asn Glu Val Lys Lys Ile Arg Thr Val Gly
                85                  90                  95

Ile Gly Ala Asp Asp Ile Ile Asn Lys Asn Leu Lys Leu Thr Leu Gly
            100                 105                 110

Leu Thr Trp Thr Cys Ile Asn Lys Phe Met Ile Glu Glu Ile Ser Val
            115                 120                 125

Glu Glu Ala Thr Ala Arg Asp Ala Leu Leu Leu Trp Ala Lys Lys Asn
            130                 135                 140
```

```
Thr Gln Gly Tyr Glu His Val Ala Val Asn Asn Phe Thr Ser Trp
145                 150                 155                 160

Asn Thr Gly Leu Ala Phe Ala Ala Leu Ile Asn Lys Phe Arg Pro Asn
                165                 170                 175

Leu Leu Asp Tyr Ser Ala Leu Asp Tyr Asn Asp His Lys Gly Ala Cys
            180                 185                 190

Glu Lys Ala Phe Ala Ala Cys Lys Glu Leu Gly Ile Tyr Val Tyr Leu
        195                 200                 205

Asp Pro Glu Asp Val Ile Asp Thr Thr Pro Asp Lys Ser Val Val
    210                 215                 220

Thr Gln Val Ala Glu Phe Phe His Phe Phe Ala Ser Glu Ser Lys Ile
225                 230                 235                 240

Ala Ala Met Ala Asp Lys Ile Lys Arg Thr Val Ala Ile Gln Lys Gln
                245                 250                 255

Ile Asp Glu Leu Lys Asn Thr Tyr Ile Glu Asp Ala Lys Ala Ala Ile
            260                 265                 270

Glu Lys Met Thr Val Asp Glu Lys Leu Lys Ala Asp Asp Tyr Glu
        275                 280                 285

Lys Thr Ile Pro Gly Ile Arg Gly Lys Leu Ala Ser Val Ile Ser Tyr
    290                 295                 300

Asn Arg Asp Ile Arg Pro Glu Ile Val Asp His Arg Ala Lys Ala Met
305                 310                 315                 320

Arg Ser Trp Ala Ala Leu Val Thr Lys Cys Lys Ser Gly Asn Arg Pro
                325                 330                 335

Ile Pro Glu Ile Pro Gln Gly Leu Glu Pro Glu Ala Leu Thr Asn Lys
            340                 345                 350

Phe Asn Glu Ile Glu Gln Thr Ser Thr Thr Arg Arg Asp Glu Leu Thr
        355                 360                 365

Gln Glu Leu Asn Asp Met Ile Lys Lys Val Glu Asp Phe Met Ala
    370                 375                 380

Lys Cys Met Asp Ile Ile Asn Lys Cys Asp Ala Ile His Glu Glu Val
385                 390                 395                 400

Lys Thr Ile Glu Gly Thr Thr Ala Glu Lys Lys Asp Lys Val Glu Gln
                405                 410                 415

Lys Leu His Glu Ala Glu Asp Leu Gln Pro Ala Leu Ala Glu Leu Thr
            420                 425                 430

Pro Leu Phe Gln Glu Leu Val Glu Leu Arg Ile Asn Thr Leu Ser Ser
        435                 440                 445

Gln Thr Asp Asp Ser Val Asn Arg His His Ser Gln Leu Ile Thr Tyr
    450                 455                 460

Ile Lys His Leu Leu Glu Gln Leu Asn Gly Lys Leu Phe Glu Glu Thr
465                 470                 475                 480

Asn Glu Ala Arg Ile Asn Glu Tyr Asn Ala Leu Ala Gln Pro Leu Tyr
                485                 490                 495

Asp Glu Ala Ile Ala Phe Lys Glu Glu Val Leu Ala Ile Ser Gly Glu
            500                 505                 510

Leu Arg Glu Arg Arg Thr Gln Phe Leu Ala Lys Gln Ala Glu Ala Pro
        515                 520                 525

Thr Lys Arg Glu His Val Asn Glu Ile Asp Pro Ile Phe Asp Gly Leu
    530                 535                 540

Glu Lys Asp Ser Leu His Leu Arg Val Asn His Ser Pro Thr Glu Ile
545                 550                 555                 560

Arg Asn Val Tyr Ala Val Thr Leu Gln His Ile Ile Thr Glu Leu Asn
```

```
            565                 570                 575
Lys Ile Phe Glu Glu Met Val Ala Asn Phe Asp Ala Thr Ala Val Pro
            580                 585                 590
Ile Ile Asp Gly Ile Thr Ala Leu Val Thr Ser Ser His Gln Ile Pro
            595                 600                 605
Gly Asp Ala Ala Val Lys Ala Gln Val Glu Glu Asn Leu Ala Ser
    610                 615                 620
Leu Asp Gly Phe Ala Glu Lys Ile Gln Ala Leu Gln Asp Pro Tyr Asn
625                 630                 635                 640
Glu Leu Val Glu Phe Lys Leu Asn Tyr Lys Val Thr Tyr Thr Tyr Ser
                645                 650                 655
Asp Ala Thr Gly Glu Leu Asp Gln Ala Arg Leu Asp Leu Lys Gln Ile
            660                 665                 670
Ile Leu Ala Lys Lys Thr Phe Leu Glu Glu Glu Arg Lys Ala Arg
            675                 680                 685
Ile Asn Asn Tyr Thr Val Lys Ala Asp Glu His Met Asn Glu Ala His
    690                 695                 700
Ala Leu Asp Gly Lys Ile Asn Ser Val Asp Gly Glu Leu Glu Pro Lys
705                 710                 715                 720
Arg Gln Lys Leu Tyr Glu Val Arg Glu Val Asn Ala Lys Lys Glu
                725                 730                 735
Lys Ala Ala Glu Glu Leu Thr Pro Ile Tyr Glu Asp Leu Glu Lys Asp
            740                 745                 750
Gln Leu His Leu Glu Ile Thr Ser Thr Pro Ala Ser Ile Asn Ile Phe
            755                 760                 765
Phe Glu Asn Leu Ile Ala His Ile Asp Thr Leu Val Lys Glu Ile Asp
    770                 775                 780
Ala Ala Ile Ala Ala Lys Gly Leu Glu Ile Ser Glu Glu Leu
785                 790                 795                 800
Asn Glu Phe Lys Asp Thr Phe Lys Tyr Phe Asp Lys Asp Lys Ser Asn
                805                 810                 815
Ser Leu Glu Tyr Phe Glu Leu Lys Ala Cys Leu Thr Ala Leu Gly Glu
            820                 825                 830
Asp Ile Thr Asp Gly Gln Ala Lys Glu Tyr Cys Lys Lys Tyr Asn Ser
            835                 840                 845
Lys Gly Glu Gly Thr Ala Leu Glu Phe Asp Asp Tyr Val Arg Phe Met
    850                 855                 860
Leu Asp His Phe Ser Lys Ala Glu Thr Thr Glu Thr Met Glu Ala
865                 870                 875                 880
Phe Lys Ala Ile Ala Gln Asn Gln Pro Val Leu Thr Asp Ala Gln Leu
            885                 890                 895
Asp Gln Tyr Phe Ser Ala Glu Asp Ala Ala Tyr Leu Arg Ser Gln Leu
        900                 905                 910
Lys Gln Gly Glu Asn Gly Tyr Glu Phe Ala Asp Trp Val Asn Ser Leu
    915                 920                 925
Tyr Asn His
    930

<210> SEQ ID NO 52
<211> LENGTH: 792
<212> TYPE: PRT
<213> ORGANISM: Neisseria gonorrhoeae

<400> SEQUENCE: 52
```

-continued

```
Met Lys Leu Lys Gln Ile Ala Ser Ala Leu Met Met Leu Gly Ile Ser
1               5                   10                  15

Pro Leu Ala Phe Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
50                  55                  60

Leu Tyr Ala Thr Gly Phe Phe Asp Asp Val Arg Val Glu Thr Ala Asp
65                  70                  75                  80

Gly Leu Leu Leu Leu Thr Val Ile Val Cys Pro Thr Ile Gly Ser Leu
                85                  90                  95

Asn Ile Thr Gly Ala Lys Met Leu Gln Asn Asp Ala Ile Lys Lys Asn
                100                 105                 110

Leu Glu Ser Phe Gly Leu Ala Gln Ser Gln Tyr Phe Asn Gln Ala Thr
            115                 120                 125

Leu Asn Gln Ala Val Ala Gly Leu Lys Glu Glu Tyr Leu Gly Arg Gly
            130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
                180                 185                 190

Met Arg Gln Met Ser Leu Thr Glu Gly Gly Ile Trp Thr Trp Leu Thr
            195                 200                 205

Arg Ser Asp Arg Phe Asp Arg Gln Lys Phe Ala Gln Asp Met Glu Lys
            210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Arg Gln Thr Ile Lys
                245                 250                 255

Ile Thr Val His Glu Gly Gly Arg Phe Arg Trp Gly Lys Val Ser Ile
                260                 265                 270

Glu Gly Asp Thr Asn Glu Val Pro Lys Ala Glu Leu Glu Lys Leu Leu
            275                 280                 285

Thr Met Lys Pro Gly Lys Trp Tyr Glu Arg Gln Gln Met Thr Ala Val
290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Gly Thr Lys Thr Val Asp
                325                 330                 335

Phe Val Leu His Ile Glu Pro Gly Arg Lys Ile Tyr Val Asn Glu Ile
                340                 345                 350

His Ile Thr Gly Asn Asn Lys Thr Arg Asp Glu Val Val Arg Arg Glu
            355                 360                 365

Leu Arg Gln Met Glu Ser Ala Pro Tyr Asp Thr Ser Lys Leu Gln Arg
            370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
```

```
            420                 425                 430
Val Gln Asp Thr Gly Leu Val Met Ser Ala Gly Val Ser Gln Asp Asn
            435                 440                 445
Leu Phe Gly Thr Gly Lys Ser Ala Ala Leu Arg Ala Ser Arg Ser Lys
    450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Ile Tyr Gly Lys Ala Phe Asp Pro
                485                 490                 495
Arg Lys Ala Ser Thr Ser Val Lys Gln Tyr Lys Thr Thr Ala Gly
            500                 505                 510
Gly Gly Val Arg Met Gly Ile Pro Val Thr Glu Tyr Asp Arg Val Asn
            515                 520                 525
Phe Gly Leu Ala Ala Glu His Leu Thr Val Asn Thr Tyr Asn Lys Ala
            530                 535                 540
Pro Lys Arg Tyr Ala Asp Phe Ile Lys Gln Tyr Gly Lys Thr Asp Gly
545                 550                 555                 560
Ala Asp Gly Ser Phe Lys Gly Leu Leu Tyr Lys Gly Thr Val Gly Trp
                565                 570                 575
Gly Arg Asn Lys Thr Asp Ser Ala Leu Trp Pro Thr Arg Gly Tyr Leu
            580                 585                 590
Thr Gly Val Asn Ala Glu Ile Ala Leu Pro Gly Ser Lys Leu Gln Tyr
            595                 600                 605
Tyr Ser Ala Thr His Asn Gln Thr Trp Phe Phe Pro Leu Ser Lys Thr
            610                 615                 620
Phe Thr Leu Met Leu Gly Gly Glu Val Gly Ile Ala Gly Gly Tyr Gly
625                 630                 635                 640
Arg Thr Lys Glu Ile Pro Phe Phe Glu Asn Phe Tyr Gly Gly Gly Leu
                645                 650                 655
Gly Ser Val Arg Gly Tyr Glu Ser Gly Thr Leu Gly Pro Lys Val Tyr
            660                 665                 670
Asp Glu Tyr Gly Glu Lys Ile Ser Tyr Gly Gly Asn Lys Lys Ala Asn
            675                 680                 685
Val Ser Ala Glu Leu Leu Phe Pro Met Pro Gly Ala Lys Asp Ala Arg
            690                 695                 700
Thr Val Arg Leu Ser Leu Phe Ala Asp Ala Gly Ser Val Trp Asp Gly
705                 710                 715                 720
Arg Thr Tyr Thr Ala Ala Glu Asn Gly Asn Asn Lys Ser Val Tyr Ser
                725                 730                 735
Glu Asn Ala His Lys Ser Thr Phe Thr Asn Glu Leu Arg Tyr Ser Ala
            740                 745                 750
Gly Gly Ala Val Thr Trp Leu Ser Pro Leu Gly Pro Met Lys Phe Ile
            755                 760                 765
Tyr Ala Tyr Pro Leu Lys Lys Lys Pro Glu Asp Glu Ile Gln Arg Phe
            770                 775                 780
Gln Phe Gln Leu Gly Thr Thr Phe
785                 790

<210> SEQ ID NO 53
<211> LENGTH: 792
<212> TYPE: PRT
<213> ORGANISM: Neisseria gonorrhoeae

<400> SEQUENCE: 53
```

```
Met Lys Leu Lys Gln Ile Ala Ser Ala Leu Met Met Leu Gly Ile Ser
1               5                   10                  15

Pro Leu Ala Phe Ala Asp Phe Thr Ile Gln Asp Ile Arg Val Glu Gly
                20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asp Arg Phe Asp Arg Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Arg Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Gly Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
```

```
                420             425             430
Val Gln Asp Thr Gly Leu Val Met Ser Ala Gly Val Ser Gln Asp Asn
            435                 440                 445

Leu Phe Gly Thr Gly Lys Ser Ala Ala Leu Arg Ala Ser Arg Ser Lys
450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Ile Tyr Gly Lys Ala Phe Asp Pro
                485                 490                 495

Arg Lys Ala Ser Thr Ser Val Lys Gln Tyr Lys Thr Thr Ala Gly
            500                 505                 510

Gly Gly Val Arg Met Gly Ile Pro Val Thr Glu Tyr Asp Arg Val Asn
            515                 520                 525

Phe Gly Leu Ala Ala Glu His Leu Thr Val Asn Thr Tyr Asn Lys Ala
            530                 535                 540

Pro Lys Arg Tyr Ala Asp Phe Ile Lys Gln Tyr Gly Lys Thr Asp Gly
545                 550                 555                 560

Ala Asp Gly Ser Phe Lys Gly Leu Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
            595                 600                 605

Tyr Ser Ala Thr His Asn Gln Thr Trp Phe Phe Pro Leu Ser Lys Thr
610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
            675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Arg Thr Tyr Thr Ala Ala Glu Asn Gly Asn Asn Lys Ser Val Tyr Ser
                725                 730                 735

Glu Asn Ala His Lys Ser Thr Phe Thr Asn Glu Leu Arg Tyr Ser Ala
            740                 745                 750

Gly Gly Ala Val Thr Trp Leu Ser Pro Leu Gly Pro Met Lys Phe Ser
            755                 760                 765

Tyr Ala Tyr Pro Leu Lys Lys Lys Pro Glu Asp Glu Ile Gln Arg Phe
770                 775                 780

Gln Phe Gln Leu Gly Thr Thr Phe
785                 790
```

<210> SEQ ID NO 54
<211> LENGTH: 326
<212> TYPE: PRT
<213> ORGANISM: Neisseria gonorrhoeae

<400> SEQUENCE: 54

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Ala His His Gly Ala Gln Ala Asp Arg Val Lys
        35                  40                  45

Thr Ala Thr Glu Ile Ala Asp Leu Gly Ser Lys Ile Gly Phe Lys Gly
50                  55                  60

Gln Glu Asp Leu Gly Asn Gly Leu Lys Ala Ile Trp Gln Leu Glu Gln
65                  70                  75                  80

Lys Ala Tyr Val Ser Gly Thr Asp Thr Gly Trp Gly Asn Arg Gln Ser
                85                  90                  95

Phe Ile Gly Leu Lys Gly Gly Phe Gly Lys Val Arg Val Gly Arg Leu
                100                 105                 110

Asn Ser Val Leu Lys Asp Thr Gly Gly Phe Asn Pro Trp Glu Gly Lys
                115                 120                 125

Ser Tyr Tyr Leu Gly Leu Ser Asn Ile Ala Gln Pro Glu Glu Arg His
                130                 135                 140

Val Ser Val Arg Tyr Asp Ser Pro Glu Phe Ala Gly Phe Arg Ala Val
145                 150                 155                 160

Gln Tyr Val Pro Asn Asp Asn Ser Gly Lys Asn His Ser Glu Ser Tyr
                165                 170                 175

His Ala Gly Phe Asn Tyr Lys Asn Ser Gly Phe Phe Val Gln Tyr Ala
                180                 185                 190

Gly Phe Tyr Lys Arg His Ser Tyr Thr Thr Glu Lys His Gln Val His
                195                 200                 205

Arg Leu Val Gly Gly Tyr Asp His Asp Ala Leu Tyr Ala Ser Val Ala
210                 215                 220

Val Gln Gln Gln Asp Ala Lys Leu Thr Trp Arg Asn Asp Asn Ser His
225                 230                 235                 240

Asn Ser Gln Thr Glu Val Ala Ala Thr Ala Tyr Arg Phe Gly Asn
                245                 250                 255

Val Thr Pro Arg Val Ser Tyr Ala His Gly Phe Lys Gly Ser Val Tyr
                260                 265                 270

Asp Ala Asp Asn Asp Asn Thr Tyr Asp Gln Val Val Val Gly Ala Glu
                275                 280                 285

Tyr Asp Phe Ser Lys Arg Thr Ser Ala Leu Val Ser Ala Gly Trp Leu
                290                 295                 300

Gln Arg Gly Lys Gly Thr Glu Lys Phe Val Ala Thr Val Gly Gly Val
305                 310                 315                 320

Gly Leu Arg His Lys Phe
                325

<210> SEQ ID NO 55
<211> LENGTH: 392
<212> TYPE: PRT
<213> ORGANISM: Neisseria gonorrhoeae

<400> SEQUENCE: 55

Met Lys Arg Gln Ala Leu Ala Ala Met Ile Ala Ser Leu Phe Ala Leu
1               5                   10                  15

Ala Ala Cys Gly Gly Glu Gln Ala Ala Gln Pro Ala Glu Thr Pro
            20                  25                  30

Ala Ala Ser Ala Glu Ala Ala Ser Ser Ala Ala Gln Ala Thr Ala Glu
            35                  40                  45

```
Thr Pro Ala Gly Glu Leu Pro Val Ile Asp Ala Val Thr His Ala
 50                  55                  60

Pro Glu Val Pro Pro Ala Ile Asp Arg Asp Tyr Pro Ala Lys Val Arg
 65                  70                  75                  80

Val Lys Met Glu Thr Val Glu Lys Thr Met Lys Met Asp Asp Gly Val
                 85                  90                  95

Glu Tyr Arg Tyr Trp Thr Phe Asp Gly Asp Val Pro Gly Arg Met Ile
            100                 105                 110

Arg Val Arg Glu Gly Asp Thr Val Glu Val Glu Phe Ser Asn Asn Pro
        115                 120                 125

Ser Ser Thr Val Pro His Asn Val Asp Phe His Ala Ala Thr Gly Gln
130                 135                 140

Gly Gly Gly Ala Ala Thr Phe Thr Ala Pro Gly Arg Thr Ser Thr
145                 150                 155                 160

Phe Ser Phe Lys Ala Leu Gln Pro Gly Leu Tyr Ile Tyr His Cys Ala
                165                 170                 175

Val Ala Pro Val Gly Met His Ile Ala Asn Gly Met Tyr Gly Leu Ile
            180                 185                 190

Leu Val Glu Pro Lys Glu Gly Leu Pro Lys Val Asp Lys Glu Phe Tyr
        195                 200                 205

Ile Val Gln Gly Asp Phe Tyr Thr Lys Gly Lys Lys Gly Ala Gln Gly
210                 215                 220

Leu Gln Pro Phe Asp Met Asp Lys Ala Val Ala Glu Gln Pro Glu Tyr
225                 230                 235                 240

Val Val Phe Asn Gly His Val Gly Ser Ile Ala Gly Asp Asn Ala Leu
                245                 250                 255

Lys Ala Lys Ala Gly Glu Thr Val Arg Met Tyr Val Gly Asn Gly Gly
            260                 265                 270

Pro Asn Leu Val Ser Ser Phe His Val Ile Gly Glu Ile Phe Asp Lys
        275                 280                 285

Val Tyr Val Glu Gly Gly Lys Leu Ile Asn Glu Asn Val Gln Ser Thr
290                 295                 300

Ile Val Pro Ala Gly Gly Ser Ala Ile Val Glu Phe Lys Val Asp Ile
305                 310                 315                 320

Pro Gly Ser Tyr Thr Leu Val Asp His Ser Ile Phe Arg Ala Phe Asn
                325                 330                 335

Lys Gly Ala Leu Gly Gln Leu Lys Val Glu Gly Ala Glu Asn Pro Glu
            340                 345                 350

Ile Met Thr Gln Lys Leu Ser Asp Thr Ala Tyr Ala Gly Ser Gly Ala
        355                 360                 365

Ala Ser Ala Pro Ala Ala Ser Ala Pro Ala Ala Ser Ala Pro Ala Ala
370                 375                 380

Ser Ala Ser Glu Lys Ser Val Tyr
385                 390

<210> SEQ ID NO 56
<211> LENGTH: 467
<212> TYPE: PRT
<213> ORGANISM: Neisseria gonorrhoeae

<400> SEQUENCE: 56

Met Asn Thr Thr Leu Lys Thr Thr Leu Thr Ser Val Ala Ala Ala Phe
  1               5                  10                  15

Ala Leu Ser Ala Cys Thr Met Ile Pro Gln Tyr Glu Gln Pro Lys Val
```

-continued

```
                    20                  25                  30
Glu Val Ala Glu Thr Phe Gln Asn Asp Thr Ser Val Ser Ser Ile Arg
                35                  40                  45
Ala Val Asp Leu Gly Trp His Asp Tyr Phe Ala Asp Pro Arg Leu Gln
 50                  55                  60
Lys Leu Ile Asp Ile Ala Leu Glu Arg Asn Thr Ser Leu Arg Thr Ala
 65                  70                  75                  80
Val Leu Asn Ser Glu Ile Tyr Arg Lys Gln Tyr Met Ile Glu Arg Asn
                85                  90                  95
Asn Leu Leu Pro Thr Leu Ala Ala Asn Ala Asn Gly Ser Arg Gln Gly
                100                 105                 110
Ser Leu Ser Gly Gly Asn Val Ser Ser Tyr Asn Val Gly Leu Gly
                115                 120                 125
Ala Ala Ser Tyr Glu Leu Asp Leu Phe Gly Arg Val Arg Ser Ser Ser
                130                 135                 140
Glu Ala Ala Leu Gln Gly Tyr Phe Ala Ser Val Ala Asn Arg Asp Ala
145                 150                 155                 160
Ala His Leu Ser Leu Ile Ala Thr Val Ala Lys Ala Tyr Phe Asn Glu
                165                 170                 175
Arg Tyr Ala Glu Glu Ala Met Ser Leu Ala Gln Arg Val Leu Lys Thr
                180                 185                 190
Arg Glu Glu Thr Tyr Asn Ala Val Arg Ile Ala Val Gln Gly Arg Arg
                195                 200                 205
Asp Phe Arg Arg Pro Ala Pro Ala Glu Ala Leu Ile Glu Ser Ala
                210                 215                 220
Lys Ala Asp Tyr Ala His Ala Ala Arg Ser Arg Gln Ala Arg Asn
225                 230                 235                 240
Ala Leu Ala Thr Leu Ile Asn Arg Pro Ile Pro Glu Asp Leu Pro Ala
                245                 250                 255
Gly Leu Pro Leu Asp Lys Gln Phe Phe Val Glu Lys Leu Pro Ala Gly
                260                 265                 270
Leu Ser Ser Glu Val Leu Leu Asp Arg Pro Asp Ile Arg Ala Ala Glu
                275                 280                 285
His Ala Leu Lys Gln Ala Asn Ala Asn Ile Gly Ala Ala Arg Ala Ala
                290                 295                 300
Phe Phe Pro Ser Ile Arg Leu Thr Gly Ser Val Gly Thr Gly Ser Val
305                 310                 315                 320
Glu Leu Gly Gly Leu Phe Lys Ser Gly Thr Gly Val Trp Ala Phe Ala
                325                 330                 335
Pro Ser Ile Thr Leu Pro Ile Phe Thr Trp Gly Thr Asn Lys Ala Asn
                340                 345                 350
Leu Asp Val Ala Lys Leu Arg Gln Gln Ala Gln Ile Val Ala Tyr Glu
                355                 360                 365
Ser Ala Val Gln Ser Ala Phe Gln Asp Val Ala Asn Ala Leu Ala Ala
                370                 375                 380
Arg Glu Gln Leu Asp Lys Ala Tyr Asp Ala Leu Ser Lys Gln Ser Arg
385                 390                 395                 400
Ala Ser Lys Glu Ala Leu Arg Leu Val Gly Leu Arg Tyr Lys His Gly
                405                 410                 415
Val Ser Gly Ala Leu Asp Leu Leu Asp Ala Glu Arg Ser Ser Tyr Ser
                420                 425                 430
Ala Glu Gly Ala Ala Leu Ser Ala Gln Leu Thr Arg Ala Glu Asn Leu
                435                 440                 445
```

Ala Asp Leu Tyr Lys Ala Leu Gly Gly Gly Leu Lys Arg Asp Thr Gln
    450                 455                 460

Thr Gly Lys
465

<210> SEQ ID NO 57
<211> LENGTH: 594
<212> TYPE: PRT
<213> ORGANISM: Neisseria gonorrhoeae (strain ATCC 700825 / FA 1090)

<400> SEQUENCE: 57

Met Ala Leu Val Glu Leu Lys Val Pro Asp Ile Gly Gly His Glu Asn
1               5                   10                  15

Val Asp Ile Ile Ala Val Glu Val Asn Val Gly Asp Thr Ile Ala Val
            20                  25                  30

Asp Asp Thr Leu Ile Thr Leu Glu Thr Asp Lys Ala Thr Met Asp Val
        35                  40                  45

Pro Ala Glu Val Ala Gly Val Ile Lys Glu Val Lys Val Lys Val Gly
    50                  55                  60

Asp Lys Ile Ser Glu Gly Gly Leu Ile Val Val Glu Ala Glu Gly
65                  70                  75                  80

Ala Ala Ala Ala Pro Lys Ala Glu Ala Ala Ala Pro Ala Gln Glu
                85                  90                  95

Ala Pro Lys Ala Ala Pro Ala Pro Gln Ala Ala Gln Phe Gly Gly
            100                 105                 110

Ala Ala Asp Ala Glu Tyr Asp Val Val Leu Gly Gly Gly Pro Gly
        115                 120                 125

Gly Tyr Ser Ala Ala Phe Ala Ala Ala Asp Glu Gly Leu Lys Val Ala
    130                 135                 140

Ile Val Glu Arg Tyr Lys Thr Leu Gly Gly Val Cys Leu Asn Val Gly
145                 150                 155                 160

Cys Ile Pro Ser Lys Ala Leu Leu His Asn Ala Ala Val Ile Asp Glu
                165                 170                 175

Val Arg His Leu Ala Ala Asn Gly Ile Lys Tyr Pro Lys Pro Glu Leu
            180                 185                 190

Asp Ile Asp Met Leu Arg Ala Tyr Lys Asp Gly Val Val Ser Arg Leu
        195                 200                 205

Thr Gly Gly Leu Ala Gly Met Ala Lys Ser Arg Lys Val Asp Val Ile
    210                 215                 220

Gln Gly Asp Gly Gln Phe Leu Asp Pro His His Leu Glu Val Ser Leu
225                 230                 235                 240

Thr Ala Gly Asp Ala Tyr Glu Gln Ala Ala Pro Thr Gly Glu Lys Lys
                245                 250                 255

Ile Val Ala Phe Lys Asn Cys Ile Ile Ala Ala Gly Ser Arg Val Thr
            260                 265                 270

Lys Leu Pro Phe Ile Pro Glu Asp Pro Arg Ile Ile Asp Ser Ser Gly
        275                 280                 285

Ala Leu Ala Leu Lys Glu Val Pro Gly Lys Leu Leu Ile Ile Gly Gly
    290                 295                 300

Gly Ile Ile Gly Leu Glu Met Gly Thr Val Tyr Ser Thr Leu Gly Ser
305                 310                 315                 320

Arg Leu Asp Val Val Glu Met Met Asp Gly Leu Met Gln Gly Ala Asp
                325                 330                 335

Arg Asp Leu Val Lys Val Trp Gln Lys Gln Asn Glu Tyr Arg Phe Asp

```
                    340                 345                 350
Asn Ile Met Val Asn Thr Lys Thr Val Ala Val Glu Pro Lys Glu Asp
                355                 360                 365
Gly Val Tyr Val Thr Phe Glu Gly Ala Asn Ala Pro Lys Glu Pro Gln
            370                 375                 380
Arg Tyr Asp Ala Val Leu Val Ala Ala Gly Arg Ala Pro Asn Gly Lys
385                 390                 395                 400
Leu Ile Ser Ala Glu Lys Ala Gly Val Ala Val Thr Asp Arg Gly Phe
                405                 410                 415
Ile Glu Val Asp Lys Gln Met Arg Thr Asn Val Pro His Ile Tyr Ala
                420                 425                 430
Ile Gly Asp Ile Val Gly Gln Pro Met Leu Ala His Lys Ala Val His
            435                 440                 445
Glu Gly His Val Ala Ala Glu Asn Cys Ala Gly His Lys Ala Tyr Phe
            450                 455                 460
Asp Ala Arg Val Ile Pro Gly Val Ala Tyr Thr Ser Pro Glu Val Ala
465                 470                 475                 480
Trp Val Gly Glu Thr Glu Leu Ser Ala Lys Ala Ser Gly Arg Lys Ile
                485                 490                 495
Thr Lys Ala Asn Phe Pro Trp Ala Ala Ser Gly Arg Ala Ile Ala Asn
                500                 505                 510
Gly Cys Asp Asn Gly Phe Thr Lys Leu Ile Phe Asp Ala Glu Thr Gly
            515                 520                 525
Arg Ile Ile Gly Gly Gly Ile Val Gly Pro Asn Gly Gly Asp Met Ile
            530                 535                 540
Gly Glu Val Cys Leu Ala Ile Glu Met Gly Cys Asp Ala Ala Asp Ile
545                 550                 555                 560
Gly Lys Thr Ile His Pro His Pro Thr Leu Gly Glu Ser Ile Gly Met
                565                 570                 575
Ala Ala Glu Val Ala Leu Gly Val Cys Thr Asp Leu Pro Pro Gln Lys
            580                 585                 590
Lys Lys

<210> SEQ ID NO 58
<211> LENGTH: 236
<212> TYPE: PRT
<213> ORGANISM: Neisseria gonorrhoeae (strain NCCP11945)

<400> SEQUENCE: 58

Met Thr Lys Gln Leu Lys Leu Ser Ala Leu Phe Val Ala Leu Leu Ala
1               5                   10                  15
Ser Gly Thr Ala Val Ala Gly Glu Ala Ser Val Gln Gly Tyr Thr Val
                20                  25                  30
Ser Gly Gln Ser Asn Glu Ile Val Arg Asn Asn Tyr Gly Glu Cys Trp
            35                  40                  45
Lys Asn Ala Tyr Phe Asp Lys Ala Ser Gln Gly Arg Val Glu Cys Gly
        50                  55                  60
Asp Ala Val Ala Val Pro Glu Pro Glu Pro Ala Pro Val Ala Val Val
65                  70                  75                  80
Glu Gln Ala Pro Gln Tyr Val Asp Glu Thr Ile Ser Leu Ser Ala Lys
                85                  90                  95
Thr Leu Phe Gly Phe Asp Lys Asp Ser Leu Arg Ala Glu Ala Gln Asp
                100                 105                 110
Asn Leu Lys Val Leu Ala Gln Arg Leu Ser Arg Thr Asn Val Gln Ser
```

```
              115                 120                 125
Val Arg Val Glu Gly His Thr Asp Phe Met Gly Ser Glu Lys Tyr Asn
    130                 135                 140

Gln Ala Leu Ser Glu Arg Arg Ala Tyr Val Val Ala Asn Asn Leu Val
145                 150                 155                 160

Ser Asn Gly Val Pro Ala Ser Arg Ile Ser Ala Val Gly Leu Gly Glu
                165                 170                 175

Ser Gln Ala Gln Met Thr Gln Val Cys Gln Ala Glu Val Ala Lys Leu
                180                 185                 190

Gly Ala Lys Ala Ser Lys Ala Lys Arg Glu Ala Leu Ile Ala Cys
        195                 200                 205

Ile Glu Pro Asp Arg Arg Val Asp Val Lys Ile Arg Ser Ile Val Thr
    210                 215                 220

Arg Gln Val Val Pro Ala Arg Asn His His Gln His
225                 230                 235

<210> SEQ ID NO 59
<211> LENGTH: 642
<212> TYPE: PRT
<213> ORGANISM: Neisseria gonorrhoeae (strain ATCC 700825 / FA 1090)

<400> SEQUENCE: 59

Met Ala Lys Val Ile Gly Ile Asp Leu Gly Thr Thr Asn Ser Cys Leu
1               5                   10                  15

Ala Ile Ser Glu Asn Gly Gln Thr Lys Val Ile Glu Asn Ala Glu Gly
                20                  25                  30

Ala Arg Thr Thr Pro Ser Ile Ala Tyr Leu Asp Gly Gly Glu Ile
            35                  40                  45

Leu Val Gly Ala Pro Ala Lys Arg Gln Ala Val Thr Asn Ala Lys Asn
50                  55                  60

Thr Ile Tyr Ala Ala Lys Arg Leu Ile Gly His Lys Phe Glu Asp Lys
65                  70                  75                  80

Glu Val Gln Arg Asp Ile Glu Ser Met Pro Phe Glu Ile Ile Lys Ala
                85                  90                  95

Asp Asn Gly Asp Ala Trp Val Lys Ala Gln Gly Lys Glu Leu Ser Pro
            100                 105                 110

Pro Gln Ile Ser Ala Glu Val Leu Arg Lys Met Lys Glu Ala Ala Glu
        115                 120                 125

Ala Tyr Leu Gly Glu Lys Val Thr Glu Ala Val Ile Thr Val Pro Ala
    130                 135                 140

Tyr Phe Asn Asp Ser Gln Arg Gln Ala Thr Lys Asp Ala Gly Arg Ile
145                 150                 155                 160

Ala Gly Leu Asp Val Lys Arg Ile Ile Asn Glu Pro Thr Ala Ala Ala
                165                 170                 175

Leu Ala Phe Gly Met Asp Lys Gly Asp Asn Lys Asp Arg Lys Ile Ala
            180                 185                 190

Val Tyr Asp Leu Gly Gly Gly Thr Phe Asp Ile Ser Ile Glu Ile
        195                 200                 205

Ala Asn Leu Asp Gly Asp Lys Gln Phe Glu Val Leu Ala Thr Asn Gly
    210                 215                 220

Asp Thr Phe Leu Gly Gly Glu Asp Phe Asp Gln Arg Leu Ile Asp Tyr
225                 230                 235                 240

Ile Ile Asp Glu Phe Lys Lys Glu Gln Gly Ile Asp Leu Lys Gln Asp
                245                 250                 255
```

Val Met Ala Leu Gln Arg Leu Lys Glu Ala Ala Glu Lys Ala Lys Ile
            260                 265                 270

Glu Leu Ser Ser Gly Gln Gln Thr Glu Ile Asn Leu Pro Tyr Ile Thr
        275                 280                 285

Met Asp Ala Thr Gly Pro Lys His Leu Ala Met Lys Ile Thr Arg Ala
    290                 295                 300

Lys Phe Glu Ser Leu Val Glu Asp Leu Ile Ala Arg Ser Ile Glu Pro
305                 310                 315                 320

Cys Arg Thr Ala Leu Lys Asp Ala Gly Leu Ser Thr Gly Asp Ile Asp
                325                 330                 335

Asp Val Ile Leu Val Gly Gly Gln Ser Arg Met Pro Lys Val Gln Glu
            340                 345                 350

Ala Val Lys Asp Phe Phe Gly Lys Glu Pro Arg Lys Asp Val Asn Pro
        355                 360                 365

Asp Glu Ala Val Ala Val Gly Ala Ala Ile Gln Gly Glu Val Leu Ser
    370                 375                 380

Gly Gly Arg Ser Asp Val Leu Leu Leu Asp Val Thr Pro Leu Ser Leu
385                 390                 395                 400

Gly Ile Glu Thr Met Gly Gly Val Met Thr Lys Leu Ile Gln Lys Asn
                405                 410                 415

Thr Thr Ile Pro Thr Lys Ala Ser Gln Val Phe Ser Thr Ala Glu Asp
            420                 425                 430

Asn Gln Ser Ala Val Thr Ile His Val Leu Gln Gly Glu Arg Glu Arg
        435                 440                 445

Ala Ser Ala Asn Lys Ser Leu Gly Gln Phe Asn Leu Gly Asp Ile Ala
    450                 455                 460

Pro Ala Pro Arg Gly Met Pro Gln Ile Glu Val Thr Phe Asp Ile Asp
465                 470                 475                 480

Ala Asn Gly Ile Leu His Val Ser Ala Lys Asp Lys Gly Thr Gly Lys
                485                 490                 495

Ala Ala Asn Ile Thr Ile Gln Gly Ser Ser Gly Leu Ser Glu Glu Glu
            500                 505                 510

Ile Glu Arg Met Val Lys Asp Ala Glu Ala Asn Ala Glu Glu Asp Lys
        515                 520                 525

Lys Leu Thr Glu Leu Val Ala Ser Arg Asn Gln Ala Glu Ala Leu Ile
    530                 535                 540

His Ser Val Lys Lys Ser Leu Ala Asp Tyr Gly Asp Lys Leu Asp Ala
545                 550                 555                 560

Ala Glu Lys Glu Lys Ile Glu Ala Ala Leu Lys Glu Ala Glu Ala
                565                 570                 575

Val Lys Gly Asp Asp Lys Thr Ala Ile Asp Ala Lys Ala Glu Ala Leu
            580                 585                 590

Gly Thr Ala Ser Gln Lys Leu Gly Glu Met Val Tyr Ala Gln Ala Gln
        595                 600                 605

Ala Glu Ala Gln Ala Gly Glu Gly Ala Gln Ala Asn Ala Ser Ala Lys
    610                 615                 620

Lys Asp Asp Asp Val Val Asp Ala Asp Phe Glu Glu Val Lys Asp Asp
625                 630                 635                 640

Lys Lys

<210> SEQ ID NO 60
<211> LENGTH: 544
<212> TYPE: PRT
<213> ORGANISM: Neisseria gonorrhoeae

<400> SEQUENCE: 60

Met Ala Ala Lys Asp Val Gln Phe Gly Asn Glu Val Arg Gln Lys Met
1               5                   10                  15

Val Asn Gly Val Asn Ile Leu Ala Asn Ala Val Arg Val Thr Leu Gly
            20                  25                  30

Pro Lys Gly Arg Asn Val Val Asp Arg Ala Phe Gly Gly Pro His
        35                  40                  45

Ile Thr Lys Asp Gly Val Thr Val Ala Lys Glu Ile Glu Leu Lys Asp
    50                  55                  60

Lys Phe Glu Asn Met Gly Ala Gln Met Val Lys Glu Val Ala Ser Lys
65                  70                  75                  80

Thr Asn Asp Val Ala Gly Asp Gly Thr Thr Thr Ala Thr Val Leu Ala
                85                  90                  95

Gln Ser Ile Val Ala Glu Gly Ile Lys Ala Val Thr Ala Gly Met Asn
            100                 105                 110

Pro Thr Asp Leu Lys Arg Gly Ile Asp Lys Ala Val Ala Ala Leu Val
        115                 120                 125

Glu Glu Leu Lys Asn Ile Ala Lys Pro Cys Asp Thr Ser Lys Glu Ile
130                 135                 140

Ala Gln Val Gly Ser Ile Ser Ala Asn Ser Asp Glu Gln Val Gly Ala
145                 150                 155                 160

Ile Ile Ala Glu Ala Met Glu Lys Val Gly Lys Glu Gly Val Ile Thr
                165                 170                 175

Val Glu Asp Gly Lys Ser Leu Glu Asn Glu Leu Asp Val Val Glu Gly
            180                 185                 190

Met Gln Phe Asp Arg Gly Tyr Leu Ser Pro Tyr Phe Ile Asn Asp Ala
        195                 200                 205

Glu Lys Gln Ile Ala Gly Leu Asp Asn Pro Phe Val Leu Leu Phe Asp
210                 215                 220

Lys Lys Ile Ser Asn Ile Arg Asp Leu Leu Pro Val Leu Glu Gln Val
225                 230                 235                 240

Ala Lys Ala Ser Arg Pro Leu Leu Ile Ile Ala Glu Asp Val Glu Gly
                245                 250                 255

Glu Ala Leu Ala Thr Leu Val Val Asn Asn Ile Arg Gly Val Leu Lys
            260                 265                 270

Thr Val Ala Val Lys Ala Pro Gly Phe Gly Asp Arg Arg Lys Ala Met
        275                 280                 285

Leu Gln Asp Ile Ala Ile Leu Thr Gly Ala Val Val Ile Ser Glu Glu
    290                 295                 300

Val Gly Leu Ser Leu Glu Lys Ala Thr Leu Asp Asp Leu Gly Gln Ala
305                 310                 315                 320

Lys Arg Ile Glu Ile Gly Lys Glu Asn Thr Thr Val Ile Asp Gly Phe
                325                 330                 335

Gly Asp Ala Ala Gln Ile Glu Ala Arg Val Ala Glu Ile Arg Gln Gln
            340                 345                 350

Ile Glu Thr Ala Thr Ser Asp Tyr Asp Lys Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Asp Arg Val Glu Asp Ala Leu
385                 390                 395                 400

His Ala Thr Arg Ala Ala Val Glu Glu Gly Val Val Ala Gly Gly Gly

```
                405                 410                 415
Val Ala Leu Leu Arg Ala Arg Ala Ala Leu Glu Asn Leu His Thr Gly
            420                 425                 430

Asn Ala Asp Gln Asp Ala Gly Val Gln Ile Val Leu Arg Ala Val Glu
        435                 440                 445

Ser Pro Leu Arg Gln Ile Val Ala Asn Ala Gly Gly Glu Pro Ser Val
    450                 455                 460

Val Val Asn Lys Val Leu Glu Gly Lys Gly Asn Tyr Gly Tyr Asn Ala
465                 470                 475                 480

Gly Ser Gly Glu Tyr Gly Asp Met Ile Gly Met Gly Val Leu Asp Pro
                485                 490                 495

Ala Lys Val Thr Arg Ser Ala Leu Gln His Ala Ala Ser Ile Ala Gly
            500                 505                 510

Leu Met Leu Thr Thr Asp Cys Met Ile Ala Glu Ile Pro Glu Glu Lys
        515                 520                 525

Pro Ala Val Pro Asp Met Gly Gly Met Gly Gly Met Gly Gly Met Met
    530                 535                 540

<210> SEQ ID NO 61
<211> LENGTH: 96
<212> TYPE: PRT
<213> ORGANISM: Neisseria gonorrhoeae (strain ATCC 700825 / FA 1090)

<400> SEQUENCE: 61

Met Thr Ile Arg Pro Leu His Asp Arg Val Val Lys Arg Leu Glu
1               5                   10                  15

Ala Glu Glu Lys Thr Ala Ser Gly Ile Val Leu Pro Gly Ala Ala Ala
            20                  25                  30

Glu Lys Pro Asp Met Gly Glu Val Ile Ala Val Gly Ala Gly Lys Ile
        35                  40                  45

Gly Lys Asp Gly Ala Arg Arg Pro Leu Asp Val Lys Ala Gly Asp Lys
    50                  55                  60

Ile Ile Phe Gly Lys Tyr Ser Gly Gln Thr Val Lys Ala Asp Gly Glu
65                  70                  75                  80

Glu Leu Leu Val Met Arg Glu Glu Asp Ile Phe Gly Ile Val Glu Lys
                85                  90                  95

<210> SEQ ID NO 62
<211> LENGTH: 89
<212> TYPE: PRT
<213> ORGANISM: Neisseria gonorrhoeae (strain NCCP11945)

<400> SEQUENCE: 62

Met Asn Lys Ser Glu Leu Ile Glu Ala Ile Ala Gln Glu Ala Asp Ile
1               5                   10                  15

Ser Lys Ala Ala Ala Gln Lys Ala Leu Asp Ala Thr Thr Asn Ala Val
            20                  25                  30

Thr Asn Ala Leu Lys Gln Gly Asp Thr Val Thr Leu Val Gly Phe Gly
        35                  40                  45

Thr Phe Tyr Val Gly Glu Arg Ala Glu Arg Gln Gly Arg Asn Pro Lys
    50                  55                  60

Thr Gly Glu Pro Leu Thr Ile Ala Ala Lys Thr Leu Lys Phe Arg
65                  70                  75                  80

Ala Gly Lys Ala Leu Lys Asp Ala Leu
                85
```

<210> SEQ ID NO 63
<211> LENGTH: 236
<212> TYPE: PRT
<213> ORGANISM: Neisseria gonorrhoeae (strain ATCC 700825 / FA 1090)

<400> SEQUENCE: 63

```
Met Thr Lys Gln Leu Lys Leu Ser Ala Leu Phe Val Ala Leu Leu Ala
1               5                   10                  15

Ser Gly Thr Ala Val Ala Gly Glu Ala Ser Val Gln Gly Tyr Thr Val
            20                  25                  30

Ser Gly Gln Ser Asn Glu Ile Val Arg Asn Asn Tyr Gly Glu Cys Trp
        35                  40                  45

Lys Asn Ala Tyr Phe Asp Lys Ala Ser Gln Gly Arg Val Glu Cys Gly
    50                  55                  60

Asp Ala Val Ala Val Pro Glu Pro Glu Pro Ala Pro Val Ala Val Val
65                  70                  75                  80

Glu Gln Ala Pro Gln Tyr Val Asp Glu Thr Ile Ser Leu Ser Ala Lys
                85                  90                  95

Thr Leu Phe Gly Phe Asp Lys Asp Ser Leu Arg Ala Glu Ala Gln Asp
            100                 105                 110

Asn Leu Lys Val Leu Ala Gln Arg Leu Ser Arg Thr Asn Val Gln Ser
        115                 120                 125

Val Arg Val Glu Gly His Thr Asp Phe Met Gly Ser Glu Lys Tyr Asn
    130                 135                 140

Gln Ala Leu Ser Glu Arg Arg Ala Tyr Val Val Ala Asn Asn Leu Val
145                 150                 155                 160

Ser Asn Gly Val Pro Ala Ser Arg Ile Ser Ala Val Gly Leu Gly Glu
                165                 170                 175

Ser Gln Ala Gln Met Thr Gln Val Cys Gln Ala Glu Val Ala Lys Leu
            180                 185                 190

Gly Ala Lys Ala Ser Lys Ala Lys Arg Glu Ala Leu Ile Ala Cys
        195                 200                 205

Ile Glu Pro Asp Arg Arg Val Asp Val Lys Ile Arg Ser Ile Val Thr
    210                 215                 220

Arg Gln Val Val Pro Ala Arg Asn His His Gln His
225                 230                 235
```

<210> SEQ ID NO 64
<211> LENGTH: 801
<212> TYPE: PRT
<213> ORGANISM: Neisseria gonorrhoeae (strain ATCC 700825 / FA 1090)

<400> SEQUENCE: 64

```
Met Ala Arg Leu Phe Ser Leu Lys Pro Leu Val Leu Ala Leu Gly Phe
1               5                   10                  15

Cys Phe Gly Thr His Cys Ala Ala Asp Thr Val Ala Ala Glu Glu Ala
            20                  25                  30

Asp Gly Arg Val Ala Glu Gly Gly Ala Gln Gly Ala Ser Glu Ser Ala
        35                  40                  45

Gln Ala Ser Asp Leu Thr Leu Gly Ser Thr Cys Leu Phe Cys Ser Asn
    50                  55                  60

Glu Ser Gly Ser Pro Glu Arg Thr Glu Ala Ala Val Gln Gly Ser Gly
65                  70                  75                  80

Glu Ala Ser Val Pro Glu Asp Tyr Thr Arg Ile Val Ala Asp Arg Met
                85                  90                  95

Glu Gly Gln Ser Lys Val Lys Val Arg Ala Glu Gly Ser Val Ile Ile
```

```
                100                 105                 110
Glu Arg Asp Gly Ala Val Leu Asn Thr Asp Trp Ala Asp Tyr Asp Gln
            115                 120                 125

Ser Gly Asp Thr Val Thr Val Gly Asp Arg Phe Ala Leu Gln Gln Asp
130                 135                 140

Gly Thr Leu Ile Arg Gly Glu Thr Leu Thr Tyr Asn Leu Asp Gln Gln
145                 150                 155                 160

Thr Gly Glu Ala His Asn Val Arg Met Glu Thr Glu Gln Gly Gly Arg
                165                 170                 175

Arg Leu Gln Ser Val Ser Arg Thr Ala Glu Met Leu Gly Glu Gly Arg
            180                 185                 190

Tyr Lys Leu Thr Glu Thr Gln Phe Asn Thr Cys Ser Ala Gly Asp Ala
            195                 200                 205

Gly Trp Tyr Val Lys Ala Ser Val Glu Ala Asp Arg Gly Lys Gly
            210                 215                 220

Ile Gly Val Ala Lys His Ala Ala Phe Val Phe Gly Gly Val Pro Leu
225                 230                 235                 240

Phe Tyr Thr Pro Trp Ala Asp Phe Pro Leu Asp Gly Asn Arg Lys Ser
                245                 250                 255

Gly Leu Leu Val Pro Ser Val Ser Ala Gly Ser Asp Gly Val Ser Leu
            260                 265                 270

Ser Val Pro Tyr Tyr Phe Asn Leu Ala Pro Asn Phe Asp Ala Thr Phe
            275                 280                 285

Ala Pro Gly Ile Ile Gly Glu Arg Gly Ala Thr Phe Asp Gly Gln Ile
            290                 295                 300

Arg Tyr Leu Arg Pro Asp Tyr Ser Gly Gln Thr Asp Leu Thr Trp Leu
305                 310                 315                 320

Pro His Asp Lys Lys Ser Gly Arg Asn Asn Arg Tyr Gln Ala Lys Trp
                325                 330                 335

Gln His Arg His Asp Ile Ser Asp Thr Leu Gln Ala Gly Val Asp Phe
                340                 345                 350

Asn Gln Val Ser Asp Ser Gly Tyr Tyr Arg Asp Phe Tyr Gly Gly Glu
            355                 360                 365

Glu Ile Ala Gly Asn Val Asn Leu Asn Arg Arg Val Trp Leu Asp Tyr
            370                 375                 380

Gly Gly Arg Ala Ala Gly Gly Ser Leu Asn Ala Gly Leu Ser Val Gln
385                 390                 395                 400

Lys Tyr Gln Thr Leu Ala Asn Gln Ser Gly Tyr Lys Asp Glu Pro Tyr
                405                 410                 415

Ala Ile Met Pro Arg Leu Ser Ala Asp Trp His Lys Asn Ala Gly Arg
                420                 425                 430

Ala Gln Ile Gly Val Ser Ala Gln Phe Thr Arg Phe Ser His Asp Gly
            435                 440                 445

Arg Gln Asp Gly Ser Arg Leu Val Val Tyr Pro Gly Ile Lys Trp Asp
450                 455                 460

Phe Ser Asn Ser Trp Gly Tyr Val Arg Pro Lys Leu Gly Leu His Ala
465                 470                 475                 480

Thr Tyr Tyr Ser Leu Asp Ser Phe Gly Lys Ala Ser Arg Ser Val
                485                 490                 495

Gly Arg Val Leu Pro Val Val Asn Ile Asp Gly Gly Thr Thr Phe Glu
            500                 505                 510

Arg Asn Thr Arg Leu Phe Gly Gly Val Val Gln Thr Ile Glu Pro
            515                 520                 525
```

```
Arg Leu Phe Tyr Asn Tyr Ile Pro Ala Lys Ser Gln Asn Asp Leu Pro
            530                 535                 540

Asn Phe Asp Ser Ser Glu Ser Ser Phe Gly Tyr Gly Gln Leu Phe Arg
545                 550                 555                 560

Glu Asn Leu Tyr Tyr Gly Asn Asp Arg Ile Asn Ala Ala Asn Ser Leu
                565                 570                 575

Ser Thr Ala Val Gln Ser Arg Ile Leu Asp Gly Ala Thr Gly Glu Glu
            580                 585                 590

Arg Phe Arg Ala Gly Ile Gly Gln Lys Phe Tyr Phe Lys Asp Asp Ala
            595                 600                 605

Val Met Leu Asp Gly Ser Val Gly Lys Asn Pro Arg Ser Arg Ser Asp
            610                 615                 620

Trp Val Ala Phe Ala Ser Gly Gly Ile Gly Gly Arg Phe Thr Leu Asp
625                 630                 635                 640

Ser Ser Ile His Tyr Asn Gln Asn Asp Lys Arg Ala Glu His Tyr Ala
                645                 650                 655

Val Gly Ala Gly Tyr Arg Pro Ala Pro Gly Lys Val Leu Asn Ala Arg
            660                 665                 670

Tyr Lys Tyr Gly Arg Asn Glu Lys Ile Tyr Leu Gln Ala Asp Gly Ser
            675                 680                 685

Tyr Phe Tyr Asp Lys Leu Ser Gln Leu Asp Leu Ser Ala Gln Trp Pro
            690                 695                 700

Leu Thr Arg Asn Leu Ser Ala Val Val Arg Tyr Asn Tyr Gly Phe Glu
705                 710                 715                 720

Ala Lys Lys Pro Ile Glu Met Leu Ala Gly Ala Glu Tyr Lys Ser Ser
                725                 730                 735

Cys Gly Cys Trp Gly Ala Gly Val Tyr Ala Gln Arg Tyr Val Thr Gly
            740                 745                 750

Glu Asn Thr Tyr Lys Asn Ala Val Phe Phe Ser Leu Gln Leu Lys Asp
            755                 760                 765

Leu Ser Ser Val Gly Arg Asn Pro Ala Gly Arg Met Asp Val Ala Val
            770                 775                 780

Pro Gly Tyr Ile Pro Ala His Ser Leu Ser Ala Gly Arg Asn Lys Arg
785                 790                 795                 800

Pro

<210> SEQ ID NO 65
<211> LENGTH: 88
<212> TYPE: PRT
<213> ORGANISM: Chlamydia trachomatis

<400> SEQUENCE: 65

Met Lys Lys Thr Ala Leu Leu Ala Ala Leu Cys Ser Val Val Ser Leu
1               5                   10                  15

Ser Ser Cys Cys Arg Ile Val Asp Cys Cys Phe Glu Asp Pro Cys Ala
            20                  25                  30

Pro Ile Gln Cys Ser Pro Cys Glu Ser Lys Lys Asp Val Asp Gly
            35                  40                  45

Gly Cys Asn Ser Cys Asn Gly Tyr Val Pro Ala Cys Lys Pro Cys Gly
        50                  55                  60

Gly Asp Thr His Gln Asp Ala Glu His Gly Pro Gln Ala Arg Glu Ile
65                  70                  75                  80

Pro Val Asp Gly Lys Cys Arg Gln
                85
```

-continued

<210> SEQ ID NO 66
<211> LENGTH: 512
<212> TYPE: PRT
<213> ORGANISM: Chlamydia trachomatis (strain D/UW-3/Cx)

<400> SEQUENCE: 66

| | | | | | | | | | | | | | | | |
|---|---|---|---|---|---|---|---|---|---|---|---|---|---|---|---|
| Met | Pro | His | Asp | Asn | Asn | Glu | Met | His | Arg | Asn | Thr | Ile | His | Gln | Leu |
| 1 | | | | 5 | | | | | 10 | | | | | 15 | |
| Phe | Thr | Gly | Leu | Asp | Lys | Ala | Tyr | Gln | Ile | Val | Lys | Gly | Phe | Tyr | Gly |
| | | | 20 | | | | | 25 | | | | | 30 | | |
| Pro | Ala | Tyr | Ser | Ser | Ser | Ser | Lys | Asp | Phe | Phe | Lys | Gly | Arg | Gly | Tyr |
| | | | 35 | | | | | 40 | | | | | 45 | | |
| His | Ile | Leu | Ser | Arg | Ile | Glu | Leu | Ser | Asp | Pro | Phe | Glu | Arg | Ile | Gly |
| | 50 | | | | | 55 | | | | | 60 | | | | |
| Val | Tyr | Phe | Ala | Arg | Ser | Leu | Ala | Lys | Arg | Ile | His | Lys | Arg | His | Ala |
| 65 | | | | | 70 | | | | | 75 | | | | | 80 |
| Asp | Gly | Val | Ile | Ser | Ser | Val | Ile | Leu | Leu | Arg | Ala | Phe | Leu | Lys | Ala |
| | | | | 85 | | | | | 90 | | | | | 95 | |
| Ser | Ile | Pro | Phe | Ile | Asp | Gln | Gly | Leu | Ser | Pro | Arg | Leu | Leu | Ala | Ser |
| | | | 100 | | | | | 105 | | | | | 110 | | |
| Ala | Leu | Ala | Ser | Gln | Lys | Glu | Ala | Val | Cys | Ala | Tyr | Leu | His | Ser | His |
| | | | 115 | | | | | 120 | | | | | 125 | | |
| Ser | Phe | Leu | Leu | Lys | Asp | Ala | Ser | Lys | Val | Leu | Gly | Leu | Ile | Arg | Ser |
| | | 130 | | | | | 135 | | | | | 140 | | | |
| His | Leu | Pro | Asp | Pro | Leu | Ile | Gly | Glu | Ala | Phe | Ala | Glu | Ala | Val | Ala |
| 145 | | | | | 150 | | | | | 155 | | | | | 160 |
| Tyr | Thr | Gly | His | Glu | Gly | Ala | Val | Ala | Leu | Ser | Gln | Arg | Ser | Gly | Ser |
| | | | | 165 | | | | | 170 | | | | | 175 | |
| Thr | Leu | His | Leu | Val | Lys | Gly | Ile | Gln | Thr | Gln | Lys | Gly | Tyr | Arg | Val |
| | | | 180 | | | | | 185 | | | | | 190 | | |
| Pro | Ser | Phe | Phe | Pro | His | Asp | Ser | Phe | His | Glu | Asn | Pro | Ile | Val | Ala |
| | | | 195 | | | | | 200 | | | | | 205 | | |
| Pro | Lys | Ile | Phe | Val | Thr | Asp | Gln | Lys | Ile | His | Cys | Leu | Phe | Pro | Phe |
| | 210 | | | | | 215 | | | | | 220 | | | | |
| Leu | Pro | Leu | Leu | Lys | Lys | Phe | Ser | Glu | Glu | Gln | Thr | Pro | Leu | Ile | Ile |
| 225 | | | | | 230 | | | | | 235 | | | | | 240 |
| Phe | Cys | Lys | Glu | Ile | Ala | Pro | Asp | Pro | Leu | Ala | Thr | Cys | Ile | Ala | Asn |
| | | | | 245 | | | | | 250 | | | | | 255 | |
| Arg | Ile | Ala | Gly | Leu | Leu | Asp | Val | Leu | Val | Thr | Ile | Pro | Asp | Thr | |
| | | | 260 | | | | | 265 | | | | | 270 | | |
| Thr | Leu | Leu | Glu | Asp | Ile | Ala | Leu | Leu | Thr | Gly | Thr | Val | Phe | Ser | |
| | | | 275 | | | | | 280 | | | | | 285 | | |
| Ser | Pro | Pro | Phe | Ser | Asn | Lys | Pro | Pro | Ile | Glu | Leu | Pro | Leu | Leu | Gly |
| | | 290 | | | | | 295 | | | | | 300 | | | |
| Ser | Cys | Thr | Trp | Ala | Glu | Leu | Ser | Arg | Asp | His | Thr | Leu | Leu | Val | Cys |
| 305 | | | | | 310 | | | | | 315 | | | | | 320 |
| Glu | Asn | Leu | Val | Pro | Glu | Val | Val | Lys | Leu | Lys | Val | Arg | Gln | Leu | Asp |
| | | | | 325 | | | | | 330 | | | | | 335 | |
| His | Ala | Ile | His | Asn | Ala | Glu | Asp | Glu | Thr | Ser | Arg | Lys | Leu | Leu | Lys |
| | | | 340 | | | | | 345 | | | | | 350 | | |
| Lys | Arg | Lys | His | Arg | Leu | Glu | Asn | Ser | Ile | Ala | Ile | Ile | Pro | Val | Lys |
| | | | 355 | | | | | 360 | | | | | 365 | | |
| Gln | Asp | Thr | Thr | Pro | Leu | His | Glu | Leu | Ala | Leu | Lys | Thr | Leu | Asn | Ser |

```
                370               375               380
Thr Gln Glu Ser Gly Phe Val Leu Gly Gly Ala Leu Leu Tyr
385               390               395               400

Ala Thr Gln Ser Leu Ser Ser Pro Glu His Ser Gln Glu Gln
              405               410               415

Ala Ala Val Gln Ile Leu Gln Thr Ala Cys Arg Thr Leu Glu Gln
          420               425               430

Leu Val Asn Ser Val Tyr Met Asp Gly Lys Leu Val Ala Asp Lys Leu
              435               440               445

Cys Ser Leu Gly Thr Pro Ser Leu Gly Phe Asn Val Val Ser Gln Gln
              450               455               460

Ile Glu Asp Met Ile Ser Ala Gly Ile Ile Thr Pro Leu Asn Val Val
465               470               475               480

Leu Asp Ile Phe Ser Cys Ser Leu His Thr Ala Val Asp Leu Leu Leu
              485               490               495

Ala Ser Phe Thr Thr Pro Pro Thr Pro Ala Ala Lys Glu Lys Lys Thr
              500               505               510

<210> SEQ ID NO 67
<211> LENGTH: 394
<212> TYPE: PRT
<213> ORGANISM: Chlamydia trachomatis serovar L2 (strain 434/Bu/ATCC VR-
      902-B)

<400> SEQUENCE: 67

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
                20                  25                  30

Leu Met Ile Asp Gly Ile Leu Trp Glu Gly Phe Gly Gly Asp Pro Cys
            35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Gln Thr Asp Val Asn Lys
65                  70                  75                  80

Glu Phe Gln Met Gly Ala Lys Pro Thr Thr Ala Thr Gly Asn Ala Ala
                85                  90                  95

Ala Pro Ser Thr Cys Thr Ala Arg Glu Asn Pro Ala Tyr Gly Arg His
            100                 105                 110

Met Gln Asp Ala Glu Met Phe Thr Asn Ala Ala Tyr Met Ala Leu Asn
        115                 120                 125

Ile Trp Asp Arg Phe Asp Val Phe Cys Thr Leu Gly Ala Thr Ser Gly
130                 135                 140

Tyr Leu Lys Gly Asn Ser Ala Ser Phe Asn Leu Val Gly Leu Phe Gly
145                 150                 155                 160

Asp Asn Glu Asn His Ala Thr Val Ser Asp Ser Lys Leu Val Pro Asn
                165                 170                 175

Met Ser Leu Asp Gln Ser Val Val Glu Leu Tyr Thr Asp Thr Thr Phe
            180                 185                 190

Ala Trp Ser Ala Gly Ala Arg Ala Ala Leu Trp Glu Cys Gly Cys Ala
        195                 200                 205

Thr Leu Gly Ala Ser Phe Gln Tyr Ala Gln Ser Lys Pro Lys Val Glu
    210                 215                 220

Glu Leu Asn Val Leu Cys Asn Ala Ala Glu Phe Thr Ile Asn Lys Pro
225                 230                 235                 240
```

```
Lys Gly Tyr Val Gly Gln Glu Phe Pro Leu Asp Leu Lys Ala Gly Thr
                245                 250                 255

Asp Gly Val Thr Gly Thr Lys Asp Ala Ser Ile Asp Tyr His Glu Trp
            260                 265                 270

Gln Ala Ser Leu Ala Leu Ser Tyr Arg Leu Asn Met Phe Thr Pro Tyr
        275                 280                 285

Ile Gly Val Lys Trp Ser Arg Ala Ser Phe Asp Ala Asp Thr Ile Arg
    290                 295                 300

Ile Ala Gln Pro Lys Ser Ala Thr Thr Val Phe Asp Val Thr Thr Leu
305                 310                 315                 320

Asn Pro Thr Ile Ala Gly Ala Gly Asp Val Lys Ala Ser Ala Glu Gly
                325                 330                 335

Gln Leu Gly Asp Thr Met Gln Ile Val Ser Leu Gln Leu Asn Lys Met
            340                 345                 350

Lys Ser Arg Lys Ser Cys Gly Ile Ala Val Gly Thr Thr Ile Val Asp
        355                 360                 365

Ala Asp Lys Tyr Ala Val Thr Val Glu Thr Arg Leu Ile Asp Glu Arg
    370                 375                 380

Ala Ala His Val Asn Ala Gln Phe Arg Phe
385                 390

<210> SEQ ID NO 68
<211> LENGTH: 102
<212> TYPE: PRT
<213> ORGANISM: Chlamydia trachomatis (strain D/UW-3/Cx)

<400> SEQUENCE: 68

Met Ser Asp Gln Ala Thr Thr Leu Lys Ile Lys Pro Leu Gly Asp Arg
1               5                   10                  15

Ile Leu Val Lys Arg Glu Glu Ala Ser Thr Ala Arg Gly Gly Ile
            20                  25                  30

Ile Leu Pro Asp Thr Ala Lys Lys Gln Asp Arg Ala Glu Val Leu
        35                  40                  45

Ala Leu Gly Thr Gly Lys Lys Asp Asp Lys Gly Gln Gln Leu Pro Phe
50                  55                  60

Glu Val Gln Val Gly Asn Ile Val Leu Ile Asp Lys Tyr Ser Gly Gln
65                  70                  75                  80

Glu Leu Thr Val Glu Gly Glu Tyr Val Ile Val Gln Met Ser Glu
            85                  90                  95

Val Ile Ala Val Leu Gln
            100

<210> SEQ ID NO 69
<211> LENGTH: 102
<212> TYPE: PRT
<213> ORGANISM: Chlamydia trachomatis

<400> SEQUENCE: 69

Met Ser Asp Gln Ala Thr Thr Leu Lys Ile Lys Pro Leu Gly Asp Arg
1               5                   10                  15

Ile Leu Val Lys Arg Glu Glu Ala Ser Thr Ala Arg Gly Gly Ile
            20                  25                  30

Ile Leu Pro Asp Thr Ala Lys Lys Gln Asp Arg Ala Glu Val Leu
        35                  40                  45

Ala Leu Gly Thr Gly Lys Lys Asp Asp Lys Gly Gln Gln Leu Pro Phe
50                  55                  60
```

```
Glu Val Gln Val Gly Asn Ile Val Leu Ile Asp Lys Tyr Ser Gly Gln
 65                  70                  75                  80

Glu Leu Thr Val Glu Gly Glu Tyr Val Ile Val Gln Met Ser Glu
                 85                  90                  95

Val Ile Ala Val Leu Gln
            100
```

<210> SEQ ID NO 70
<211> LENGTH: 89
<212> TYPE: PRT
<213> ORGANISM: Chlamydia trachomatis

<400> SEQUENCE: 70

```
Met Leu Lys Pro Leu Lys Asp Arg Val Val Ile Gln Met Val Glu Gln
  1               5                  10                  15

Glu Glu Lys Thr Ala Gly Gly Leu Phe Leu Pro Thr Ala Ala Gln Glu
                 20                  25                  30

Lys Leu Gln Phe Ala Thr Val Leu Ala Val Ser Glu Phe Thr Glu Glu
             35                  40                  45

Lys Asp Arg Gln Val Gln Val Gly Asp Arg Val Val Phe Glu Lys Tyr
         50                  55                  60

Thr Gly Thr Glu Val Lys Leu Asp Gly Gln Glu Tyr Ile Ile Val Lys
 65                  70                  75                  80

Glu Gln Asp Ile Ile Ala Ile Val Gln
                 85
```

<210> SEQ ID NO 71
<211> LENGTH: 660
<212> TYPE: PRT
<213> ORGANISM: Chlamydia trachomatis serovar L2 (strain 434/Bu/ATCC VR-
      902-B)

<400> SEQUENCE: 71

```
Met Ser Glu Lys Arg Lys Ser Asn Lys Ile Ile Gly Ile Asp Leu Gly
  1               5                  10                  15

Thr Thr Asn Ser Cys Val Ser Val Met Glu Gly Gly Gln Pro Lys Val
                 20                  25                  30

Ile Ala Ser Ser Glu Gly Thr Arg Thr Thr Pro Ser Ile Val Ala Phe
             35                  40                  45

Lys Gly Gly Glu Thr Leu Val Gly Ile Pro Ala Lys Arg Gln Ala Val
         50                  55                  60

Thr Asn Pro Glu Lys Thr Leu Ala Ser Thr Lys Arg Phe Ile Gly Arg
 65                  70                  75                  80

Lys Phe Ser Glu Val Glu Ser Glu Ile Lys Thr Val Pro Tyr Lys Val
                 85                  90                  95

Ala Pro Asn Ser Lys Gly Asp Ala Val Phe Asp Val Glu Gln Lys Leu
                100                 105                 110

Tyr Thr Pro Glu Glu Ile Gly Ala Gln Ile Leu Met Lys Met Lys Glu
            115                 120                 125

Thr Ala Glu Ala Tyr Leu Gly Glu Thr Val Thr Glu Ala Val Ile Thr
        130                 135                 140

Val Pro Ala Tyr Phe Asn Asp Ser Gln Arg Ala Ser Thr Lys Asp Ala
145                 150                 155                 160

Gly Arg Ile Ala Gly Leu Asp Val Lys Arg Ile Ile Pro Glu Pro Thr
                165                 170                 175

Ala Ala Ala Leu Ala Tyr Gly Ile Asp Lys Glu Gly Asp Lys Lys Ile
```

```
                180             185                 190
Ala Val Phe Asp Leu Gly Gly Gly Thr Phe Asp Ile Ser Ile Leu Glu
                195                 200                 205

Ile Gly Asp Gly Val Phe Glu Val Leu Ser Thr Asn Gly Asp Thr His
            210                 215                 220

Leu Gly Gly Asp Asp Phe Asp Gly Val Ile Ile Asn Trp Met Leu Asp
225                 230                 235                 240

Glu Phe Lys Lys Gln Glu Gly Ile Asp Leu Ser Lys Asp Asn Met Ala
                245                 250                 255

Leu Gln Arg Leu Lys Asp Ala Ala Glu Lys Ala Lys Ile Glu Leu Ser
            260                 265                 270

Gly Val Ser Ser Thr Glu Ile Asn Gln Pro Phe Ile Thr Ile Asp Ala
            275                 280                 285

Asn Gly Pro Lys His Leu Ala Leu Thr Leu Thr Arg Ala Gln Phe Glu
            290                 295                 300

His Leu Ala Ser Ser Leu Ile Glu Arg Thr Lys Gln Pro Cys Ala Gln
305                 310                 315                 320

Ala Leu Lys Asp Ala Lys Leu Ser Ala Ser Asp Ile Asp Asp Val Leu
                325                 330                 335

Leu Val Gly Gly Met Ser Arg Met Pro Ala Val Gln Ala Val Val Lys
                340                 345                 350

Glu Ile Phe Gly Lys Glu Pro Asn Lys Gly Val Asn Pro Asp Glu Val
                355                 360                 365

Val Ala Ile Gly Ala Ala Ile Gln Gly Gly Val Leu Gly Gly Glu Val
            370                 375                 380

Lys Asp Val Leu Leu Leu Asp Val Ile Pro Leu Ser Leu Gly Ile Glu
385                 390                 395                 400

Thr Leu Gly Gly Val Met Thr Pro Leu Val Glu Arg Asn Thr Thr Ile
                405                 410                 415

Pro Thr Gln Lys Lys Gln Ile Phe Ser Thr Ala Ala Asp Asn Gln Pro
            420                 425                 430

Ala Val Thr Ile Val Val Leu Gln Gly Glu Arg Pro Met Ala Lys Asp
                435                 440                 445

Asn Lys Glu Ile Gly Arg Phe Asp Leu Thr Asp Ile Pro Pro Ala Pro
            450                 455                 460

Arg Gly His Pro Gln Ile Glu Val Thr Phe Asp Ile Asp Ala Asn Gly
465                 470                 475                 480

Ile Leu His Val Ser Ala Lys Asp Ala Ala Ser Gly Arg Glu Gln Lys
                485                 490                 495

Ile Arg Ile Glu Ala Ser Ser Gly Leu Lys Glu Asp Glu Ile Gln Gln
            500                 505                 510

Met Ile Arg Asp Ala Glu Leu His Lys Glu Glu Asp Lys Gln Arg Lys
            515                 520                 525

Glu Ala Ser Asp Val Lys Asn Glu Ala Asp Gly Met Ile Phe Arg Ala
530                 535                 540

Glu Lys Ala Val Lys Asp Tyr His Asp Lys Ile Pro Ala Glu Leu Val
545                 550                 555                 560

Lys Glu Ile Glu Glu His Ile Glu Lys Val Arg Gln Ala Ile Lys Glu
                565                 570                 575

Asp Ala Ser Thr Thr Ala Ile Lys Ala Ala Ser Asp Glu Leu Ser Thr
            580                 585                 590

Arg Met Gln Lys Ile Gly Glu Ala Met Gln Ala Gln Ser Ala Ser Ala
            595                 600                 605
```

```
Ala Ala Ser Ser Ala Ala Asn Ala Gln Gly Gly Pro Asn Ile Asn Ser
    610                 615                 620

Glu Asp Leu Lys Lys His Ser Phe Ser Thr Arg Pro Pro Ala Gly Gly
625                 630                 635                 640

Ser Ala Ser Ser Thr Asp Asn Ile Glu Asp Ala Asp Val Glu Ile Val
                645                 650                 655

Asp Lys Pro Glu
            660

<210> SEQ ID NO 72
<211> LENGTH: 232
<212> TYPE: PRT
<213> ORGANISM: Chlamydia trachomatis serovar L2 (strain 434/Bu/ATCC VR-
      902-B)

<400> SEQUENCE: 72

Met Thr Lys His Gly Lys Arg Ile Arg Gly Ile Gln Glu Thr Tyr Asp
1               5                   10                  15

Leu Ala Lys Ser Tyr Ser Leu Gly Glu Ala Ile Asp Ile Leu Lys Gln
            20                  25                  30

Cys Pro Thr Val Arg Phe Asp Gln Thr Val Asp Val Ser Val Lys Leu
        35                  40                  45

Gly Ile Asp Pro Arg Lys Ser Asp Gln Gln Ile Arg Gly Ser Val Ser
    50                  55                  60

Leu Pro His Gly Thr Gly Lys Val Leu Arg Ile Leu Val Phe Ala Ala
65                  70                  75                  80

Gly Asp Lys Ala Ala Glu Ala Ile Glu Ala Gly Ala Asp Phe Val Gly
                85                  90                  95

Ser Asp Asp Leu Val Glu Lys Ile Lys Gly Gly Trp Val Asp Phe Asp
            100                 105                 110

Val Ala Val Ala Thr Pro Asp Met Met Arg Glu Val Gly Lys Leu Gly
        115                 120                 125

Lys Val Leu Gly Pro Arg Asn Leu Met Pro Thr Pro Lys Ala Gly Thr
    130                 135                 140

Val Thr Thr Asp Val Val Lys Thr Ile Ala Glu Leu Arg Lys Gly Lys
145                 150                 155                 160

Ile Glu Phe Lys Ala Asp Arg Ala Gly Val Cys Asn Val Gly Val Ala
                165                 170                 175

Lys Leu Ser Phe Asp Ser Ala Gln Ile Lys Glu Asn Val Glu Ala Leu
            180                 185                 190

Cys Ala Ala Leu Val Lys Ala Lys Pro Ala Thr Ala Lys Gly Gln Tyr
        195                 200                 205

Leu Val Asn Phe Thr Ile Ser Ser Thr Met Gly Pro Gly Val Thr Val
    210                 215                 220

Asp Thr Arg Glu Leu Ile Ala Leu
225                 230

<210> SEQ ID NO 73
<211> LENGTH: 1014
<212> TYPE: PRT
<213> ORGANISM: Chlamydia trachomatis serovar A (strain A2497)

<400> SEQUENCE: 73

Met Met Gln Thr Ser Phe His Lys Phe Phe Leu Ser Met Ile Leu Ala
1               5                   10                  15

Tyr Ser Cys Cys Ser Leu Asn Gly Gly Gly Tyr Ala Ala Glu Ile Met
```

-continued

```
            20                  25                  30
Val Pro Gln Gly Ile Tyr Asp Gly Glu Thr Leu Thr Val Ser Phe Pro
             35                  40                  45
Tyr Thr Val Ile Gly Asp Pro Ser Gly Thr Thr Val Phe Ser Ala Gly
         50                  55                  60
Glu Leu Thr Leu Lys Asn Leu Asp Asn Ser Ile Ala Ala Leu Pro Leu
 65                  70                  75                  80
Ser Cys Phe Gly Asn Leu Leu Gly Ser Phe Thr Val Leu Gly Arg Gly
                 85                  90                  95
His Ser Leu Thr Phe Glu Asn Ile Arg Thr Ser Thr Asn Gly Ala Ala
                100                 105                 110
Leu Ser Asp Ser Ala Asn Ser Gly Leu Phe Thr Ile Glu Gly Phe Lys
            115                 120                 125
Glu Leu Ser Phe Ser Asn Cys Asn Ser Leu Leu Ala Val Leu Pro Ala
        130                 135                 140
Ala Thr Asn Asn Gly Ser Gln Thr Pro Thr Thr Ser Thr Pro
145                 150                 155                 160
Ser Asn Gly Thr Ile Tyr Ser Lys Thr Asp Leu Leu Leu Asn Asn
                165                 170                 175
Glu Lys Phe Ser Phe Tyr Ser Asn Leu Val Ser Gly Asp Gly Ala
            180                 185                 190
Ile Asp Ala Lys Ser Leu Thr Val Gln Gly Ile Ser Lys Leu Cys Val
            195                 200                 205
Phe Gln Glu Asn Thr Ala Gln Ala Asp Gly Ala Cys Gln Val Val
        210                 215                 220
Thr Ser Phe Ser Ala Met Ala Asn Glu Ala Pro Ile Ala Phe Val Ala
225                 230                 235                 240
Asn Val Ala Gly Val Arg Gly Gly Ile Ala Ala Val Gln Asp Gly
                245                 250                 255
Gln Gln Gly Val Ser Ser Ser Thr Ser Thr Glu Asp Pro Val Val Ser
            260                 265                 270
Phe Ser Arg Asn Thr Ala Val Glu Phe Asp Gly Asn Val Ala Arg Val
        275                 280                 285
Gly Gly Gly Ile Tyr Ser Tyr Gly Asn Val Ala Phe Leu Asn Asn Gly
        290                 295                 300
Lys Thr Leu Phe Leu Asn Asn Val Ala Ser Pro Val Tyr Ile Ala Ala
305                 310                 315                 320
Glu Gln Pro Thr Asn Gly Gln Ala Ser Asn Thr Ser Asp Asn Tyr Gly
                325                 330                 335
Asp Gly Gly Ala Ile Phe Cys Lys Asn Gly Ala Gln Ala Ala Gly Ser
            340                 345                 350
Asn Asn Ser Gly Ser Val Ser Phe Asp Gly Glu Gly Val Phe Phe
        355                 360                 365
Ser Ser Asn Val Ala Ala Gly Lys Gly Gly Ala Ile Tyr Ala Lys Lys
            370                 375                 380
Leu Ser Val Ala Asn Cys Gly Pro Val Gln Phe Leu Gly Asn Ile Ala
385                 390                 395                 400
Asn Asp Gly Gly Ala Ile Tyr Leu Gly Glu Ser Gly Glu Leu Ser Leu
                405                 410                 415
Ser Ala Asp Tyr Gly Asp Met Ile Phe Asp Gly Asn Leu Lys Arg Thr
            420                 425                 430
Ala Lys Glu Asn Ala Ala Asp Val Asn Gly Val Thr Val Ser Ser Gln
        435                 440                 445
```

```
Ala Ile Ser Met Gly Ser Gly Lys Ile Thr Thr Leu Arg Ala Lys
    450                 455                 460

Ala Gly His Gln Ile Leu Phe Asn Asp Pro Ile Glu Met Ala Asn Gly
465                 470                 475                 480

Asn Asn Gln Pro Ala Gln Ser Ser Glu Pro Leu Lys Ile Asn Asp Gly
                485                 490                 495

Glu Gly Tyr Thr Gly Asp Ile Val Phe Ala Asn Gly Asn Ser Thr Leu
                500                 505                 510

Tyr Gln Asn Val Thr Ile Glu Gln Gly Arg Ile Val Leu Arg Glu Lys
            515                 520                 525

Ala Lys Leu Ser Val Asn Ser Leu Ser Gln Thr Gly Gly Ser Leu Tyr
530                 535                 540

Met Glu Ala Gly Ser Thr Leu Asp Phe Val Thr Pro Gln Pro Pro Gln
545                 550                 555                 560

Gln Pro Pro Ala Ala Asn Gln Leu Ile Thr Leu Ser Asn Leu His Leu
                565                 570                 575

Ser Leu Ser Ser Leu Leu Ala Asn Asn Ala Val Thr Asn Pro Pro Thr
                580                 585                 590

Asn Pro Pro Ala Gln Asp Ser His Pro Ala Val Ile Gly Ser Thr Thr
            595                 600                 605

Ala Gly Ser Val Thr Ile Ser Gly Pro Ile Phe Phe Glu Asp Leu Asp
610                 615                 620

Asp Thr Ala Tyr Asp Arg Tyr Asp Trp Leu Gly Ser Asn Gln Lys Ile
625                 630                 635                 640

Asp Val Leu Lys Leu Gln Leu Gly Thr Gln Pro Pro Ala Asn Ala Pro
                645                 650                 655

Ser Asp Leu Thr Leu Gly Asn Glu Met Pro Lys Tyr Gly Tyr Gln Gly
                660                 665                 670

Ser Trp Lys Leu Ala Trp Asp Pro Asn Thr Ala Asn Asn Gly Pro Tyr
            675                 680                 685

Thr Leu Lys Ala Thr Trp Thr Lys Thr Gly Tyr Asn Pro Gly Pro Glu
690                 695                 700

Arg Val Ala Ser Leu Val Pro Asn Ser Leu Trp Gly Ser Ile Leu Asp
705                 710                 715                 720

Ile Arg Ser Ala His Ser Ala Ile Gln Ala Ser Val Asp Gly Arg Ser
                725                 730                 735

Tyr Cys Arg Gly Leu Trp Val Ser Gly Val Ser Asn Phe Phe Tyr His
                740                 745                 750

Asp Arg Asp Ala Leu Gly Gln Gly Tyr Arg Tyr Ile Ser Gly Gly Tyr
            755                 760                 765

Ser Leu Gly Ala Asn Ser Tyr Phe Gly Ser Ser Met Phe Gly Leu Ala
770                 775                 780

Phe Thr Glu Val Phe Gly Arg Ser Lys Asp Tyr Val Val Cys Arg Ser
785                 790                 795                 800

Asn His His Ala Cys Ile Gly Ser Val Tyr Leu Ser Thr Lys Gln Ala
                805                 810                 815

Leu Cys Gly Ser Tyr Val Phe Gly Asp Ala Phe Ile Arg Ala Ser Tyr
                820                 825                 830

Gly Phe Gly Asn Gln His Met Lys Thr Ser Tyr Thr Phe Ala Glu Glu
            835                 840                 845

Ser Asp Val Arg Trp Asp Asn Asn Cys Leu Val Gly Glu Ile Gly Val
850                 855                 860
```

```
Gly Leu Pro Ile Val Ile Thr Pro Ser Lys Leu Tyr Leu Asn Glu Leu
865                 870                 875                 880

Arg Pro Phe Val Gln Ala Glu Phe Ser Tyr Ala Asp His Glu Ser Phe
            885                 890                 895

Thr Glu Glu Gly Asp Gln Ala Arg Ala Phe Arg Ser Gly His Leu Met
        900                 905                 910

Asn Leu Ser Val Pro Val Gly Val Lys Phe Asp Arg Cys Ser Ser Thr
    915                 920                 925

His Pro Asn Lys Tyr Ser Phe Met Gly Ala Tyr Ile Cys Asp Ala Tyr
    930                 935                 940

Arg Thr Ile Ser Gly Thr Gln Thr Thr Leu Leu Ser His Gln Glu Thr
945                 950                 955                 960

Trp Thr Thr Asp Ala Phe His Leu Ala Arg His Gly Val Ile Val Arg
                965                 970                 975

Gly Ser Met Tyr Ala Ser Leu Thr Ser Asn Ile Glu Val Tyr Gly His
            980                 985                 990

Gly Arg Tyr Glu Tyr Arg Asp Thr  Ser Arg Gly Tyr Gly  Leu Ser Ala
        995                 1000                1005

Gly Ser  Lys Val Arg Phe
    1010

<210> SEQ ID NO 74
<211> LENGTH: 547
<212> TYPE: PRT
<213> ORGANISM: Chlamydia trachomatis

<400> SEQUENCE: 74

Met Asn Lys Leu Ile Arg Arg Ala Val Thr Ile Phe Ala Val Thr Ser
1               5                   10                  15

Val Ala Ser Leu Phe Ala Ser Gly Val Leu Thr Ser Met Ala Glu
            20                  25                  30

Ser Leu Ser Thr Asn Val Ile Ser Leu Ala Asp Thr Lys Ala Lys Asp
        35                  40                  45

Asn Thr Ser His Lys Ser Lys Lys Ala Arg Lys Asn His Ser Lys Glu
    50                  55                  60

Thr Leu Val Asp Arg Lys Glu Val Ala Pro Val His Glu Ser Lys Ala
65                  70                  75                  80

Thr Gly Pro Lys Gln Asp Ser Cys Phe Gly Arg Met Tyr Thr Val Lys
                85                  90                  95

Val Asn Asp Asp Arg Asn Val Glu Ile Thr Gln Ala Val Pro Glu Tyr
            100                 105                 110

Ala Thr Val Gly Ser Pro Tyr Pro Ile Glu Ile Thr Ala Thr Gly Lys
        115                 120                 125

Arg Asp Cys Val Asp Val Ile Ile Thr Gln Gln Leu Pro Cys Glu Ala
    130                 135                 140

Glu Phe Val Arg Ser Asp Pro Ala Thr Pro Thr Ala Asp Gly Lys
145                 150                 155                 160

Leu Val Trp Lys Ile Asp Arg Leu Gly Gln Gly Glu Lys Ser Lys Ile
                165                 170                 175

Thr Val Trp Val Lys Pro Leu Lys Glu Gly Cys Cys Phe Thr Ala Ala
            180                 185                 190

Thr Val Cys Ala Cys Pro Glu Ile Arg Ser Val Thr Lys Cys Gly Gln
        195                 200                 205

Pro Ala Ile Cys Val Lys Gln Glu Gly Pro Glu Asn Ala Cys Leu Arg
    210                 215                 220
```

```
Cys Pro Val Val Tyr Lys Ile Asn Val Val Asn Gln Gly Thr Ala Ile
225                 230                 235                 240

Ala Arg Asn Val Val Glu Asn Pro Val Pro Asp Gly Tyr Ala His
            245                 250                 255

Ser Ser Gly Gln Arg Val Leu Thr Phe Thr Leu Gly Asp Met Gln Pro
            260                 265                 270

Gly Glu His Arg Thr Ile Thr Val Glu Phe Cys Pro Leu Lys Arg Gly
            275                 280                 285

Arg Ala Thr Asn Ile Ala Thr Val Ser Tyr Cys Gly His Lys Asn
            290                 295                 300

Thr Ala Ser Val Thr Thr Val Ile Asn Glu Pro Cys Val Gln Val Ser
305                 310                 315                 320

Ile Ala Gly Ala Asp Trp Ser Tyr Val Cys Lys Pro Val Glu Tyr Val
                325                 330                 335

Ile Ser Val Ser Asn Pro Gly Asp Leu Val Leu Arg Asp Val Val Val
                340                 345                 350

Glu Asp Thr Leu Ser Pro Gly Val Thr Val Leu Glu Ala Ala Gly Ala
            355                 360                 365

Gln Ile Ser Cys Asn Lys Val Val Trp Thr Val Lys Glu Leu Asn Pro
            370                 375                 380

Gly Glu Ser Leu Gln Tyr Lys Val Leu Val Arg Ala Gln Thr Pro Gly
385                 390                 395                 400

Gln Phe Thr Asn Asn Val Val Lys Ser Cys Ser Asp Cys Gly Thr
                405                 410                 415

Cys Thr Ser Cys Ala Glu Ala Thr Thr Tyr Trp Lys Gly Val Ala Ala
                420                 425                 430

Thr His Met Cys Val Val Asp Thr Cys Asp Pro Val Cys Val Gly Glu
            435                 440                 445

Asn Thr Val Tyr Arg Ile Cys Val Thr Asn Arg Gly Ser Ala Glu Asp
            450                 455                 460

Thr Asn Val Ser Leu Met Leu Lys Phe Ser Lys Glu Leu Gln Pro Val
465                 470                 475                 480

Ser Phe Ser Gly Pro Thr Lys Gly Thr Ile Thr Gly Asn Thr Val Val
                485                 490                 495

Phe Asp Ser Leu Pro Arg Leu Gly Ser Lys Glu Thr Val Glu Phe Ser
            500                 505                 510

Val Thr Leu Lys Ala Val Ser Ala Gly Asp Ala Arg Gly Glu Ala Ile
            515                 520                 525

Leu Ser Ser Asp Thr Leu Thr Val Pro Val Ser Asp Thr Glu Asn Thr
530                 535                 540

His Ile Tyr
545

<210> SEQ ID NO 75
<211> LENGTH: 635
<212> TYPE: PRT
<213> ORGANISM: Neisseria gonorrhoeae (strain ATCC 700825 / FA 1090)

<400> SEQUENCE: 75

Met Pro Ser Glu Ala Ser Arg Pro Val Arg Thr Val Leu Glu Ser Lys
1               5                   10                  15

Ser Ala Thr Pro Met His Asp Thr Arg Thr Met Met Ile Lys Pro Thr
            20                  25                  30

Ala Leu Leu Leu Pro Ala Leu Phe Phe Phe Pro His Ala Tyr Ala Pro
```

```
            35                  40                  45
Ala Ala Asp Leu Ser Glu Asn Lys Ala Gly Phe Ala Leu Phe Lys
             50                  55                  60
Ser Lys Ser Pro Asp Thr Glu Ser Val Lys Leu Lys Pro Lys Phe Pro
 65                  70                  75                  80
Val Arg Ile Asp Thr Gln Asp Ser Glu Ile Lys Asp Met Val Glu Glu
                 85                  90                  95
His Leu Pro Leu Ile Thr Gln Gln Glu Glu Val Leu Asp Lys Glu
                100                 105                 110
Gln Thr Gly Phe Leu Ala Glu Ala Pro Asp Asn Val Lys Thr Met
             115                 120                 125
Leu Arg Ser Lys Gly Tyr Phe Ser Ser Lys Val Ser Leu Thr Glu Lys
130                 135                 140
Asp Gly Ala Tyr Thr Val His Ile Thr Pro Gly Pro Arg Thr Lys Ile
145                 150                 155                 160
Ala Asn Val Gly Val Ala Ile Leu Gly Asp Ile Leu Ser Asp Gly Asn
                165                 170                 175
Leu Ala Glu Tyr Tyr Arg Asn Ala Leu Glu Asn Trp Gln Gln Pro Val
            180                 185                 190
Gly Ser Asp Phe Asp Gln Asp Ser Trp Glu Asn Ser Lys Thr Ser Val
            195                 200                 205
Leu Gly Ala Val Thr Arg Lys Gly Tyr Pro Leu Ala Lys Leu Gly Asn
210                 215                 220
Thr Arg Ala Ala Val Asn Pro Asp Thr Ala Thr Ala Asp Leu Asn Val
225                 230                 235                 240
Val Val Asp Ser Gly Arg Pro Ile Ala Phe Gly Asp Phe Glu Ile Thr
                245                 250                 255
Gly Thr Gln Arg Tyr Pro Glu Gln Thr Val Ser Gly Leu Ala Arg Phe
            260                 265                 270
Gln Pro Gly Thr Pro Tyr Asp Leu Asp Leu Leu Asp Phe Gln Gln
            275                 280                 285
Ala Leu Glu Gln Asn Gly His Tyr Ser Gly Ala Ser Val Gln Ala Asp
        290                 295                 300
Phe Asp Arg Leu Gln Gly Asp Arg Val Pro Val Lys Val Ser Val Thr
305                 310                 315                 320
Glu Val Lys Arg His Lys Leu Glu Thr Gly Ile Arg Leu Asp Ser Glu
                325                 330                 335
Tyr Gly Leu Gly Gly Lys Ile Ala Tyr Asp Tyr Asn Leu Phe Asn
            340                 345                 350
Lys Gly Tyr Ile Gly Ser Val Val Trp Asp Met Asp Lys Tyr Glu Thr
        355                 360                 365
Thr Leu Ala Ala Gly Ile Ser Gln Pro Arg Asn Tyr Arg Gly Asn Tyr
        370                 375                 380
Trp Thr Ser Asn Val Ser Tyr Asn Arg Ser Thr Thr Gln Asn Leu Glu
385                 390                 395                 400
Lys Arg Ala Phe Ser Gly Ile Trp Tyr Val Arg Asp Arg Ala Gly
                405                 410                 415
Ile Asp Ala Arg Leu Gly Ala Glu Phe Leu Ala Glu Gly Arg Lys Ile
            420                 425                 430
Pro Gly Ser Asp Val Asp Leu Gly Asn Ser His Ala Thr Met Leu Thr
        435                 440                 445
Ala Ser Trp Lys Arg Gln Leu Leu Asn Asn Val Leu His Pro Glu Asn
450                 455                 460
```

-continued

Gly His Tyr Leu Asp Gly Lys Ile Gly Thr Thr Leu Gly Thr Phe Leu
465                 470                 475                 480

Ser Ser Thr Ala Leu Ile Arg Thr Ser Arg Ala Gly Tyr Phe Phe
            485                 490                 495

Thr Pro Glu Asn Lys Lys Leu Gly Thr Phe Ile Ile Arg Gly Gln Ala
            500                 505                 510

Gly Tyr Thr Val Ala Arg Asp Asn Ala Asp Val Pro Ser Gly Leu Met
            515                 520                 525

Phe Arg Ser Gly Gly Ala Ser Ser Val Arg Gly Tyr Glu Leu Asp Ser
            530                 535                 540

Ile Gly Leu Ala Gly Pro Asn Gly Ser Val Leu Pro Glu Arg Ala Leu
545                 550                 555                 560

Leu Val Gly Ser Leu Glu Tyr Gln Leu Pro Phe Thr Arg Thr Leu Ser
                565                 570                 575

Gly Ala Val Phe His Asp Met Gly Asp Ala Ala Asn Phe Lys Arg
                580                 585                 590

Met Lys Leu Lys His Gly Ser Gly Leu Gly Val Arg Trp Phe Ser Pro
            595                 600                 605

Leu Ala Pro Phe Ser Phe Asp Ile Ala Tyr Gly His Ser Asp Lys Lys
            610                 615                 620

Ile Arg Trp His Ile Ser Leu Gly Thr Arg Phe
625                 630                 635

<210> SEQ ID NO 76
<211> LENGTH: 467
<212> TYPE: PRT
<213> ORGANISM: Neisseria gonorrhoeae

<400> SEQUENCE: 76

Met Lys Lys Ile Gln Ala Asp Ile Val Val Ile Gly Gly Gly Thr Ala
1               5                   10                  15

Gly Met Gly Ala Phe Arg Asn Ala Arg Leu His Ser Asp Asn Val Tyr
                20                  25                  30

Leu Ile Glu Asn Asn Val Phe Gly Thr Thr Cys Ala Arg Val Gly Cys
            35                  40                  45

Met Pro Ser Lys Leu Leu Ile Ala Ala Glu Ala Arg His His Ala
        50                  55                  60

Leu His Thr Asp Pro Phe Gly Val His Leu Asp Lys Asp Ser Ile Val
65                  70                  75                  80

Val Asn Gly Glu Glu Val Met Arg Arg Val Lys Ser Glu Arg Asp Arg
                85                  90                  95

Phe Val Gly Phe Val Val Thr Asp Val Glu Glu Trp Pro Ala Asp Lys
            100                 105                 110

Arg Ile Met Gly Ser Ala Lys Phe Ile Asp Glu His Thr Val Gln Ile
        115                 120                 125

Asp Asp His Ile Gln Ile Ala Ala Lys Ser Phe Val Ile Ala Thr Gly
    130                 135                 140

Ser Arg Pro Val Ile Leu Pro Gln Trp Gln Ser Leu Gly Asp Arg Leu
145                 150                 155                 160

Ile Ile Asn Asp Asp Val Phe Ser Trp Asp Thr Leu Pro Lys Arg Val
                165                 170                 175

Ala Val Phe Gly Pro Gly Val Ile Gly Leu Glu Leu Gly Gln Ala Leu
            180                 185                 190

His Arg Leu Gly Val Lys Val Glu Ile Phe Gly Leu Gly Gly Ile Ile

```
        195                 200                 205
Gly Gly Ile Ser Asp Pro Val Val Ser Asp Glu Ala Lys Ala Val Phe
    210                 215                 220

Gly Glu Glu Leu Lys Leu His Leu Asp Ala Lys Thr Glu Val Lys Leu
225                 230                 235                 240

Asp Ala Asp Gly Asn Val Glu Val His Trp Glu Gln Asp Gly Glu Lys
                245                 250                 255

Gly Val Phe Val Ala Glu Tyr Met Leu Ala Ala Val Gly Arg Arg Pro
            260                 265                 270

Asn Val Asp Asn Ile Gly Leu Glu Asn Ile Asn Ile Asp Lys Asp Ala
        275                 280                 285

Arg Gly Val Pro Val Ala Asp Pro Leu Thr Met Gln Thr Ser Ile Pro
    290                 295                 300

His Ile Phe Ile Ala Gly Asp Ala Ser Asn Gln Leu Pro Leu Leu His
305                 310                 315                 320

Glu Ala Ala Asp Gln Gly Lys Ile Ala Gly Asp Asn Ala Gly Arg Tyr
                325                 330                 335

Pro Asn Ile Gly Ser Gly Leu Arg Arg Ser Thr Ile Gly Val Val Phe
            340                 345                 350

Thr Ser Pro Gln Ile Gly Phe Val Gly Leu Lys Tyr Ala Gln Val Ala
        355                 360                 365

Ala Gln Tyr Gln Ala Asp Glu Phe Val Ile Gly Glu Val Ser Phe Lys
    370                 375                 380

Asn Gln Gly Arg Ser Arg Val Met Leu Val Asn Lys Gly His Met Arg
385                 390                 395                 400

Leu Tyr Ala Glu Lys Ala Thr Gly Arg Phe Ile Gly Ala Glu Ile Val
                405                 410                 415

Gly Pro Ala Ala Glu His Leu Ala His Leu Leu Ala Trp Ala His Gln
            420                 425                 430

Met Lys Met Thr Val Pro Gln Met Leu Asp Met Pro Phe Tyr His Pro
        435                 440                 445

Val Ile Glu Glu Gly Leu Arg Thr Ala Leu Arg Asp Ala Asp Ala Lys
    450                 455                 460

Leu Lys Ala
465

<210> SEQ ID NO 77
<211> LENGTH: 297
<212> TYPE: PRT
<213> ORGANISM: Neisseria gonorrhoeae

<400> SEQUENCE: 77

Met Ile Ile Ala Glu Asp Val Glu Gly Glu Ala Leu Ala Thr Leu Val
1               5                   10                  15

Val Asn Asn Ile Arg Gly Ile Leu Lys Thr Val Ala Lys Ala Pro
        20                  25                  30

Gly Phe Gly Asp Arg Arg Lys Ala Met Leu Gln Asp Ile Ala Ile Leu
            35                  40                  45

Thr Gly Gly Val Val Ile Ser Glu Glu Val Gly Leu Ser Leu Glu Lys
        50                  55                  60

Ala Thr Leu Asp Asp Leu Gly Gln Ala Lys Arg Ile Glu Ile Gly Lys
65                  70                  75                  80

Glu Asn Thr Thr Val Ile Asp Gly Phe Gly Asp Ala Ala Gln Ile Glu
                85                  90                  95
```

Ala Arg Val Ala Glu Ile Arg Gln Gln Ile Glu Thr Ala Thr Ser Asp
            100                 105                 110

Tyr Asp Lys Glu Lys Leu Gln Glu Arg Val Ala Lys Leu Ala Gly Gly
        115                 120                 125

Val Ala Val Ile Lys Val Gly Ala Ala Thr Glu Val Glu Met Lys Glu
    130                 135                 140

Lys Lys Asp Arg Val Glu Asp Ala Leu His Ala Thr Arg Ala Ala Val
145                 150                 155                 160

Glu Glu Gly Val Val Ala Gly Gly Val Ala Leu Leu Arg Ala Arg
                165                 170                 175

Ala Ala Leu Glu Asn Leu His Thr Gly Asn Ala Asp Gln Asp Ala Gly
            180                 185                 190

Val Gln Ile Val Leu Arg Ala Val Glu Ser Pro Leu Arg Gln Ile Val
        195                 200                 205

Ala Asn Ala Gly Gly Glu Pro Ser Val Val Asn Lys Val Leu Glu
    210                 215                 220

Gly Lys Gly Asn Tyr Gly Tyr Asn Ala Gly Ser Gly Glu Tyr Gly Asp
225                 230                 235                 240

Met Ile Gly Met Gly Val Leu Asp Pro Ala Lys Val Thr Arg Ser Ala
                245                 250                 255

Leu Gln His Ala Ala Ser Ile Ala Gly Leu Met Leu Thr Thr Asp Cys
            260                 265                 270

Met Ile Ala Glu Ile Pro Glu Glu Lys Pro Ala Val Pro Asp Met Gly
        275                 280                 285

Gly Met Gly Gly Met Gly Gly Met Met
    290                 295

<210> SEQ ID NO 78
<211> LENGTH: 90
<212> TYPE: PRT
<213> ORGANISM: Neisseria gonorrhoeae (strain ATCC 700825 / FA 1090)

<400> SEQUENCE: 78

Met Arg Lys Thr Phe Leu Ile Leu Thr Val Ser Ala Ala Leu Leu Ser
1               5                   10                  15

Gly Cys Ala Trp Glu Thr Tyr Gln Asp Gly Asn Gly Lys Thr Ala Val
            20                  25                  30

Arg Gln Lys Tyr Pro Ala Gly Thr Pro Val Tyr Gln Asp Gly Ser
        35                  40                  45

Tyr Ser Lys Asn Met Asn Tyr Asn Gln Tyr Arg Pro Glu Arg Arg Ala
    50                  55                  60

Val Leu Pro Asp Gln Thr Gly Asn Asn Ala Asp Glu Glu His Arg Gln
65                  70                  75                  80

His Trp Gln Lys Pro Lys Phe Gln Asn Arg
            85                  90

<210> SEQ ID NO 79
<211> LENGTH: 288
<212> TYPE: PRT
<213> ORGANISM: Neisseria gonorrhoeae (strain ATCC 700825 / FA 1090)

<400> SEQUENCE: 79

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
            20                  25                  30

-continued

Ala Ala Pro Ser Ala Asp Asn Gly Ala Ala Lys Lys Glu Ile Val Phe
            35                  40                  45

Gly Thr Thr Val Gly Asp Phe Gly Asp Met Val Lys Glu Gln Ile Gln
 50                  55                  60

Ala Glu Leu Glu Lys Lys Gly Tyr Thr Val Lys Leu Val Glu Phe Thr
 65                  70                  75                  80

Asp Tyr Val Arg Pro Asn Leu Ala Leu Ala Glu Gly Glu Leu Asp Ile
                 85                  90                  95

Asn Val Phe Gln His Lys Pro Tyr Leu Asp Asp Phe Lys Lys Glu His
            100                 105                 110

Asn Leu Asp Ile Thr Glu Ala Phe Gln Val Pro Thr Ala Pro Leu Gly
            115                 120                 125

Leu Tyr Pro Gly Lys Leu Lys Ser Leu Glu Glu Val Lys Asp Gly Ser
130                 135                 140

Thr Val Ser Ala Pro Asn Asp Pro Ser Asn Phe Ala Arg Ala Leu Val
145                 150                 155                 160

Met Leu Asn Glu Leu Gly Trp Ile Lys Leu Lys Asp Gly Ile Asn Pro
                165                 170                 175

Leu Thr Ala Ser Lys Ala Asp Ile Ala Glu Asn Leu Lys Asn Ile Lys
            180                 185                 190

Ile Val Glu Leu Glu Ala Ala Gln Leu Pro Arg Ser Arg Ala Asp Val
            195                 200                 205

Asp Phe Ala Val Val Asn Gly Asn Tyr Ala Ile Ser Ser Gly Met Lys
            210                 215                 220

Leu Thr Glu Ala Leu Phe Gln Glu Pro Ser Phe Ala Tyr Val Asn Trp
225                 230                 235                 240

Ser Ala Val Lys Thr Ala Asp Lys Asp Ser Gln Trp Leu Lys Asp Val
                245                 250                 255

Thr Glu Ala Tyr Asn Ser Asp Ala Phe Lys Ala Tyr Ala His Lys Arg
            260                 265                 270

Phe Glu Gly Tyr Lys Tyr Pro Ala Ala Trp Asn Glu Gly Ala Ala Lys
            275                 280                 285

<210> SEQ ID NO 80
<211> LENGTH: 751
<212> TYPE: PRT
<213> ORGANISM: Trichomonas vaginalis G3

<400> SEQUENCE: 80

Met Phe Cys Ser Leu Leu Ile Thr Ser Ala Phe Ala Ile His Asn Arg
 1               5                  10                  15

Thr Glu Asn Ile Thr Leu Lys Asp Asp Gln Thr Leu Val Tyr Ser His
             20                  25                  30

Leu Lys Asn Gly Ser Tyr Leu Met Pro Leu Tyr Val Lys Asp Ile Trp
         35                  40                  45

Pro Glu Cys Glu Asn Asp Thr Ser Ile Thr Phe Cys Trp Tyr Tyr Leu
 50                  55                  60

Thr Arg Gly Asn Ala Trp Asp Phe Gly Tyr Ala Lys Leu Pro Asn Gly
 65                  70                  75                  80

Val Gln His Pro Gln Lys Gly Gln Tyr Cys Thr Asp Phe Asp Val Leu
                 85                  90                  95

Tyr Arg Gly Ala Trp Thr Thr Phe Ala Lys Thr Gly Trp Trp Pro Ile
            100                 105                 110

Trp Ser Ile Asp Asp Ser Ile Tyr Tyr Arg Ile His Gly Ser Glu Asn
            115                 120                 125

```
Gly Thr Asn Thr Leu Arg Asn Val Thr Ile Arg Thr Lys Ile Thr Gln
        130                 135                 140

Pro Ala Gly Pro Asn Tyr Leu Leu Ile Glu Phe Ile Ala His Asn His
145                 150                 155                 160

Asp Ser Gln Pro His Ile Val Asn Val Leu Ser Tyr Thr Asp Val Met
                165                 170                 175

Ile Gly Asn Lys Asp Ser Ala Pro Ile Lys Trp Tyr Pro Asn Thr
            180                 185                 190

His Asn Gly Phe Ser Met Glu Asn Glu Ala Asn Arg Thr Leu Val
        195                 200                 205

Leu Ile Gly Lys Asn Gly Phe Gly Val Asn Pro Val Asp Tyr Leu Trp
    210                 215                 220

Phe Gly Leu Tyr Ser Glu Gly Gln Thr Tyr Lys Phe Asn Lys Thr Asp
225                 230                 235                 240

Glu Ser Pro Thr Pro Ile Gly Arg Asp Thr Ala Phe Ser Leu Gly Trp
                245                 250                 255

Thr Asn Arg Arg Ile Tyr Pro Gly Gln Asn Leu Ser Phe Gly Val Leu
            260                 265                 270

Leu Gly Ile Gly Glu Phe Asn Gln Leu Lys Phe Pro Pro Thr Ile Thr
        275                 280                 285

Val Asp Glu Ser Lys Phe Lys Ile Asn Tyr Ala Pro Gly Glu Lys Ile
    290                 295                 300

Lys Ile Pro Ile Arg Val Gln Asp Lys Leu Thr Gly Ser Tyr Gly Leu
305                 310                 315                 320

Arg Val Thr Cys Glu Phe Pro Asn Asn Glu Ser Lys Thr His Asn Ile
                325                 330                 335

Ser Lys Thr Glu Gly Thr Val Asn Glu Pro Val Glu Phe Glu Tyr Asp
            340                 345                 350

Leu Gly Gln Asn Ile Ser Arg Tyr Pro Val Lys Cys Tyr Ala Glu Asn
        355                 360                 365

Tyr Asp Ile Thr Lys Thr Asp His Pro Gly Pro Lys Ser Asn Asp Phe
    370                 375                 380

Asn Arg Val Phe Leu Val Asn Glu Ala Pro Arg Leu Thr Leu Thr Ser
385                 390                 395                 400

Gln Ile Asn Asp Gln Tyr Gly Arg Gly Gly Tyr Val Asn Ile Asp Gly
                405                 410                 415

Ile Val Trp Asp Asp Thr Arg Val Thr Met Thr Tyr Gln Val Asp Asp
            420                 425                 430

Asn Phe Tyr Tyr Arg Ala Asp Gly Asp Ile Thr Cys Asp Lys Gln Glu
        435                 440                 445

Lys Leu Phe Ser Lys Gln Ile Gln Ile Ser Pro Ser Tyr Ser Tyr Gly
    450                 455                 460

Lys His Thr Leu Gln Ile Trp Ala Glu Asp Glu Phe Gly Val Lys Ser
465                 470                 475                 480

Pro Ile Val Lys Lys Glu Phe Ser Val Gln Asn His Pro Pro Glu
                485                 490                 495

Val Asn Ile Thr Glu Val Asp Asp Asn Lys Ser Gly Asn Tyr Tyr Asn
            500                 505                 510

Ser Pro Ile Thr Phe Lys Leu Gln Val Arg Asp Val Asp Val Asp Asp
        515                 520                 525

Val Ile Leu Leu Met Val Lys Thr Pro Gly Thr Asn Gln Phe Ala Gln
    530                 535                 540
```

```
Ile Met Thr Thr Pro Ala Lys Gln Gln Glu Trp Ile Asn Phe Thr Tyr
545                 550                 555                 560

Thr Tyr Asp Val Glu Ala Leu His Glu Glu Gly Asn Tyr Ala Ile Ile
            565                 570                 575

Phe Gln Ala Thr Asp Arg Ile Gly Ser Pro Ser Arg Asn Lys Glu Tyr
            580                 585                 590

Thr Phe Ile Phe Lys Lys His Pro Val Pro Thr Pro Ala Gln Pro Arg
            595                 600                 605

Ser Glu Lys Thr Asp Asn Ser Gly Asn Ile Glu Gln Cys Ala Met Val
            610                 615                 620

Thr Asp Ala Asn Gly Asp Ser Phe Leu Asn Cys Thr Met Thr His Val
625                 630                 635                 640

Ile Ile Asp Val Asn Gln Lys Thr Pro Ser Ala Ser Asn Asp Asp Gly
            645                 650                 655

Asp Ala Phe Ser Asn Gln Gly Asp Ala Asn Lys Ser Asn Ser Lys Lys
            660                 665                 670

Lys Asp Lys Tyr Leu Ile Ile Gly Ile Ala Ala Ala Val Val Ala
            675                 680                 685

Ala Ala Ile Ile Ala Ala Ile Leu Ile Ala Lys Glu Ala Ser Lys
690                 695                 700

Lys Ala Asn Asp Phe Gly Phe Asn Pro Glu Thr Glu Glu Ala Leu Gln
705                 710                 715                 720

Ala Asn Asn Asp Phe Val Gln Glu Lys Glu Asn Pro Val Tyr Asn Glu
            725                 730                 735

Asn Ala Gln Asp Asp Pro Phe Ala Asn Glu Phe Glu Asp Val Asp
            740                 745                 750

<210> SEQ ID NO 81
<211> LENGTH: 748
<212> TYPE: PRT
<213> ORGANISM: Trichomonas vaginalis G3

<400> SEQUENCE: 81

Met Leu Pro Leu Phe Tyr Thr Leu Ile Ser Ser Asp Asp Tyr Ile Val
1               5                   10                  15

Lys Thr Lys Tyr Leu Arg Ala Tyr Tyr Cys Arg His Tyr Tyr Tyr Asp
            20                  25                  30

Pro Trp Thr Asp Ile Asn Ile Gln Tyr Asn Glu Arg Ala Asp Ser Thr
            35                  40                  45

Ser Gly Gly Glu Arg Trp Val Pro Thr Thr Tyr Ser Asp Gly Gly Trp
50                  55                  60

Phe Pro Ile Phe Lys Val Asp Asp Pro Thr Lys Val Arg Ile Leu
65                  70                  75                  80

Gly Ser Asn Arg Gly Val Ser Asn Tyr Lys Gly Ile Tyr Ala Ser Thr
            85                  90                  95

Asn Val Thr Tyr His Pro Glu Ile Gly Glu Lys Tyr Leu Leu Ile Thr
            100                 105                 110

Tyr Ser Phe Lys Asn Gln Asp Thr Arg Pro His Thr Leu His Val Ala
            115                 120                 125

Ser His Thr Asp Val Gln Ile Arg Ser Asn Asp Arg Ala Thr Cys Lys
            130                 135                 140

Trp Tyr Tyr Gly Lys Arg Gly Leu Thr Met Lys Asp Pro Gly Thr Gly
145                 150                 155                 160

Ile Thr Leu Thr Leu Leu Ile Lys Gly Gly Tyr His Val Thr Asp Val
            165                 170                 175
```

```
Asp Thr Phe Trp Phe Gly Arg Trp Gln Gly Pro Asn Thr Asn Leu His
                180                 185                 190

Tyr Phe Asp Asn Tyr Thr Asp Ser Gly Asp Asn Asp Leu Val Asn Thr
            195                 200                 205

Asp Ser Ala Phe Ser Ile Gly Trp Leu Asn Arg His Ile Tyr Pro Asn
        210                 215                 220

Glu Thr Leu Asp Phe Ser Val Leu Leu Gly Val Gly Ala Asn Leu Lys
225                 230                 235                 240

Asn Pro Ala Val Leu Thr Val Asn Asp Asn Phe Ala Asp Asn Asn Met
                245                 250                 255

Pro Asn Gln Glu Ile Thr Val Thr Gly Thr Val Asn Asp Phe Asp Pro
            260                 265                 270

Asp Glu Asn Val Thr Val Tyr Tyr Gln Phe Asn Gly Gly Pro Glu Thr
        275                 280                 285

Lys Val Glu Thr Phe Pro Thr Gly Ala Ser Gly Gly Ile Ser Asn Gly
        290                 295                 300

Ala Phe Ser Phe Lys Val Thr Leu Gly Pro Asp Val Ala Gln Tyr Pro
305                 310                 315                 320

Leu Lys Val Tyr Ala Arg Asp Ser Phe Gly Leu Thr Ser Asn Val Phe
                325                 330                 335

Glu Lys Asn Leu Leu Val Asn Glu Ile Pro Arg Leu Val Leu Thr Arg
            340                 345                 350

Ala Pro Pro Ser Thr Phe Phe Thr Gly Gly Thr Val Ile Leu Glu Gly
        355                 360                 365

Thr Ile Trp Asp Asp Arg Lys Ala Thr Leu Lys Tyr Gln Val Asp Asn
        370                 375                 380

Gly Tyr Asn Trp Asn Thr Gly Asp Glu Glu Phe Val Cys Asn Arg Ala
385                 390                 395                 400

Thr Lys Pro Phe Arg Lys Ser Phe Pro Ile Gln Glu Asp Tyr Ile Asn
                405                 410                 415

Tyr Gly His His Val Ile Lys Ile Trp Ala Gln Asp Asp Phe Gly Val
            420                 425                 430

Gln Ser Glu Pro Ile Ile Ala Glu Phe Asp Tyr Val Gln Leu His Ala
        435                 440                 445

Pro Glu Met Lys Pro Ser Gln Ala Gln Thr Ser Ile Pro Glu Val His
        450                 455                 460

Val Gly Lys Lys Phe Thr Ile Ser Gly Gln Ala Arg Asp Ile Asp Ser
465                 470                 475                 480

Gly Glu Arg Val Ser Val Tyr Tyr Lys Tyr Pro Glu Asp Thr Pro Gly
                485                 490                 495

Thr Gln Pro Arg Pro Leu Phe Thr Phe Asp Ser Asn Thr Gly Trp Gln
            500                 505                 510

Glu Trp Glu Ile Glu Tyr Glu Val Pro Asp Arg Lys Leu Pro Phe Asp
        515                 520                 525

Gln Glu Val Lys Val Ile Leu Tyr Ala Glu Asp Thr Arg Gly Gly Thr
        530                 535                 540

Ser Ala Asp Leu Glu Phe Lys Phe Ile Val Lys Lys Val Gln Thr Ile
545                 550                 555                 560

Pro Pro Thr Pro Tyr Asp Gly Glu Val Pro Asn Pro Ser Asp Asn
                565                 570                 575

Pro Asn Ile Pro Asp Ser Ser Tyr Ser Gly Leu Thr Ala Thr Ser Glu
            580                 585                 590
```

```
Val Pro Thr Ile Val Cys Glu Glu His Thr Asp Val Asn Gly Asp Thr
            595                 600                 605

Tyr Thr Arg Cys Asp Leu Gly Thr Thr Tyr Ile Val Ile Thr Thr Asp
    610                 615                 620

Ala Thr Pro Ala Pro Thr Gln Ser Ala Thr Pro Ser Ala Ser Pro Glu
625                 630                 635                 640

Pro Gly Ala Phe Pro Glu Glu Asp Asn Ala Lys Glu Val Ser Ala Ser
                645                 650                 655

Lys Glu Lys Ser Asn Lys Lys Lys Met Leu Ile Ile Gly Leu Ala Ala
                660                 665                 670

Gly Gly Val Ala Ala Ala Val Ala Ala Ala Ile Ile Ile His
            675                 680                 685

Glu Ala Thr Lys Ala Pro Lys Asp Phe Val Phe Asn Glu Glu Asn Gly
            690                 695                 700

Glu Phe Met Glu Val Asp Gly Asp Ala Cys Gln Asp Ala Asp Asn Pro
705                 710                 715                 720

Ile Tyr Asp Glu Asn Gly Ala Asp Pro Phe Ala Asn Glu Phe Asp
                725                 730                 735

Glu Asp Asp Gly Pro Val Glu Gly Ile Phe Pro Ala
            740                 745
```

<210> SEQ ID NO 82
<211> LENGTH: 613
<212> TYPE: PRT
<213> ORGANISM: Trichomonas vaginalis G3

<400> SEQUENCE: 82

```
Met Phe Asn Leu Phe Leu Ala Thr Val Ser Ser Glu Lys Arg Pro Gln
1               5                   10                  15

Ile Glu Ala Asp Lys Val Arg Phe Gln Gly Tyr Gly Lys Phe Ser Lys
            20                  25                  30

Thr Gly His Gln Ile Ala Ile Ser Ser Asn Gln Arg Leu Tyr Tyr Tyr
        35                  40                  45

Ala Ser Val His Ile Ile Asn Ala Tyr Phe Ser Asn Cys Val Ala Asn
    50                  55                  60

Asp Leu Asn Leu Lys Trp Gln Met Ser Cys Gly Gly Ala Ile Phe Leu
65              70                  75                  80

Asn Lys Gly Ser Leu Tyr Phe Glu Arg Lys Asp Gly Ser Tyr Ser Ser
                85                  90                  95

Ser Phe Asp Gln Cys Gln Ala Thr Asp Lys Gly Gly Ala Ile Tyr Ala
            100                 105                 110

Tyr Asp Ser Ala Cys Asp Ile Phe Gln Val Asn Phe Arg Cys Lys
        115                 120                 125

Ala Gly Asn Glu Gly Gly Ala Tyr Tyr His Asp Gly Met Arg Tyr Ser
    130                 135                 140

Arg Pro Tyr Tyr Ala Asn Ala Lys Tyr Asn Thr Leu Ile Ile Glu Tyr
145                 150                 155                 160

Cys Thr Phe Lys Gly Asn Leu Ala Asp Ser Tyr Gly Gly Ala Leu Ala
                165                 170                 175

Val Lys Gly Ala Val Pro Phe Thr Leu Lys Asn Ser Lys Phe Leu Asn
            180                 185                 190

Asn Gly Ala Val Ala Gly Gly Ala Leu Tyr Gly Asp Tyr Ser Asp Ile
        195                 200                 205

Thr Met Thr Asn Asn Leu Phe Val Leu Asn Phe Gly Asp His Thr Arg
    210                 215                 220
```

```
Pro Cys Gln Asn Asn Lys Lys Cys Gly Ser Pro Asn Tyr Gln Ser Phe
225                 230                 235                 240

Lys Tyr Val Pro Ala Gly Ala Ile Leu Ile Arg Ser Ser Pro Glu Tyr
            245                 250                 255

Phe Pro Val Asp Val Tyr Ser Ala Glu Asn Cys Phe Asn Gln Asn Phe
                260                 265                 270

Leu Leu Asn Asn Arg Trp Pro Asp Lys Ser Lys Thr Ser Val Asn Ile
            275                 280                 285

Leu Leu Leu Phe Ala Val Arg Phe Lys Ser Val Asn Asp Lys Met Lys
        290                 295                 300

Trp His Thr Val Asn Val Ile Asp Asn Met Thr Leu Ala Lys Lys Phe
305                 310                 315                 320

Asn Tyr Pro Lys Glu Tyr Pro Ser Lys Tyr Ile Gln Leu Arg Ala Asn
                325                 330                 335

Gly Ile Asn Ile Arg Ser Phe Glu Met Thr Gly Thr Arg Gln Asp Val
            340                 345                 350

Glu Gly Cys Lys Ile Asp Gly Phe Pro Ala Val Thr Pro Ile Pro Pro
        355                 360                 365

Ala Thr Pro Ile Pro Thr Pro Tyr Pro Thr Val Pro Thr Pro Asp Pro
370                 375                 380

Thr Gln Pro Pro Pro Thr Arg Ser Leu Ala Ala Thr Pro Tyr Pro
385                 390                 395                 400

Thr Ile Pro Pro Pro Arg Thr Pro Phe Pro Ser Ala Thr Ile Pro Pro
                405                 410                 415

Ala Thr Lys Lys Lys Asp Thr Pro Phe Pro Thr Leu Ala Pro Pro Gln
            420                 425                 430

Thr Pro Ala Pro Thr Pro Ser Pro Ile Pro Thr Arg Glu Pro Thr Ala
            435                 440                 445

Pro Pro Thr Ala Thr Pro Ala Ala Thr Arg Ser Ala Ile Pro Thr Pro
        450                 455                 460

Ile Ser Val Pro Pro Thr Ile Asn Ile Thr Ile Pro Ala Asn Ala Ser
465                 470                 475                 480

Val Asp Glu Glu Ile Asn Thr Ser Asp Cys Gly Glu Met Cys Lys Thr
                485                 490                 495

Glu His Ile Pro Met Arg Thr Pro Asn Ala Ile Thr Ile Asn Tyr Glu
                500                 505                 510

Ser Pro Val Pro Asn Thr Glu Asp Ser Ala Asn Asn Ala Lys Asn Ala
            515                 520                 525

Val Ile Gly Arg Asn Thr Ala Ala Pro Asp Glu Ser Ala Val Gly Phe
            530                 535                 540

Val Ile Ala Ala Val Ala Ala Val Ala Ala Val Gly Val Ile Ala Gly
545                 550                 555                 560

Ile Ile Tyr Thr Leu Thr Arg Ser Lys Pro Pro Pro Met Asp Leu Glu
                565                 570                 575

Asn Ala Glu Arg Val Asn Met Gly Asn Asp Asn Asn Ala Val Glu Asn
                580                 585                 590

Asp Asn Pro Ile Tyr Asn Asn Asn Ala Ala Gln Asp Pro Phe Ala Asp
            595                 600                 605

Glu Phe Glu Asp Ala
610

<210> SEQ ID NO 83
<211> LENGTH: 596
```

<212> TYPE: PRT
<213> ORGANISM: Trichomonas vaginalis G3

<400> SEQUENCE: 83

```
Met Ser Ser Asp Lys Ser Ser Arg Val Thr Ser Glu Glu Asn Ile Glu
1               5                   10                  15

Lys Thr Thr Thr Thr Gly Phe Glu Met Phe Glu Cys Leu Lys Leu Phe
            20                  25                  30

Arg Asn Lys Ala Ile Leu Phe Leu Val Tyr Phe Ile Ser Leu Gly Asn
        35                  40                  45

Gly Ala Leu Pro Ile Phe Asn Met Met Ile Leu Gly Asp Val Thr Ser
    50                  55                  60

Ser Ala Ser Thr Asp Pro Thr Lys Thr Ala Thr Lys Leu Met Thr Pro
65                  70                  75                  80

Leu Leu Leu Lys Leu Thr Tyr Ile Ser Ile Ala Gln Ala Val Ile Leu
                85                  90                  95

Leu Ile Thr Ile Met Cys Lys Ser Tyr Ile Ile Pro Thr Phe Thr Val
            100                 105                 110

Asp Ile Arg Gln Ala Met Phe Asn Ser Ile Met Thr Gln Pro Ile Asp
        115                 120                 125

Phe Phe Asp Lys Thr Ser Ser Gly Val Leu Met Gly Arg Phe Ser Glu
130                 135                 140

Asp Ile Thr Ile Ile Arg Asp Val Tyr Ile Glu Lys Asn Cys Ala Met
145                 150                 155                 160

Leu Gln Gly Met Thr Met Ser Leu Ile Ala Ile Ile Met Gly Phe Ile
                165                 170                 175

Arg Leu Pro Tyr Val Ser Leu Ser Tyr Phe Val Ala Ile Pro Leu Leu
            180                 185                 190

Val Ala Ser Tyr Ile Leu Ser Glu Lys Tyr Ile Asp Lys Leu Trp Lys
        195                 200                 205

Asn His Asn Ile Gln Ser Thr Ser Ile Ala Ser Lys Thr Glu Glu Val
    210                 215                 220

Ile Ser Gln Tyr Arg Thr Val Lys Ala Phe Cys Glu Lys Lys Glu
225                 230                 235                 240

Cys Asp Asp Tyr Asn Asp Leu Leu Asp Asn Val Asp Ile Tyr Arg
                245                 250                 255

Lys Thr Ala Ile Ala Gln Gly Leu Lys Glu Ala Phe Ser Ser Ile Ile
            260                 265                 270

Ala Asn Gly Leu Thr Val Phe Val Tyr Phe Ile Ala Tyr Leu Met
        275                 280                 285

Met Val Lys Lys Asn Thr Lys Val Lys Ser Gly Asp Ser Leu Ser Met
290                 295                 300

Met Met Tyr Ile Met Leu Gly Thr Met Gly Phe Ser Gln Ile Leu Ser
305                 310                 315                 320

Ala Ser Asp Ser Tyr Lys Lys Ala Asn Met Ala Ala Leu Lys Ile Leu
                325                 330                 335

Asn Ile Ile Asn Arg Lys Val Glu Asn Asp Ser Glu Asn Gln Thr Glu
            340                 345                 350

Ile Gly Lys Ile Glu Gly Lys Ile Glu Phe Gln Asn Val Ser Phe Lys
        355                 360                 365

Tyr Ser Thr Arg Asp Glu Tyr Ala Ile Arg Asn Leu Thr Phe Glu Ile
    370                 375                 380

Lys Pro Gly Glu Thr Val Ala Leu Val Gly Glu Ser Gly Cys Gly Lys
385                 390                 395                 400
```

```
Thr Thr Thr Leu Ser Leu Leu Gln Arg Phe Tyr Asp Val Ser Glu Gly
            405                 410                 415

Lys Ile Leu Ile Asp Gly Lys Asp Ile Ser Asn Phe Ser Ala Ser Ser
            420                 425                 430

Leu Arg Ser Gln Ile Ser Cys Val Pro Gln Ser Pro Val Leu Phe Ser
            435                 440                 445

Met Ser Ile Leu Asp Asn Val Lys Tyr Gly Lys Pro Glu Ser Ser Phe
450                 455                 460

Asp Glu Val Lys Thr Ala Ala Glu Ile Gly Asn Ala His Asn Phe Ile
465                 470                 475                 480

Cys Gln Met Glu Asn Gln Tyr Asp Gln Glu Val Gln Gln Ile Ser Leu
            485                 490                 495

Ser Gly Gly Gln Lys Gln Arg Ile Cys Ile Ser Arg Ala Val Leu Cys
            500                 505                 510

Asn Ala Pro Ile Leu Leu Leu Asp Glu Ala Thr Ala Ser Leu Asp Ala
            515                 520                 525

Glu Ser Glu Gln Leu Val Gln Glu Ser Leu Glu Lys Val Arg Lys Gly
            530                 535                 540

Lys Thr Ala Ile Ile Val Ala His Arg Leu Ser Thr Val Lys Asn Ala
545                 550                 555                 560

Asp Arg Ile Leu Val Phe Asp Asn Gly Thr Ile Val Glu Thr Gly Thr
                565                 570                 575

His Glu Glu Leu Leu Glu Lys Gly Gly Ile Tyr Ser Asn Leu Val Lys
            580                 585                 590

Phe Gln Leu Gln
            595

<210> SEQ ID NO 84
<211> LENGTH: 846
<212> TYPE: PRT
<213> ORGANISM: Trichomonas vaginalis G3

<400> SEQUENCE: 84

Met Tyr Leu Gly Phe Leu Ile Ser Phe Ala Ser Ser Asn Gln Asn Lys
1               5                   10                  15

Pro Val Leu Glu Asn Cys Asn Tyr Tyr Ser Thr Tyr Asn Tyr Ser Cys
            20                  25                  30

Ala Thr Ile Pro Ser Gly Met Asn Tyr Ile Asp Gly Leu Leu Arg Cys
            35                  40                  45

Asn Ser Ser Ser Gln Val Ile Asp Leu Thr Ser Asp Glu Met Thr Cys
50                  55                  60

Ile Asp Tyr Ala Ser Gly Thr Lys Val Leu Tyr Asp Thr Ala Val Val
65                  70                  75                  80

Ser Glu Asn Thr Thr Gly Leu Ser Ser Lys Met Ile Val Phe Phe Asp
                85                  90                  95

Gln Ser Asp Lys Phe Ser Ser Arg Leu Ser Thr Asp Tyr Gly Asn Leu
            100                 105                 110

Leu Asp Asp Ala Val Lys Ala Cys Lys Ser Asn Tyr Ala Gln Met Tyr
            115                 120                 125

Thr Pro Cys Gln Ile Val Ala Ser Gly Cys Ala Leu Ser Ser Tyr Tyr
            130                 135                 140

Pro His Ser Pro Ala Cys Ile Ala Tyr Asn Ala Leu Pro Ala Ala Asn
145                 150                 155                 160

Ser Thr Thr Tyr Glu Tyr Lys Tyr Trp Pro Ala Asn Arg Pro Phe Ile
```

```
            165                 170                 175
Glu Tyr Gly Val Gln Ala Ser Lys Val Ile Asp Glu His Ile Met Asn
            180                 185                 190

Thr Thr Phe Ser Lys Glu Glu Gln Ile Asn Ile Val Leu Ala Arg Tyr
            195                 200                 205

Ser Gln Asn Gly Thr Phe Leu Gly Tyr Val Pro Leu Thr Asn Gln Phe
            210                 215                 220

Asp Ile Cys Thr Glu Lys Arg Asp Val Asn Leu Met Trp Gln Leu Tyr
225                 230                 235                 240

Gly Thr Gly Tyr Val Ser Glu Cys Glu Val Asn Ile Met Asp Ile Phe
            245                 250                 255

Asn Ser Thr Thr Thr Asp Val Tyr Asp Pro Phe Leu Val Gln Glu Val
            260                 265                 270

Ser Gly Thr Asn Val Leu Arg Pro Ile Pro Val Asn Val Leu Ser Tyr
            275                 280                 285

Arg Asp Ala Asn Glu Ile Pro Val Asn Gln Arg Ser Ile Glu Arg Lys
            290                 295                 300

Lys Arg Leu Phe Arg Arg Phe Phe Ala Leu Asp Asn Tyr Thr Asn Pro
305                 310                 315                 320

Ile Phe Ile Gln Tyr Leu Ser Ser Met Ser Ile Lys Phe Glu His Phe
            325                 330                 335

Asn Glu Thr Ser Glu Glu Arg Ile Pro Val Ile Thr Val Gly Tyr Thr
            340                 345                 350

Thr Val Arg Arg Ser Asp Leu Gln Glu Ser Asp Tyr Pro Ile Tyr Leu
            355                 360                 365

Asp Val Glu Ser Phe Thr Thr Ser Asn Tyr Ser Phe Ser Ile Glu Phe
            370                 375                 380

Ser Thr Asn Ile Glu Ser Tyr Trp Glu Ala Ala Leu Ile Thr Leu Ile
385                 390                 395                 400

Val Leu Ala Ile Ile Cys Ile Ile Ile Trp Leu Tyr Arg Ala Val Val
            405                 410                 415

Thr Val Lys Arg Tyr Gly Thr Glu Gly Ile Asp Phe Lys Val Ile Ala
            420                 425                 430

Ala Leu Phe Ala Glu Ala Phe Asn Ile Val Ala Trp Leu Leu Phe Ile
            435                 440                 445

Met Ala Phe Val Phe Ser Phe Ala Ile Phe Cys Ala Tyr Lys Trp Thr
            450                 455                 460

Pro Ser Ser Lys Tyr Thr Ile Leu Gly Asn Glu Phe Gly Ile Leu Thr
465                 470                 475                 480

Gly Phe Ile Trp Ala Ala Trp Val Leu Ser Phe Ile Gly Leu Val Ile
            485                 490                 495

Lys Tyr Val Leu Met Leu Thr Ser Glu Thr Phe Leu Ile Asp Trp Glu
            500                 505                 510

Pro Arg Arg Pro Ser Ile Pro Val Ser Ala Trp Arg Arg Ile Leu Val
            515                 520                 525

Gly Asn Glu Phe Leu Lys Leu His Thr Arg Arg Ser Tyr Asn Ile Pro
            530                 535                 540

Phe Thr Val Ile Thr Leu Val Phe Ile Leu Gly Gly Phe Gly Val Asp
545                 550                 555                 560

Lys Leu Gln Ala Val Leu Pro Ser Ser Thr Leu Ile Glu Ser Gly Ser
            565                 570                 575

Asn Tyr Gly Val Leu Arg Phe Ala Ile Val Thr Phe Ile Tyr Ile Leu
            580                 585                 590
```

```
Leu Leu Ile Phe Gln Tyr Ile Val Thr Arg Ile Val Trp Leu Ile Ser
            595                 600                 605

Gly Ser Pro Tyr Glu Asp Phe Ala Arg Leu Cys Gly Thr Ala Asn Val
        610                 615                 620

Ser Val Leu Thr Leu Leu Ser Pro Ser Trp Ala Ile Tyr Leu Asn Gly
625                 630                 635                 640

Arg Ala Met Lys Pro Ala Asp Glu Gly Asp Ile Lys Leu Ile Gln Ser
                645                 650                 655

Ile Ser Glu Ala Glu Lys Gly Ala Leu Ser Ile Lys Pro Leu Ser Glu
            660                 665                 670

Asn Arg Pro Glu Gln Val Tyr Glu Cys Phe Phe Ala Pro Lys Leu Arg
                675                 680                 685

Glu Pro Leu Tyr Gln Ala Tyr Asp Arg Ile Val Glu Met His His Met
        690                 695                 700

Arg Pro Lys Asn Leu Lys Arg Ala Asn Thr Ser Ile Val Ser Leu Glu
705                 710                 715                 720

Ala Met Ser Ser Phe Glu Gln Leu Asn Val Phe Leu Gln Arg Phe Phe
                725                 730                 735

Gly Ala Glu Gly Lys Asp Arg Glu Tyr Asp Val Trp Lys Thr Pro Phe
            740                 745                 750

Gly Tyr Lys Leu Ser Arg Met Pro Pro Glu Pro Glu Arg Ser Leu
        755                 760                 765

Leu Tyr Ala Gln Ser Thr Asn Ser Leu Arg Lys Ala Ile Asp Gly Tyr
        770                 775                 780

Gly Glu Trp Leu Leu Ala Leu Phe Asp Leu Leu Phe Val Cys Val
785                 790                 795                 800

Asp Tyr Gln Ala Ser Ser Thr Pro Ile Ala Ala Phe Val Thr Leu Ile
                805                 810                 815

Ile Asp Ala Val Met Met Ala Ala Trp Arg Ser Ala Ala Lys Arg Asn
            820                 825                 830

Leu Ala Arg Lys Ser Leu Ile Asp Asn Arg Phe Phe Leu Asn
        835                 840                 845

<210> SEQ ID NO 85
<211> LENGTH: 454
<212> TYPE: PRT
<213> ORGANISM: Trichomonas vaginalis G3

<400> SEQUENCE: 85

Met Gly Glu Asp Val Ser Glu Val Asp Glu Gln Ser Pro Lys Ser Asn
1               5                   10                  15

Leu Leu Lys Trp Ile Phe Ile Ala Val Ala Val Val Val Ile Val
            20                  25                  30

Ile Ile Val Thr Val Thr Val Val Leu Val Leu Lys Lys Lys Arg Asn
        35                  40                  45

Glu Lys Tyr Pro Gly Phe Leu Tyr Leu Asn Asp Ile His Ile Asp Leu
    50                  55                  60

Ser Tyr Asn Pro Lys Ser Asn Lys Asp Trp Cys His Ser Gln Thr Asn
65                  70                  75                  80

Asn Leu Leu Glu Ser Trp Glu Phe Gly Gln Tyr Asn Cys Asp Pro Pro
                85                  90                  95

Pro Lys Leu Tyr Asp Ser Leu Val Glu Ser Leu Lys Thr Asn Val Pro
            100                 105                 110

Ser Val Asp Phe Ile Leu Leu Gly Gly Asp Leu Pro Ser His Asp Leu
```

```
                115                 120                 125
Gly Gly Asn Tyr Thr Phe Leu Lys Glu His Phe Arg Leu Ile Thr Asp
            130                 135                 140

Pro Leu Glu Lys Leu Tyr Pro Asn Lys Lys Ile Phe Ile Thr Leu Gly
145                 150                 155                 160

Asn Asn Asp Phe Gln Glu Asn Tyr Gly Ser Phe Lys Thr Asp Leu Lys
                165                 170                 175

Asp Phe Glu Asn Ala His Glu Val Phe Gly Lys Trp Met Asn Glu Glu
            180                 185                 190

Gln Ser Lys Thr Phe Lys Lys Gly Gly Tyr Tyr Glu Asp Met Pro
        195                 200                 205

Glu Leu Lys Leu Arg Leu Leu Leu Asn Thr Val Met Tyr Thr Asn
    210                 215                 220

Thr Lys Ser Arg Val Phe Asn Glu Ser Leu Lys Asp Pro Tyr Asp Gln
225                 230                 235                 240

Phe Ala Trp Ile Arg Gln Thr Tyr Lys Glu Gly Val Asp Lys Gly Tyr
                245                 250                 255

Lys Val Gly Val Ala Leu His Val Pro Pro Gly Ile Val Tyr Tyr Lys
            260                 265                 270

Gly Ile Pro Gly Phe Pro Ser Met Tyr Leu Glu Glu Phe Gly Lys Val
        275                 280                 285

Phe Glu Glu Cys Asp Phe Ser Phe Thr Ile Ser Gly His Ser His Ile
    290                 295                 300

Asp Thr Leu Asn Pro Leu Tyr Lys Ala Asn Val Glu Glu Asp Asn Ile
305                 310                 315                 320

Gln Tyr Ser Leu Ser Ala Val Ser Val Ser Pro Ser His Tyr Asn Asn
                325                 330                 335

Pro Gly Tyr Arg Tyr Phe Glu Ile Lys Asp Gly Val Leu Gln Asp Tyr
            340                 345                 350

Thr Gln Phe Tyr Ala Asp Ile Met Met Asn Pro Asp Ser Pro Lys Trp
        355                 360                 365

Glu Val Glu Tyr Lys Phe Arg Asp Ala Tyr Lys Val Lys Asp Leu Ser
    370                 375                 380

Lys Lys Ser Leu Asn Asp Ala Thr Arg Tyr Ile Arg Ser Lys Gly Ser
385                 390                 395                 400

Val Ile Trp Ser Tyr Arg Gly Tyr Ile Tyr Ser Gln Ala Glu Lys Tyr
                405                 410                 415

Asn Pro Phe Phe Tyr Cys Ala Leu Arg Ala Leu Thr Lys Glu Asp Val
            420                 425                 430

Phe Lys Cys Ser Leu Asp Leu Asn Val Asn Leu Ser Ser Ile Met Pro
        435                 440                 445

Tyr Ser Asn Arg Gly Asp
    450

<210> SEQ ID NO 86
<211> LENGTH: 1576
<212> TYPE: PRT
<213> ORGANISM: Trichomonas vaginalis G3

<400> SEQUENCE: 86

Met Asn Pro Ser Glu Ser Ser Val Ser Lys Ser Thr Ser Ser Val Ser
1               5                   10                  15

Ser Ile Gly Val Asn Lys Asp Ser Val Ile Gln Gly Lys Tyr Ser Leu
            20                  25                  30
```

```
Ser Asp Gln Ile Phe Pro Val Tyr Asp Gln Met Met Gln Lys Ala Ile
         35                  40                  45

Leu Pro Lys Trp Phe Leu Ala Phe Val Ala Phe Tyr Ile Met Leu Gln
 50                  55                  60

Ile Leu Ile Ile Ala Phe Trp Val Tyr Thr Glu Pro Phe Leu Arg Ile
 65                  70                  75                  80

Asn Ser Lys Tyr Ser Lys Phe Phe Glu Ile Phe Leu Lys Val Phe Ile
                 85                  90                  95

Tyr Gly Asp Ala Ile His Tyr Thr Glu Val Lys Gly Leu Asn Met Tyr
                100                 105                 110

Arg Thr Leu Ile Val Ser Leu Phe Ala Phe Phe Trp Val Phe Phe Val
                115                 120                 125

Ile Tyr Tyr His Lys Leu Lys Tyr Ser Ile Pro Val Pro Leu Leu Tyr
                130                 135                 140

Ile Thr Ser Leu Ile Val Asp Ile Leu Val Pro Val Phe Ile Thr Pro
145                 150                 155                 160

Ser Ala Tyr Val Ala Cys His Gly Ile Val Asn Leu Lys Tyr Ala His
                165                 170                 175

Asn Ser Thr Ile Ile Gly Glu Ile Ile Ile Gly Phe Ile Ser Tyr Gly
                180                 185                 190

Ile Thr Leu Met Asn Phe Ser Ile Thr Thr Leu Lys Ala Arg Ser
                195                 200                 205

Val Ala Leu Thr Asn Leu Thr Phe Pro Leu Phe Asp Ser Ser Ile
                210                 215                 220

Val Val Trp Thr Ile Ser Thr Thr Leu Cys Cys Ile Leu Ser Ala Ile
225                 230                 235                 240

Leu Thr Tyr Phe Glu Asn Trp Thr Gln Ile Ile Val Ile Val Ile His
                245                 250                 255

Ala Ile Ile Ser Cys Tyr Leu Cys Tyr Arg Leu Leu Phe Ile Pro Phe
                260                 265                 270

Tyr Asp Leu Tyr Arg Asn Ala Ser Val Leu Ala Phe Ala Ile Thr Ser
                275                 280                 285

Ile Val Leu Asp Ile Tyr Ser Ile Leu Met Gln Leu Ile Lys Ser Ile
                290                 295                 300

Pro Tyr Glu Tyr Ile Pro Phe Ile Leu Ile Gly Ser Leu Ile Ile Ser
305                 310                 315                 320

Phe Ile Phe Ala Ser Ile Phe Tyr Lys Arg Lys Val Lys Gln Ile Lys
                325                 330                 335

Glu Asp Leu Thr Phe Arg Thr Asp Asn Pro Lys Ala Pro Glu Tyr Leu
                340                 345                 350

Ala Ser Leu Asn Ile Asp Ser Thr Gln Leu Arg Ala Met Glu Tyr Ile
                355                 360                 365

Val Val Gly Leu Thr Gln Ile Cys Asp Tyr Phe Val Asp Gly Ser Leu
                370                 375                 380

Thr Asp Tyr Ile Ile Lys Val Asp Glu Phe Glu Gly Ile Leu Ala Ile
385                 390                 395                 400

Leu Leu Gln Val Val Thr Phe Phe Pro Cys Glu Ser Arg Lys Met Asp
                405                 410                 415

Val Leu Tyr Lys Lys Leu Ile Met Lys Arg Lys Leu Ser Phe Ala Asp
                420                 425                 430

Arg Phe Leu Leu Tyr Gln Val Tyr Arg Ile Lys Thr Arg Arg Leu Val
                435                 440                 445

Thr Asp Thr Lys Ser Thr Leu Glu Thr Tyr Thr Lys Leu Lys Ala Arg
```

```
              450                 455                 460
Asn Asp Glu Cys Lys Gln Ser Ile Arg Ser Phe Trp Asp Phe Pro Ser
465                 470                 475                 480

Cys Lys Ile Asn Tyr Leu Ser Ser Leu Ser Ile Thr Val Asn Asp Ile
                485                 490                 495

Asn Ser Leu Phe Ile Asn Thr Ile Gln Glu Asn Pro Asn Asn Val Arg
                500                 505                 510

Ile Ala Thr Glu Tyr Ser Asp Phe Leu Ile Glu Cys Met Thr Asn Phe
                515                 520                 525

Asp Glu Ala Ile Arg Gln Lys Val Lys Val Glu Arg Ile Leu Asn Gly
            530                 535                 540

Thr Asn Phe Asn Val Asp Ile Ser Phe Arg Ser Leu Val Asn Lys Phe
545                 550                 555                 560

Pro Arg Tyr Leu Lys Asp Lys Ile Leu Asp Thr Lys Gly Arg Leu Ile
                565                 570                 575

Met Arg Leu Lys Glu Arg Asn Ser Asp Pro Leu Asn Asp Asn Ser Ser
            580                 585                 590

Asn Gln Ser Lys Ser Gly Ser Ser Lys Glu Thr Asn Thr Ser Thr
                595                 600                 605

Leu Thr Val Asp Leu Glu Thr Gln Glu Val Val Ser Lys Arg Val Leu
            610                 615                 620

Arg Asp Ser Lys Val Arg Leu Ala Phe His Gln Ser Ile His Thr Leu
625                 630                 635                 640

His Pro His His Met Lys Asn Leu Thr Ile Leu Ala Asn Ser Ile Leu
                645                 650                 655

Val Val Cys Phe Ser Ile Phe Ile Ala Tyr Tyr Ala Tyr Gln Lys Asp
                660                 665                 670

Lys Leu Lys Trp Arg Arg Asp Ala Phe Val Glu Phe Arg Tyr Met Ser
            675                 680                 685

Leu Ala Leu Asp Lys Thr Tyr Tyr Ala Ser Phe Val Leu Thr Leu Glu
            690                 695                 700

Trp Ala Arg Met His Asp Arg Tyr Asp Asn Ser Thr Glu Ile Met Gly
705                 710                 715                 720

Asn Ile Ser Ile Asp Phe Glu Asp Asn Pro Ile Ala Lys Asn Lys Trp
                725                 730                 735

Glu Pro Ala Tyr Glu Thr Ile Tyr Gln Thr Val Asp Gln Ala Lys Asp
                740                 745                 750

Phe Leu Glu Thr Leu Tyr Gln Ser Met Ala Asp Ser Ala Arg Thr Glu
            755                 760                 765

Asp Ile Tyr Glu Ile Ile Pro Leu Leu Leu Lys Pro Arg Ser Lys Ile
            770                 775                 780

Tyr Ala Cys Thr Asn Tyr Glu Ile Ser His Asp Met Pro Gly Asn Leu
785                 790                 795                 800

Lys Asp Gln Phe Val Ile Ile His Phe Gln Asp Asn Phe Ala Gly
                805                 810                 815

Asp Phe His Val Met Asp Lys Asp Ile Pro Asn Ile Tyr Gln Asn Asp
            820                 825                 830

Phe Tyr Cys Gln Leu Phe Ala Asn Ser Tyr Ile Leu Ser Lys Asn Ala
            835                 840                 845

Glu Glu Ser Ile Glu Asn Ile Leu Asp Tyr Ser Val Glu Lys Ser Gln
            850                 855                 860

Lys Leu Ile Asp Asp Val Trp Leu Trp Thr Gly Ile Gly Gly Gly Ile
865                 870                 875                 880
```

```
Val Leu Phe Val Thr Phe Ile Pro Met Ile Ile Ile Ile Asn Tyr
                885             890                 895

Tyr Lys Ile Val Asn Gly Leu Leu Lys Val Leu Leu Glu Leu Pro Asn
        900                 905                 910

Ser Ala Lys Glu Asp Ala Lys Lys Arg Leu Asn Ile Glu Asn Thr Asp
        915                 920                 925

Glu Ile Val Glu Thr Ser Asn Lys Thr Lys Lys Ser Lys Leu Leu Glu
930                 935                 940

Ile Ser Ile Phe Ile Tyr Phe Ala Ser Ala Ala Leu Ile Thr Val Leu
945                 950                 955                 960

Tyr Cys Leu Ser Gly Leu Tyr Thr Tyr Tyr Phe Asn Asp Leu Met Ala
                965                 970                 975

Asn Leu Leu Asp Trp Tyr Tyr Ile Ser Cys Val Arg Asn Val Ala Ser
                980                 985                 990

Ser Glu Leu Arg Asn Asn Ile Leu His Ile Ile Leu Leu Asn Asp Ser
                995                 1000                1005

Leu Pro Asn Lys Ile Ile Pro Leu Glu Asp Ile Tyr Gln Ala Ala
        1010            1015            1020

Leu Asp Glu Ile Asp Leu Leu Lys Arg Tyr Asn Gln Tyr Leu Ile
    1025            1030            1035

Glu Gly Gly Asn Asn Phe Glu Arg Phe Ile Gly Phe Asp Ala Glu
    1040            1045            1050

Ser Asp Ser Tyr Gln Phe Met Glu Val Cys Glu Leu Gly Arg Asp
    1055            1060            1065

Pro Lys Ser Met His Asp Met Tyr Ala Cys Ser Ser Ile Asp Lys
    1070            1075            1080

Gln Ile Ala Phe Leu Thr Thr Asn Val Arg Asp Ile Met Lys Asn
    1085            1090            1095

Pro Asp Lys Leu Ser Gly Ala Ile Asn Asp Glu Val Thr Gln Asn
    1100            1105            1110

Val Met His Leu Ile Asn Asn His Phe Tyr Pro Leu Thr Val Leu
    1115            1120            1125

Ala Ala Thr Arg Val Lys Ser Leu Leu Gln Asp Asn Phe Asp Ala
    1130            1135            1140

Gly Met Lys Lys Leu Thr Ile Tyr Leu Val Ile Glu Leu Leu Ile
    1145            1150            1155

Ser Leu Phe Leu Phe Ile Leu Pro Leu Phe Ile Arg Ala Val Ile
    1160            1165            1170

Trp Glu Asn Tyr Lys Met Leu Leu Met Leu Leu Lys His Leu Pro
    1175            1180            1185

Pro Gln Val Ile Ile Asp Thr Pro Glu Ile Leu Asp Phe Phe Arg
    1190            1195            1200

Glu Lys Ser Lys His His His Thr Glu Ala Met Thr Ile Ser Lys
    1205            1210            1215

Ser Val Val Tyr Asn Thr Ser Glu Cys Ile Ala Ile Thr Asn Gln
    1220            1225            1230

Asn Ala Ile Ile Glu Ile Val Asn Gln Ser Leu Thr Ala Asn Ile
    1235            1240            1245

Asn Ile Thr Pro Asp Gln Ile Leu Gly Gln Ser Ile Thr Asn Ile
    1250            1255            1260

Ile Ser Leu Ser Glu His Asp Arg Ile Gly Asn Gln Ile Gln Leu
    1265            1270            1275
```

Met Thr Thr Gly Gln Gly Ser Ser Val Trp Gln Asp His Thr Lys
1280                1285                1290

Leu Val Lys Asp Asp Gly Ser Glu Val Pro Phe Gly Ile Thr Ile
1295                1300                1305

Ile Gly Met Lys Glu Asn Glu Gly Ser Ala Asp Ile Thr Ser Leu
1310                1315                1320

Val Phe Ile Leu Glu Asn Glu Glu Lys Ile Lys Gln Lys Lys
1325                1330                1335

Leu Ala Glu Glu Ser Lys Ala Lys Ser Glu Lys Leu Leu Tyr Gln
1340                1345                1350

Ile Leu Pro Lys Asp Ile Val Val Arg Leu Asn Arg Gly Glu Thr
1355                1360                1365

Asp Ile Ser Phe Thr Ile Pro Ser Ala Thr Ile Phe Phe Ile Asp
1370                1375                1380

Ile Val Lys Phe Ser Ser Tyr Ala Glu Leu Leu Thr Pro Ser Glu
1385                1390                1395

Ile Met Ala Asn Leu Ser Leu Val Phe Ala Thr Phe Asp Gly Ile
1400                1405                1410

Val Ser Glu Phe Gln Ser Ile Thr Lys Ile Lys Leu Ile Gly Asp
1415                1420                1425

Val Tyr Met Ala Ala Ala Gly Leu Phe Gln Asp Pro Lys Glu Glu
1430                1435                1440

Ser Lys Gln His Ala Glu Asp Ala Val Arg Cys Cys Leu Lys Cys
1445                1450                1455

Ala Lys Ser Met Glu Glu Ile Asn Met Lys Leu Asn Ala Ser Leu
1460                1465                1470

Glu Val Arg Ile Gly Cys Asn Ser Gly Gly Pro Leu Ile Gly Gly
1475                1480                1485

Val Leu Gly Thr Asp Lys Pro Thr Phe Asp Ile Ile Gly Asp Thr
1490                1495                1500

Ile Asn Val Ala Ala Arg Leu Gln Ser Thr Asp Ile Pro Gly Asn
1505                1510                1515

Val Gln Ile Ser Ala Ser Thr Lys Glu Met Ile Glu His Leu Asp
1520                1525                1530

Phe Val Ile Glu Glu Arg Gly Leu Ile Tyr Leu Lys Gly Lys Gly
1535                1540                1545

Lys Gln Met Thr Tyr Phe Val Ser Phe Lys Asn Asn Asp Gly Asn
1550                1555                1560

Lys Ser Ser Phe Asp Ser Ser Phe Thr Leu Lys Leu Asn
1565                1570                1575

<210> SEQ ID NO 87
<211> LENGTH: 370
<212> TYPE: PRT
<213> ORGANISM: Trichomonas vaginalis G3

<400> SEQUENCE: 87

Met Phe Arg Gln Leu Leu Ala Gly Ser Leu Pro Thr Asp Met Ile Val
1               5                   10                  15

Pro Asn Phe Thr His Val Tyr Pro Glu Cys Asp Lys Lys Leu Glu Lys
                20                  25                  30

Thr Met Asn Phe Thr Thr Leu Tyr Thr Lys Glu Leu Glu Ala Gly Glu
            35                  40                  45

Ile Ile Cys Phe Tyr Lys Thr Tyr Ala Ile Ala Gly Asn Ala Ala Tyr
        50                  55                  60

```
Thr Val Asn Ala Thr Tyr Phe Asn Pro Glu Asn Thr Ser Ile Tyr Glu
 65                  70                  75                  80

Thr Lys Phe Ala Glu Ser Pro Phe Leu Val Ser Gly Pro Ile Ser Pro
                 85                  90                  95

Lys Val Ile Pro Val Ser Lys Val Ala Cys Lys Asp Ser Ser Lys Lys
            100                 105                 110

Cys Lys Ile Gln Phe Ile Ser Ile Thr Pro Ser Gly His Gln Lys Leu
        115                 120                 125

Glu Glu Ser Asp Leu Tyr Val Asp Asn Ile Phe Asp Ser Tyr Leu Ser
    130                 135                 140

Thr Lys Lys Lys Gln Ser Phe Ser Lys Ser Tyr Ser Met Glu Phe His
145                 150                 155                 160

Ile Ser Ser Lys Asn Asn Lys Val Lys Arg Val Met Asn Ser Ser Thr
                165                 170                 175

Phe Ile Ser Thr His Ile Gly Ser Lys Ser Arg Thr Ile Thr Val Ser
            180                 185                 190

Pro Asp Ser Leu Tyr Val Phe Ala Asp Gly Lys Lys Gln Glu Lys Asn
        195                 200                 205

Thr Gly Thr Gly Lys Ala Leu Ser Phe Ala Pro Ser Gln Glu Phe Ser
    210                 215                 220

Leu Ser Leu Val Asn Met Ser Glu Leu Gln Thr Lys Ile Gln Thr Asp
225                 230                 235                 240

Lys Lys Asp Gly Lys Ile Asn Asp Ser Tyr Lys Ile Asp Lys Lys Gly
                245                 250                 255

Ser Gln Thr Ile Thr Val Ser Ile Ser Glu Pro Lys Ser Ser Ser Glu
            260                 265                 270

Asp Glu Glu Phe Phe Phe Asp Glu Asp Lys Glu Tyr Tyr Leu Lys Gly
        275                 280                 285

Asp Ala Ser Leu Lys Ser Lys Lys Glu Val Glu Glu Asp Thr Lys Glu
    290                 295                 300

Asn Pro Pro Gly Ser Ser Phe Pro Ala Trp Glu Ile Ala Val Ile
305                 310                 315                 320

Val Ile Val Ile Ile Leu Ile Ile Val Ile Ile Ile Ile Ile Ile Phe
                325                 330                 335

Cys Cys Cys Cys Cys Cys Cys Ser Cys Cys Ser Cys Lys Lys Gly Ser
            340                 345                 350

Ser Asn Val Gly Ser Ala Lys Asp Asp Glu Asp Ser Gly Ser Gly Val
        355                 360                 365

Asn Val
    370

<210> SEQ ID NO 88
<211> LENGTH: 567
<212> TYPE: PRT
<213> ORGANISM: Trichomonas vaginalis

<400> SEQUENCE: 88

Met Leu Ala Ser Ser Val Ala Ala Pro Val Arg Asn Ile Cys Arg Ala
1               5                   10                  15

Lys Leu Pro Ala Leu Lys Thr Gly Met Thr Leu Leu Gln Asp Gly Asp
                20                  25                  30

Leu Ser Lys Gly Ser Ala Phe Thr Lys Glu Glu Arg Asp Arg Leu Asn
        35                  40                  45

Leu Arg Gly Leu Leu Pro Tyr Lys Val Phe Thr Lys Asp Glu Gln Ala
```

```
            50                  55                  60
Ala Arg Ile Arg Arg Gln Phe Glu Leu Met Pro Thr Pro Leu Leu Lys
 65                  70                  75                  80

Tyr Ile Phe Leu Ala Asn Glu Arg Glu Lys Asn Ser Gln Ser Phe Trp
                 85                  90                  95

Arg Phe Leu Phe Thr His Pro Pro Thr Glu Thr Met Pro Val Leu Tyr
                100                 105                 110

Thr Pro Thr Val Gly Glu Ala Cys Gln Lys Trp Ala Thr His Arg Gln
                115                 120                 125

Ser Tyr Arg Gly Ile Tyr Ile Thr Pro Glu Asp Ser Gly Lys Ile Lys
130                 135                 140

Asp Ile Leu Arg Asn Tyr Pro Arg Gln Asp Ile Arg Cys Ile Val Val
145                 150                 155                 160

Thr Asp Gly Gly Arg Ile Leu Gly Leu Gly Asp Leu Gly Ala Ser Gly
                165                 170                 175

Leu Gly Ile Pro Val Gly Lys Leu Met Leu Tyr Thr Leu Ile Gly Gln
                180                 185                 190

Val His Pro Asp Gln Thr Leu Pro Val Gln Leu Asp Met Gly Thr Asp
                195                 200                 205

Arg Lys Glu Ile Leu Ala Asp Pro Leu Tyr His Gly Trp Arg His Pro
210                 215                 220

Arg Ile Arg Gly Pro Glu His Thr Lys Phe Val Ala Glu Phe Val Asp
225                 230                 235                 240

Ala Val Lys Glu Val Phe Gly Glu Thr Cys Leu Val Gln Phe Glu Asp
                245                 250                 255

Phe Glu Met Glu Thr Ala Phe Lys Leu Leu Asp His Phe Arg Trp Arg
                260                 265                 270

Cys Asn Cys Phe Asn Asp Asp Ile Glu Gly Thr Ala Ala Val Ala Ala
                275                 280                 285

Ala Thr Leu Ala Ser Ala Thr His Met Glu Gly Val Pro Asp Leu Lys
                290                 295                 300

Asn Gln Lys Ile Ile Phe Ile Gly Ala Gly Ser Ala Ala Thr Gly Ile
305                 310                 315                 320

Ala Asn Leu Ile Val Asp Met Ala Val Ser Arg Gly Ile Ser Arg
                325                 330                 335

Lys Asp Ala Glu Arg Asn Ile Ile Met Phe Asp His Lys Gly Met Val
                340                 345                 350

His Ala Asp Arg Lys Asp Leu Tyr Asp Phe Asn Lys Pro Tyr Met His
                355                 360                 365

Asp Met Glu Val Tyr Gly Ser Val Leu Glu Gly Val Lys Lys Phe Lys
                370                 375                 380

Ala Thr Cys Val Ile Gly Val Ser Gly Val Pro Gly Leu Ile Thr Lys
385                 390                 395                 400

Glu Ile Val Gln Ala Thr Cys Ala Asn Cys Glu Arg Pro Val Ile Met
                405                 410                 415

Pro Leu Ser Asn Pro Thr Val Lys Ala Glu Ala Lys Pro His Asp Val
                420                 425                 430

Tyr Gln Trp Ser Asn Gly Lys Ala Leu Cys Ala Thr Gly Ser Pro Phe
                435                 440                 445

Pro Val Glu Thr Val Asn Gly Lys Lys Thr Ile Thr Ala Gln Ala Asn
                450                 455                 460

Asn Ser Trp Ile Phe Pro Ala Val Gly Tyr Ala Leu Val Thr Thr Arg
465                 470                 475                 480
```

Ala Arg His Cys Pro Gly Lys Val Phe Glu Val Ala Ala Glu Ser Leu
            485                 490                 495

Ala Ser Leu Val Lys Lys Glu Asp His Asp Met Gly Asn Leu Leu Pro
            500                 505                 510

Pro Leu Asp Lys Ile Arg Glu Tyr Ser Phe Gly Ile Ala Leu Asp Val
            515                 520                 525

Ala Lys Tyr Leu Ile Lys Asn Glu Leu Ala Thr Ala Leu Pro Pro Lys
            530                 535                 540

Gly Thr Glu Leu Lys Asp Trp Leu Lys Ala Gln Leu Phe Asp Pro Gln
545                 550                 555                 560

Ala Glu Tyr Glu Gln Leu Tyr
            565

<210> SEQ ID NO 89
<211> LENGTH: 309
<212> TYPE: PRT
<213> ORGANISM: Trichomonas vaginalis

<400> SEQUENCE: 89

Met Leu Ser Ser Ser Phe Glu Arg Asn Leu His Gln Pro Leu Leu Phe
1               5                   10                  15

Ile Asp Lys Asp Thr Lys Val Val Ile Gln Gly Ile Gly Asn Gln Gly
            20                  25                  30

Gln Phe His Ser Arg Leu Met Arg Gln Tyr Gly Thr Lys Val Val Gly
            35                  40                  45

Ala Val His Pro Lys Lys Ala Gly Ser Ile Ile Ala Gly Leu Pro Ile
        50                  55                  60

Phe Lys Asn Met Lys Glu Val Val Lys Arg Thr Asp Ala Asn Ala Ser
65                  70                  75                  80

Leu Ile Phe Val Pro Ala Pro Gly Ala Ala Ala Cys Ile Glu Ala
                85                  90                  95

Ala Gln Ala Gly Met Gly Leu Val Val Cys Ile Thr Glu His Ile Pro
            100                 105                 110

Gln His Asp Met Ile Lys Val Lys Lys Val Met Lys Glu Thr Gly Cys
            115                 120                 125

Gln Leu Ile Gly Pro Asn Cys Pro Gly Leu Ile Gln Pro Gly Thr His
        130                 135                 140

Thr Lys Leu Gly Ile Ile Pro Thr Asn Ile Phe Asn Asn Gly Lys Ile
145                 150                 155                 160

Gly Ile Val Ser Arg Ser Gly Thr Leu Thr Tyr Glu Ala Ala Tyr Ala
            165                 170                 175

Thr Thr Leu Ala Gly Leu Gly Gln Ser Thr Val Val Gly Ile Gly Gly
            180                 185                 190

Asp Pro Phe Ala Gly Gln Leu His Thr Asp Val Val Lys Arg Phe Ala
        195                 200                 205

Ala Asp Pro Gln Thr Glu Gly Ile Ile Leu Ile Gly Glu Ile Gly Gly
        210                 215                 220

Thr Ser Glu Glu Asp Ala Ala Glu Trp Ile Ala Lys Thr Lys Leu Thr
225                 230                 235                 240

Gln Glu Lys Pro Val Val Ala Phe Ile Ala Gly Ala Thr Ala Pro Pro
                245                 250                 255

Gly Lys Arg Met Gly His Ser Gly Ala Ile Val Ser Gly Gly Lys Gly
            260                 265                 270

Thr Ala Glu Gly Lys Tyr Lys Ala Leu Glu Ala Ala Gly Val Arg Ile

```
                275                 280                 285
Ala Arg His Pro Gly Asn Met Gly Lys Phe Ile Phe Glu Glu Met Lys
            290                 295                 300
Arg Met Gly Lys Ile
305

<210> SEQ ID NO 90
<211> LENGTH: 931
<212> TYPE: PRT
<213> ORGANISM: Trichomonas vaginalis

<400> SEQUENCE: 90

Met Ser Val Arg Arg Glu Gly Leu Leu Asp Asp Ala Trp Glu Lys Thr
1               5                   10                  15

Gln Ile Lys Val Phe Ser Arg Trp Val Gln Lys Gln Leu Leu Ala Arg
            20                  25                  30

Gln Ile Gln Phe Glu Thr Ile Glu Thr Asp Phe Glu Asp Gly Thr Lys
        35                  40                  45

Leu Leu Asn Leu Leu Glu Ile Ile Gly Lys Glu Pro Met Pro Ser Lys
    50                  55                  60

Trp His Lys Gln Pro Lys Met Met Val Gln Lys Arg Glu Asn Val Asp
65                  70                  75                  80

Leu Ala Leu Lys Tyr Ile Asn Glu Val Lys Lys Ile Arg Thr Val Gly
                85                  90                  95

Ile Gly Ala Asp Asp Ile Ile Asn Lys Asn Leu Lys Leu Thr Leu Gly
            100                 105                 110

Leu Thr Trp Thr Cys Ile Asn Lys Phe Met Ile Glu Ile Ser Val
        115                 120                 125

Glu Glu Ala Thr Ala Arg Asp Ala Leu Leu Leu Trp Ala Lys Lys Asn
130                 135                 140

Thr Gln Gly Tyr Glu His Val Ala Val Asn Asn Phe Thr Thr Ser Trp
145                 150                 155                 160

Asn Thr Gly Leu Ala Phe Ala Ala Leu Ile Asn Lys Phe Arg Pro Asn
                165                 170                 175

Leu Leu Asp Tyr Ser Ala Leu Asp Tyr Asn Asp His Lys Gly Ala Cys
            180                 185                 190

Glu Lys Ala Phe Ala Ala Cys Lys Glu Leu Gly Ile Tyr Val Tyr Leu
        195                 200                 205

Asp Pro Glu Asp Val Ile Asp Thr Thr Pro Asp Glu Lys Ser Val Val
    210                 215                 220

Thr Gln Val Ala Glu Phe His Phe Phe Ala Ser Glu Ser Lys Ile
225                 230                 235                 240

Ala Ala Met Ala Asp Lys Ile Lys Arg Thr Val Ala Ile Gln Lys Gln
                245                 250                 255

Ile Asp Glu Leu Lys Asn Thr Tyr Ile Glu Asp Ala Lys Ala Ala Ile
            260                 265                 270

Glu Lys Met Thr Val Glu Asp Glu Lys Leu Lys Ala Asp Asp Tyr Glu
        275                 280                 285

Lys Thr Ile Pro Gly Ile Arg Gly Lys Leu Ala Ser Val Ile Ser Tyr
    290                 295                 300

Asn Arg Asp Ile Arg Pro Glu Ile Val Asp His Arg Ala Lys Ala Met
305                 310                 315                 320

Arg Ser Trp Ala Ala Leu Val Thr Lys Cys Lys Ser Gly Asn Arg Pro
                325                 330                 335
```

```
Ile Pro Glu Ile Pro Gln Gly Leu Glu Pro Glu Ala Leu Thr Asn Lys
                340                 345                 350

Phe Asn Glu Ile Glu Gln Thr Ser Thr Thr Arg Arg Asp Glu Leu Thr
            355                 360                 365

Gln Glu Leu Asn Asp Met Ile Lys Lys Val Glu Asp Phe Met Ala
370                 375                 380

Lys Cys Met Asp Ile Ile Asn Lys Cys Asp Ala Ile His Glu Glu Val
385                 390                 395                 400

Lys Thr Ile Glu Gly Thr Thr Ala Glu Lys Lys Asp Lys Val Glu Gln
                405                 410                 415

Lys Leu His Glu Ala Glu Asp Leu Gln Pro Ala Leu Ala Glu Leu Thr
            420                 425                 430

Pro Leu Phe Gln Glu Leu Val Glu Leu Arg Ile Asn Thr Leu Ser Ser
            435                 440                 445

Gln Thr Asp Asp Ser Val Asn Arg His His Ser Gln Leu Ile Thr Tyr
        450                 455                 460

Ile Lys His Leu Leu Glu Gln Leu Asn Gly Lys Leu Phe Glu Glu Thr
465                 470                 475                 480

Asn Glu Ala Arg Ile Asn Glu Tyr Asn Ala Leu Ala Gln Pro Leu Tyr
                485                 490                 495

Asp Glu Ala Ile Ala Phe Lys Glu Glu Val Leu Ala Ile Ser Gly Glu
            500                 505                 510

Leu Arg Glu Arg Arg Thr Gln Phe Leu Ala Lys Gln Ala Glu Ala Pro
            515                 520                 525

Thr Lys Arg Glu His Val Asn Glu Ile Asp Pro Ile Phe Asp Gly Leu
530                 535                 540

Glu Lys Asp Ser Leu His Leu Arg Val Asn His Ser Pro Thr Glu Ile
545                 550                 555                 560

Arg Asn Val Tyr Ala Val Thr Leu Gln His Ile Ile Thr Glu Leu Asn
                565                 570                 575

Lys Ile Phe Glu Glu Met Val Ala Asn Phe Asp Ala Thr Ala Val Pro
            580                 585                 590

Ile Ile Asp Gly Ile Thr Ala Leu Val Thr Ser Ser His Gln Ile Pro
            595                 600                 605

Gly Asp Ala Ala Ala Val Lys Ala Gln Val Glu Glu Asn Leu Ala Ser
610                 615                 620

Leu Asp Gly Phe Ala Glu Lys Ile Gln Ala Leu Gln Asp Pro Tyr Asn
625                 630                 635                 640

Glu Leu Val Glu Phe Lys Leu Asn Tyr Lys Val Thr Tyr Thr Tyr Ser
                645                 650                 655

Asp Ala Thr Gly Glu Leu Asp Gln Ala Arg Leu Asp Leu Lys Gln Ile
            660                 665                 670

Ile Leu Ala Lys Lys Thr Phe Leu Glu Glu Glu Arg Lys Ala Arg
            675                 680                 685

Ile Asn Asn Tyr Thr Val Lys Ala Asp Glu His Met Asn Glu Ala His
690                 695                 700

Ala Leu Asp Gly Lys Ile Asn Ser Val Asp Gly Glu Leu Glu Pro Lys
705                 710                 715                 720

Arg Gln Lys Leu Tyr Glu Val Arg Glu Val Asn Ala Lys Lys Glu
                725                 730                 735

Lys Ala Ala Glu Glu Leu Thr Pro Ile Tyr Glu Asp Leu Glu Lys Asp
            740                 745                 750

Gln Leu His Leu Glu Ile Thr Ser Thr Pro Ala Ser Ile Asn Ile Phe
```

-continued

```
                    755                 760                 765
Phe Glu Asn Leu Ile Ala His Ile Asp Thr Leu Val Lys Glu Ile Asp
    770                 775                 780

Ala Ala Ile Ala Ala Ala Lys Gly Leu Glu Ile Ser Glu Glu Glu Leu
785                 790                 795                 800

Asn Glu Phe Lys Asp Thr Phe Lys Tyr Phe Asp Lys Asp Lys Ser Asn
                805                 810                 815

Ser Leu Glu Tyr Phe Glu Leu Lys Ala Cys Leu Thr Ala Leu Gly Glu
                820                 825                 830

Asp Ile Thr Asp Gly Gln Ala Lys Glu Tyr Cys Lys Lys Tyr Asn Ser
                835                 840                 845

Lys Gly Glu Gly Thr Ala Leu Glu Phe Asp Asp Tyr Val Arg Phe Met
    850                 855                 860

Leu Asp His Phe Ser Lys Ala Glu Thr Thr Glu Thr Thr Met Glu Ala
865                 870                 875                 880

Phe Lys Ala Ile Ala Gln Asn Gln Pro Val Leu Thr Asp Ala Gln Leu
                885                 890                 895

Asp Gln Tyr Phe Ser Ala Glu Asp Ala Ala Tyr Leu Arg Ser Gln Leu
                900                 905                 910

Lys Gln Gly Glu Asn Gly Tyr Glu Phe Ala Asp Trp Val Asn Ser Leu
    915                 920                 925

Tyr Asn His
    930
```